(12) United States Patent
Long et al.

(10) Patent No.: US 8,785,424 B2
(45) Date of Patent: Jul. 22, 2014

(54) NGCYCLOARTANONE DERIVATIVES WITH ANTICANCER ACTIVITY

(75) Inventors: Christophe Long, Vielmur sur Agout (FR); Yves Guminski, Lagarrigue (FR); Fadila Derguini, Toulouse (FR); Joséphine Beck, Toulouse (FR); Frédéric Cantagrel, Talence (FR)

(73) Assignees: Pierre Fabre Medicament, Boulogne-Billancourt (FR); Centre National de la Recherche Scientifique (CNRS), Paris (FR)

( * ) Notice: Subject to any disclaimer, the term of this patent is extended or adjusted under 35 U.S.C. 154(b) by 262 days.

(21) Appl. No.: 13/321,440

(22) PCT Filed: May 20, 2010

(86) PCT No.: PCT/EP2010/057006
§ 371 (c)(1),
(2), (4) Date: Nov. 18, 2011

(87) PCT Pub. No.: WO2010/133687
PCT Pub. Date: Nov. 25, 2010

(65) Prior Publication Data
US 2012/0077777 A1 Mar. 29, 2012

(30) Foreign Application Priority Data
May 20, 2009 (EP) .................................. 0953385

(51) Int. Cl.
A61K 31/58 (2006.01)
C07J 53/00 (2006.01)
C07J 71/00 (2006.01)

(52) U.S. Cl.
USPC ................ 514/176; 552/510; 540/50; 540/76

(58) Field of Classification Search
USPC .......................... 514/176; 540/50, 76; 552/510
See application file for complete search history.

(56) References Cited

PUBLICATIONS

Ausseil et al., "High-Throughput Bioluminescence Screening of Ubiquitin-Proteasome Pathway Inhibitors from Chemical and Natural Source", Journal of Biomolecular Screening, vol. 12 (2007) pp. 106-116.
Grando et al., "Antineoplastic 31-Norcycloartanones from Solanum cerniuum Vell.", Journal of Biosciences, vol. 63 (2008) pp. 507-514.
Kikuchi et al., "Cancer Chemopreventive Effects of Cycloartane-Type and Related Triterpenoids in in Vitro and in Vivo Models", J. Nat, Prod., vol. 70 (2007) pp. 918-922.
Rakhimov et al., "Triterperne Alkaloids of Thalictrum foetidum L. and Thalictrum minus L. and Their Antitumorigenic Activity", J. Pharma. Chem, vol. 21 (1987) pp. 848-850.
Vandenberghe et al., "Physalin B, a novel inhibitor of the ubiquitin-proteasome pathway, triggers NOXA-associated apoptosis", Biochemical Pharmacology, vol. 76 (2006) pp. 463-462.

*Primary Examiner* — Barbara P Badio
(74) *Attorney, Agent, or Firm* — Birch, Stewart, Kolasch & Birch, LLP

(57) ABSTRACT

The present invention relates to a compound of following formula (I):

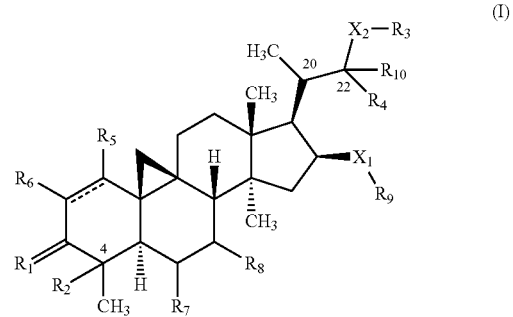

or to a pharmaceutically acceptable salt thereof, as well as to pharmaceutical compositions including same and to the use thereof as a drug, in particular for treating a proliferative disease such as cancer.

22 Claims, No Drawings

NGCYCLOARTANONE DERIVATIVES WITH ANTICANCER ACTIVITY

The present invention relates to novel derivatives that can be used as a drug, notably for treating a proliferative disease such as cancer.

Thus, the present invention relates to a compound of following formula (I):

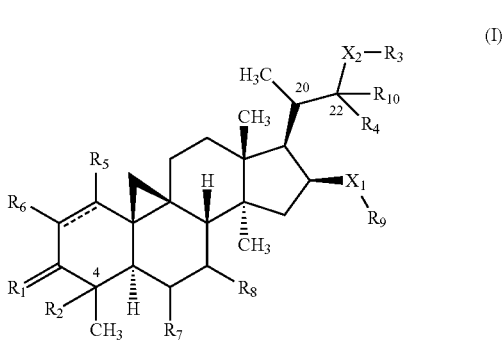

or to a pharmaceutically acceptable salt thereof, wherein:
⎯⎯ indicates a single bond or a double bond, $X_1$ and $X_2$ represent, independently of each other, an oxygen or sulfur atom, and notably an oxygen atom, $R_1$ represents an oxygen atom, a sulfur atom or an $N-OR_{11}$ or $N-NHCO-NH_2$ group, $R_2$ represents a hydrogen atom or an $OR_{12}$ or $SR_{12}$ group, $R_3$ represents a hydrogen atom, $-SO_2R_{55}$, $-CH_2OCH_2CH_2SiR_{61}R_{62}R_{63}$ or a $-CO-(C_1-C_6)$ alkyl, such as $-COCH_3$, or $-CO-(C_2-C_6)$alkenyl group, wherein said group is optionally substituted by a halogen atom or a COOH group, or $-NR_{56}R_{57}$, with for example $R_{56}=R_{57}=H$, $R_4$ represents a group selected from:
  a hydrogen atom,
  a saturated or unsaturated linear or branched hydrocarbon chain comprising 1 to 15, for example 1 to 10, carbon atoms, one or more, for example 1 to 2, non-consecutive carbon atoms may be replaced by an oxygen atom, wherein said chain is optionally substituted by one or more groups selected from a halogen atom, =O, -OH, $-OSO_2R_{13}$, $-N_3$, $(C_1-C_6)$alkoxy, $-Z_1C(X)R_{14}$, $-C(X)Z_2R_{15}$, $-Z_3C(X)Z_4R_{16}$, $-NH-OR_{17}$, $=N-OR_{18}$, $=N-NR_{53}R_{54}$, $-OSiR_{19}R_{20}R_{21}$, $-SiR_{58}R_{59}R_{60}$, $-OP(O)(OR_{22})(OR_{23})$, $-NR_{24}R_{25}$, a heterocycle with 5 or 6 members, an epoxide, a sugar residue and an inositol residue, one or more hydroxy groups of said sugar and inositol residues are optionally substituted by an acetyl group or $-P(O)(OH)_2$, and
  a heterocycle with 5 or 6 members or a polycycle with 10 to 15 members, wherein said heterocycle or polycycle comprises at least one oxygen atom and is optionally substituted by one or more groups selected from $-OH$, =O, $-NH_2$, $-N_3$, =$CH_2$, $-COOR_{26}$, $(C_2-C_6)$alkenyl, $(C_1-C_6)$alkoxy, and a $(C_1-C_6)$alkyl group, such as methyl, optionally substituted by a halogen atom or an $-N_3$, $-OH$, $(C_1-C_6)$alkoxy, $-NH-COR_{27}$ or $-NR_{28}-OC(O)R_{29}$ group, $R_5$ and $R_6$ each represent a hydrogen atom when ⎯⎯ represents a double bond, or $R_5$ and $R_6$ each represent, independently of each other, a hydrogen atom or an $OR_{48}$ group, such as OH, or $R_5$ and $R_6$ together form, with the carbon atoms that carry them, an epoxide ring, when ⎯⎯ represents a single bond, $R_7$ represents a hydrogen atom or an $OR_{49}$ group, such as OH, $R_8$ represents a hydrogen atom, or $R_7$ and $R_8$ together form, with the carbon atoms that carry them, an epoxide ring, $R_9$ represents a $-CO-(C_1-C_6)$alkyl or $-CO-(C_2-C_6)$alkenyl group, $R_{10}$ represents a hydrogen atom, or $R_{10}$ and $R_3$ together form a bond, i.e., the bond between carbon atom 22 and $X_2$ is a double bond, or $R_{10}$ and $R_9$ together form a bond, i.e., $X_1$ and carbon atom 22 are linked by a single bond.

with:

$R_{11}$, $R_{26}$, $R_{28}$, $R_{30}$, $R_{31}$, $R_{36}$, $R_{37}$, $R_{41}$, $R_{42}$, $R_{43}$, $R_{48}$, $R_{49}$ and $R_{50}$ representing, independently of one another, a hydrogen atom or a $(C_1-C_6)$alkyl, $(C_2-C_6)$alkenyl, aryl or aryl-$(C_1-C_6)$alkyl group, $R_{12}$ representing a hydrogen atom or a $(C_1-C_6)$alkyl or $(C_2-C_6)$alkenyl group, and notably a hydrogen atom, $R_{13}$ and $R_{55}$ represent, independently of each other, an $-OH$, $(C_1-C_6)$alkoxy, aryl, $-NR_{30}R_{31}$ or $(C_1-C_6)$alkyl-aryl group, or a $(C_1-C_6)$alkyl group optionally substituted by an $-NR_{30}R_{31}$ group, $R_{14}$ representing a $(C_1-C_6)$alkyl, $(C_2-C_6)$alkenyl, aryl, $(C_1-C_6)$alkyl-aryl or aryl-$(C_1-C_6)$alkyl group, wherein said group is optionally substituted by a group selected from a halogen atom, an $-NR_{32}-[(CH_2)_a-NR_{33}]_d-[(CH_2)_b-NR_{34}-(CH_2)_c-NR_{35}]_e-R_{52}$, $-P(O)(OH)_2$ or $-COOH$ group, with a, b and c representing an integer between 1 and 5 and d and e each representing 0 or 1, $R_{15}$ and $R_{16}$ representing, independently of each other, a hydrogen atom or a $(C_1-C_6)$alkyl, $(C_2-C_6)$alkenyl, aryl, $(C_1-C_6)$alkyl-aryl or aryl-$(C_1-C_6)$alkyl group, wherein said group is optionally substituted by a group selected from a halogen atom, an $-NR_{32}-[(CH_2)_a-NR_{33}]_d[(CH_2)_b-NR_{34}-(CH_2)_c-N-R_{35}]_e-R_{52}$ or $-COOH$ group, with a, b, c, d and e as defined above, $R_{17}$ and $R_{18}$ representing, independently of each other, a hydrogen atom or a $(C_1-C_6)$alkyl, $(C_2-C_6)$alkenyl, aryl or aryl-$(C_1-C_6)$alkyl group, $R_{19}$, $R_{20}$, $R_{21}$, $R_{58}$, $R_{59}$, $R_{60}$, $R_{61}$, $R_{62}$ and $R_{63}$ representing, independently of one another, a $(C_1-C_6)$alkyl, $(C_2-C_6)$alkenyl or aryl group, $R_{22}$ and $R_{23}$, identical or different, and notably identical, representing a hydrogen atom or a $(C_1-C_6)$alkyl or $(C_2-C_6)$alkenyl group, wherein said group is optionally substituted by an $-OC(O)-(C_1-C_6)$alkyl, $NR_{36}R_{37}$ and $-N^+R_{38}R_{39}R_{40}$ group, or optionally $R_{22}$ and $R_{23}$ together form, with the oxygen atoms that carry them and the phosphorous atom, a ring, notably with 5 or 6 members, $R_{24}$ and $R_{25}$, representing, independently of each other, a hydrogen atom or a $-CO-(C_1-C_6)$alkyl, $-CO-(C_2-C_6)$alkenyl, $(C_2-C_6)$alkenyl, $(C_3-C_7)$cycloalkyl or $(C_1-C_6)$alkyl group optionally substituted by an $NR_{41}R_{42}$ group, or $R_{24}$ and $R_{25}$ together form, with the nitrogen atom that carries them, a heterocycle with 5 or 6 members, wherein said heterocycle may comprise, in addition to the nitrogen atom carrying $R_{24}$ and $R_{25}$, one or more heteroatoms selected from nitrogen, oxygen and sulfur, and is optionally substituted by a $(C_1-C_6)$alkyl group, $R_{27}$ representing an aryl, $(C_1-C_6)$alkyl or $(C_2-C_6)$alkenyl group, for example $(C_1-C_6)$alkyl or $(C_2-C_6)$alkenyl, wherein said group is optionally substituted by one or more halogen atoms, $R_{29}$ representing a $(C_1-C_6)$alkyl, $(C_2-C_6)$alkenyl, aryl or aryl-$(C_1-C_6)$alkyl group, $R_{32}$, $R_{33}$, $R_{34}$, $R_{35}$, $R_{52}$, $R_{53}$, $R_{54}$, $R_{56}$ and $R_{57}$ representing, independently of one another, a hydrogen atom or a $(C_1-C_6)$alkyl, $(C_2-C_6)$alkenyl, —CO—$(C_1-C_6)$alkyl, —CO—$(C_2-C_6)$alkenyl, —CO$_2$—$(C_1-C_6)$alkyl or —CO$_2$—$(C_2-C_6)$alkenyl group, for example $R_{52}$ representing a hydrogen atom, $R_{38}$, $R_{39}$ and $R_{40}$ representing, independently of one another, a $(C_1-C_6)$alkyl or $(C_2-C_6)$alkenyl group, X representing O, S or $NR_{50}$, and notably O, $Z_1$, $Z_2$, $Z_3$ and $Z_4$ representing, independently of one another, O or $NR_{43}$, or $Z_2R_{15}$ and/or $Z_4R_{16}$ representing, independently of each other, a heterocycle with 5 or 6 members optionally substituted by a $(C_1-C_6)$alkyl group, wherein the heterocycle comprises at least one nitrogen atom by which it is linked to the rest of the molecule.

In the present invention, "pharmaceutically acceptable" refers to what is useful in the preparation of a pharmaceutical composition that is generally safe, nontoxic and neither biologically nor otherwise undesirable and that is acceptable for veterinary use as well as for human pharmaceuticals.

"Pharmaceutically acceptable salts" of a compound refers to salts that are pharmaceutically acceptable, as defined herein, and that have the desired pharmacological activity of the parent compound. Such salts include:

(1) hydrates and solvates, (2) acid addition salts formed with inorganic acids such as hydrochloric acid, hydrobromic acid, sulfuric acid, nitric acid, phosphoric acid and the like; or formed with organic acids such as acetic acid, benzenesulfonic acid, benzoic acid, camphorsulfonic acid, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalene-sulfonic acid, propionic acid, salicylic acid, succinic acid, dibenzoyl-L-tartaric acid, tartaric acid, p-toluenesulfonic acid, trimethylacetic acid, trifluoroacetic acid and the like, or (3) salts formed when an acid proton present in the parent compound is either replaced by a metal ion, for example an alkaline metal ion, an alkaline-earth metal ion or an aluminum ion or is coordinated with an organic or inorganic base. Acceptable organic bases include diethanolamine, ethanolamine, N-methylglucamine, triethanolamine, tromethamine and the like. Acceptable inorganic bases include aluminum hydroxide, calcium hydroxide, potassium hydroxide, sodium carbonate and sodium hydroxide.

In the context of the present invention, "halogen atom" refers to fluorine, chlorine, bromine and iodine atoms.

In the context of the present invention, "non-consecutive carbon atoms" refers to carbon atoms that are not linked to each other.

In the context of the present invention, "$(C_1-C_6)$alkyl" group refers to a saturated linear or branched hydrocarbon chain comprising 1 to 6, in particular 1 to 4, carbon atoms. As an example, mention may be made of methyl, ethyl, propyl, isopropyl, butyl, isobutyl, sec-butyl, tert-butyl, pentyl and hexyl groups.

In the context of the present invention, "$(C_2-C_6)$alkenyl" group refers to a linear or branched hydrocarbon chain comprising at least one double bond and comprising 2 to 6 carbon atoms. As an example, mention may be made of ethenyl and allyl groups.

In the context of the present invention, "$(C_1-C_6)$alkoxy" group refers to a $(C_1-C_6)$alkyl group, as defined above, linked to the molecule via an oxygen atom. As an example, mention may be made of methoxy, ethoxy, propoxy, isopropoxy, butoxy and tert-butoxy groups.

In the context of the present invention, "$(C_2-C_6)$alkenoxy" group refers to a $(C_2-C_6)$alkenyl group, as defined above, linked to the rest of the molecule via an oxygen atom. As an example, mention may be made of the —OCH$_2$CH=CH$_2$ group.

In the context of the present invention, "$(C_3-C_7)$cycloalkyl" group refers to a cyclic saturated hydrocarbon chain comprising 3 to 7 cyclic carbon atoms. As an example, mention may be made of the cyclopropyl, cyclopentyl, cyclohexyl and cycloheptyl groups.

In the context of the present invention, "acetyl" group refers to a —C(O)—R group where R represents a $(C_1-C_6)$ alkyl, aryl, $(C_1-C_6)$alkyl-aryl or aryl-$(C_1-C_6)$alkyl group, as defined in the context of the present invention. R may represent in particular a methyl, benzyl or phenyl group, and more particularly a methyl group.

In the context of the present invention, "aryl" represents an aromatic group comprising notably from 5 to 10 carbon atoms, and comprising one or more fused rings, such as for example a phenyl or naphthyl group. Advantageously, it is a phenyl group.

In the context of the present invention, "aryl-$(C_1-C_6)$alkyl" or "aralkyl" refers to an aryl group, as defined above, linked to the molecule via a $(C_1-C_6)$alkyl chain, as defined above. As an example, mention may be made of the benzyl group.

In the context of the present invention, "$(C_1-C_6)$alkyl-aryl" refers to a $(C_1-C_6)$alkyl group, as defined above, linked to the molecule via an aryl group, as defined above. As an example, mention may be made of the methyl-phenyl group, also called tolyl.

In the context of the present invention, "heterocycle with 5 or 6 members" refers a saturated, unsaturated or aromatic ring with 5 or 6 members and containing one or more, advantageously 1 to 4, even more advantageously 1 or 2, heteroatoms, such as for example sulfur, nitrogen or oxygen atoms. It may be notably a pyrrolidinyl, piperidinyl, piperazinyl, morpholinyl, dihydrofuranyl, tetrahydrofuranyl, imidazolyl or triazolyl group.

If $R_4$ represents a heterocycle, it will be advantageously a dihydrofuranyl or a tetrahydrofuranyl, such as 2,3-dihydrofuran-5-yl or tetrahydrofuran-2-yl, wherein said heterocycle is optionally substituted as indicated above.

If $Z_2R_{15}$ or $Z_4R_{16}$ represents a heterocycle, it will be advantageously a heterocycle with 5 or 6 members comprising a nitrogen atom and optionally another heteroatom such as an oxygen or nitrogen atom. Said heterocycle will advantageously be saturated. It may be in particular a piperidinyl, pyrrolidinyl, piperazinyl or morpholinyl group. The piperazinyl group may then be optionally substituted by a $(C_1-C_6)$ alkyl group at its second nitrogen atom.

In the context of the present invention, "polycycle with 10 to 15 members" refers to a polycyclic hydrocarbon system comprising at least 2, for example 2 or 3, fused rings, wherein each ring may be saturated, unsaturated or aromatic and may optionally contain one or more, for example 0 or 1, heteroatoms such as a sulfur, nitrogen or oxygen atom. It may be notably a bi- or tri-cyclic system combining rings with 5, 6 or 7 members comprising notably an acetal group. Advantageously, the polycycle will have the following structure:

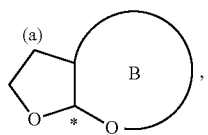

where B represents a saturated, unsaturated or aromatic mono- or bi-cyclic system optionally comprising one or more, advantageously 0 or 1, additional heteroatoms notably selected from O, S and N. The link to the rest of the molecule is made at the carbon marked with an asterisk (*) and the carbon marked with an (a) is advantageously substituted by a methyl group. Other substitutions can obviously be envisaged as indicated above. Thus, they may notably be the following rings:

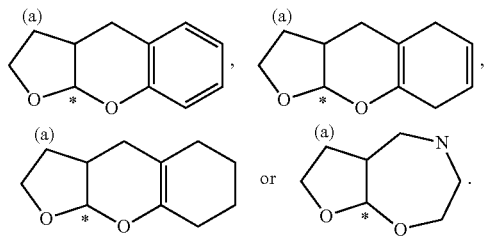

In the context of the present invention, "epoxy" refers to a

ring.

In the context of the present invention, "sugar" refers notably to erythrose, threose, ribose, arabinose, xylose, lyxose, allose, altrose, glucose, mannose, gulose, idose, galactose, talose, erythrulose, ribulose, xylulose, psicose, fructose, sorbose, sophrose or tagatose, in D or L form.

In the context of the present invention, "sugar residue" refers to a sugar molecule, for example substituted or unsubstituted, as defined above, that is linked to the rest of the molecule via the oxygen atom located in the anomeric position, and optionally via a second oxygen atom.

In the context of the present invention, "inositol" refers to a saturated hydrocarbon ring with 6 members substituted on each carbon atom by an OH group.

In the context of the present invention, "inositol residue" refers to a molecule of inositol, as defined above, that is linked to the rest of the molecule via one of its oxygen atoms.

$R_9$ and $R_4$ may also together form a bond, i.e., $X_1$ and carbon atom 22 are linked together by a single bond or $R_9$ may form a bond with the carbon atom of the $R_4$ group located in the a position in relation to carbon atom 22, i.e., $X_1$ is linked by a single bond to carbon 23 located in the a position relative to carbon atom 22.

In particular, $R_3$ represents a hydrogen atom, or a —CO—$(C_1-C_6)$alkyl, such as —COCH$_2$, or —OC—$(C_2-C_6)$alkenyl group, wherein said group is optionally substituted by an NH$_2$ group.

In particular, the $R_4$ group may represent a group selected from:

a hydrogen atom, a saturated or unsaturated linear or branched hydrocarbon chain comprising 1 to 10 carbon atoms, and optionally substituted by one or more groups selected from a halogen atom, =O, —OH, —OSO$_2R_{13}$, —N$_3$, $(C_1-C_6)$alkoxy, —Z$_1$C(X)R$_{14}$, —C(X)Z$_2R_{15}$, —Z$_3$C(X)Z$_4R_{16}$, —NH—OR$_{17}$, =N—NR$_{53}R_{54}$, —OSiR$_{19}R_{20}R_{21}$, —OP(O)(OR$_{22}$)(OR$_{23}$), —NR$_{29}R_{25}$, a heterocycle with 5 or 6 members, an epoxide, a sugar residue and an inositol residue, wherein one or more hydroxy groups of said sugar and inositol residues are optionally substituted by an acetyl or —P(O)(OH)$_2$ group, and a heterocycle with 5 or 6 members or a polycycle with 10 to 15 members, wherein said heterocycle or polycycle comprises at least one oxygen atom and is optionally substituted by one or more groups selected from —OH, =O, —NH$_2$, —N$_3$, =CH$_2$, —COOR$_{26}$, $(C_2-C_6)$alkenyl, $(C_1-C_6)$alkoxy, and a $(C_1-C_6)$alkyl group, such as methyl, optionally substituted by a halogen atom or an —N$_3$, —OH, $(C_1-C_6)$alkoxy, —NHCOR$_{27}$ or —NR$_{28}$—OC(O)R$_{29}$ group.

The methyl group located at position (4) may for example be located on the same side of the ring with 6 members as the neighboring hydrogen atom.

Furthermore, carbon (20) is for example of configuration (S).

$R_1$ is for example selected from an oxygen atom, an N—OH, —N—OMe, —N—OBn and —N—NHCO—NH$_2$ group; for example $R_1$ is an oxygen atom.

$R_2$ represents for example a hydrogen atom or an OR$_{12}$ group, and more particularly a hydrogen atom.

Advantageously, $R_5$ and $R_6$ each represent a hydrogen atom and ≕ represents a double bond.

$R_8$ represents, for example, a hydrogen atom and $R_7$ represents a hydrogen atom or an OH group, and notably a hydrogen atom.

$R_9$ represents, for example, a —CO—$(C_1-C_6)$alkyl group, such as a —COCH$_3$ group.

Advantageously, $X_2$—$R_3$ represents an —OH or —OC(O)CH$_3$ group and $R_{10}$ represents a hydrogen atom or $R_3$ and $R_{10}$ together form a bond. Notably, $X_2$—$R_3$ represents an —OH or —OC(O)CH$_3$ group and $R_{10}$ represents a hydrogen atom.

Thus, the compounds of the invention advantageously are of following formula (Ia) or formula (Ib):

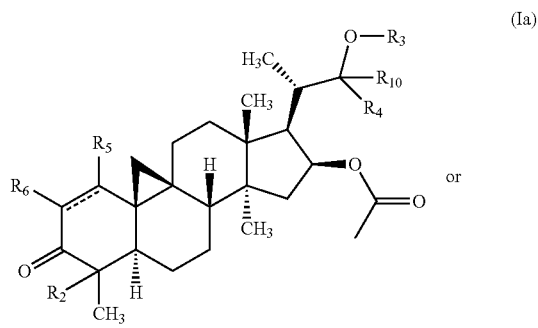

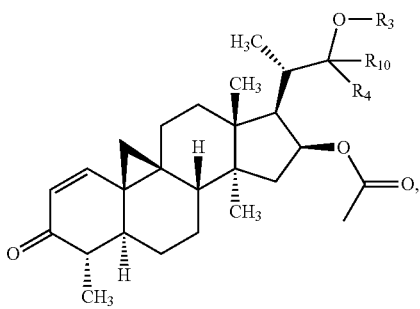

(Ib)

wherein $R_2$, $R_3$, $R_4$, $R_5$, $R_6$ and $R_{10}$ are as defined above.

According to a first particular embodiment of the invention, $R_4$ represents, in formula (I), (Ia) or (Ib) above:

a

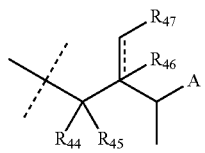

chain, such as a

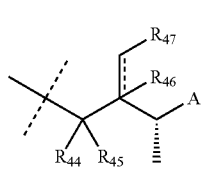

chain,
wherein:
- - - represents a single bond or a double bond, $R_{44}$ represents a hydrogen atom and $R_{45}$ represents an OH group, or $R_{44}$ and $R_{45}$ together form an =O or =N—$OR_{48}$ group, $R_{46}$ represents a hydrogen atom and $R_{47}$ represents a hydrogen atom, a ($C_1$-$C_6$)alkoxy group, —NH—$OR_{49}$ or a heterocycle with 5 or 6 members linked to the rest of the molecule via a nitrogen atom, such as an imidazolyl, when - - - represents a single bond, or $R_{46}$ is absent and $R_{47}$ represents a hydrogen atom when - - - represents a double bond, and A represents a —CHO, —COOH or —$CH_2A_1$ group with $A_1$ representing a halogen atom, —OH, —$OSO_2R_{13}$, —$N_3$, ($C_1$-$C_6$)alkoxy, —$Z_1C(X)R_{14}$, —$Z_3C(X)Z_4R_{16}$, —NH—$OR_{17}$, —$OSiR_{19}R_{20}R_{21}$, —OP(O)($OR_{22}$)($OR_{23}$)—$NR_{24}R_{25}$, a heterocycle with 5 or 6 members or a sugar residue, wherein one or more hydroxy groups of said sugar residue are optionally substituted by an acetyl or —P(O)(OH)$_2$ group, with $R_{48}$ and $R_{49}$ representing, independently of each other, a hydrogen atom or a ($C_1$-$C_6$)alkyl, aryl or aryl-($C_1$-$C_6$) alkyl group.

$A_1$ may also represent a hydrogen atom, a ($C_2$-$C_6$)alkenoxy group, a ($C_1$-$C_6$)alkoxy group optionally substituted by one or more OH groups, or a —$OCH_2OR_{66}$ group with $R_{66}$ representing a —CO—(($C_1$-$C_6$)alkyl) or ($C_1$-$C_6$)alkyl group optionally substituted by a $SiR_{67}R_{68}R_{69}$ group wherein $R_{67}$, $R_{68}$ and $R_{69}$ represent, independently of one another, a ($C_1$-$C_6$)alkyl group.

$R_{44}$ may also form a bond with $R_9$, i.e., $X_1$ and the carbon atom carrying the $R_{45}$ group are linked by a bond.

Advantageously, $R_{44}$ and $R_{45}$ together form an =O group.

In particular, $R_{46}$ is absent and $R_{47}$ represents a hydrogen atom and - - - represents a double bond.

Moreover, A may represent a —$CH_2A_1$ group.

Thus, $R_4$ represents advantageously the following chain:

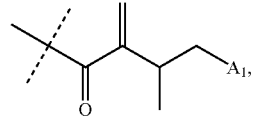

such as a

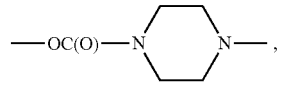

chain, with $A_1$ as defined above.

Advantageously, $A_1$ represents an —OH, —$OSO_2R_{13}$, —$N_3$, ($C_1$-$C_6$)alkoxy, —$Z_1C(X)R_{14}$, —$Z_3C(X)Z_4R_{16}$, —$OSiR_{19}R_{20}R_{21}$, —OP(O)($OR_{22}$)($OR_{23}$), —$NR_{24}R_{25}$ group, a heterocycle with 5 or 6 members or a sugar residue.

$A_1$ may represent notably one of the following groups:
- —OH; ($C_1$-$C_6$)alkoxy such as methoxy; —$OSiR_{19}R_{20}R_{21}$ such as —$OSiMe_3$ or —$OSitBuMe_2$; —$OSO_2R_{13}$ such as —$OSO_3H$, —$OSO_2CH_3$, —$OSO_2$—$C_6H_4$—$CH_3$ or —$OSO_2NMe_2$; —OP(O)($OR_{22}$)($OR_{23}$) such as —OP(O)O$^-$(OCH$_2$CH$_2$N$^+$Me$_3$), —OP(O)(OCH$_2$OC(O)CH$_3$), —OPO$_3$H$_2$, —OP(O)(OEt)$_2$, or —OP(O)(OH)(OCH$_2$CH$_2$NH$_2$); a sugar residue such as a glucose residue;
- —$Z_1C(X)R_{14}$, in particular —OC(O)$R_{14}$, such as —OC(O)CH$_3$, —OC(O)CH$_2$NMe$_2$, —OC(O)CH$_2$NH$_2$, —OC(O)CH$_2$Cl, —OC(O)—C$_6$H$_4$—COOH, —OC(O)CH$_2$CH$_2$COOH, —OC(O)CH$_2$NHCO$_2$tBu, —OC(O)CH$_2$NH(CH$_2$)$_3$NH(CH$_2$)$_4$NH(CH$_2$)$_3$NH$_2$ or —OC(O)CH$_2$NBoc(CH$_2$)$_3$NBoc(CH$_2$)$_4$NBoc(CH$_2$)$_3$NHBoc (with Boc=-COOtBu);
- —$Z_3C(X)Z_4R_{16}$, in particular —OC(O)NHR$_{16}$ (carbamates) and —OC(O)OR$_{16}$ (carbonates), such as —OC(O)NHPh, —OC(O)NHCH$_2$CH$_2$NMe$_2$ or

—OC(O)—N⌒N—, or —OC(O)— dimethylaniline (group of formula —OC(O)C$_6$H$_4$—NMe$_2$);
- —N$_3$; or —NR$_{24}$R$_{25}$ such as —NMe$_2$, morpholinyl, N-methyl-piperazinyl or —N(COOtBu)(CH$_2$CH$_2$NMe$_2$).

Thus, $A_1$ may be selected from OH, —OCH$_3$, —OSiMe$_3$, —OSitBuMe$_2$, —OSO$_3$H, —OSO$_2$CH$_3$, —OSO$_2$—C$_6$H$_4$—CH$_3$, —OSO$_2$NMe$_2$, —OP(O)O$^-$(OCH$_2$CH$_2$N$^+$Me$_3$), —OP(O)(OCH$_2$OC(O)CH$_3$), —OPO$_3$H$_2$, —OP(O)(OEt)$_2$, —OP(O)(OH)(OCH$_2$CH$_2$NH$_2$), a glucose residue, —OC(O)CH$_3$, —OC(O)CH₂NMe₂, —OC(O)CH₂NH₂, —OC(O)CH₂Cl, —OC(O)—C₆H₄—COOH, —OC(O)CH₂CH₂COOH, —OC(O)CH₂NHCO₂tBu, —OC(O)NHPh, —OC(O) NHCH₂CH₂NMe₂, —NMe₂, —OC(O)CH₂NH(CH₂)₃NH (CH₂)₄NH(CH₂)₃NH₂, —OC(O)CH₂NBoc(CH₂)₃NBoc (CH₂)₄NBoc(CH₂)₃NHBoc, —N(COOtBu) (CH₂CH₂NMe₂) and

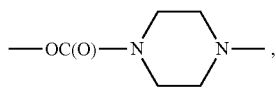

or —OC(O)C₆H₄—NMe₂.

According to a second particular embodiment of the invention, $R_4$ represents, in formula (I), (Ia) or (Ib) above, the following ring:

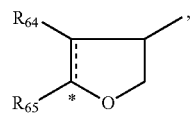

such as a

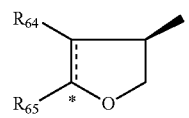

ring, linked to the rest of the molecule via the carbon atom marked with an asterisk (*) and wherein,

- ⋯ represents a single bond or a double bond,
- $R_{64}$ represents a ($C_1$-$C_8$)alkyl group, such as methyl, optionally substituted by a halogen atom or an —N₃, —OH, ($C_1$-$C_6$)alkoxy, —NHCOR₂₇ or —NR₂₈—OC(O)R₂₉ group; or a =CH₂ group, wherein said =CH₂ group may be present only when ⋯ represents a single bond, and
- $R_{65}$ is not present when ⋯ represents a double bond, or $R_{51}$ represents a hydrogen atom or a ($C_1$-$C_6$)alkoxy group when ⋯ represents a single bond, or
- $R_{64}$ and $R_{65}$ together form with the carbon atoms that carry them, when ⋯ represents a single bond, a cyclic system comprising 1 or 2 saturated, unsaturated or aromatic fused rings, each with 5 to 7 members,
  wherein said cyclic system comprises at least one oxygen atom linked to the carbon atom marked with an asterisk and optionally comprises one or more, notably 1 or 2, additional heteroatoms selected from O, S and N, and
  wherein said cyclic system is optionally substituted by one or more groups selected from =O, —OH, —COOR₂₆, and ($C_1$-$C_6$)alkyl optionally substituted by an —OH group.

$R_{65}$ may also form a bond with $R_9$, i.e., $X_1$ is linked to the carbon atom marked with an asterisk (*).

In this case, the $R_4$ group may be selected from:

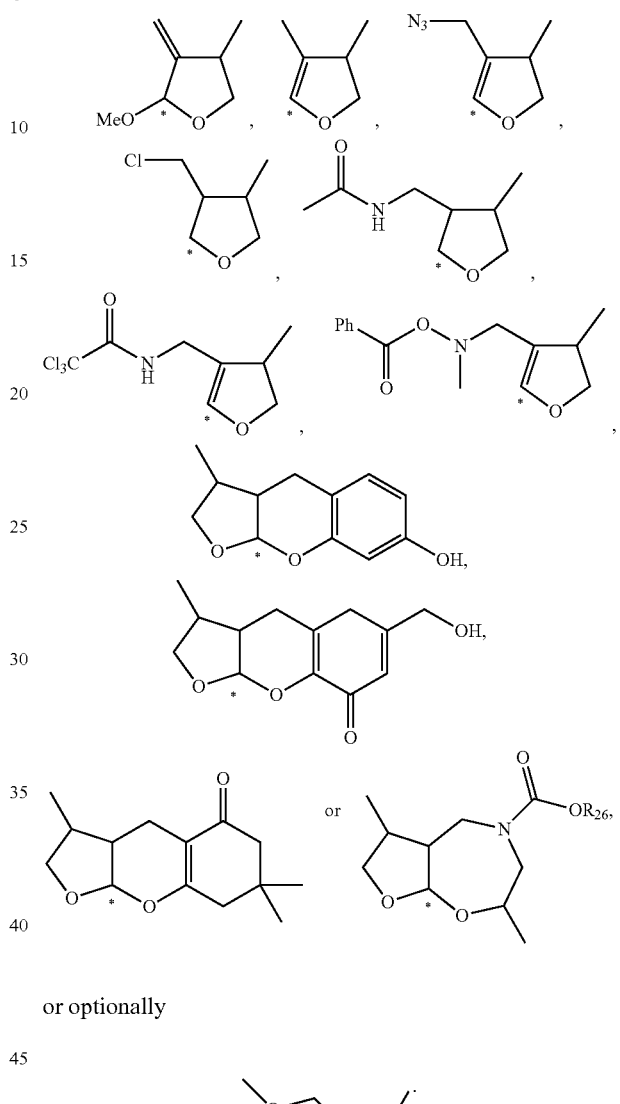

or optionally

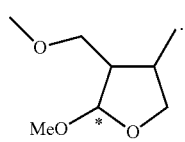

According to a particular embodiment of the invention, the compounds of the invention may be compounds of formula (I) or pharmaceutically acceptable salts thereof, wherein:

- ⋯ indicates a single bond or a double bond,
- $X_1$ and $X_2$ represent an oxygen atom,
- $R_1$ represents an oxygen atom, or a —N—OR₁₁ or —N—NHCO—NH₂ group, for example an oxygen atom,
- $R_2$ represents a hydrogen atom or an —OH group, for example a hydrogen atom,
- $R_3$ represents a hydrogen atom, or an —SO₃H, —CH₂OCH₂CH₂Si(CH₃)₃, —COCH₃, —C(O)CH₂Cl, —CO(CH₂)₂COOH, —CO(CH₂)NHCOO($C_1$-$C_6$)alkyl group such as —CO(CH₂)NHCOOtBu, $R_4$ represents a group selected from:

a hydrogen atom,

—C(O)CH=C(CH$_3$)$_2$, —C(O)CH(CH$_2$NHOCH$_3$)CH(CH$_3$)CH$_2$OH, —C(O)CH(CH$_2$NHOCH$_2$—C$_6$H$_5$)CH(CH$_3$)CH$_2$OH, —C(O)CH(CH$_2$OCH$_3$)CH(CH$_3$)CH$_2$OH, —C(O)C(=CH$_2$)CH(CH$_3$)CHO, —C(O)C(CH$_3$)=C(CH$_3$)CH=N—N(CH$_3$)$_2$, —CH(OH)C(=CH$_2$)—CH(CH$_3$)CH$_2$OH, the following chain:

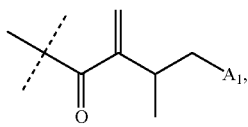

such as a

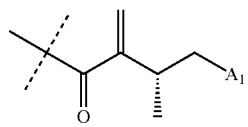

chain, with $A_1$ representing a hydrogen atom or an —OH; —COOH, (C$_1$-C$_6$)alkoxy such as methoxy; —OCH$_2$CH=CH$_2$; —OCH$_2$CH(OH)CH$_2$OH; —OCH$_2$OCOCH$_3$; —OSiMe$_3$, —OCH$_2$OCH$_2$CH$_2$SiMe$_3$; —OSitBuMe$_2$, —OSO$_3$H; —OSO$_2$CH$_3$; —OSO$_2$—C$_6$H$_4$—CH$_3$; —OSO$_2$NMe$_2$; —OP(O)O$^-$(OCH$_2$CH$_2$N$^+$Me$_3$); —OP(O)(OCH$_2$OC(O)CH$_3$)$_2$; —OPO$_3$H$_2$; —OP(O)(OEt)$_2$; —OP(O)(OH)(OCH$_2$CH$_2$NH$_2$); a sugar residue such as a glucose residue; —OC(O)CH$_3$; —OC(O)CH$_2$NMe$_2$; —OC(O)CH$_2$NH$_2$; —OC(O)CH$_2$Cl; —OC(O)—C$_6$H$_4$—COOH; —OC(O)CH$_2$CH$_2$COOH; —OC(O)CH$_2$NHCO$_2$tBu; —OC(O)(CH$_2$)$_2$N(C$_2$H$_5$)$_2$; OC(O)CH=CH$_2$; OC(O)CH$_2$NH(CH$_2$)$_3$NH(CH$_2$)$_4$NH(CH$_2$)$_3$NH$_2$; —OC(O)CH$_2$NBoc(CH$_2$)$_3$NBoc(CH$_2$)$_4$NBoc(CH$_2$)$_3$NHBoc (with Boc=-COOtBu), —OC(O)CH$_2$OPO$_3$H$_2$; —OC(O)NHPh; —OC(O)NHCH$_2$CH$_2$NMe$_2$;

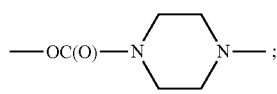

—OC(O)-dimethylaniline (—OC(O)—C$_6$H$_4$—NMe$_2$); —NMe$_2$, morpholinyl, —N-methyl-piperazinyl or —N(COOtBu)(CH$_2$CH$_2$NMe$_2$) group, or a group:

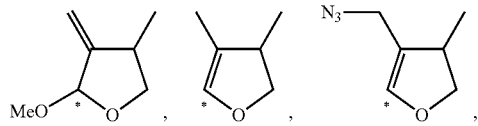

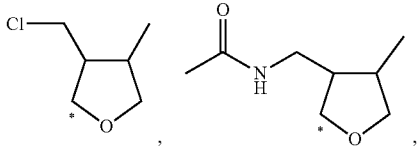

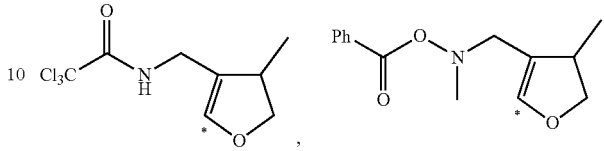

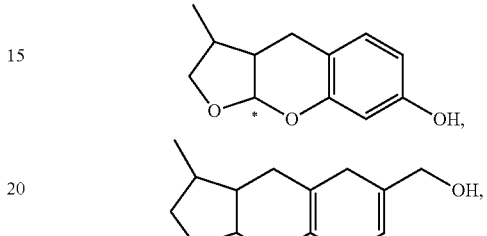

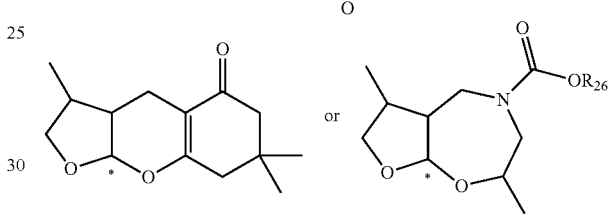

wherein an asterisk (*) indicates the carbon atom that is linked to the rest of the molecule, $R_5$ and $R_6$ each represent a hydrogen atom when ≈ represents a double bond, or $R_5$ and $R_6$ each represent, independently of each other, a hydrogen atom or an —OH group, or $R_5$ and $R_6$ together form, with the carbon atoms that carry them, an epoxide ring, when ≈ represents a single bond, $R_7$ represents a hydrogen atom or an —OH group, $R_8$ represents a hydrogen atom, or $R_7$ and $R_8$ together form, with the carbon atoms that carry them, an epoxide ring, $R_9$ represents a —CO—(C$_1$-C$_6$)alkyl group, for example —CO—CH$_3$, or $R_9$ and $R_4$ together form a bond, or $R_9$ forms a bond with carbon atom (23) of the $R_4$ group (located at the a position relative to carbon atom (22), wherein the $R_4$ group is, for example,

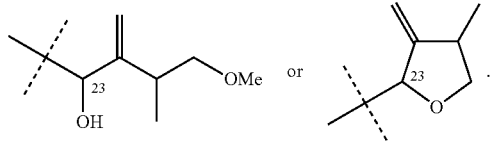

$R_{10}$ represents a hydrogen atom, or $R_{10}$ and $R_3$ together form a bond, the bond between $C_{22}$ and $X_2$ is thus a double bond, or $R_{10}$ and $R_9$ together form a bond, with:

$R_{11}$ representing a hydrogen atom, a (C$_1$-C$_6$)alkyl, for example —CH$_3$, aryl or aryl-(C$_1$-C$_6$)alkyl group, for example benzyl.

According to another particular embodiment of the invention, the compounds of the invention may be compounds of formula (I) or pharmaceutically acceptable salts thereof, wherein:

- ---- represents a double bond or a single bond,
- $X_1$ and $X_2$ each represent an oxygen atom,
- $R_1$ represents an oxygen atom, an N—OH, N—O—($C_1$-$C_6$)alkyl such as N—OCH$_3$, N—O—($C_1$-$C_6$)alkyl-aryl such as N—OBn, or N—NHCO—NH$_2$ group,
- $R_2$ represents a hydrogen atom,
- $R_3$ represents a hydrogen atom or a CO—($C_1$-$C_6$)alkyl group such as CO—CH$_3$,
- $R_4$ represents a group selected from:

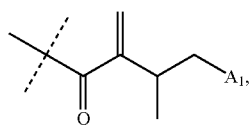

such as

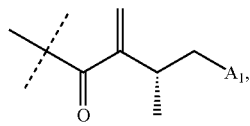

wherein $A_1$ represents an —OH group; ($C_1$-$C_6$)alkoxy such as methoxy; —OSiMe$_3$; —OSitBuMe$_2$; —OSO$_3$H; —OSO$_2$CH$_3$; —OSO$_2$—C$_6$H$_4$—CH$_3$; —OSO$_2$NMe$_2$; —OP(O)O$^-$(OCH$_2$CH$_2$N$^+$Me$_3$); —OP(O)(OCH$_2$OC(O)CH$_3$); —OPO$_3$H$_2$; —OP(O)(OEt)$_2$; —OP(O)(OH)(OCH$_2$CH$_2$NH$_2$); a sugar residue such as a glucose residue; —OC(O)CH$_3$; —OC(O)CH$_2$NMe$_{23}$; —OC(O)CH$_2$NH$_2$; —OC(O)CH$_2$Cl; —OC(O)—C$_6$H$_4$—COOH; —OC(O)NHPh; —OC(O)NHCH$_2$CH$_2$NMe$_2$; —OC(O)CH$_2$CH$_2$COOH; —OC(O)CH$_2$NHCO$_2$tBu; —NMe$_2$; N(COOtBu) (CH$_2$CH$_2$NMe$_2$; —OC(O)CH$_2$NH(CH$_2$)$_3$NH(CH$_2$)$_4$NH(CH$_2$)$_3$NH$_2$; —OC(O)CH$_2$NBoc(CH$_2$)$_3$NBoc(CH$_2$)$_4$NBoc(CH$_2$)$_3$NHBoc (with Boc=COOtBu); or

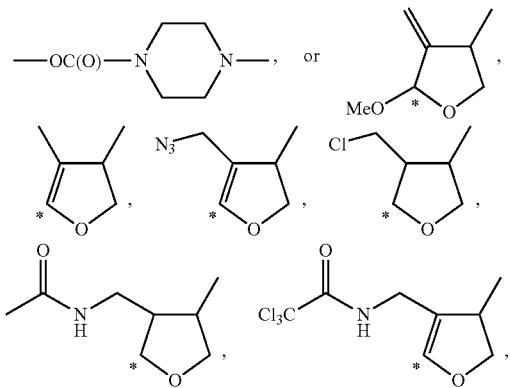

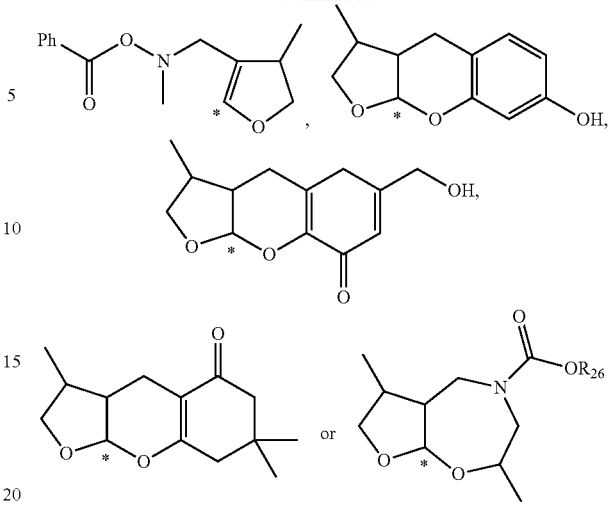

wherein * indicates the carbon atom that is linked to the rest of the molecule,

- $R_5$ and $R_6$ each represent a hydrogen atom when ---- represents a double bond, or
- $R_5$ and $R_6$ represent, independently of each other, a hydrogen atom or an OH group, or together form, with the carbon atoms that carry them, an epoxide ring, when ---- represents a single bond,
- $R_7$ represents a hydrogen atom or an OH group and $R_8$ represents a hydrogen atom, or
- $R_7$ and $R_8$ together form, with the carbon atoms that carry them, an epoxide ring,
- $R_9$ represents a CO—($C_1$-$C_6$)alkyl group such as CO—CH$_3$, and
- $R_{10}$ represents a hydrogen atom, or
- $R_{10}$ and $R_3$ together form a bond, or
- $R_{10}$ and $R_9$ together form a bond.

In particular, the compound of formula (I) of the invention may be selected from compounds 1 to 92 as exemplified in the following examples.

Another object of the present invention relates to a compound of formula (I) as defined above or a Pharmaceutically acceptable salt thereof for the use thereof as a drug, intended in particular for treating a proliferative disease such as cancer (notably by inhibiting cellular proteasomes).

The present invention thus also relates to the use of a compound of formula (I) as defined above or a pharmaceutically acceptable salt thereof for the preparation of a drug, intended notably for treating a proliferative disease such as cancer.

The present invention also relates to a method for treating a proliferative disease such as cancer comprising the administration of an effective quantity of a compound of formula (I) as defined above or of a pharmaceutically acceptable salt thereof to a patient in need thereof.

Another object of the present invention relates to a pharmaceutical composition comprising at least one compound of formula (I) as defined above or a pharmaceutically acceptable salt thereof and at least one pharmaceutically acceptable carrier.

The pharmaceutical compositions according to the invention may be formulated for oral, sublingual, subcutaneous, intramuscular, intravenous, transdermal, local or rectal administration intended for mammals, including humans.

The active ingredient may be administered in unit dosage forms of administration, in mixture with standard pharmaceutical excipients, to animals or to humans. Suitable unit dosage forms of administration include forms by oral route such as tablets, gelatin capsules, powders, granules and oral solutions or suspensions, sublingual and buccal forms of administration, subcutaneous, intramuscular, intravenous, intranasal or intraocular forms of administration and rectal forms of administration.

When a solid composition in tablet form is prepared, the main active ingredient is mixed with a pharmaceutical carrier such as gelatin, starch, lactose, magnesium stearate, talc, gum arabic or analogs. Tablets may be coated with sucrose or other suitable materials or may be treated in such a way that they have extended or delayed activity and that they continuously release a predetermined quantity of active ingredient.

A preparation in gelatin capsules is obtained by mixing the active ingredient with a diluent and by pouring the mixture obtained into soft or hard gelatin capsules.

A preparation in syrup or elixir form may contain the active ingredient together with a sweetener, an antiseptic, as well as a flavoring agent and a suitable colorant.

Water-dispersible powders or granules may contain the active ingredient in mixture with dispersion or wetting agents, or suspension agents, as well as with flavor correctors or sweeteners.

For rectal administration, suppositories that are prepared with binders that melt at rectal temperature, for example cocoa butter or polyethylene glycols, are used.

For parenteral, intranasal or intraocular administration, aqueous suspensions, isotonic saline solutions or sterile and injectable solutions that contain pharmacologically compatible dispersants and/or wetting agents are used.

The active ingredient may also be formulated in the form of microcapsules, optionally with one or more additive carriers.

The compounds of the invention as active ingredients may be used in doses between 0.01 mg and 1000 mg per day, given in a single dose once per day or in several doses throughout the day, for example twice a day in equal doses. The daily dose administered is advantageously between 5 mg and 500 mg, even more advantageously between 10 mg and 200 mg. It may be necessary to use doses beyond these ranges according to the experience of the person skilled in the art.

The pharmaceutical composition according to the invention may further comprise at least one other active ingredient such as an anticancer agent.

Another object of the present invention relates to a pharmaceutical composition comprising:
 (i) at least one compound of formula (I) as defined above or a pharmaceutically acceptable salt thereof, and
 (ii) at least one other active ingredient, such as an anticancer agent,
as combination products for simultaneous, separate or sequential use.

Another object of the present invention relates to a pharmaceutical composition according to the invention as previously defined for the use thereof as a drug, intended notably for treating a proliferative disease such as cancer.

The compounds of the invention were prepared by extraction from leaves of the genus *Neoboutonia*, and in particular from the species *Neoboutonia melleri* (Euphorbiaceae), a plant from Cameroon, or by hemisynthesis, according to functionalization reactions well known to the person skilled in the art, from the following two compounds obtained by extraction as described below, the second compound having been named neoboutomellerone:

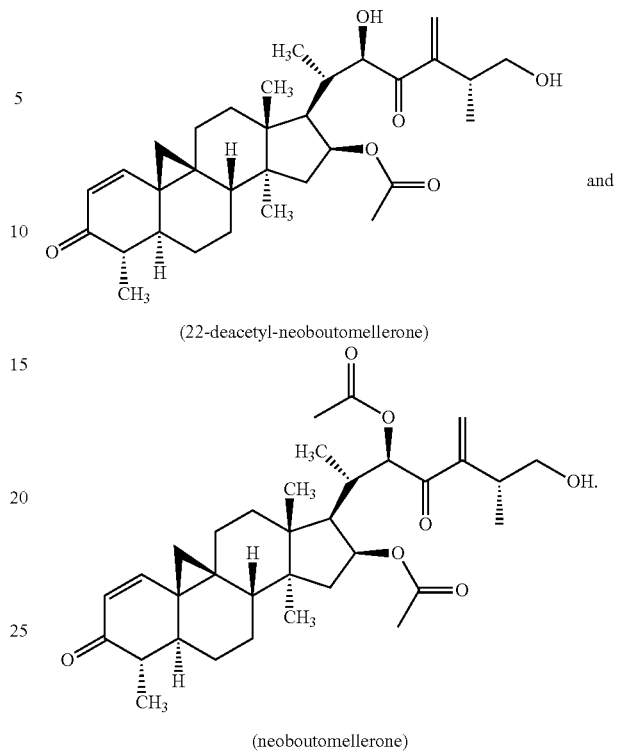

(22-deacetyl-neoboutomellerone)

(neoboutomellerone)

The present invention will be better understood upon consideration of the non-limiting examples which follow.

EXAMPLES

The following abbreviations are used in the examples which follow:

| | |
|---|---|
| ACN | Acetonitrile |
| Boc | tert-Butyloxycarbonyl |
| TLC | Thin-layer chromatography |
| DBU | 1,8-Diazabicyclo[5.4.0]undec-7-ene |
| DCC | Dicyclohexylcarbodiimide |
| DCM | Dichloromethane |
| DIAD | Diisopropyl azodicarboxylate |
| DMAP | Dimethylaminopyridine |
| DMF | Dimethylformamide |
| DMSO | Dimethylsulfoxide |
| EDC | 1-Ethyl-3-(3-dimethylaminopropyl)carbodiimide |
| Gly | Glycine |
| HPLC | High-performance liquid chromatography |
| NMG | N-methyl-D-glucamine |
| Yield | Yield |
| Rf | Retardation factor |
| NMR | Nuclear magnetic resonance |
| rt | Room temperature |
| TBAF | Tetra-n-butylammonium fluoride |
| TBDMS | tert-Butyldimethylsilyl |
| TBTU | O-benzotriazole-1-yl-N,N,N',N'-tetramethyluronium tetrafluoroborate |
| Tf | Triflate |
| THF | Tetrahydrofuran |

1. Obtention of the Compounds of the Invention
1.1. By extraction from *Neoboutonia melleri*

1 kg of leaves of *Neoboutonia melleri* (Euphorbiaceae) is extracted with 15 liters of dichloromethane at room temperature for 24 hours. After filtration, the marc of the plant is extracted again with dichloromethane under the same conditions. The filtrates are combined and dried to dryness under reduced pressure in a rotary evaporator. The dichloromethane extract obtained (45 g, yield=4.5%) is then taken up in 1 liter of dichloromethane to which 100 g of activated carbon is added. The solution thus obtained is stirred for 1 hour and then filtered. The filtrate is then evaporated to dryness under reduced pressure (32 g). This dechlorophyllated extract is liquid/liquid partitioned with methanol and cyclohexane with a little water to obtain two immiscible phases. The two phases obtained are evaporated to dryness: methanol extract (ME, 15 g) and hexane extract (HE, 17 g). Only the ME will be used to isolate the cycloartanes. The ME is first purified by medium pressure liquid chromatography (MPLC) on silica. A 600 g column is used and eluted with a 50/50 isocratic ethyl acetate/cyclohexane mixture. After analysis of the fractions obtained by thin-layer chromatography (TLC) (97/3 dichloromethane/methanol eluent), four fractions are obtained: ME1 (6 g), ME2 (5.5 g), ME3 (1.5 g) and ME4 (1 g).

The least polar fraction (ME1) is purified by preparative reverse-phase high-performance liquid chromatography (HPLC). A water/acetonitrile mixture is used as the eluent phase with a linear 20/80 to 100% acetonitrile gradient. We obtained in the order of elution 7 (10 mg, 0.001% dry weight), 18 (0.1 mg, 0.00001%), 10 (0.4 mg, 0.00004%), 9 (6 mg, 0.0006%), 8 (7 mg, 0.0007%), 5 (3.5 mg, 0.000351%).

The fractions of average polarity (ME2 and ME3) are also purified by preparative HPLC on C18 by using a linear 45/55 to 100% water/acetonitrile gradient. From fraction ME2 one of the major cycloartanes is obtained, 2 (2.5 g, 0.25%), as well as 14 (1.5 mg, 0.00015%) and 11 (10.5 mg, 0.00105%). From ME3, the second major cycloartane 1 (600 mg, 0.06%) is purified, as well as products 12 (2 mg, 0.0002%) and 3 (15 mg, 0.0015%).

Finally the most polar fraction (ME4), made it possible to obtain after purification by preparative HPLC (50/50 to 100% water/acetonitrile gradient): 15 (0.5 mg, 0.00005%), 6 (1 mg, 0.0001%), 16 (0.5 mg, 0.00005%), 4 (17 mg, 0.0017%) and 13 (0.2 mg, 0.00002%).

The products thus obtained are described below.

Example 1

22-deacetyl-neoboutomellerone

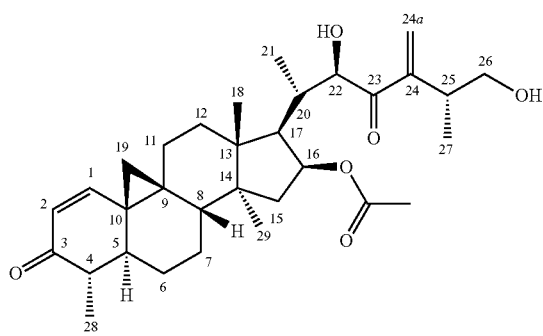

Chemical formula: $C_{32}H_{46}O_6$
Exact mass: 526.33
Molecular weight: 526.70

$^1$H NMR (500 MHz, $CD_3CN$) δ=6.94 (1H, d, J=10.1 Hz, H-1), 6.12 (1H, s, H-24a'), 5.99 (1H, d, J=0.9 Hz, H-24a"), 5.89 (1H, d, J=9.8 Hz, H-2), 5.20 (1H, td, J=7.5 Hz, J=4.6 Hz, H-16), 4.72 (1H, dd, J=6.1 Hz, J=1.8 Hz, H-22), 3.54 (1H, d, J=6.1 Hz, OH-22), 3.56 (1H, dt, J=10.6 Hz, J=6.0 Hz, H-26'), 3.41 (1H, dt, J=10.6 Hz, J=6.0 Hz, H-26"), 2.83 (1H, sxt, J=6.6 Hz, H-25), 2.67 (1H, t, J=5.6 Hz, OH-26), 2.46 (1H, dqd, J=10.7 Hz, J=6.7 Hz, J=2.1 Hz, H-20), 2.42 (1H, dd, J=10.7 Hz, J=7.0 Hz, H-17), 2.22 (1H, dd, J=13.9 Hz, J=8.1 Hz, H-15'), 2.17 (1H, dq, J=12.8 Hz, J=6.7 Hz, H-4), 2.03 (3H, s, H-16b), 1.98-2.07 (2H, m, H-8,11'), 1.95-1.98 (1H, m, H-5), 1.60-1.74 (3H, m, H-6', 12', 12"), 1.50-1.59 (1H, m, H-11"), 1.41-1.50 (1H, m, H-7'), 1.38 (1H, dd, J=14.0 Hz, J=4.0 Hz, H-15"), 1.24 (1H, d, J=4.3 Hz, H-19'), 1.15-1.26 (4H, m, H-7"), 1.17 (3H, s, H-18), 1.05 (3H, d, J=7.0 Hz, H-27), 1.03 (3H, d, J=6.7 Hz, H-28), 0.96 (3H, s, H-29), 0.94 (3H, qd, J=12.5 Hz, J=3.7 Hz, H-6"), 0.64 (3H, d, J=6.1 Hz, H-21), 0.57 (1H, d, H-19")

$^{13}$C NMR (126 MHz, $CD_3CN$) δ=205.6 (C-23), 202.4 (C-3), 171.3 (C-16a), 155.6 (C-1), 149.1 (C-24), 128.4 (C-2), 126.5 (C-24a), 77.2 (C-16), 75.8 (C-22), 66.6 (C-26), 51.4 (C-17), 48.3 (C-14), 47.6 (C-4), 46.9 (C-15), 46.7 (C-13), 45.3 (C-8), 43.6 (C-5), 37.6 (C-25), 36.3 (C-20), 33.1 (C-12), 32.9 (C-10), 28.1 (C-11), 27.7 (C-19), 27.2 (C-9), 24.3 (C-6), 24.3 (C-7), 22.1 (C-16b), 20.1 (C-29), 18.5 (C-21), 17.2 (C-27), 12.3 (C-21), 11.3 (C-28)

Example 2

Neoboutomellerone

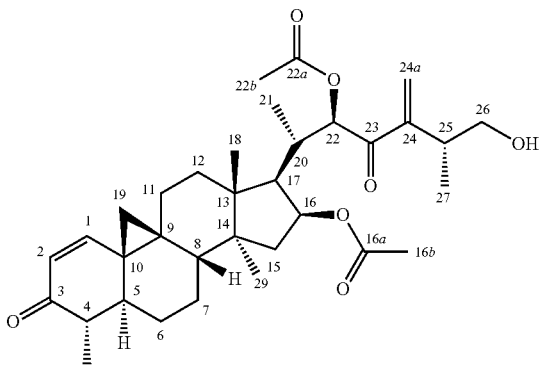

Chemical formula: $C_{34}H_{48}O_7$
Exact mass: 568.34
Molecular weight: 568.74

$^1$H NMR (500 MHz, $CD_3CN$) δ=6.94 (1H, d, J=10.1 Hz, H-1), 6.04 (1H, s, H-24a'), 5.89 (1H, d, J=1.2 Hz, H-24a"), 5.90 (1H, d, J=9.8 Hz, H-2), 5.53 (1H, d, J=2.4 Hz, H-22), 5.09 (1H, td, J=7.7 Hz, J=4.4 Hz, H-16), 3.53 (1H, dt, J=10.8 Hz, J=5.9 Hz, H-26'), 3.39 (1H, dt, J=10.5 Hz, J=6.1 Hz, H-26"), 2.77 (1H, sxt, J=6.7 Hz, H-25), 2.68 (1H, t, J=5.8 Hz, OH-26), 2.54-2.65 (1H, dqd, J=11.1 Hz, J=6.9 Hz, J=2.3 Hz, H-20), 2.29 (1H, dd, J=11.0 Hz, J=7.6 Hz, H-17), 2.14-2.22 (2H, m, H-4,15'), 2.09 (3H, s, H-22b), 2.03 (3H, s, H-16b), 1.98-2.05 (2H, m, H-8,11'), 1.95-1.98 (1H, m, H-5), 1.63-1.77 (3H, m, H-6', 12', 12"), 1.51-1.61 (1H, m, H-11"), 1.40-1.50 (1H, m, H-7'), 1.33-1.40 (1H, ddq, J=14.0 Hz, J=4.6 Hz, J=0.9 Hz, H-15"), 1.24 (1H, d, J=4.3 Hz, H-19'), 1.18 (3H, s, H-18), 1.14-1.23 (1H, m, H-7"), 1.03 (3H, d, J=7.0 Hz, H-27), 1.02 (3H, d, H-28), 0.95 (3H, d, J=0.6 Hz, H-29), 0.88-0.99 (1H, m, H-6"), 0.85 (3H, d, J=7.0 Hz, H-21), 0.58 (1H, d, J=4.6 Hz, H-19")

$^{13}$C NMR (126 MHz, $CD_3CN$) δ=202.4 (C-3), 199.6 (C-23), 171.7 (C-22a), 171.3 (C-16a), 155.5 (C-1), 150.3 (C-24), 128.4 (C-2), 124.6 (C-24a), 78.5 (C-22), 76.6 (C-16), 66.4 (C-26), 51.3 (C-17), 48.4 (C-14), 47.6 (C-4), 46.8 (C-13), 46.7 (C-15), 45.2 (C-8), 43.6 (C-5), 37.9 (C-25), 33.2 (C-20), 33.0 (C-12), 32.9 (C-10), 28.1 (C-11), 27.7 (C-19), 27.2 (C-9), 24.3 (C-7, 6), 22.1 (C-16b), 20.9 (C-22b), 20.0 (C-29), 18.2 (C-18), 17.2 (C-27), 13.3 (C-21), 11.3 (C-28)

Example 3

Diastereoisomer of Ring A of 22-deacetyl-neoboutomellerone

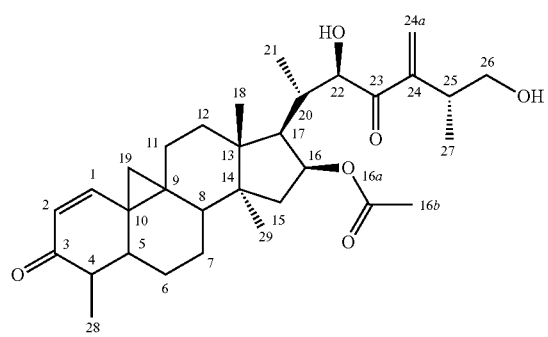

Chemical formula: $C_{32}H_{46}O_6$
Exact mass: 526.33
Molecular weight: 526.70

$^1$H NMR (500 MHz, $CD_3CN$) δ=6.49 (1H, d, J=10.1 Hz, H-1), 6.13 (1H, s, H-24a'), 5.98 (1H, d, J=0.9 Hz, H-24a"), 5.87 (1H, d, J=10.1 Hz, H-2), 5.24 (1H, td, J=7.4 Hz, J=5.0 Hz, H-16), 4.72 (1H, br. s., H-22), 3.55 (1H, br. s., OH-22), 3.55 (1H, dd, J=10.4 Hz, J=6.7 Hz, H-26'), 3.41 (1H, dd, J=10.5 Hz, J=6.6 Hz, H-26"), 2.83 (1H, sxt, J=6.6 Hz, H-25), 2.69 (1H, br. s., OH-26), 2.42-2.51 (1H, dqd, J=11.0 Hz, J=6.4 Hz, J=2.1 Hz, H-20), 2.43 (1H, dd, J=11.0 Hz, J=7.3 Hz, H-17), 2.07-2.26 (4H, m, H-4,8,11', 15'), 2.04 (3H, s, H-16b), 1.98-2.07 (1H, m, H-6'), 1.91 (1H, m, H-5), 1.81 (1H, td, J=13.3 Hz, J=4.9 Hz, H-12'), 1.59 (1H, ddd, J=13.1 Hz, J=5.3 Hz, J=1.7 Hz, H-12"), 1.33-1.44 (2H, m, H-11", 15"), 1.31 (1H, d, J=4.9 Hz, H-19'), 1.21-1.30 (2H, m, H-7', 7"), 1.12 (3H, s, H-18), 1.09-1.19 (1H, m, H-6"), 1.04 (3H, d, J=6.7 Hz, H-28), 1.04 (3H, d, J=7.3 Hz, H-27), 0.94 (3H, d, J=0.9 Hz, H-29), 0.91 (1H, d, J=5.2 Hz, H-19"), 0.65 (3H, d, J=6.4 Hz, H-21)

$^{13}$C NMR (126 MHz, $CD_3CN$) δ=205.6 (C-23), 201.0 (C-3), 171.3 (C-16a), 157.3 (C-1), 149.1 (C-24), 126.5 (C-2), 126.5 (C-24a), 77.2 (C-16), 76.0 (C-22), 66.6 (C-26), 50.6 (C-17), 48.8 (C-14), 48.5 (C-4), 46.8 (C-13), 44.7 (C-15), 41.5 (C-8), 40.4 (C-5), 37.6 (C-25), 36.4 (C-20), 35.0 (C-10), 33.0 (C-12), 31.9 (C-6), 31.6 (C-19), 30.4 (C-11), 27.7 (C-9), 22.1 (C-16b), 21.3 (C-7), 19.1 (C-29), 17.2 (C-27), 15.6 (C-18), 12.7 (C-21), 12.6 (C-28)

Example 4

Diastereoisomer of Ring A of Neoboutomellerone

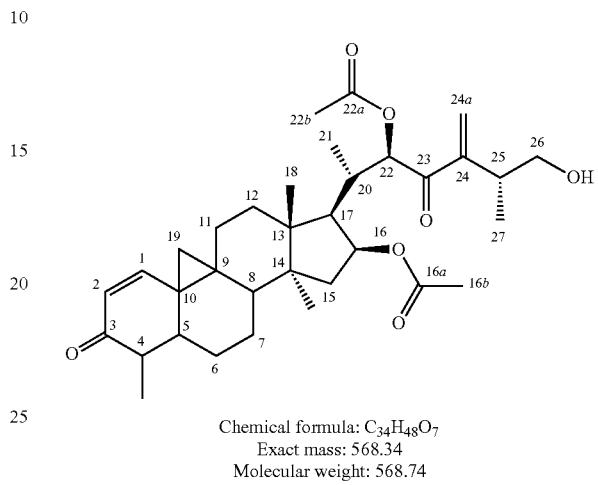

Chemical formula: $C_{34}H_{48}O_7$
Exact mass: 568.34
Molecular weight: 568.74

$^1$H NMR (500 MHz, $CD_3CN$) δ=6.49 (1H, d, J=10.1 Hz, H-1), 6.04 (1H, s, H-24a'), 5.88 (1H, d, J=0.9 Hz, H-24a"), 5.88 (1H, d, J=10.1 Hz, H-2), 5.53 (1H, d, J=2.1 Hz, H-22), 5.13 (1H, td, J=7.6 Hz, J=4.9 Hz, H-16), 3.53 (1H, dt, J=10.6 Hz, J=5.8 Hz, H-26'), 3.39 (1H, dt, J=10.7 Hz, J=6.1 Hz, H-26"), 2.76 (1H, sxt, J=6.4 Hz, H-25), 2.72 (1H, t, J=5.6 Hz, OH-26), 2.56-2.66 (1H, dqd, J=10.9 Hz, J=7.0 Hz, J=2.1 Hz, H-20), 2.28 (1H, dd, J=11.0 Hz, J=7.6 Hz, H-17), 2.15-2.26 (1H, m, H-4), 2.09 (3H, s, H-22b), 2.07-2.16 (2H, m, H-11', 15'), 2.04 (3H, s, H-16b), 1.97-2.05 (1H, m, H-6'), 1.88-1.93 (1H, m, H-5), 1.83 (1H, td, J=13.3 Hz, J=4.9 Hz, H-12'), 1.63 (1H, ddd, J=13.1 Hz, J=5.2 Hz, J=1.5 Hz, H-12"), 1.41 (1H, ddd, J=14.3 Hz, J=4.9 Hz, J=1.8 Hz, H-11"), 1.35 (1H, dd, J=13.4 Hz, J=4.3 Hz, H-15"), 1.30 (1H, d, J=5.2 Hz, H-19'), 1.20-1.29 (1H, m, H-7'), 1.10-1.18 (2H, m, H-6", 7"), 1.13 (3H, s, H-18), 1.04 (3H, d, J=6.4 Hz, H-28), 1.02 (3H, d, J=7.0 Hz, H-27), 0.92 (3H, s, H-29), 0.88-0.96 (1H, m, H-19), 0.85 (3H, d, J=7.0 Hz, H-21)

$^{13}$C NMR (126 MHz, $CD_3CN$) δ=200.9 (C-3), 199.6 (C-23), 171.6 (C-22a), 171.2 (C-16a), 157.2 (C-1), 150.3 (C-24), 126.5 (C-2), 124.6 (C-24a), 78.6 (C-22), 76.6 (C-16), 66.4 (C-26), 50.5 (C-17), 48.8 (C-14), 48.4 (C-4), 46.9 (C-13), 44.5 (C-15), 41.4 (C-8), 40.3 (C-22), 37.9 (C-25), 34.9 (C-10), 33.2 (C-20), 32.9 (C-12), 31.9 (C-6), 31.6

(C-19), 30.4 (C-11), 27.7 (C-10), 22.1 (C-16b), 21.3 (C-7), 20.9 (C-22b), 18.9 (C-29), 17.2 (C-27), 15.4 (C-18), 13.7 (C-21), 12.6 (C-28)

Example 5

Truncated Neoboutomellerone

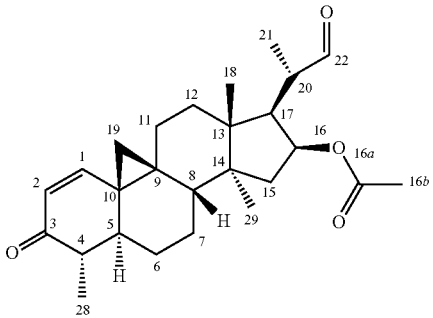

Chemical formula: $C_{26}H_{36}O_4$
Exact mass: 412.26
Molecular weight: 412.56

$^1$H NMR (500 MHz, $CD_3CN$) δ=9.59 (1H, d, J=1.8 Hz, H-22), 6.95 (1H, d, J=10.1 Hz, H-1), 5.91 (1H, d, J=9.8 Hz, H-2), 5.25 (1H, td, J=8.2 Hz, J=5.5 Hz, H-16), 2.87 (1H, dqd, J=11.0 Hz, J=7.3 Hz, J=2.0 Hz, H-20), 2.39 (1H, dd, J=11.0 Hz, J=8.2 Hz, H-17), 2.16-2.21 (1H, m, H-4), 2.04-2.11 (2H, m, H-8a, 15'), 1.96-2.04 (2H, m, H-5a, 11'), 1.90 (3H, s, H-16b), 1.70-1.78 (1H, m, H-12'), 1.58-1.70 (3H, m, H-6', 11", 12"), 1.42-1.51 (1H, m, H-7'), 1.33 (1H, ddq, J=13.4 Hz, J=5.6 Hz, J=1.1 Hz, H-15"), 1.27 (1H, d, J=4.3 Hz, H-19'), 1.19-1.26 (1H, m, H-7"), 1.17 (3H, s, H-18), 1.09 (3H, d, J=7.3 Hz, H-21), 1.02 (3H, d, J=6.7 Hz, H-28), 0.96 (3H, d, J=0.9 Hz, H-29), 0.89-1.00 (1H, m, H-6"), 0.56 (1H, d, J=4.3 Hz, H-19")
$^{13}$C NMR (126 MHz, $CD_3CN$) δ=205.2 (C-22), 202.3 (C-3), 170.9 (C-16a), 155.4 (C-1), 128.5 (C-2), 75.1 (C-16), 50.7 (C-17), 48.4 (C-14), 47.6 (C-4), 46.5 (C-13), 45.3 (C-15), 45.1 (C-20), 44.3 (C-8), 43.3 (C-5), 33.0 (C-10), 32.6 (C-12), 28.0 (C-11), 27.3 (C-9), 26.9 (C-19), 24.1 (C-6), 24.0 (C-7), 21.3 (C-16b), 19.4 (C-29), 18.4 (C-18), 13.4 (C-21), 11.3 (C-28)

Example 6

6-hydroxy-neoboutomellerone

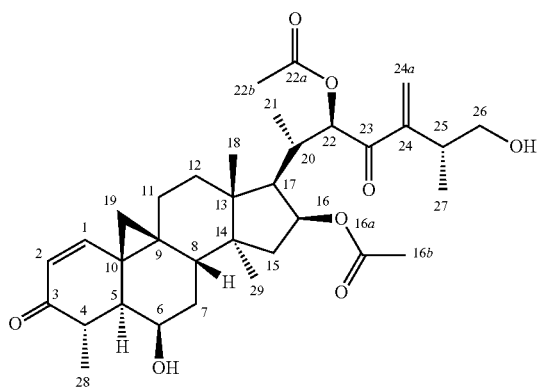

Chemical formula: $C_{34}H_{48}O_8$
Exact mass: 584.33
Molecular weight: 584.74

$^1$H NMR (500 MHz, $CD_3CN$) δ=6.84 (1H, d, J=9.8 Hz, H-1), 6.06 (1H, s, H-24a'), 5.90 (1H, d, J=0.9 Hz, H-24a"), 5.82 (1H, d, J=9.8 Hz, H-2), 5.55 (1H, d, J=2.1 Hz, H-22), 5.09 (1H, td, J=7.6 Hz, J=4.3 Hz, H-16), 4.05 (1H, br. s., H-6), 3.54 (1H, dd, J=10.2 Hz, J=6.3 Hz, H-26'), 3.39 (1H, dd, J=10.2 Hz, J=6.6 Hz, H-26"), 2.77 (1H, sxt, J=6.6 Hz, H-25), 2.69 (1H, br. s., OH-26), 2.57-2.65 (2H, m, OH-6, H-20), 2.48 (1H, dq, J=13.0 Hz, J=6.8 Hz, H-4), 2.25-2.36 (2H, m, H-8, 17), 2.18-2.25 (1H, m, H-11'), 2.22 (1H, dd, J=14.0 Hz, J=7.9 Hz, H-15'), 2.10 (3H, s, H-22b), 2.04 (3H, s, H-16b), 1.93-1.95 (1H, m, H-5), 1.81 (1H, d, J=3.4 Hz, H-19'), 1.64-1.79 (2H, m, H-12', 12"), 1.52 (1H, dt, J=13.4 Hz, J=4.7 Hz, H-7'), 1.43 (1H, dd, J=13.1 Hz, J=1.8 Hz, H-7"), 1.37 (1H, dd, J=13.7 Hz, J=4.9 Hz, H-15"), 1.33-1.41 (1H, m, H-11"), 1.24 (3H, s, H-18), 1.14 (3H, d, J=6.7 Hz, H-28), 1.03 (3H, d, J=7.0 Hz, H-27), 1.00 (3H, s, H-29), 0.86 (3H, d, J=7.0 Hz, H-21), 0.68 (1H, d, J=3.4 Hz, H-19")
$^{13}$C NMR (126 MHz, $CD_3CN$) δ=203.4 (C-3), 199.5 (C-23), 171.7 (C-22a), 171.4 (C-16a), 156.2 (C-1), 150.3 (C-24), 127.5 (C-2), 124.7 (C-24a), 78.5 (C-22), 76.8 (C-16), 66.4 (C-26), 65.6 (C-6), 51.5 (C-17), 51.4, 50.5, 47.7 (C-14), 47.5 (C-15), 47.1 (C-13), 46.6 (C-5), 44.9 (C-4), 41.1 (C-8), 37.9 (C-25), 33.2 (C-20), 33.1 (C-12), 33.0 (C-19), 32.7 (C-7), 30.8 (C-10), 28.1 (C-9), 27.7 (C-11), 22.1 (C-16b), 20.9 (C-22b), 20.7 (C-29), 19.4 (C-18), 17.2 (C-27), 13.2 (C-21), 11.0 (C-28)

Example 7

22-deacetyl,26-dehydroxy-neoboutomellerone

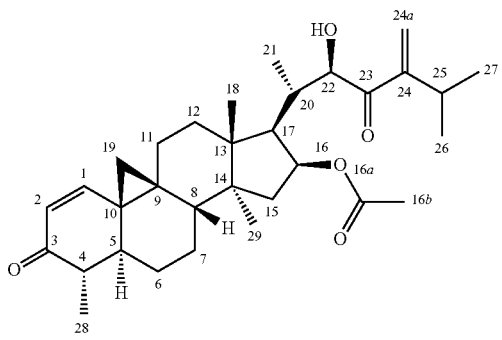

Chemical formula: $C_{32}H_{46}O_5$
Exact mass: 510.33
Molecular weight: 510.70

$^1$H NMR (500 MHz, $CD_3CN$) δ=6.94 (1H, d, J=9.8 Hz, H-1), 6.03 (1H, s, H-24a'), 5.94 (1H, d, J=1.2 Hz, H-24a"), 5.89 (1H, d, J=10.1 Hz, H-2), 5.20 (1H, td, J=7.6 Hz, J=4.4 Hz, H-16), 4.71 (1H, d, J=5.8 Hz, H-22), 3.54 (1H, d, J=5.8 Hz, OH-22), 2.79-2.91 (1H, m, J=6.9 Hz, J=0.9 Hz, H-25), 2.38-2.49 (2H, m, H-17, 20), 2.22 (1H, dd, J=13.9 Hz, J=7.8 Hz, H-15'), 2.16-2.21 (1H, m, H-4), 2.03 (3H, s, H-16b), 1.98-2.06 (2H, m, H-8,11'), 1.94-1.98 (1H, m, H-5), 1.61-1.74 (3H, m, H-6', 12', 12"), 1.50-1.59 (1H, m, H-11"), 1.41-1.49 (1H, m, H-7'), 1.38 (1H, dd, J=13.9 Hz, J=4.4 Hz, H-15"), 1.24 (1H, d, J=4.3 Hz, H-19'), 1.18-1.26 (1H, m, H-7"), 1.17 (3H, s, H-18), 1.10 (3H, d, J=7.0 Hz, H-26), 1.03 (3H, d, J=6.7 Hz, H-28), 1.02 (3H, d, J=6.7 Hz, H-27), 0.96 (3H, d, J=0.6 Hz, H-29), 0.94 (1H, qd, J=12.5 Hz, J=3.7 Hz, H-6"), 0.64 (3H, d, J=6.4 Hz, H-21), 0.57 (1H, d, J=4.3 Hz, H-19")

$^{13}$C NMR (126 MHz, CD$_3$CN) δ=205.4 (C-23), 202.5 (C-3), 171.3 (C-16a), 155.7 (C-1), 153.1 (C-24), 128.3 (C-2), 124.3 (C-24a), 77.3 (C-16), 75.8 (C-22), 51.4 (C-17), 48.3 (C-14), 47.6 (C-4), 46.9 (C-15), 46.7 (C-13), 45.3 (C-8), 43.6 (C-5), 36.2 (C-20), 33.1 (C-12), 33.0 (C-10), 29.5 (C-25), 28.1 (C-11), 27.7 (C-19), 27.2 (C-9), 24.3 (C-7), 24.3 (C-6), 22.6 (C-27), 22.1 (C-16b), 22.0 (C-26), 20.1 (C-29), 18.5 (C-18), 12.3 (C-21), 11.3 (C-28)

Example 8

26-dehydroxy-neoboutomellerone

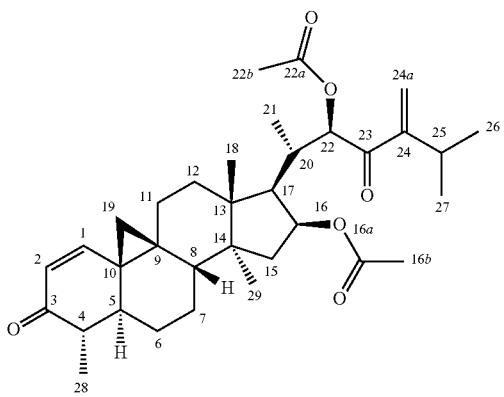

Chemical formula: C$_{34}$H$_{48}$O$_6$
Exact mass: 552.35
Molecular weight: 552.74

$^1$H NMR (500 MHz, CD$_3$CN) δ=6.94 (1H, d, J=9.8 Hz, H-1), 5.94 (1H, s, H-24a'), 5.90 (1H, d, J=10.1 Hz, H-2), 5.83 (1H, d, J=1.2 Hz, H-24a"), 5.51 (1H, d, J=2.4 Hz, H-22), 5.09 (1H, td, J=7.6 Hz, J=4.3 Hz, H-16), 2.73-2.86 (1H, m, J=7.0 Hz, J=0.9 Hz, H-25), 2.50-2.61 (1H, dqd, J=11.0 Hz, J=7.0 Hz, J=2.1 Hz, H-20), 2.29 (1H, dd, J=11.0 Hz, J=7.3 Hz, H-17), 2.16-2.22 (2H, m, H-4, 15'), 2.09 (3H, s, H-22b), 2.02 (3H, s, H-16b), 1.98-2.06 (2H, m, H-8,11'), 1.94-1.98 (1H, m, H-5), 1.62-1.77 (3H, m, H-6', 12', 12"), 1.51-1.61 (1H, m, H-11"), 1.40-1.49 (1H, m, H-7'), 1.36 (1H, ddd, J=14.0 Hz, J=4.3 Hz, J=0.9 Hz, H-15"), 1.24 (1H, d, J=4.6 Hz, H-19'), 1.18 (3H, s, H-18), 1.13-1.22 (1H, m, H-7"), 1.07 (3H, d, J=6.7 Hz, H-26), 1.02 (3H, d, J=7.0 Hz, H-28), 1.00 (3H, d, J=7.0 Hz, H-27), 0.95 (3H, s, H-29), 0.94 (1H, qd, J=12.5 Hz, J=4.0 Hz, H-6"), 0.85 (3H, d, J=7.0 Hz, H-21), 0.58 (1H, d, H-19")

$^{13}$C NMR (126 MHz, CD$_3$CN) δ=202.5 (C-3), 199.5 (C-23), 171.7 (C-22a), 171.3 (C-16a), 155.6 (C-1), 154.3 (C-24), 128.4 (C-2), 122.3 (C-24a), 78.5 (C-22), 76.6 (C-16), 51.3 (C-17), 48.4 (C-14), 47.6 (C-4), 46.8 (C-13), 46.7 (C-15), 45.2 (C-8), 43.6 (C-5), 33.0 (C-20), 32.9 (C-12), 29.7 (C-25), 28.1 (C-11), 27.7 (C-19), 27.2 (C-7, 6), 22.4 (C-27), 22.1 (C-16b), 21.6 (C-26), 20.9 (C-22b), 20.0 (C-29), 18.2 (C-18), 13.2 (C-21), 11.3 (C-28)

Example 9

26-dehydroxy,24,25-dehydro-nor-neoboutomellerone

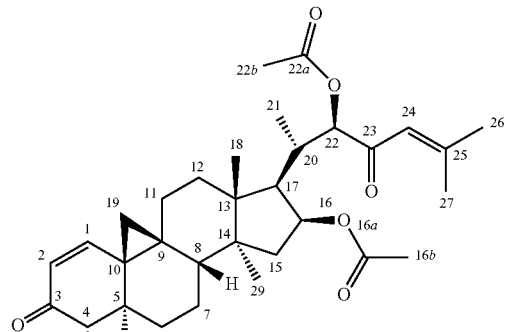

Chemical formula: C$_{33}$H$_{46}$O$_6$
Exact mass: 538.33
Molecular weight: 538.71

$^1$H NMR (500 MHz, CD$_3$CN) δ=6.94 (1H, d, J=9.8 Hz, H-1), 6.14 (1H, spt, J=1.3 Hz, H-24), 5.90 (1H, d, J=9.8 Hz, H-2), 5.10 (1H, td, J=7.8 Hz, J=4.6 Hz, H-16), 4.86 (1H, d, J=1.8 Hz, H-22), 2.56-2.64 (1H, dqd, J=10.9 Hz, J=7.0 Hz, J=1.5 Hz, H-20), 2.12 (3H, d, J=1.2 Hz, H-27), 2.10 (3H, s, H-22b), 2.09 (3H, s, H-16b), 2.04-2.22 (4H, m, H-4,8a, 15', 17), 1.95-2.03 (2H, m, H-5, 11'), 1.98 (3H, m, H-26), 1.63-1.73 (3H, m, H-6', 12', 12"), 1.53-1.63 (1H, m, H-11"), 1.42-1.51 (1H, m, H-7'), 1.38 (1H, dd, J=13.7 Hz, J=4.6 Hz, H-15"), 1.26 (1H, d, J=4.3 Hz, H-19'), 1.20 (3H, s, H-18), 1.17-1.24 (1H, m, H-7"), 1.02 (3H, d, J=6.7 Hz, H-28), 0.94 (3H, d, J=0.9 Hz, H-29), 0.89-0.99 (1H, m, H-6"), 0.86 (3H, d, J=7.0 Hz, H-21), 0.57 (1H, d, J=4.3 Hz, H-19")

$^{13}$C NMR (126 MHz, CD$_3$CN) δ=202.6 (C-3), 196.9 (C-23), 171.7 (C-22a), 171.3 (C-16a), 159.8 (C-25), 155.7 (C-1), 128.4 (C-2), 120.5 (C-24), 81.5 (C-22), 76.1 (C-16), 51.1 (C-17), 47.6 (C-4), 46.7 (C-13), 46.1 (C-15), 44.9 (C-8), 43.5 (C-5), 32.7 (C-12), 28.1 (C-26), 28.0 (C-11), 27.4 (C-19), 24.2 (C-6), 24.2 (C-7), 21.8 (C-16b), 21.2 (C-22b), 21.0 (C-27), 19.8 (C-29), 18.1 (C-18), 13.2 (C-21), 11.3 (C-28)

Example 10

22-deacetyl,26-dehydroxy,24,25-dehydro-nor-neoboutomellerone

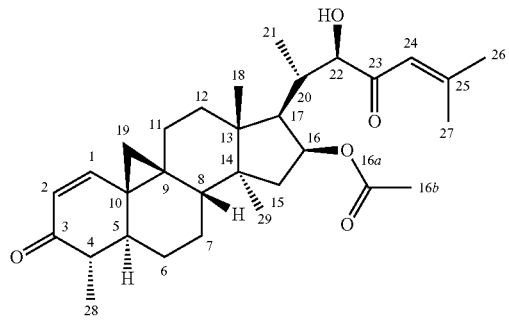

Chemical formula: C$_{31}$H$_{44}$O$_5$
Exact mass: 496.32
Molecular weight: 496.68

$^1$H NMR (500 MHz, CD$_3$CN) δ=6.94 (1H, d, J=10.1 Hz, H-1), 6.17 (1H, spt, J=1.3 Hz, H-24), 5.90 (1H, d, J=10.1 Hz, H-2), 5.20 (1H, td, J=7.9 Hz, J=4.7 Hz, H-16), 4.00 (1H, dd, J=4.9 Hz, J=1.2 Hz, H-22), 3.55 (1H, d, J=5.2 Hz, OH-22), 2.44-2.53 (1H, dqd, J=11.3 Hz, J=7.0 Hz, J=1.8 Hz, H-20), 2.35 (1H, dd, J=11.0 Hz, J=7.6 Hz, H-17), 2.17 (3H, d, J=1.2 Hz, H-27), 2.16-2.20 (1H, m, H-4), 2.06 (3H, s, H-16b), 2.04-2.13 (2H, m, H-8,15'), 1.96-2.02 (2H, m, H-5,11'), 1.94 (3H, m, H26), 1.61-1.73 (3H, m, H-6', 12', 12"), 1.53-1.61 (1H, m, H-11"), 1.43-1.50 (1H, m, H-7'), 1.39 (1H, dd, J=13.6 Hz, J=5.0 Hz, H-15"), 1.26 (1H, d, J=4.6 Hz, H-19'), 1.20-1.30 (1H, m, H-7"), 1.20 (3H, s, H-18), 1.03 (3H, d, J=6.7 Hz, H-28), 0.96 (3H, d, J=0.6 Hz, H-29), 0.91-1.00 (1H, m, H-6"), 0.65 (3H, d, J=6.7 Hz, H-21), 0.57 (1H, d, J=4.3 Hz, H-19")

$^{13}$C NMR (126 MHz, CD$_3$CN) δ=202.5 (C-23, 3), 171.3 (C-16a), 159.9 (C-25), 155.7 (C-1), 128.4 (C-2), 120.3 (C-24), 79.0 (C-22), 76.5 (C-16), 51.2 (C-17), 48.4 (C-14), 47.6 (C-4), 46.6 (C-13), 46.3 (C-15), 45.0 (C-8), 43.5 (C-5), 34.4 (C-20), 32.9 (C-12), 28.1 (C-11), 28.1 (C-26), 27.4 (C-19), 24.3 (C-6), 24.2 (C-7), 21.8 (C-16b), 21.3 (C-27), 19.9 (C-29), 18.3 (C-18), 12.2 (C-21), 11.3 (C-28)

Example 11

1,2-dihydro-neoboutomellerone

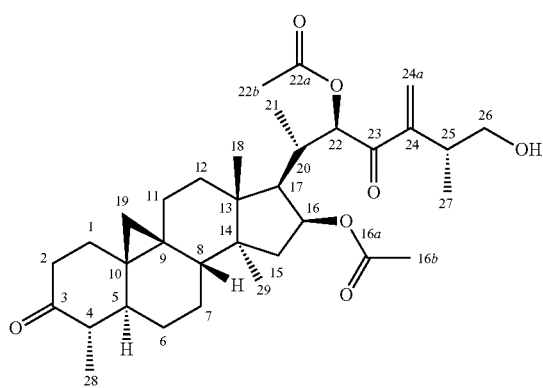

Chemical formula: C$_{34}$H$_{50}$O$_7$
Exact mass: 570.36
Molecular weight: 570.76

$^1$H NMR (500 MHz, CD$_3$CN) δ=6.05 (1H, s, H-24a'), 5.90 (1H, d, J=0.9 Hz, H-24a"), 5.53 (1H, d, J=2.1 Hz, H-22), 5.08 (1H, td, J=7.6 Hz, J=4.3 Hz, H-16), 3.53 (1H, dt, J=10.6 Hz, J=5.8 Hz, H-26'), 3.39 (1H, dt, J=10.5 Hz, J=6.1 Hz, H-26"), 2.77 (1H, sxt, J=6.7 Hz, H-25), 2.68 (1H, t, J=5.6 Hz, OH-26), 2.55-2.64 (1H, dqd, J=10.7 Hz, J=6.7 Hz, J=1.8 Hz, H-20), 2.43 (1H, td, J=13.6 Hz, J=6.4 Hz, H-2'), 2.23-2.32 (3H, m, H-2", 4, 17), 2.20 (1H, dd, J=14.0 Hz, J=7.9 Hz, H-15'), 2.09 (3H, s, H-22b), 2.07-2.13 (1H, m, H-11'), 2.03 (3H, s, H-16b), 1.77-1.87 (1H, m, H-1'), 1.63-1.75 (4H, m, H-6', 8, 12', 12"), 1.50-1.62 (2H, m, H-1", 5), 1.36 (1H, dd, J=14.5 Hz, J=4.1 Hz, H-15"), 1.23 (3H, s, H-18), 1.20-1.34 (2H, m, H-7', 11"), 1.10 (1H, qd, J=12.8 Hz, J=2.7 Hz, H-7"), 1.03 (3H, d, J=7.0 Hz, H-27), 0.97 (3H, s, H-29), 0.91 (3H, d, J=6.7 Hz, H-28), 0.84 (3H, d, J=7.0 Hz, H-21), 0.75 (1H, qd, J=12.6 Hz, J=2.4 Hz, H-6"), 0.65 (1H, d, J=3.7 Hz, H-19'), 0.47 (1H, d, H-19")

$^{13}$C NMR (126 MHz, CD$_3$CN) δ=213.2 (C-3), 199.6 (C-23), 171.7 (C-22a), 171.3 (C-16a), 150.3 (C-24), 124.6 (C-24a), 78.5 (C-22), 76.9 (C-16), 66.4 (C-26), 51.4 (C-17), 50.5 (C-4), 48.6 (C-8), 48.0 (C-14), 47.6 (C-15), 47.0 (C-5), 46.8 (C-13), 41.5 (C-2), 37.9 (C-25), 33.5 (C-1), 33.3 (C-12), 33.2 (C-20), 30.3 (C-10), 28.0 (C-19), 27.4 (C-11), 26.5 (C-6), 26.2 (C-7), 25.4 (C-9), 22.1 (C-16b), 20.9 (C-22b), 20.6 (C-29), 19.3 (C-18), 17.2 (C-27), 13.2 (C-21), 11.2 (C-28)

Example 12

6,7-epoxy-neoboutomellerone

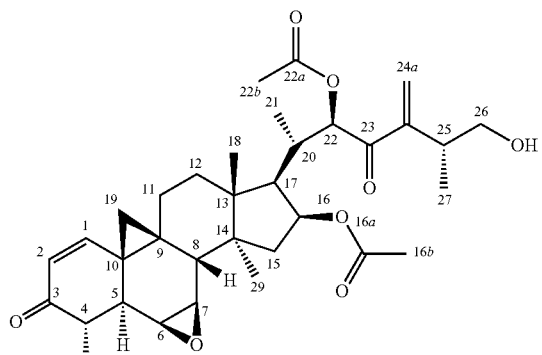

Chemical formula: C$_{34}$H$_{46}$O$_8$
Exact mass: 582.32
Molecular weight: 582.72

$^1$H NMR (500 MHz, CD$_3$CN) δ=6.94 (1H, d, J=10.1 Hz, H-1), 6.06 (1H, s, H-24a'), 5.91 (1H, d, J=10.1 Hz, H-2), 5.90 (1H, s, H-24a"), 5.54 (1H, d, J=2.1 Hz, H-22), 5.16 (1H, td, J=7.7 Hz, J=4.7 Hz, H-16), 3.53 (1H, dd, J=10.4 Hz, J=6.4 Hz, H-26'), 3.39 (1H, dd, J=10.5 Hz, J=6.6 Hz, H-26"), 3.15 (1H, dd, J=4.3 Hz, J=1.5 Hz, H-6), 3.00 (1H, dd, J=4.3 Hz, J=1.8 Hz, H-7), 2.83 (1H, d, J=1.2 Hz, H-8), 2.77 (1H, sxt, J=6.7 Hz, H-25), 2.70 (1H, br. s., OH-26), 2.59-2.68 (1H, dqd, J=10.8 Hz, J=7.0 Hz, J=2.1 Hz, H-20), 2.55 (1H, dq, J=12.5 Hz, J=7.0 Hz, H-4), 2.45 (1H, d, J=11.3 Hz, H-5), 2.33 (1H, dd, J=13.4 Hz, J=7.9 Hz, H-15'), 2.28 (1H, dd, J=10.8 Hz, J=7.8 Hz, H-17), 2.08 (3H, s, H-22b), 2.06 (3H, s, H-16b), 2.02-2.05 (2H, m, H-11', 19'), 1.51-1.73 (3H, m, H-12', 12", 15"), 1.40 (1H, dd, J=15.9 Hz, J=3.1 Hz, H-11"), 1.23 (3H, d, J=7.0 Hz, H-28), 1.20 (3H, s, H-18), 1.03 (3H, d, J=7.0 Hz, H-27), 0.94 (3H, s, H-29), 0.86 (3H, d, J=7.0 Hz, H-21), 0.03 (1H, d, J=4.0 Hz, H-19")

$^{13}$C NMR (126 MHz, CD$_3$CN) δ=202.1 (C-3), 199.6 (C-23), 171.7 (C-22a), 171.3 (C-16a), 154.2 (C-1), 150.3 (C-24), 128.4 (C-2), 124.7 (C-24a), 78.6 (C-22), 76.3 (C-16), 66.4 (C-26), 55.0 (C-7), 52.8 (C-6), 49.7 (C-17), 47.3 (C-14), 47.1 (C-13), 45.6 (C-4), 44.7 (C-15), 41.5 (C-5), 38.9 (C-8), 38.0 (C-25), 33.2 (C-20), 32.1 (C-12), 31.8 (C-10), 27.4

(C-11), 27.2 (C-9), 22.1 (C-16b, 19), 22.1, 20.9 (C-22b), 19.6 (C-29), 17.2 (C-27), 15.2 (C-18), 13.7 (C-21), 11.3 (C-28), 1.8

Example 13

Diastereoisomer on the Side Chain of Neoboutomellerone

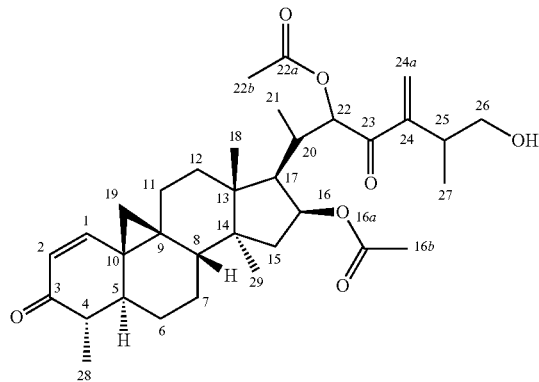

Chemical formula: $C_{34}H_{48}O_7$
Exact mass: 568.34
Molecular weight: 568.74

$^1$H NMR (500 MHz, CDCl$_3$) δ=6.82 (1H, d, J=9.8 Hz, H-1), 6.11 (1H, s, H-24a'), 5.98 (1H, d, J=10.1 Hz, H-2), 5.83 (1H, d, J=0.9 Hz, H-24a"), 5.52 (1H, d, J=2.1 Hz, H-22), 5.07 (1H, td, J=7.7 Hz, J=4.4 Hz, H-16), 3.56 (2H, t, J=6.0 Hz, H-26), 2.96 (1H, sxt, J=6.7 Hz, H-25), 2.55-2.63 (1H, m, H-20), 2.21-2.33 (2H, m, H-15', 17), 2.14-2.22 (1H, m, H-4), 2.14 (3H, s, H-22b), 2.06 (3H, s, H-16b), 1.91-2.03 (3H, m, H-5,8,11'), 1.62-1.77 (3H, m, H-6', 12', 12"), 1.48-1.59 (1H, m, H-11"), 1.41-1.48 (1H, m, H-7'), 1.30 (1H, dd, J=14.2 Hz, J=4.7 Hz, H-15"), 1.18 (1H, d, J=4.0 Hz, H-19'), 1.15-1.21 (1H, m, H-7"), 1.16 (3H, s, H-18), 1.09 (3H, d, J=7.0 Hz, H-27), 1.08 (3H, d, J=6.7 Hz, H-28), 0.93 (3H, s, H-29), 0.89 (3H, d, J=7.0 Hz, H-21), 0.86-0.89 (1H, m, H-6"), 0.55 (1H, d, J=4.6 Hz, H-19")

$^{13}$C NMR (126 MHz, CDCl$_3$) δ=202.0 (C-3), 198.6 (C-23), 170.7 (C-22a), 170.1 (C-16a), 153.7 (C-1), 149.2 (C-24), 128.3 (C-2), 124.3 (C-24a), 77.8 (C-22), 75.9 (C-16), 66.8 (C-26), 50.3 (C-17), 47.4 (C-14), 46.9 (C-4), 46.0 (C-15), 45.6 (C-13), 44.3 (C-8), 42.5 (C-5), 37.9 (C-25), 32.2 (C-20), 32.1 (C-12), 31.9 (C-10), 27.4 (C-11), 27.0 (C-19), 23.5 (C-7), 23.4 (C-6), 21.7 (C-16b), 20.7 (C-22b), 19.6 (C-29), 17.8 (C-18), 15.5 (C-27), 12.7 (C-21), 10.8 (C-28)

Example 14

1,2-dihydro-22-deacetyl-neoboutomellerone

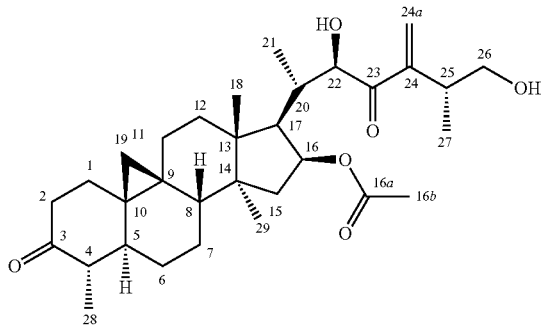

Chemical formula: $C_{32}H_{48}O_6$
Exact mass: 528.35
Molecular weight: 528.72

$^1$H NMR (500 MHz, CD$_3$CN) δ=6.12 (1H, s, H-24a'), 5.99 (1H, d, J=0.9 Hz, H-24a"), 5.20 (1H, td, J=7.6 Hz, J=4.4 Hz, H-16), 4.72 (1H, dd, J=6.1 Hz, J=2.1 Hz, H-22), 3.56 (1H, dt, J=10.7 Hz, J=5.8 Hz, H-26'), 3.54 (1H, d, J=6.1 Hz, OH-22), 3.41 (1H, dt, J=10.5 Hz, J=6.0 Hz, H-26"), 2.83 (1H, sxt, J=6.7 Hz, H-25), 2.67 (1H, t, J=5.8 Hz, OH-26), 2.34-2.50 (3H, m, H-2', 17, 20), 2.19-2.34 (3H, m, H-2", 4, 15'), 2.05-2.13 (1H, m, H-11'), 2.03 (3H, s, H-16b), 1.77-1.87 (1H, tdd, J=13.5 Hz, J=3.7 Hz, J=1.2 Hz, H-1'), 1.62-1.75 (4H, m, H-6', 8, 12', 12"), 1.50-1.62 (2H, m, H-1", 5), 1.35-1.41 (1H, ddq, J=14.2 Hz, J=4.4 Hz, J=0.9 Hz, H-15"), 1.21-1.37 (2H, m, H-7', 11"), 1.22 (3H, s, H-18), 1.12 (1H, qd, J=12.8 Hz, J=2.7 Hz, H-7"), 1.05 (3H, d, J=7.3 Hz, H-27), 0.97 (3H, d, J=0.6 Hz, H-29), 0.91 (3H, d, J=6.7 Hz, H-28), 0.75 (1H, qd, J=12.5 Hz, J=2.4 Hz, H-6"), 0.61-0.67 (1H, m, H-19'), 0.64 (3H, d, J=6.4 Hz, H-21), 0.47 (1H, d, J=4.0 Hz, H-19")

$^{13}$C NMR (126 MHz, CD$_3$CN) δ=213.3 (C-3), 205.6 (C-23), 171.3 (C-16a), 149.1 (C-24), 126.5 (C-24a), 77.5 (C-16), 75.8 (C-22), 66.7 (C-26), 51.5 (C-17), 50.5 (C-4), 48.6 (C-8), 47.9 (C-14), 47.8 (C-15), 47.0 (C-5), 46.7 (C-13), 41.5 (C-2), 37.6 (C-25), 36.3 (C-20), 33.5 (C-1), 33.5 (C-12), 30.3 (C-10), 28.0 (C-19), 27.4 (C-11), 26.5 (C-6), 26.2 (C-7), 25.4 (C-9), 22.1 (C-16b), 20.7 (C-29), 19.5 (C-18), 17.2 (C-27), 12.2 (C-21), 11.2 (C-28)

Example 15

1-hydroxy-2-hydro-22-deacetyl-neoboutomellerone

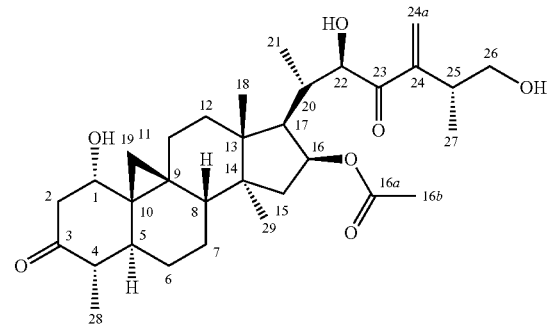

Chemical formula: $C_{32}H_{48}O_7$
Exact mass: 544.34
Molecular weight: 544.72

$^1$H NMR (500 MHz, CD$_3$CN) δ=6.12 (1H, s, H-24a'), 5.99 (1H, d, J=0.9 Hz, H-24a"), 5.21 (1H, td, J=7.5 Hz, J=4.3 Hz, H-16), 4.72 (1H, dd, J=5.3 Hz, J=1.7 Hz, H-22), 3.81 (1H, t, J=3.1 Hz, H-1), 3.55 (2H, d, J=6.1 Hz, OH-22), 3.50-3.61 (1H, m, H-26'), 3.34-3.45 (1H, m, H-26"), 2.83 (1H, sxt, J=6.4 Hz, H-25), 2.80 (1H, br. s., OH-1), 2.69 (1H, br. s., OH-26), 2.64 (1H, dd, J=14.0 Hz, J=3.7 Hz, H-2'), 2.41-2.50 (1H, dqd, J=11.0 Hz, J=6.7 Hz, J=2.1 Hz, H-20), 2.41 (1H, dd, J=11.0 Hz, J=7.0 Hz, H-17), 2.20-2.34 (4H, m, H-2", 4, 11', 15'), 2.10-2.14 (1H, m, H-5), 2.03 (3H, s, H-16b), 1.70-1.79 (1H, m, H-6'), 1.64-1.71 (3H, m, H-8, 12', 12"), 1.25-1.42 (3H, m, H-7', 11", 15"), 1.21 (3H, s, H-18), 1.12 (1H, qd, J=12.8 Hz, J=2.1 Hz, H-7"), 1.05 (3H, d, J=7.0 Hz, H-27), 1.01 (3H, s, H-29), 0.92 (3H, d, J=6.4 Hz, H-28), 0.80 (1H, qd, J=12.6 Hz, J=2.4 Hz, H-6"), 0.73 (1H, d, J=4.3 Hz, H-19'), 0.64 (3H, d, H-21), 0.48 (1H, d, J=4.3 Hz, H-19")

$^{13}$C NMR (126 MHz, CD$_3$CN) δ=212.2 (C-3), 205.6 (C-23), 171.3 (C-16a), 149.1 (C-24), 126.5 (C-24a), 77.5 (C-16), 75.8 (C-22), 74.0 (C-1), 66.7 (C-26), 51.5 (C-17), 50.5 (C-4), 49.3 (C-2), 48.7 (C-8), 47.9 (0-14), 47.9 (C-15), 46.6 (C-13), 39.5 (C-5), 37.6 (C-25), 36.3 (C-20), 34.0 (C-10), 33.3 (C-12), 28.1 (C-19), 26.5 (C-11), 26.2 (C-7), 26.1 (C-6), 26.0 (C-9), 22.1 (C-16b), 20.7 (C-29), 19.6 (C-18), 17.2 (C-27), 12.2 (C-21), 11.0 (C-28)

Example 16

6-hydroxy-22-deacetyl-neoboutomellerone

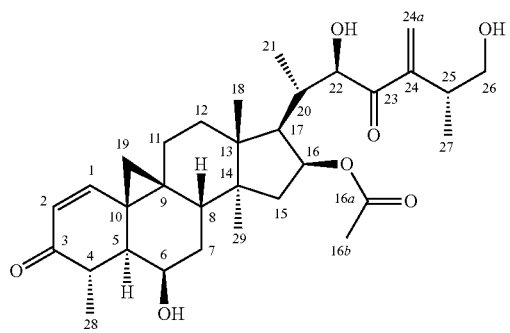

Chemical formula: C$_{32}$H$_{46}$O$_7$
Exact mass: 542.32
Molecular weight: 542.70

$^1$H NMR (500 MHz, CDCL$_3$) δ=6.74 (1H, d, J=10.1 Hz, H-1), 6.16 (1H, s, H-24a'), 6.01 (1H, s, H-24a"), 5.92 (1H, d, J=9.8 Hz, H-2), 5.33 (1H, td, J=7.1 Hz, J=4.4 Hz, H-16), 4.72 (1H, s, H-22), 4.16 (1H, br. s., H-6), 3.62 (2H, d, J=6.1 Hz, H-26), 3.57 (1H, d, J=5.5 Hz, OH-22), 2.94 (1H, sxt, J=6.4 Hz, H-25), 2.52-2.59 (1H, m, H-4), 2.47-2.54 (1H, m, H-17), 2.39-2.47 (1H, m, H-20), 2.35 (1H, dd, J=13.7 Hz, J=7.9 Hz, H-15'), 2.27 (1H, dd, J=12.7 Hz, J=4.4 Hz, H-8), 2.15-2.24 (1H, m, H-11'), 2.07 (3H, s, H-16b), 1.96 (1H, dd, J=12.8 Hz, J=2.4 Hz, H-5), 1.82 (1H, d, J=3.1 Hz, H-19'), 1.65-1.79 (2H, m, H-12', 12"), 1.56 (1H, td, J=12.9 Hz, J=4.4 Hz, H-7'), 1.47 (1H, t, J=13.1 Hz, H-7"), 1.35 (1H, dd, J=15.1 Hz, J=4.4 Hz, H-15"), 1.26-1.39 (1H, m, H-11"), 1.21 (3H, br. s., H-18), 1.21 (3H, d, J=7.3 Hz, H-28), 1.11 (3H, d, J=7.0 Hz, H-27), 1.01 (3H, s, H-29), 0.68 (1H, d, J=3.1 Hz, H-19"), 0.65 (3H, d, J=6.4 Hz, H-21)

$^{13}$C NMR (126 MHz, CDCL$_3$) δ=204.4 (C-23), 202.7 (C-3), 170.2 (C-16a), 154.6 (C-1), 147.9 (C-24), 127.3 (C-2), 125.8 (C-24a), 77.1 (C-16), 74.8 (C-22), 74.8, 67.0 (C-26), 65.6 (C-6), 50.9, 50.4 (C-17), 46.9 (C-15), 46.7 (C-14), 46.1 (C-13), 45.7 (C-5), 43.8 (C-4), 40.2 (C-8), 36.6 (C-25), 35.8 (C-20), 32.7 (C-19), 32.3 (C-12), 31.9 (C-7), 29.7 (C-10), 27.2 (C-11), 25.4 (C-9), 21.8 (C-16b), 20.3 (C-29), 19.3 (C-18), 16.5 (C-27), 11.5 (C-21), 10.8 (C-28)

1.2. By Hemisynthesis

Example 1

22-deacetyl-neoboutomellerone

Compound 1 can be obtained by extraction from the leaves of *Neoboutonia melleri* as described above or can be prepared by synthesis from neoboutomellerone as described below.

In a sealed test tube, 100 mg (0.178 mmol) of compound 2 is dissolved in 3.2 ml of an alcohol used as solvent such as isopropanol or tert-butanol. Potassium carbonate (123 mg, 0.889 mmol, 5 eq) and 0.8 ml of water are then added. The test tube is sealed and the reaction is left for 72 hours at 40° C.

The reaction is diluted with ethyl acetate and the organic phase is separated and then washed successively with water and brine. The product is purified on a silica gel column and is eluted with a 60/40 cyclohexane/ethyl acetate mixture to lead to the isolation of compound 1 with a yield of 70%.

The same reaction carried out at 70° C. using scandium triflate (20%, 18 mg, 0.036 mmol) in a tert-butanol/water mixture (1 ml/0.2 ml) leads to the same compound 1 with a conversion of 50%.

Example 17

26-acetyl-22-deacetyl-neoboutomellerone

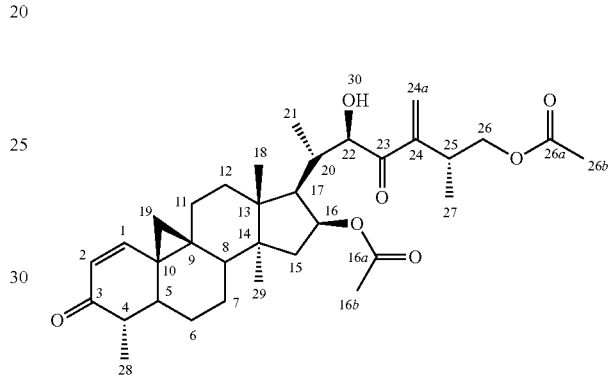

Chemical formula: C$_{34}$H$_{48}$O$_7$
Exact mass: 568.34
Molecular weight: 568.74

Protocol A: 200 mg (0.380 mmol) of compound 1 is dissolved in 16 ml of DCM. The reaction is cooled to 0° C. and then 1 eq (0.380 mmol, 45 µl) of lutidine is added, followed by 0.75 eq (0.285 mmol, 27 µl) of acetic anhydride and finally 5 mg of DMAP (10%). After 1 h, the reaction is hydrolyzed with water. The organic phase is washed with water, copper sulfate solution, water and then brine. After drying on sodium sulfate and evaporation of the solvent, 240 mg of crude reaction product is collected. The product is purified on a silica gel column and is eluted with an 80/20 cyclohexane/ethyl acetate mixture. 94.6 mg (58%) of product 17 (Rf: 0.68; 50/50 cyclohexane/ethyl acetate), and 76 mg (38%) of starting product 1 (Rf: 0.31; 50/50 cyclohexane/ethyl acetate) are obtained.

Protocol B: 200 mg (0.352 mmol) of compound 2 is dissolved in 25 ml of acetonitrile. To this solution, 195 mg (4 eq, 1.4 mmol) of potassium carbonate and 11 mg (0.1 eq, 0.035 mmol) of tetrabutylammonium bromide are added. The reaction is left under stirring at 40° C. overnight and then the reaction medium is filtered. The product is purified on a silica gel column under the same conditions as before and leads to 136 mg (69%) of compound 17 (Rf: 0.68; 50/50 cyclohexane/ethyl acetate).

$^1$H NMR (500 MHz, CD$_3$CN) δ=6.94 (1H, d, J=10.1 Hz, H-1), 6.17 (1H, s, H-24aa), 6.04 (1H, d, J=0.6 Hz, H-24ab), 5.89 (1H, d, J=9.8 Hz, H-2), 5.20 (1H, td, J=7.5 Hz, J=4.6 Hz, H-16), 4.72 (1H, dd, J=6.3 Hz, J=1.7 Hz, H-22), 3.99-4.10 (2H, m, H-26<">, 26<'>), 3.52 (1H, d, J=6.1 Hz, H-30), 3.05 (1H, sxt, J=6.8 Hz, H-25), 2.37-2.49 (2H, m, H-20, 17), 2.22 (1H, dd, J=13.9 Hz, J=7.8 Hz, H-15<'>), 2.15-2.21 (1H, m, H-4), 2.03 (3H, s, H-16b), 1.98-2.07 (2H, m, H-8, 11<'>), 1.97 (3H, s, H-26b), 1.94-1.98 (1H, m, H-5), 1.60-1.74 (3H, m, H-6<'>, 12<">, 12<'>), 1.50-1.59 (1H, m, H-11<">), 1.41-1.49 (1H, m, H-7<'>), 1.38 (1H, dd, J=13.6 Hz, J=4.4 Hz, H-15<">), 1.24 (1H, d, J=4.6 Hz, H-19<'>), 1.17-1.23 (1H, m, H-7<">), 1.17 (3H, s, H-18), 1.09 (3H, d, J=7.0 Hz, H-27), 1.03 (3H, d, J=7.0 Hz, H-28), 0.96 (3H, s, H-29), 0.94 (1H, qd, J=12.8 Hz, J=4.0 Hz, H-6<">), 0.64 (3H, d, J=6.1 Hz, H-21), 0.57 (1H, d, J=4.3 Hz, H-19<">)

$^{13}$C NMR (126 MHz, CD$_3$CN) δ=205.0 (C-23), 202.4 (C-3), 171.6 (C-26a), 171.3 (C-16a), 155.6 (C-1), 148.0 (C-24), 128.4 (C-2), 127.4 (C-24a), 77.3 (C-16), 75.8 (C-22), 68.0 (C-26), 51.4 (C-17), 48.3 (C-14), 47.6 (C-4), 46.9 (C-15), 46.7 (C-13), 45.3 (C-8), 43.6 (C-5), 36.4 (C-20), 34.7 (C-25), 33.1 (C-12), 32.9 (C-10), 28.1 (C-11), 27.7 (C-19), 27.2 (C-9), 24.3 (C-6), 24.3 (C-7), 22.1 (C-16b), 21.1 (C-26b), 20.1 (C-29), 18.5 (C-18), 17.3 (C-27), 12.3 (C-21), 11.3 (C-28)

Example 18

26-acetyl-neoboutomellerone

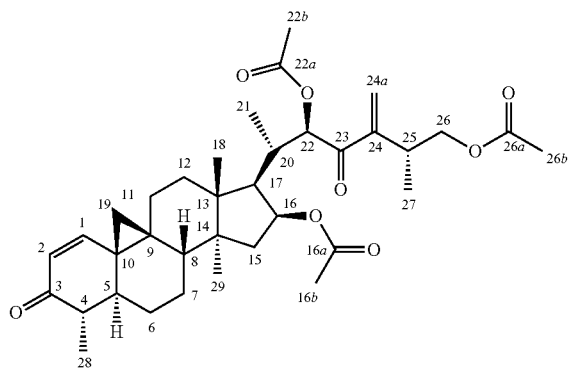

Chemical formula: C$_{36}$H$_{50}$O$_8$
Exact mass: 610.35
Molecular weight: 610.78

Protocol: 50 mg (0.088 mmol) of 2 is dissolved in 4 ml of DCM. The reaction is cooled to 0° C., then 300 μl (3.7 mmol) of pyridine is added, followed by 10 eq (0.88 mmol, 60 μl) of acetyl chloride. The reaction is left under stirring overnight. Excess acetyl chloride is neutralized with methanol, and the solvents are evaporated. The crude reaction product is purified on a silica gel column and eluted with a 70/30 cyclohexane/ethyl acetate mixture, which leads to 40.52 mg (75%) of compound 18 (Rf: 0.68; 50/50 cyclohexane/ethyl acetate).

$^1$H NMR (500 MHz, CD$_3$CN) δ=6.94 (1H, d, J=10.1 Hz, H-1), 6.10 (1H, s, H-24a'), 5.96 (1H, d, J=0.6 Hz, H-24a"), 5.90 (1H, d, J=10.1 Hz, H-2), 5.52 (1H, d, J=2.1 Hz, H-22), 5.09 (1H, td, J=7.6 Hz, J=4.6 Hz, H-16), 3.96-4.09 (2H, m, H-26', 26"), 3.00 (1H, sxt, J=6.9 Hz, H-25), 2.53-2.63 (1H, dqd, J=11.0 Hz, J=7.0 Hz, J=2.1 Hz, H-20), 2.30 (1H, dd, J=11.0 Hz, J=7.6 Hz, H-17), 2.14-2.24 (2H, m, H-15', 4), 2.09 (3H, s, H-22b), 2.03 (3H, s, H-16b), 1.99-2.06 (2H, m, H-11', 8), 1.97 (3H, s, H-26b), 1.95-1.98 (1H, m, H-5), 1.63-1.77 (3H, m, H-6', 12', 12"), 1.52-1.62 (1H, m, H-11"), 1.41-1.49 (1H, m, H-7'), 1.37 (1H, dd, J=14.5 Hz, J=4.1 Hz, H-15"), 1.24 (1H, d, J=4.6 Hz, H-19'), 1.19 (3H, s, H-18), 1.14-1.22 (1H, m, H-7"), 1.07 (3H, d, J=7.0 Hz, H-27), 1.03 (3H, d, J=6.7 Hz, H-28), 0.95 (3H, s, H-29), 0.89-0.99 (1H, m, H-6"), 0.85 (3H, d, J=7.0 Hz, H-21), 0.58 (1H, d, H-19")

$^{13}$C NMR (126 MHz, CD$_3$CN) δ=202.4 (C-3), 198.9 (C-23), 171.6 (C-22a), 171.6 (C-26a), 171.3 (C-16a), 155.5 (C-1), 149.2 (C-24), 128.4 (C-2), 125.6 (C-24a), 78.3 (C-22), 76.7 (C-16), 67.8 (C-26), 51.3 (C-17), 48.4 (C-14), 47.6 (C-4), 46.9 (C-13), 46.7 (C-15), 45.2 (C-8), 43.6 (C-5), 34.9 (C-25), 33.2 (C-20), 32.9 (C-12), 28.1 (C-11), 27.6 (C-19), 27.2 (C-9), 24.3 (C-6, 7), 22.1 (C-16b), 21.1 (C-26b), 20.9 (C-22b), 20.0 (C-29), 18.3 (C-18), 17.3 (C-27), 13.3 (C-21), 11.3 (C-28)

Example 19

26-methoxy-neoboutomellerone

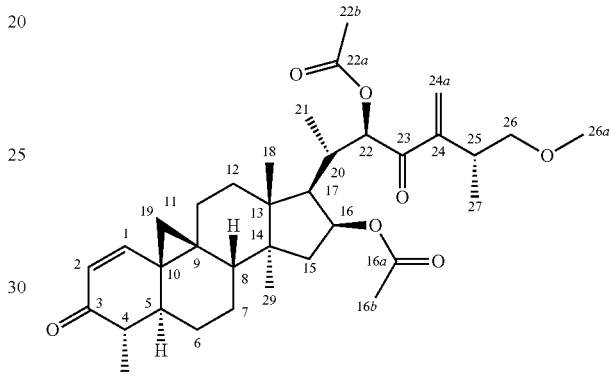

Chemical formula: C$_{35}$H$_{50}$O$_7$
Exact mass: 582.36
Molecular weight: 582.77

Protocol: 51 mg (0.089 mmol) of 2 is dissolved in 1 ml of DCM. At 0° C., 70 μl (3.5 eq, 0.31 mmol) of 2-6-(di-tert-butyl)-pyridine and then 69 mg (3 eq, 0.27 mmol) of silver triflate are added and the reaction medium is protected from light. Finally, 94 μl (6 eq, 0.54 mmol) of iodomethane is added. After 23 h, the reaction medium is filtered on Celite® and the filtrate is washed successively with a 4% hydrochloric acid solution, a solution of sodium bicarbonate and brine. After drying on sodium sulfate and evaporation of the solvents, 240 mg of crude reaction product is collected. The product is purified on a silica gel column and is eluted with a 100/0 to 0/100 cyclohexane/ethyl acetate gradient. Product 19 (Rf: 0.73; 60/40 cyclohexane/ethyl acetate) is finally obtained with a 77% yield (40.5 mg).

$^1$H NMR (500 MHz, CD$_3$CN) δ=6.94 (1H, d, J=10.1 Hz, H-1), 6.01 (1H, s, H-24a'), 5.90 (1H, d, J=10.1 Hz, H-2), 5.87 (1H, d, J=0.9 Hz, H-24a"), 5.51 (1H, d, J=2.1 Hz, H-22), 5.09 (1H, td, J=7.7 Hz, J=4.4 Hz, H-16), 3.40 (1H, dd, J=9.3 Hz, J=6.9 Hz, H-26'), 3.25 (3H, s, H-26a), 3.26 (1H, dd, J=9.3 Hz, J=6.6 Hz, H-26"), 2.90 (1H, sxt, J=7.0 Hz, H-25), 2.53-2.64 (1H, dqd, J=11.0 Hz, J=7.0 Hz, J=2.1 Hz, H-20), 2.28 (1H, dd, J=11.1 Hz, J=7.5 Hz, H-17), 2.15-2.22 (2H, m, H-15', 4), 2.09 (3H, s, H-22b), 1.98-2.05 (2H, m, H-11', 8), 2.02 (3H, s, H-16b), 1.94-1.98 (1H, m, H-5), 1.62-1.76 (3H, m, H-6', 12', 12"), 1.52-1.62 (1H, m, H-11"), 1.41-1.49 (1H, m, H-7'), 1.36 (1H, dd, J=13.9 Hz, J=3.5 Hz, H-15"), 1.24 (1H, d, J=4.6 Hz, H-19'), 1.15-1.22 (1H, m, H-7"), 1.18 (3H, s, H-18), 1.04 (3H, d, J=7.0 Hz, H-28), 1.02 (3H, d, J=6.4 Hz, H-27), 0.95 (3H, s, H-29), 0.94 (1H, qd, J=12.5 Hz, J=3.7 Hz, H-6"), 0.85 (3H, d, J=6.7 Hz, H-21), 0.58 (1H, d, J=4.3 Hz, H-19")

$^{13}$C NMR (126 MHz, CD$_3$CN) δ=202.4 (C-3), 199.3 (C-23), 171.7 (C-22a), 171.3 (C-16a), 155.5 (C-1), 150.3 (C-24), 128.4 (C-2), 124.7 (C-24a), 78.4 (C-22), 76.6 (C-26), 76.6 (C-16), 58.8 (C-26a), 51.3 (C-17), 48.4 (C-14), 47.6 (C-4), 46.8 (C-13), 46.7 (C-15), 45.2 (C-8), 43.6 (C-5), 36.1 (C-25), 33.0 (C-20), 32.9 (C-12), 28.1 (C-11), 27.6 (C-19), 27.2 (C-9), 24.3 (C-7, 6), 22.1 (C-16b), 20.9 (C-22b), 20.0 (C-29), 18.2 (C-18), 17.7 (C-27), 13.2 (C-21), 11.3 (C-28)

Example 20

26-N-phenylcarbamate-neoboutomellerone

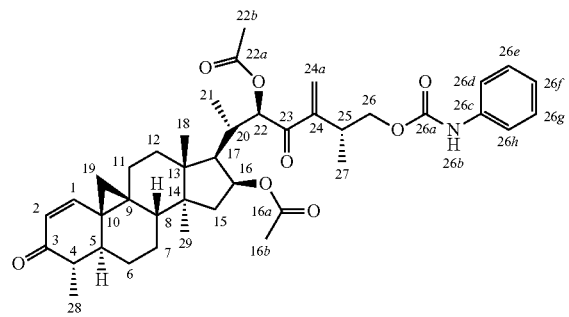

Chemical formula: C$_{41}$H$_{53}$O$_8$
Exact mass: 687.38
Molecular weight: 687.86

Protocol: 53 mg (0.093 mmol) of 2 is solubilized in 1 ml of dichloromethane under nitrogen. 6 mg (0.047 mmol, 0.5 eq) of DMAP, 11 μl (0.102 mmol, 1.1 eq) of phenyl isocyanate and 11 μl (0.102 mmol, 1.1 eq) of triethylamine are added and the reaction medium is stirred at room temperature. After 22 h, the reaction medium is diluted in ethyl acetate and the organic phase is washed successively with a 4% HCl solution, a saturated sodium bicarbonate solution and a saturated sodium chloride solution. The organic phase is dried on MgSO$_4$, filtered and concentrated in a rotary evaporator. The product is purified by silica chromatography (eluent: cyclohexane/AcOEt: 10/0 to 0/10). A white solid is obtained with a yield of 47% (30 mg).

$^1$H NMR (500 MHz, CD$_3$CN) δ=7.68 (1H, br. s., H-26b), 7.41 (2H, d, J=7.9 Hz, H-26d, 26h), 7.29 (2H, t, J=8.5 Hz, H-26g, 26e), 7.03 (1H, tt, J=7.3 Hz, J=1.2 Hz, H-26H), 6.94 (1H, d, J=10.1 Hz, H-1), 6.15 (1H, s, H-24a'), 6.02 (1H, d, J=0.6 Hz, H-24a"), 5.90 (1H, d, J=9.8 Hz, H-2), 5.54 (1H, d, J=2.1 Hz, H-22), 5.09°(1H, td, J=7.7 Hz, J=4.4 Hz, H-16), 4.13 (1H, dd, J=10.7 Hz, J=7.0 Hz, H-26'), 4.06 (1H, dd, J=10.7 Hz, J=6.4 Hz, H-26"), 3.07 (1H, sxt, J=7.0 Hz, H-25), 2.54-2.66 (1H, dqd, J=10.9 Hz, J=7.0 Hz, J=2.3 Hz, H-20), 2.30 (1H, dd, J=11.0 Hz, J=7.3 Hz, H-17), 2.15-2.22 (2H, m, H-15', 4), 2.10 (3H, s, H-22b), 2.03 (3H, s, H-16b), 1.98-2.06 (2H, m, H-8,11'), 1.94-1.98 (1H, m, H-5), 1.61-1.76 (3H, m, H-6', 12', 12"), 1.50-1.61 (1H, m, H-11"), 1.44 (1H, s, H-7'), 1.37 (1H, dd, J=13.9 Hz, J=4.1 Hz, H-15"), 1.24 (1H, d, J=4.6 Hz, H-19'), 1.18 (3H, s, H-18), 1.14-1.22 (1H, m, H-7"), 1.11 (3H, d, J=7.0 Hz, H-27), 1.02 (3H, d, J=6.7 Hz, H-28), 0.95 (3H, s, H-29), 0.88-1.00 (1H, m, H-6"), 0.85 (3H, d, J=7.0 Hz, H-21), 0.57 (1H, d, J=4.6 Hz, H-19")

$^{13}$C NMR (126 MHz, CD$_3$CN) δ=202.4 (C-3), 198.8 (C-23), 171.8 (C-22a), 171.3 (C-16), 155.5 (C-1), 149.2 (C-24), 139.9 (C-26c), 129.9 (C-26e, 26g), 128.4 (C-2), 125.7 (C-24a), 123.9 (C-26f), 119.5 (C-26d, 26h), 78.5 (C-22), 76.7 (C-16), 68.5 (C-26), 51.3 (C-17), 48.3 (C-14), 47.6 (C-4), 46.8 (C-13), 46.7 (C-15), 45.2 (C-8), 43.6 (C-5), 35.0 (C-25), 33.4 (C-20), 32.9 (C-12), 28.1 (C-11), 27.6 (C-19), 27.2 (C-9), 24.3 (C-6, 7), 22.1 (C-16b), 21.0 (C-22b), 20.0 (C-29), 18.3 (C-18), 17.1 (C-27), 13.4 (C-21), 11.3 (C-28)

Examples 21 & 22

26-N—(N-methylpiperazine)carbamate-neoboutomellerone (21) and 26-N—(N-methylpiperazine) carbamate-neoboutomellerone hydrochloride (22)

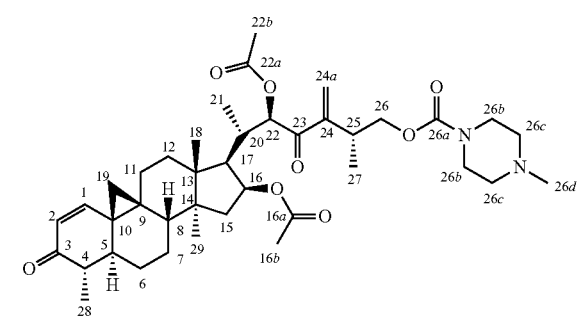

Chemical formula: C$_{40}$H$_{58}$N$_2$O$_8$
Exact mass: 694.42
Molecular weight: 694.90

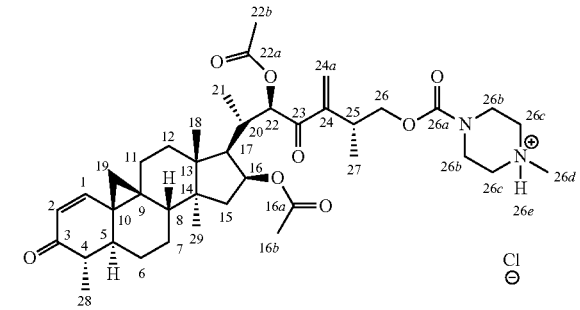

Chemical formula: C$_{40}$H$_{59}$ClN$_2$O$_8$
Exact mass: 730.40
Molecular weight: 731.36

Protocol: 200 mg of 2 (0.380 mmol) is solubilized in 1 ml of anhydrous acetonitrile. 210 mg (1.520 mmol, 4 eq) of potassium carbonate, 151 mg (0.760 mmol, 2 eq) of 4-methylpiperazine carbonyl chloride hydrochloride and 12 mg (0.035 mmol, 0.1 eq) of tetrabutylammonium bromide are added. The reaction medium is stirred for 28 hours at room temperature. The reaction medium is filtered and concentrated in a rotary evaporator. The residue is purified by silica gel chromatography (eluent: DCM/MeOH gradient: 98/2 to 95/5). Two products are isolated: the expected carbamate 21 (70 mg, 29%) and product 17 (65 mg) with a yield of 33%. 3 ml of 0.1 M HCl is added to 44 mg of carbamate 21 and the reaction medium is stirred at room temperature for 1 hour. The reaction medium is then freeze-dried in order to obtain 43 mg of hydrochloride 22 (93%).

Example 21

$^1$H NMR (500 MHz, ACETONITRILE-d$_3$) δ=6.94 (1H, d, J=9.8 Hz, H-1), 6.11 (1H, s, H-24aa), 5.96 (1H, s, H-24ab), 5.90 (1H, d, J=9.8 Hz, H-2), 5.53 (1H, d, J=2.4 Hz, H-22), 5.08 (1H, td, J=7.6 Hz, J=4.6 Hz, H-16), 4.02-4.09 (1H, m, H-26<'>), 3.99 (1H, dd, J=10.6 Hz, J=6.2 Hz, H-26<">), 3.33-3.39 (4H, m, H-26b), 2.99 (1H, sxt, J=6.8 Hz, H-25), 2.54-2.61 (1H, m, H-20), 2.29 (1H, dd, J=11.0 Hz, J=7.6 Hz, H-17), 2.21-2.28 (4H, m, H-26c,), 2.20 (3H, s, H-26d), 2.14-2.19 (2H, m, H-15<'>, 4), 2.09 (3H, s, H-22b), 2.03 (3H, s, H-16b), 1.95-2.01 (3H, m, H-11<'>, 8a, 5a), 1.64-1.75 (3H, m, H-6<'>, 12), 1.52-1.60 (1H, m, H-11<">), 1.41-1.48 (1H, m, H-7<">), 1.33-1.40 (1H, m, H-15<">), 1.22-1.26 (1H, m, H-19<">), 1.19-1.22 (1H, m, H-7<'>), 1.18 (3H, s, H-18), 1.08 (2H, d, J=7.3 Hz, H-27), 1.02 (2H, d, J=6.7 Hz, H-28), 0.95 (3H, s, H-29), 0.87-0.93 (1H, m, H-6<">), 0.84 (3H, d, J=7.0 Hz, H-21), 0.58 (1H, d, J=4.3 Hz, H-19<'>)

$^{13}$C NMR (126 MHz, ACETONITRILE-d$_3$) δ=202.4 (C-3), 198.8 (C-23), 171.6 (C-22a), 171.2 (C-16a), 155.9 (C-26a), 155.5 (C-1), 149.3 (C-24), 128.4 (C-2), 125.7 (C-24a), 78.3 (C-22), 76.7 (C-16), 68.7 (C-26), 55.5 (C-26c), 51.3 (C-17), 48.4 (C-14), 47.6 (C-4), 46.8 (C-13), 46.7 (C-15), 46.4 (C-8), 45.2 (C-26d), 44.6 (C-26b), 43.6 (C-5), 35.4 (C-25), 33.3 (C-20), 33.0 (C-12), 32.9 (C-10), 28.1 (C-11), 27.6 (C-19), 27.2 (C-9), 24.3 (C-6, 7), 22.1 (C-16b), 20.9 (C-22b), 20.0 (C-29), 18.3 (C-18), 17.2 (C-27), 13.3 (C-21), 11.3 (C-28)

Example 22

$^1$H NMR (500 MHz, DMSO-d$_6$) δ=9.97 (1H, br. s, H-26e), 6.97 (1H, d, J=10.1 Hz, H-1), 6.11 (2H, d, J=10.8 Hz, H-24ab, 24aa), 5.90 (1H, d, J=10.0 Hz, H-2), 5.43-5.49 (1H, m, H-22), 5.03 (1H, td, J=7.5 Hz, J=4.2 Hz, H-16), 3.91-4.09 (4H, m, H-26, 26b), 3.36-3.44 (1H, m, H-26c), 3.13 (2H, br. s., H-26b), 2.90-3.02 (3H, m, H-25, 26c), 2.77 (3H, br. s., H-26d), 2.46-2.48 (1H, m, H-20), 2.22 (1H, dd, J=11.0 Hz, J=7.5 Hz, H-17), 2.12-2.16 (1H, m, H-4, 15<'>), 2.11 (5H, s, H-22b), 2.06 (3H, s, H-16b), 1.94-2.02 (3H, m, H-11<'>, 8a), 1.89 (1H, td, J=12.5 Hz, J=4.2 Hz, H-5a), 1.50-1.66 (5H, m, H-12, 6<">, 11<">), 1.35-1.44 (1H, m, H-7<'>), 1.30 (1H, dd, J=13.9 Hz, J=3.7 Hz, H-15<">), 1.24 (1H, d, J=4.0 Hz, H-19<'>), 1.14-1.18 (1H, m, H-7<">), 1.13 (3H, s, H-18), 1.04 (3H, d, J=7.0 Hz, H-27), 0.98 (3H, d, J=6.7 Hz, H-28), 0.92-0.94 (1H, m, H-6<">), 0.90 (3H, s, H-29), 0.79 (3H, d, J=7.0 Hz, H-21), 0.58 (1H, d, J=4.2 Hz, H-19<">)

$^{13}$C NMR (126 MHz, DMSO-d$_6$) δ=200.6 (C-3), 197.1 (C-23), 170.2 (C-22a), 169.8 (C-16a), 154.7 (C-26a), 154.0 (C-1), 147.5 (C-24), 127.3 (C-2), 125.1 (C-24a), 76.6 (C-22), 75.1 (C-16), 68.3 (C-26), 52.0 (C-26c), 49.7 (C-17), 47.0 (C-14), 46.1 (C-4), 45.4 (C-13), 45.3 (C-15), 43.3 (C-8), 42.4 (C-26b), 42.0 (C-26d, 5), 33.1 (C-25), 31.9 (C-20), 31.7 (C-10), 31.6 (C-12), 26.6 (C-9), 26.3 (C-11), 25.9 (C-19), 22.9 (C-6), 22.8 (C-7), 21.4 (C-16b), 20.4 (C-22b), 19.1 (C-29), 17.5 (C-18), 16.6 (C-27), 12.4 (C-21), 10.7 (C-28)

Examples 23 & 24

26-N—(N-methylpiperazine)carbamate-22-deacetyl-neoboutomellerone (23) and 26-N—(N-methylpiperazine)carbamate-22-deacetyl-neoboutomellerone hydrochloride (24)

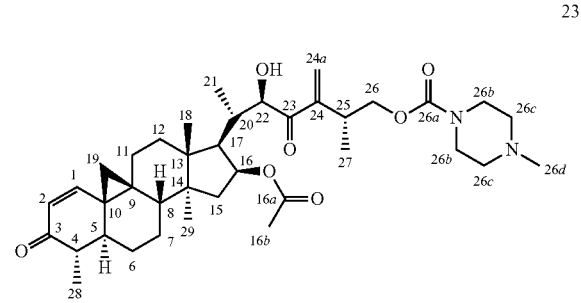

23

Chemical formula: C$_{38}$H$_{56}$N$_2$O$_7$
Exact mass: 652.41
Molecular weight: 652.86

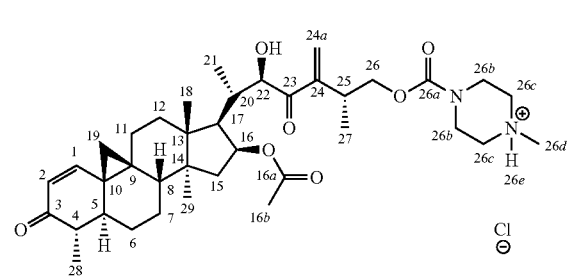

24

Chemical formula: C$_{38}$H$_{57}$ClN$_2$O$_7$
Exact mass: 688.39
Molecular weight: 689.32

Protocol: 200 mg of 1 (0.38 mmol) is solubilized in anhydrous acetonitrile. 194 mg (1.408 mmol, 4 eq) of potassium carbonate, 140 mg (0.704 mmol, 2 eq) of 4-methylpiperazine carbonyl chloride hydrochloride and 11 mg (0.035 mmol, 0.1 eq) of tetrabutylammonium bromide are added. The reaction medium is stirred for 90 hours at room temperature. The reaction medium is filtered and concentrated in a rotary evaporator. The residue is purified by silica gel chromatography (eluent: DCM/MeOH: 95/5). Two products are isolated: the carbamate 23 (87 mg, 35%), obtained in the form of a white solid and the starting product 1 (96 mg, 48%). 3 ml of 0.1 M HCl is added to 69 mg of carbamate 23 and the reaction medium is stirred at room temperature for 1 hour. The reaction medium is then freeze-dried in order to obtain 66 mg of hydrochloride 24 (90%).

Example 23

$^1$H NMR (500 MHz, ACETONITRILE-d$_3$) δ=6.94 (1H, d, J=9.8 Hz, H-1), 6.18 (1H, s, H-24aa), 6.04 (1H, d, J=0.6 Hz, H-24ab), 5.89 (1H, d, J=10.1 Hz, H-2), 5.20 (1H, td, J=7.5 Hz, J=4.6 Hz, H-16), 4.72 (1H, br. s., H-22), 4.05 (2H, d, J=6.4 Hz, H-26), 3.54 (1H, d, J=5.2 Hz, H-30), 3.32-3.40 (4H, m, H-26b), 3.00-3.10 (1H, m, H-25), 2.39-2.49 (2H, m, H-20,

17), 2.23-2.28 (4H, m, H-26c), 2.20-2.23 (1H, m, H-15<'>), 2.20 (3H, s, H-26d), 2.16-2.19 (1H, m, H-4), 2.03 (3H, s, H-16b), 1.96-2.02 (3H, m, H-11<'>, 8a, 5a), 1.58-1.74 (3H, m, H-6<''>, 12), 1.51-1.58 (1H, m, H-11<''>), 1.42-1.49 (1H, m, H-7<''>), 1.32-1.41 (1H, m, H-15<''>), 1.23 (1H, d, J=4.3 Hz, H-19<''>), 1.18-1.22 (1H, m, H-7<'>), 1.17 (3H, s, H-18), 1.10 (3H, d, J=7.3 Hz, H-27), 1.03 (3H, d, J=6.7 Hz, H-28), 0.96 (3H, s, H-29), 0.88-0.95 (1H, m, H-6<'>), 0.64 (3H, d, J=6.1 Hz, H-21), 0.57 (1H, d, J=4.6 Hz, H-19<'>)

40.5 (C-26b), 34.4 (C-20), 33.2 (C-25), 31.8 (C-10, 12), 31.6, 26.7 (C-11), 26.3 (C-9), 26.0 (C-19), 22.9 (C-6), 22.8 (C-7), 21.5 (C-16b), 19.2 (C-29), 17.7 (C-18), 16.6 (C-27), 11.8 (C-21), 10.8 (C-28)

Example 25

26-N-(4-N,N-dimethylaniline)carbamate-neoboutomellerone

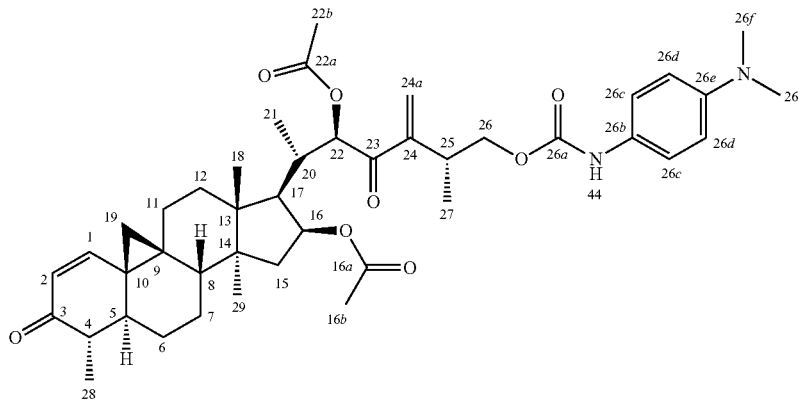

Chemical formula: $C_{43}H_{58}N_2O_8$
Exact mass: 730.42
Molecular weight: 730.93

$^{13}$C NMR (126 MHz, ACETONITRILE-$d_3$) δ=204.9 (C-23), 202.4 (C-3), 171.2 (C-16a), 156.0 (C-26a), 155.6 (C-1), 148.1 (C-24), 128.4 (C-2), 127.5 (C-24a), 77.3 (C-16), 75.8 (C-22), 68.8 (C-26), 55.5 (C-26c), 51.4 (C-17), 48.3 (C-14), 47.6 (C-4), 46.9 (C-15), 46.7 (C-13), 46.4 (C-26d), 45.3 (C-8), 44.6 (C-26b), 43.6 (C-5), 36.4 (C-20), 35.3 (C-25), 33.1 (C-12), 32.9 (C-10), 28.1 (C-11), 27.7 (C-19), 27.2 (C-9), 24.3 (C-6), 24.3 (C-7), 22.1 (C-16b), 20.1 (C-29), 18.6 (C-18), 17.2 (C-27), 13.8, 12.3 (C-21), 11.3 (C-28)

Example 24

$^1$H NMR (500 MHz, DMSO-$d_6$) δ=10.30 (1H, br. s., H-26e), 6.97 (1H, d, J=10.1 Hz, H-1), 6.10 (1H, s, H-24aa), 6.03 (1H, s, H-24ab), 5.90 (1H, d, J=10.1 Hz, H-2), 5.15 (1H, dd, J=7.4 Hz, J=4.5 Hz, H-16), 4.79 (1H, d, J=6.1 Hz, H-30), 4.60 (1H, d, J=3.7 Hz, H-22), 3.96-4.08 (4H, m, H-26, 26b), 3.34-3.42 (2H, m, H-26c), 3.09-3.21 (2H, m, H-26b), 2.89-3.03 (3H, m, H-25, 26c), 2.76 (3H, br. s., H-26d), 2.29-2.39 (2H, m, H-20, 17), 2.07-2.16 (2H, m, H-4, 15<'>), 2.02 (3H, s, H-16b), 1.93-2.00 (2H, m, H-11<'>, 8a), 1.90 (1H, td, J=12.5 Hz, J=4.4 Hz, H-5a), 1.50-1.64 (4H, m, H-12, 6<'>, 11<''>), 1.37-1.44 (1H, m, H-7<'>), 1.27-1.34 (1H, m, H-15<'>), 1.24 (1H, d, J=4.3 Hz, H-19<'>), 1.13-1.19 (1H, m, H-7<''>), 1.11 (3H, s, H-18), 1.05 (3H, d, J=7.0 Hz, H-27), 0.98 (3H, d, J=6.7 Hz, H-28), 0.93 (2H, t, J=7.3 Hz, H-6<'>), 0.90 (3H, s, H-29), 0.64 (3H, d, J=6.4 Hz, H-21), 0.55-0.59 (1H, m, H-19<'>)

$^{13}$C NMR (126 MHz, DMSO-$d_6$) δ=203.5 (C-23), 200.7 (C-3), 170.0 (C-16a), 154.8 (C-26a), 154.0 (C-1), 147.4 (C-24), 127.3 (C-2), 125.0 (C-24a), 75.3 (C-16), 74.2 (C-22), 68.5 (C-26), 51.9 (C-26c), 49.6 (C-17), 47.0 (C-14), 46.2 (C-4), 45.4 (C-15), 45.2 (C-13), 43.3 (C-8), 42.0 (C-26d, 5),

Protocol: 100 mg (0.176 mmol) of 2 are solubilized in 1 ml anhydrous dichloromethane under nitrogen. 11 mg (0.080 mmol, 0.5 eq) of DMAP, 43 mg (0.264 mmol, 1.5 eq) of dimethylaminophenyl isocyanate and 40 μl (0.264 mmol, 1.5 eq) of triethylamine are added and the reaction medium is stirred at room temperature. After 24 h, 1 equivalent (m=29 mg) of dimethylaminophenyl isocyanate is added and the reaction medium is stirred at room temperature for 18 hours. The reaction medium is diluted in ethyl acetate and the organic phase is washed successively with a 4% HCl solution, a saturated sodium bicarbonate solution and a saturated sodium chloride solution. The organic phase is dried on MgSO$_4$, filtered and concentrated in a rotary evaporator. The product is purified by silica chromatography (eluent: cyclohexane/AcOEt: 6/4). A white solid 25 is obtained with a yield of 79% (101 mg).

$^1$H NMR (500 MHz, ACETONITRILE-$d_3$) δ=7.32 (1H, br. s., H-44), 7.20 (2H, d, J=8.2 Hz, H-26c), 6.94 (1H, d, J=9.8 Hz, H-1), 6.71 (2H, d, J=9.1 Hz, H-26d), 6.13 (1H, s, H-24aa), 5.99 (1H, s, H-24ab), 5.90 (1H, d, J=10.1 Hz, H-2), 5.55 (1H, d, J=2.1 Hz, H-22), 5.10 (1H, td, J=7.6 Hz, J=4.3 Hz, H-16), 4.11 (1H, dd, J=10.6 Hz, J=7.1 Hz, H-26<'>), 4.03 (1H, dd, J=10.6 Hz, J=6.3 Hz, H-26<''>), 3.05 (1H, sxt, J=6.9 Hz, H-25), 2.86 (6H, s, H-26f), 2.56-2.65 (1H, m, H-20), 2.30 (1H, dd, J=11.0 Hz, J=7.6 Hz, H-17), 2.14-2.22 (2H, m, H-4, 15<'>), 2.10 (3H, s, H-22b), 2.03 (3H, s, H-16b), 1.96-2.01 (3H, m, H-11<'>, 8a, 5a), 1.62-1.76 (3H, m, H-6<'>, 12), 1.56 (1H, qd, J=8.7 Hz, J=6.3 Hz, H-11<''>), 1.41-1.49 (1H, m, H-7<'>), 1.37 (1H, dd, J=13.9 Hz, J=3.8 Hz, H-15<''>), 1.24 (1H, d, J=4.3 Hz, H-19<'>), 1.20-1.23 (1H, m, H-7<''>), 1.18 (3H, s, H-18), 1.10 (3H, d, J=7.0 Hz, H-27), 1.03 (3H, d, J=7.0 Hz, H-28), 0.96 (3H, s, H-29), 0.88-0.94 (1H, m, H-6<''>), 0.86 (3H, d, J=6.7 Hz, H-21), 0.57 (1H, d, J=4.3 Hz, H-19<'>)

$^{13}C$ NMR (126 MHz, ACETONITRILE-$d_3$) δ=202.4 (C-3), 198.9 (C-23), 171.8 (C-22a), 171.3 (C-16a), 155.5 (C-1), 155.1 (C-26a), 149.4 (C-24), 148.8 (C-26e), 129.4 (C-26b), 128.5 (C-2), 125.5 (C-24a), 121.8 (C-26c, 26c), 114.2 (C-26d, 26d), 78.5 (C-22), 76.7 (C-16), 68.3 (C-26), 51.4 (C-17), 48.4 (C-14), 47.7 (C-4), 46.9 (C-13), 46.8 (C-15), 45.2 (C-8), 43.6 (C-5), 41.3 (C-26f, 26f), 35.3 (C-25), 33.4 (C-20), 33.0 (C-12), 33.0 (C-10), 28.1 (C-11), 27.7 (C-19), 27.3 (C-9), 24.3 (C-7, 6), 22.1 (C-16b), 21.0 (C-22b), 20.0 (C-29), 18.3 (C-18), 17.2 (C-27), 13.4 (C-21), 11.3 (C-28)

Example 26

26-N-(4-N,N-dimethylaniline)carbamate-22-deacetyl-neoboutomellerone

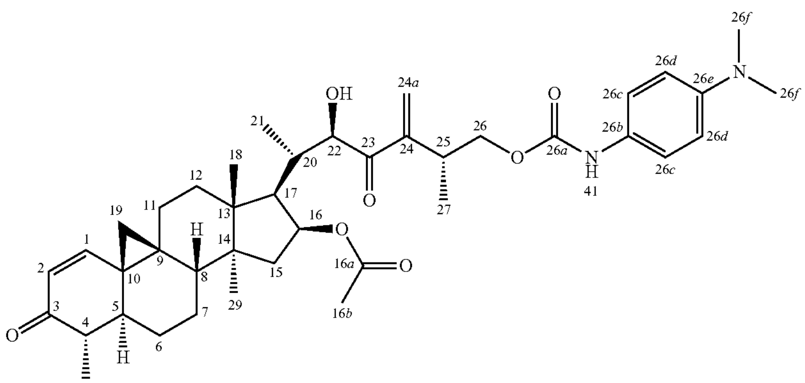

Chemical formula: $C_{41}H_{56}N_2O_7$
Exact mass: 688.41
Molecular weight: 688.89

Protocol: 100 mg (0.19 mmol) of 2 is solubilized in 1 ml of anhydrous dichloromethane under nitrogen. 12 mg (0.095 mmol, 0.5 eq) of DMAP, 76 mg (0.475 mmol, 2.5 eq) of dimethylaminophenyl isocyanate and 40 μl (0.285 mmol, 1.5 eq) of triethylamine are added and the reaction medium is stirred at room temperature. After 22 h, the reaction medium is diluted in ethyl acetate and the organic phase is washed successively with a 4% HCl solution, a saturated sodium bicarbonate solution and a saturated sodium chloride solution. The organic phase is dried on $MgSO_4$, filtered and concentrated in a rotary evaporator. The product is purified by silica chromatography (eluent: cyclohexane/AcOEt: 7/3). A white solid 26 is obtained with a yield of 60% (79 mg).

$^1H$ NMR (500 MHz, ACETONITRILE-$d_3$) δ=7.32 (1H, br. s, H-41a), 7.19 (2H, br. s., H-26c), 6.93 (1H, d, J=10.1 Hz, H-1), 6.71 (2H, d, J=8.9 Hz, H-26d), 6.19 (1H, s, H-24aa), 6.09 (1H, d, J=16.2 Hz, H-24ab), 5.89 (1H, d, J=9.8 Hz, H-2), 5.21 (1H, td, J=7.5 Hz, J=4.9 Hz, H-16), 4.72 (1H, dd, J=6.1 Hz, J=1.5 Hz, H-22), 4.14 (1H, dd, J=10.7 Hz, J=6.5 Hz, H-26<'>), 4.08 (1H, dd, J=10.6 Hz, J=6.3 Hz, H-26<">), 3.53 (1H, d, J=6.2 Hz, H-30), 3.08 (1H, sxt, J=6.9 Hz, H-25), 2.86 (6H, s, H-26f), 2.40-2.51 (2H, m, H-20, 17), 2.14-2.25 (2H, m, H-4, 15<'>), 2.03-2.07 (1H, m, H-11<'>), 2.02 (3H, s, H-16b), 1.97-2.01 (2H, m, H-8a, 5a), 1.60-1.72 (3H, m, H-6<'>, 12), 1.54 (1H, qd, J=8.8 Hz, J=5.9 Hz, H-11<">), 1.42-1.48 (1H, m, H-7<'>), 1.38 (1H, dd, J=14.6 Hz, J=4.5 Hz, H-15<">), 1.24 (1H, d, J=4.6 Hz, H-19<'>), 1.19-1.21 (1H, m, H-7<">), 1.17 (3H, s, H-18), 1.13 (3H, d, J=7.0 Hz, H-27), 1.03 (3H, d, J=7.0 Hz, H-28), 0.96 (3H, s, H-29), 0.90-0.94 (1H, m, H-6<">), 0.65 (3H, d, J=6.1 Hz, H-21), 0.57 (1H, d, J=4.3 Hz, H-19<">)

$^{13}C$ NMR (126 MHz, ACETONITRILE-$d_3$) δ=205.0 (C-23), 202.4 (C-3), 171.3 (C-16a), 155.6 (C-26a, 1), 155.2, 148.8 (C-26e), 148.2 (C-24), 129.5 (C-26b), 128.4 (C-2), 127.3 (C-24a), 121.9 (C-26c, 26c), 114.2 (C-26d, 26d), 77.3 (C-22), 75.9 (C-16), 68.3 (C-26), 51.5 (C-17), 48.4 (C-14), 47.7 (C-4), 46.9 (C-15), 46.7 (C-13), 45.4 (C-8), 43.7 (C-5), 41.3 (C-26f, 26f), 36.4 (C-25), 35.2 (C-20), 33.2 (C-12), 33.0 (C-10), 28.2 (C-11), 27.8 (C-19), 27.3 (C-9), 24.4 (C-7, 6), 22.1 (C-16b), 20.2 (C-29), 18.6 (C-18), 17.3 (C-27), 12.4 (C-21), 11.3 (C-28)

Examples 27 & 28

3-anti-oxime-neoboutomellerone (27) and
3-syn-oxime-neoboutomellerone (28)

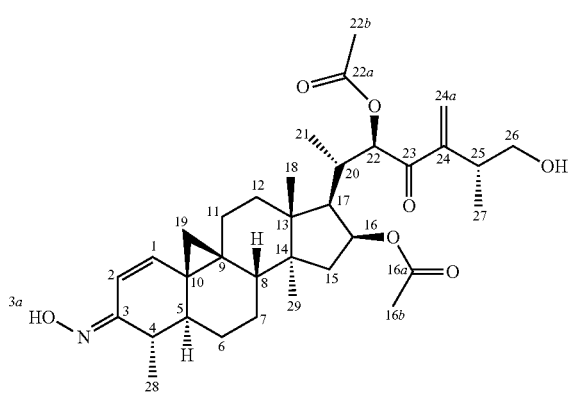

27

Chemical formula: $C_{34}H_{49}O_7$
Exact mass: 583.35
Molecular weight: 583.76

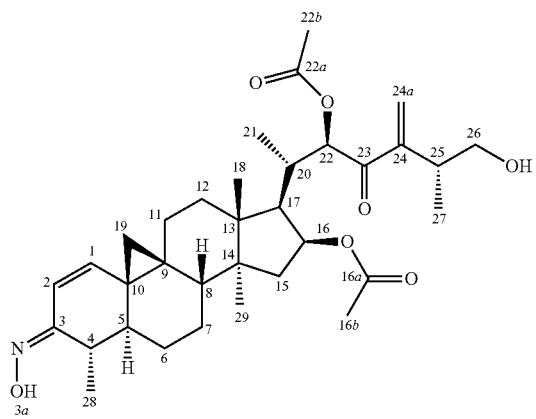

28

Chemical formula: $C_{34}H_{49}O_7$
Exact mass: 583.35
Molecular weight: 583.76

Protocol: 28.40 mg (0.05 mmol) of 2 is solubilized in 700 μl of a dioxane/methanol mixture (1/1) and 20.84 mg (0.15 mmol, 6 eq) of hydroxylamine hydrochloride in solution in 200 μl water is added. After 20 hours of stirring at room temperature, the reaction medium is diluted in dichloromethane and filtered on Celite®. After the filtrate is concentrated in a rotary evaporator, the product is purified by silica gel chromatography (eluent: DCM/MeOH: 100/0 to 98/2) in order to obtain 27 (5 mg, 2%) and 28 (2.88 mg, 1%).

Example 27

$^1$H NMR (500 MHz, CD$_3$CN) δ=8.29 (1H, s, H-3a), 6.70 (1H, d, J=10.4 Hz, H-2), 6.21 (1H, d, J=10.1 Hz, H-1), 6.04 (1H, s, H-24a'), 5.89 (1H, d, J=0.9 Hz, H-24a"), 5.53 (1H, d, J=2.1 Hz, H-22), 5.08 (1H, td, J=7.7 Hz, J=4.4 Hz, H-16), 3.53 (1H, dt, J=10.8 Hz, J=5.6 Hz, H-26'), 3.39 (1H, dt, J=10.9 Hz, J=5.7 Hz, H-26"), 2.77 (1H, sxt, J=6.7 Hz, H-25), 2.69 (1H, t, J=5.6 Hz, OH-26), 2.53-2.64 (1H, dqd, J=11.2 Hz, J=2.1 Hz, H-20), 2.28 (1H, dd, J=11.0 Hz, J=7.6 Hz, H-17), 2.24 (1H, dq, J=11.6 Hz, J=6.7 Hz, H-4), 2.15 (1H, m, H-15'), 2.09 (3H, s, H-22b), 2.02 (3H, s, H-16b), 1.96-2.04 (2H, m, H-11', 8), 1.61-1.76 (4H, m, H-6', 12', 12", 5), 1.50-1.60 (1H, m, H-11"), 1.40-1.49 (1H, m, H-7'), 1.35 (1H, dd, J=14.0 Hz, J=4.0 Hz, H-15"), 1.17 (3H, s, H-18), 1.13-1.20 (1H, m, H-7"), 1.07 (3H, d, J=6.7 Hz, H-28), 1.03 (3H, d, J=7.0 Hz, H-27), 1.00 (1H, d, J=4.6 Hz, H-19'), 0.93 (3H, s, H-29), 0.84 (3H, d, J=7.0 Hz, H-21), 0.78-0.90 (1H, m, H-6"), 0.41 (1H, d, J=4.3 Hz, H-19")

$^{13}$C NMR (126 MHz, CD$_3$CN) δ=199.6 (C-23), 171.7 (C-22a), 171.3 (C-16a), 157.7 (C-3), 150.3 (C-24), 143.3 (C-1), 124.6 (C-24a), 116.4 (C-2), 78.5 (C-22), 76.6 (C-16), 66.4 (C-26), 51.2 (C-17), 48.4 (C-14), 46.8 (C-13), 46.6 (C-15), 44.7 (C-8), 43.4 (C-5), 39.7 (C-4), 37.9 (C-25), 33.2 (C-20), 33.0 (C-12), 32.7 (C-10), 28.1 (C-11), 27.5 (C-19), 26.7 (C-9), 24.2 (C-7), 23.7 (C-6), 22.1 (C-16b), 20.9 (C-22b), 19.9 (C-29), 18.1 (C-18), 17.2 (C-27), 13.3 (C-21), 13.1 (C-28)

Example 28

$^1$H NMR (500 MHz, CD$_3$CN) δ=8.44 (1H, br. s., H-3a), 6.25 (1H, d, J=9.8 Hz, H-1), 6.11 (1H, d, J=10.1 Hz, H-2), 6.04 (1H, s, H-24a'), 5.89 (1H, d, J=0.9 Hz, H-24a"), 5.53 (1H, d, J=2.1 Hz, H-22), 5.08 (1H, td, J=7.6 Hz, J=4.3 Hz, H-16), 3.53 (1H, dt, J=10.7 Hz, J=6.0 Hz, H-26'), 3.39 (1H, dt, J=10.7 Hz, J=6.1 Hz, H-26"), 2.77 (1H, sxt, J=6.7 Hz, H-25), 2.69 (1H, t, J=5.8 Hz, OH-26), 2.54-2.65 (1H, dqd, J=11.0 Hz, J=7.0 Hz, J=2.3 Hz, H-20), 2.41 (1H, dq, J=11.0 Hz, J=6.7 Hz, H-4), 2.29 (1H, dd, H-17), 2.16-2.21 (1H, m, H-15'), 2.09 (3H, s, H-22b), 2.08-2.12 (1H, m, H-11'), 2.02 (3H, s, H-16b), 1.82-1.88 (2H, m, H-6', 8), 1.65-1.77 (2H, m, H-12', 12"), 1.61 (1H, td, J=11.4 Hz, J=4.1 Hz, H-5), 1.36 (1H, dd, J=13.6 Hz, J=4.4 Hz, H-15"), 1.33-1.41 (1H, m, H-7'), 1.29 (3H, d, J=6.4 Hz, H-28), 1.24-1.33 (1H, m, H-11"), 1.18 (3H, s, H-18), 1.14-1.21 (1H, m, H-7"), 1.03 (3H, d, J=7.0 Hz, H-27), 0.97 (3H, s, H-29), 0.82-0.84 (1H, m, H-19'), 0.84 (3H, d, J=7.0 Hz, H-21), 0.73 (1H, qd, J=13.1 Hz, J=3.1 Hz, H-6"), 0.26 (1H, d, H-19")

$^{13}$C NMR (126 MHz, CD$_3$CN) δ=199.6 (C-23), 171.7 (C-22a), 171.3 (C-16a), 160.5 (C-3), 150.3 (C-24), 140.7 (C-1), 126.3 (C-2), 124.7 (C-24a), 78.5 (C-22), 76.8 (C-16), 66.4 (C-26), 51.3 (C-17), 48.2 (C-14), 47.2 (C-15), 47.0 (C-13), 46.9 (C-8), 44.7 (C-5), 37.9 (C-25), 37.7 (C-4), 33.2 (C-20), 33.2 (C-12), 28.6 (C-19), 28.5 (C-11), 25.3 (C-7), 25.0 (C-6), 22.1 (C-16b), 20.9 (C-22b), 20.3 (C-29), 18.9 (C-18), 17.2 (C-27), 16.0 (C-28), 13.3 (C-21)

Examples 29, 30 and 31

3-anti-O-methyloxime-neoboutomellerone (29), 3-anti-O-methyloxime-24a-O-methylhydroxylamine-neoboutomellerone (30) and 24a-O-methylhydroxylamine-neoboutomellerone (31)

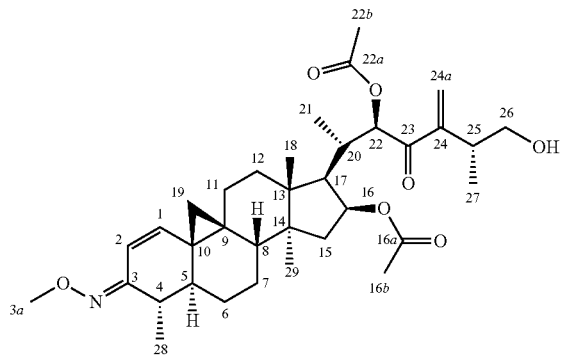

Chemical formula: $C_{35}H_{51}O_7$
Exact Mass: 597.37
Molecular weight: 597.78

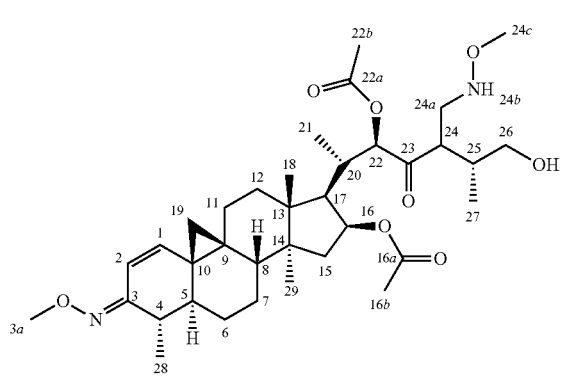

Chemical formula: $C_{36}H_{56}N_2O_8$
Exact Mass: 644.40
Molecular weight: 644.84

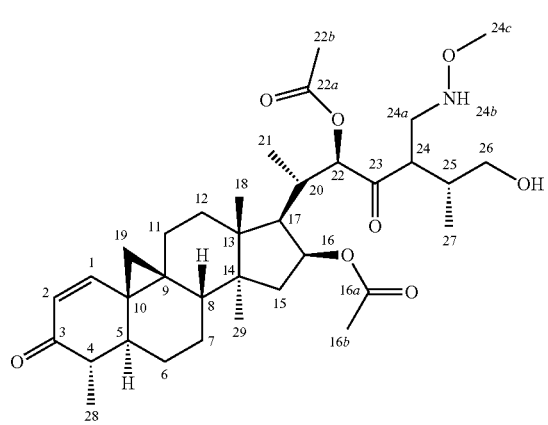

Chemical formula: $C_{35}H_{53}NO_8$
Exact Mass: 615.38
Molecular weight: 615.80

Protocol: 21.7 mg (0.26 mmol, 4 eq) of O-methylhydroxylamine hydrochloride and 38 mg (0.286 mmol, 4.4 eq) of sodium acetate are dissolved in 1.3 ml of methanol. 37 mg (0.065 mmol) of 2 is then added. After 10 hours of stirring at room temperature, the reaction medium is diluted in ethyl acetate and the organic phase is washed with distilled water. The aqueous phase is extracted three times in ethyl acetate and the combined organic phases are washed with saturated sodium chloride solution and dried on $MgSO_4$. After concentration in a rotary evaporator, the product is purified by silica gel chromatography (eluent: cyclohexane/AcOEt: 8/2 to 4/6) in order to obtain products 29 (24 mg, 62%), 30 (3.2 mg, 8%) and 31 (0.75 mg, 2%).

Example 29

$^1$H NMR (500 MHz, $CD_3CN$) δ=6.61 (1H, d, J=10.1 Hz, H-2), 6.24 (1H, d, J=10.1 Hz, H-1), 6.04 (1H, s, H-24a'), 5.89 (1H, d, J=0.9 Hz, H-24a"), 5.53 (1H, d, J=2.1 Hz, H-22), 5.08 (1H, td, J=7.6 Hz, J=4.6 Hz, H-16), 3.78 (3H, s, H-3a), 3.53 (1H, dt, J=10.7 Hz, J=6.0 Hz, H-26'), 3.39 (1H, dt, J=10.4 Hz, J=6.3 Hz, H-26"), 2.76 (1H, sxt, J=6.8 Hz, H-25), 2.68 (1H, t, J=5.8 Hz, OH-26), 2.54-2.64 (1H, m, H-20), 2.20-2.33 (2H, m, H-4, 17), 2.13-2.18 (1H, m, H-15'), 2.02 (3H, s, H-16b), 1.96-2.05 (2H, m, H-8,11'), 1.97 (3H, s, H-22b), 1.60-1.76 (4H, m, H-6', 5, 12', 12"), 1.50-1.59 (1H, m, H-11"), 1.40-1.49 (1H, m, H-7'), 1.35 (1H, dd, J=14.2 Hz, J=4.1 Hz, H-15"), 1.16-1.21 (1H, m, H-7"), 1.17 (3H, s, H-18), 1.09 (3H, d, J=6.7 Hz, H-28), 1.01 (1H, d, J=4.6 Hz, H-19'), 1.03 (3H, d, J=7.0 Hz, H-27), 0.92 (3H, s, H-29), 0.79-0.88 (1H, m, H-6"), 0.84 (3H, d, J=7.0 Hz, H-21), 0.41 (1H, d, J=4.6 Hz, H-19")

$^{13}$C NMR (126 MHz, $CD_3CN$) δ=199.6 (C-23), 171.7 (C-22a), 171.3 (C-16a), 157.4 (C-3), 150.3 (C-24), 144.4 (C-1), 124.6 (C-24a), 116.7 (C-2), 78.5 (C-22), 76.6 (C-16), 66.4 (C-26), 61.8 (C-3a), 51.2 (C-17), 48.4 (C-14), 46.8 (C-13), 46.6 (C-15), 44.7 (C-8), 43.4 (C-5), 39.7 (C-4), 37.9 (C-25), 33.2 (C-20), 33.0 (C-12), 32.7 (C-10), 28.1 (C-11), 27.5 (C-19), 26.8 (C-9), 24.2 (C-7), 23.7 (C-6), 22.1 (C-16b), 21.2 (C-22b), 19.9 (C-29), 18.0 (C-18), 17.2 (C-27), 13.3 (C-21), 13.1 (C-28)

Example 30

$^1$H NMR (500 MHz, $CD_3CN$) δ=6.61 (1H, d, J=10.4 Hz, H-2), 6.24 (1H, d, J=10.1 Hz, H-1), 6.20 (1H, br. s., H-24b), 5.09 (1H, td, J=7.6 Hz, J=4.6 Hz, H-16), 4.99 (1H, d, J=0.6 Hz, H-22), 3.78 (3H, s, H-3a), 3.46-3.53 (1H, m, H-26'), 3.39-3.46 (1H, m, H-26"), 3.37 (3H, s, H-24c), 3.25 (1H, td, J=8.1 Hz, J=4.6 Hz, H-24), 3.07-3.17 (1H, m, J=14.3 Hz, H-24a'), 2.94-3.03 (1H, m, J=9.8 Hz, H-24a"), 2.83 (1H, t, J=4.7 Hz, OH-26), 2.70-2.80 (1H, m, H-20), 2.22-2.30 (1H, m, H-4), 2.19 (1H, dd, J=11.3 Hz, J=7.6 Hz, H-17), 2.14-2.16 (1H, m, H-15'), 2.11 (3H, s, H-22b), 2.08 (3H, s, H-16b), 2.04 (1H, dd, J=9.3 Hz, J=7.2 Hz, H-8), 1.92-1.94 (1H, m, H11'), 1.82-1.89 (1H, m, H-25), 1.52-1.76 (5H, m, H-12', 12", 5, 11', 6'), 1.42-1.51 (1H, m, H-7'), 1.36 (1H, dd, J=13.6 Hz, J=4.1 Hz, H-15"), 1.19 (3H, s, H-18), 1.17-1.23 (1H, m, H-7"), 1.09 (3H, d, J=6.7 Hz, H-28), 1.02 (1H, d, J=4.0 Hz, H-19'), 0.90 (3H, s, H-29), 0.90 (3H, d, J=6.7 Hz, H-27), 0.85-0.92 (1H, m, H-6"), 0.86 (3H, d, J=6.7 Hz, H-21), 0.40 (1H, d, J=4.3 Hz, H-19")

$^{13}$C NMR (126 MHz, $CD_3CN$) δ=210.8 (C-23), 172.4 (C-22a), 171.5 (C-16a), 157.4 (C-3), 144.3 (C-1), 116.8 (C-2), 82.3 (C-22), 76.2 (C-16), 64.9, 61.8 (C-3a), 61.3 (C-24c), 52.8 (C-24a), 51.2 (C-17), 48.5 (C-14), 48.3 (C-24), 46.7 (C-13), 46.3 (C-15), 44.2 (C-19), 43.2 (C-5), 39.6 (C-4), 36.6 (C-25), 32.8 (C-10), 32.7 (C-12), 30.4 (C-20), 28.0 (C-11), 27.1 (C-19), 26.8 (C-9), 24.0 (C-7), 23.6 (C-6), 22.1 (C-16b), 21.0 (C-22b), 19.7 (C-29), 17.7 (C-18), 16.3 (C-27), 13.4 (C-21), 13.1 (C-28)

Example 31

$^1$H NMR (500 MHz, $CD_3CN$) δ=6.94 (1H, d, J=10.1 Hz, H-1), 6.20 (1H, dd, J=9.8 Hz, J=5.2 Hz, H-24b), 5.90 (1H, d, J=10.1 Hz, H-2), 5.10 (1H, td, J=7.8 Hz, J=4.6 Hz, H-16), 5.00 (1H, d, J=0.6 Hz, H-22), 3.49 (1H, dq, J=10.8 Hz, J=5.4 Hz, H-26'), 3.38-3.46 (1H, m, H-26"), 3.37 (3H, s, H-24c), 3.21-3.29 (1H, m, H-24), 3.13 (1H, ddd, J=12.9 Hz, J=8.8 Hz, J=4.3 Hz, H-24a'), 2.99 (1H, ddd, J=13.0 Hz, J=8.3 Hz, J=4.9 Hz, H-24a"), 2.84 (1H, t, J=5.3 Hz, OH-26), 2.71-2.80 (1H, m, H-20), 2.16-2.23 (3H, m, H-4, 15', 17), 2.11 (3H, s, H-22b), 2.08 (3H, s, H-16b), 2.06-2.10 (1H, m, H-8), 1.93-1.98 (2H, m, H-5,11'), 1.83-1.90 (1H, m, H-25), 1.63-1.75 (3H, m, H-6', 12', 12"), 1.55-1.63 (2H, m, H-11"), 1.41-1.50 (1H, m, H-7'), 1.37 (1H, dd, J=14.0 Hz, J=4.6 Hz, H-15"), 1.26 (1H, d, J=4.3 Hz, H-19'), 1.20 (3H, s, H-18), 1.18-1.22 (1H, m, H-7"), 1.02 (3H, d, J=6.7 Hz, H-28), 0.93 (3H, s, H-29), 0.90 (3H, d, J=7.0 Hz, H-27), 0.87 (3H, d, J=7.0 Hz, H-21), 0.56 (1H, d, J=4.6 Hz, H-19")

$^{13}$C NMR (126 MHz, $CD_3CN$) δ=210.8 (C-23), 202.4 (C-3), 172.4 (C-22a), 171.5 (C-16a), 155.5 (C-1), 128.4 (C-2), 82.3 (C-22), 76.2 (C-16), 64.9 (C-26), 61.3 (C-24c), 52.8 (C-24a), 51.3 (C-17), 48.5 (C-14), 48.3 (C-24), 47.6 (C-4), 46.7 (C-13), 46.4 (C-15), 44.7 (C-8), 43.4 (C-5), 36.7 (C-25), 33.0 (C-10), 32.7 (C-12), 30.4 (C-20), 28.0 (C-11), 27.7 (C-9), 27.3 (C-19), 24.2 (C-7), 24.1 (C-6), 22.1 (C-16b), 21.0 (C-22b), 19.8 (C-29), 17.9 (C-18), 16.3 (C-27), 13.3 (C-21), 11.3 (C-28)

Examples 32, 33 & 34

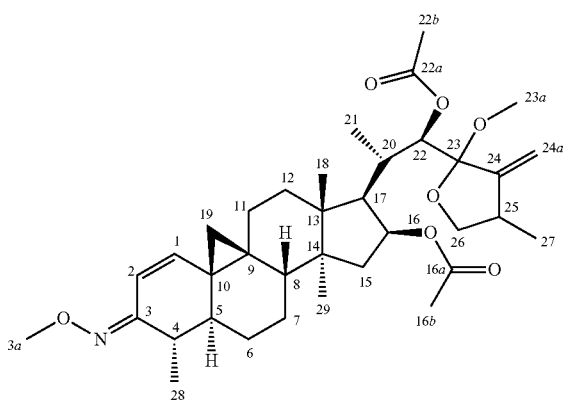

Chemical formula: $C_{36}H_{53}NO_7$
Exact Mass: 611.38
Molecular weight: 611.81

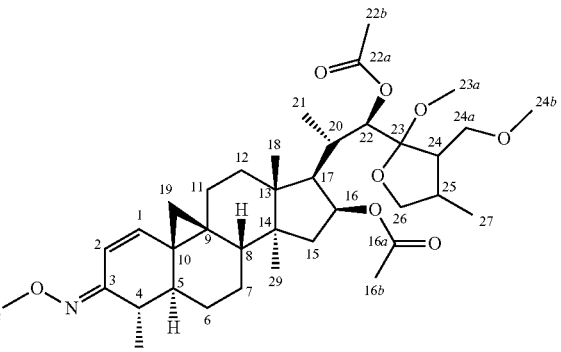

Chemical formula: $C_{37}H_{57}NO_8$
Exact Mass: 643.41
Molecular weight: 643.85

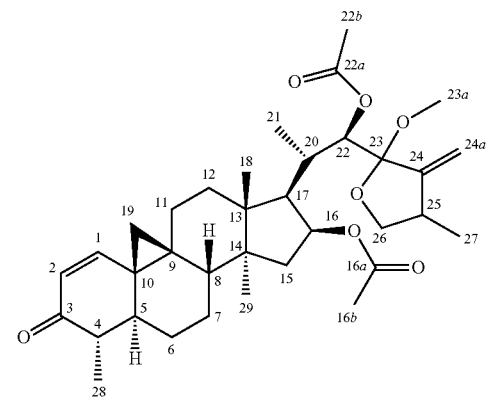

Chemical formula: $C_{35}H_{50}O_7$
Exact Mass: 582.36
Molecular weight: 582.77

Protocol: 50 mg of O-methylhydroxylamine hydrochloride is added to 114 mg of compound 2 solubilized in a MeOH and dioxane mixture (1/1, 2.8 ml). After 30 minutes of stirring at room temperature, the reaction medium is diluted in ethyl acetate and the organic phase is washed with distilled water. The aqueous phase is extracted three times with ethyl acetate and the combined organic phases are washed with a saturated sodium chloride solution and dried on $MgSO_4$. After concentration in a rotary evaporator, the crude residue is purified by silica gel chromatography (eluent: cyclohexane/AcOEt: 8/2 to 5/5) in order to obtain products 32 (13 mg, 11%), 33 (4.5 mg, 4%) and 34 (18 mg, 15%).

Example 32

$^1$H NMR (500 MHz, $CD_3CN$) δ=6.60 (1H, d, J=10.1 Hz, H-2), 6.23 (1H, d, J=10.1 Hz, H-1), 5.55 (1H, td, J=7.9 Hz, J=4.9 Hz, H-16), 5.13 (1H, d, J=3.1 Hz, H-24a'), 4.97 (1H, d, J=3.1 Hz, H-24a"), 4.91 (1H, s, H-22), 4.21 (1H, t, J=8.2 Hz, H-26'), 3.77 (3H, s, H-3a), 3.42 (1H, dd, J=9.2 Hz, J=7.9 Hz, H-26"), 3.09 (3H, s, H-23a), 2.73-2.82 (1H, m, H-25), 2.64-2.73 (1H, m, H-20), 2.23 (1H, dq, J=13.1 Hz, J=6.7 Hz, H-4), 1.97-2.05 (2H, m, H-15', 8), 1.94-1.97 (6H, m, H-16b, 22b), 1.81-1.91 (2H, m, H-11', 17), 1.65-1.74 (2H, m, H-5, H6'), 1.53-1.65 (3H, m, H-12', 12", 11), 1.42-1.50 (1H, m, H-7'), 1.31 (1H, dd, J=14.2 Hz, J=5.0 Hz, H-15"), 1.16 (3H, s, H-18), 1.13-1.18 (1H, m, H-7"), 1.10 (3H, d, J=6.7 Hz, H-21), 1.08 (3H, d, J=6.7 Hz, H-28), 1.03 (3H, d, J=6.7 Hz, H-27), 1.02 (1H, d, J=3.0 Hz, H-19'), 0.83-0.90 (1H, m, H-6"), 0.81 (3H, s, H-29), 0.38 (1H, d, J=4.6 Hz, H-19")

$^{13}$C NMR (126 MHz, CD$_3$CN) δ=171.5 (C-16a), 171.4 (C-22a), 157.4 (C-3), 154.3 (C-24), 144.4 (C-1), 116.7 (C-2), 110.5 (C-23), 109.3 (C-24a), 78.2 (C-22), 75.1 (C-16), 75.0 (C-26), 61.8 (C-3a), 52.9 (C-17), 49.8 (C-23a), 48.5 (C-14), 46.6 (C-13), 45.3 (C-15), 43.9 (C-8), 43.1 (C-5), 39.6 (C-4), 38.0 (C-25), 32.9 (C-12), 32.8 (C-10), 31.8 (C-20), 28.1 (C-11), 27.0 (C-9), 26.8 (C-19), 23.9 (C-7), 23.6 (C-6), 21.7 (C-16b), 21.3 (C-22b), 19.6 (C-29), 17.4 (C-18), 16.2 (C-27), 13.8 (C-21), 13.1 (C-28)

Example 33

$^1$H NMR (500 MHz, CD$_3$CN) δ=6.60 (1H, d, J=10.1 Hz, H-2), 6.23 (1H, d, J=10.1 Hz, H-1), 5.35 (1H, td, J=7.9 Hz, J=4.9 Hz, H-16), 4.89 (1H, s, H-22), 4.06 (1H, t, J=8.1 Hz, H-26<'>), 3.77 (3H, s, H-3a), 3.54 (1H, dd, J=9.8 Hz, J=4.6 Hz, H-24a'), 3.29-3.37 (2H, m, H-26", 24a"), 3.23 (3H, s, H-24b), 3.15 (3H, s, H-23a), 2.47-2.59 (1H, m, H-20), 2.23 (1H, dq, J=13.1 Hz, 6.4 Hz, H-4), 2.16-2.19 (1H, m, H-25), 2.06 (3H, s, H-22b), 1.99-2.08 (2H, m, H-15', 8), 1.97 (3H, s, H-16b), 1.77-1.92 (3H, m, H-11', 24, 17), 1.49-1.75 (5H, m, H-11", 6', 12", 12', 5), 1.39-1.49 (1H, m, H-7'), 1.28 (1H, dd, J=13.4 Hz, J=4.3 Hz, H-15"), 1.14-1.23 (1H, m, H-7"), 1.14 (3H, s, H-18), 1.08 (3H, d, J=6.4 Hz, H-28), 1.05 (3H, d, J=7.0 Hz, H-21), 1.02 (1H, d, J=4.6 Hz, H-19'), 1.03 (3H, d, J=6.4 Hz, H-27), 0.83 (3H, s, H-29), 0.81-0.88 (1H, m, H-6"), 0.38 (1H, d, J=4.6 Hz, H-19")

$^{13}$C NMR (126 MHz, CD$_3$CN) δ=171.8 (C-22a), 171.4 (C-16a), 157.4 (C-3), 144.4 (C-1), 116.8 (C-2), 109.6 (C-23), 75.7 (C-26), 75.6 (C-16), 75.4 (C-22), 73.2 (C-24a), 61.8 (C-3a), 59.1 (C-24b), 53.3 (C-24), 52.8 (C-17), 50.1 (C-23a), 45.7 (C-15), 43.9 (C-8), 43.1 (C-5), 39.6 (C-4), 38.6 (C-25), 33.0 (C-12), 32.7 (C-10), 31.5 (C-20), 28.1 (C-11), 26.8 (C-19), 23.9 (C-7), 23.6 (C-6), 21.8 (C-16b), 21.2 (C-22b), 19.7 (C-29), 17.6 (C-27), 17.4 (C-18), 14.0 (C-21), 13.1 (C-28)

Example 34

$^1$H NMR (500 MHz, CD$_3$CN) δ=6.93 (1H, d, J=10.1 Hz, H-1), 5.89 (1H, d, J=9.8 Hz, H-2), 5.57 (1H, td, J=7.9 Hz, J=4.9 Hz, H-16), 5.13 (1H, d, J=3.1 Hz, H-24a'), 4.97 (1H, d, J=3.4 Hz, H-24a"), 4.91 (1H, s, H-22), 4.22 (1H, t, J=8.1 Hz, H-26'), 3.42 (1H, dd, J=9.2 Hz, J=7.9 Hz, H-26"), 3.09 (3H, s, H-23a), 2.73-2.82 (1H, m, H-25), 2.65-2.74 (1H, m, H-20), 2.10-2.15 (1H, m, H-4), 1.97-2.05 (2H, m, H-15', 8), 1.93-1.97 (8H, m, H-16b, 22b, 11', 5), 1.85 (1H, dd, J=11.4 Hz, J=7.8 Hz, H-17), 1.62-1.70 (3H, m, H-6', 12', 12"), 1.53-1.62 (1H, m, H-11"), 1.40-1.50 (1H, m, H-7'), 1.32 (1H, dd, J=13.6 Hz, J=4.4 Hz, H-15"), 1.25 (1H, d, J=4.3 Hz, H-19'), 1.16-1.23 (1H, m, J=7.2 Hz, J=7.2 Hz, H-7"), 1.18 (3H, s, H-18), 1.11 (3H, d, J=6.7 Hz, H-21), 1.04 (3H, d, J=6.7 Hz, H-27), 1.02 (3H, d, J=6.7 Hz, H-28), 0.90-1.00 (1H, m, H-6"), 0.85 (3H, s, H-29), 0.55 (1H, d, J=4.6 Hz, H-19")

$^{13}$C NMR (126 MHz, CD$_3$CN) δ=202.4 (C-3), 171.5 (C-16a), 171.4 (C-22a), 155.6 (C-1), 154.3 (C-24), 128.4 (C-2), 110.5 (C-23), 109.5 (C-24a), 78.2 (C-22), 75.1 (C-16), 75.0 (C-26), 52.9 (C-17), 49.8 (C-23a), 48.5 (C-14), 47.6 (C-4), 46.6 (C-13), 45.4 (C-15), 44.5 (C-8), 43.4 (C-5), 38.0 (C-25), 32.9 (C-12), 31.7 (C-20), 28.1 (C-11), 27.4 (C-10), 27.1 (C-19), 24.3 (C-9), 24.2 (C-7), 24.0 (C-6), 21.7 (C-16b), 21.3 (C-22b), 19.7 (C-29), 17.7 (C-18), 16.2 (C-27), 13.8 (C-21), 11.3 (C-28)

Example 35

3-semicarbazone-neoboutomellerone

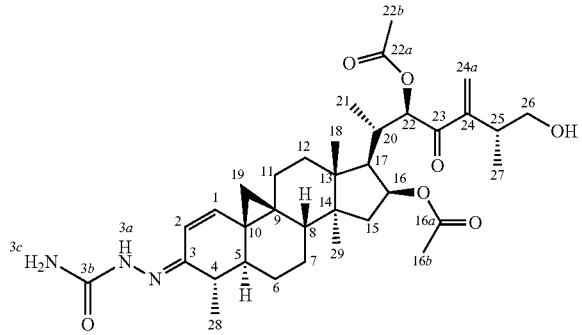

Chemical formula: C$_{35}$H$_{51}$NO$_7$
Exact mass: 625.37
Molecular weight: 625.80

Protocol: 49 mg (0.44 mmol, 5 eq) of semicarbazide hydrochloride and 67 mg (0.48 mmol, 5.5 eq) of sodium acetate are dissolved in 2 ml of methanol. 51 mg (0.089 mmol) of 2 is then added and the reaction medium is stirred at room temperature. After 20 h, the reaction medium is diluted in ethyl acetate and the organic phase is washed with distilled water. The aqueous phase is extracted three times with ethyl acetate and the combined organic phases are dried on MgSO$_4$. After concentration in a rotary evaporator, the product is purified by silica gel chromatography (eluent: DCM/MeOH: 97.5/2.5 to 92.5/7.5) in order to obtain a white solid (36 mg, 66%).

$^1$H NMR (500 MHz, CD$_3$CN) δ=8.04 (1H, s, NH-3a), 6.41 (1H, d, J=10.4 Hz, H-2), 6.33 (1H, d, J=10.1 Hz, H-1), 6.04 (1H, s, H-24a'), 5.89 (1H, d, a=0.9 Hz, H-24a"), 5.53 (1H, d, J=2.1 Hz, H-22), 5.08 (1H, td, J=7.7 Hz, J=4.4 Hz, H-16), 3.53 (1H, dd, J=10.7 Hz, J=6.1 Hz, H-26'), 3.39 (1H, dd, J=10.4 Hz, J=6.4 Hz, H-26"), 2.76 (1H, sxt, J=6.8 Hz, H-25), 2.54-2.64 (1H, dqd, J=10.9 Hz, J=6.9 Hz, J=2.1 Hz, H-20), 2.23-2.33 (2H, m, H-17, 4), 2.12-2.17 (1H, m, H-15'), 2.09 (3H, s, H-22b), 2.03 (3H, s, H-16b), 1.96-2.11 (2H, m, H-11', 8), 1.64-1.77 (4H, m, H-5, 12', 12", 6'), 1.53-1.64 (1H, m, H-11"), 1.41-1.50 (1H, m, H-7'), 1.35 (1H, dd, J=13.9 Hz, J=3.8 Hz, H-15"), 1.17-1.24 (1H, m, H-7"), 1.17 (3H, s, H-18), 1.12 (3H, d, J=6.7 Hz, H-28), 1.06 (1H, d, J=4.6 Hz, H-19'), 1.03 (3H, d, J=7.0 Hz, H-27), 0.92 (3H, s, H-29), 0.85-0.95 (1H, m, H-6"), 0.84 (3H, d, J=7.0 Hz, H-21), 0.46 (1H, d, J=4.3 Hz, H-19")

$^{13}$C NMR (126 MHz, CD$_3$CN) δ=199.6 (C-23), 171.7 (C-22a), 171.3 (C-16a), 158.4 (C-3b), 150.3 (C-24), 150.2 (C-3), 145.4 (C-1), 124.7 (C-24a), 116.4 (C-2), 78.5 (C-22), 76.6 (C-16), 66.4 (C-26), 51.2 (C-17), 48.4 (C-14), 46.8 (C-13), 46.6 (C-15), 44.6 (C-8), 43.3 (C-5), 41.2 (C-4), 37.9 (C-25), 33.2 (C-20), 33.1 (C-10), 33.0 (C-12), 28.1 (C-11), 27.7 (C-19), 27.1 (C-9), 24.1 (C-7), 23.9 (C-6), 22.1 (C-16b), 20.9 (C-22b), 19.9 (C-29), 18.0 (C-18), 17.2 (C-27), 13.3 (C-21), 13.2 (C-28)

Examples 36 & 37

3-anti-O-benzyloxime-neoboutomellerone (36) and
3-anti-O-benzyloxime-24a-O-benzylhydroxylamine-neoboutomellerone (37)

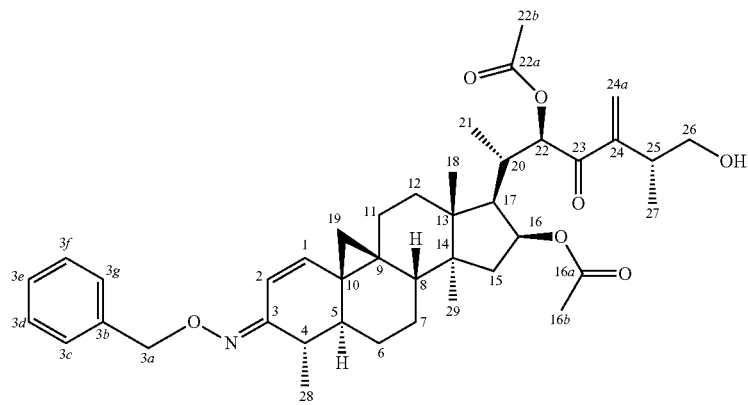

36

Chemical formula: $C_{41}H_{55}NO_7$
Exact mass: 673.40
Molecular weight: 673.88

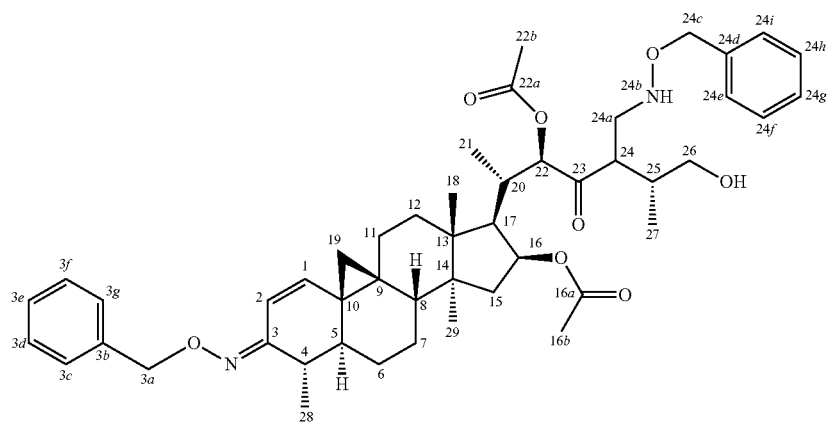

37

Chemical formula: $C_{48}H_{64}N_2O_7$
Exact mass: 796.47
Molecular weight: 797.03

Protocol: 81.64 mg (0.6 mmol, 3 eq) of sodium acetate, 35 μl (0.48 mmol, 5.5 eq) of acetic acid and 5 drops of distilled water are added to 4 ml of dioxane. The reaction medium is cooled to 0° C. and 95.7 mg (0.6 mmol, 3 eq) of O-benzyl-hydroxylamine hydrochloride is added. At room temperature, 114 mg of (0.2 mmol) is introduced and the reaction medium is stirred at room temperature for 6 hours. The reaction medium is diluted in ethyl acetate and the organic phase is washed with distilled water. The aqueous phase is extracted three times with ethyl acetate and the combined organic phases are washed with a saturated sodium chloride solution and dried on $MgSO_4$. After concentration in a rotary evaporator, the product is purified by silica chromatography (eluent: cyclohexane/AcOEt: 8/2 to 5/5) and by HPLC (eluent: cyclohexane/AcOEt: 6/4). 36 is obtained with a yield of 17%.

A fraction of the silica gel chromatography is repurified by reversed-phase chromatography (eluent: MeOH/$H_2O$: 100/5 to 100/0) and then by normal-phase HPLC (eluent: cyclohexane/ethyl acetate: 6/4). Compound 37 is isolated with a yield of 17% (26.6 mg).

Example 36

$^1$H NMR (500 MHz, $CD_3CN$) δ=7.20-7.43 (5H, m, H-3c, 3d, 3e, 3f, 3g), 6.67 (1H, d, J=10.4 Hz, H-2), 6.25 (1H, d, J=10.4 Hz, H-1), 6.04 (1H, s, H-24a'), 5.89 (1H, d, J=0.9 Hz, H-24a"), 5.52 (1H, d, J=2.4 Hz, H-22), 5.05-5.11 (1H, m, H-16), 4.99-5.11 (2H, m, H-3a', 3a"), 3.53 (1H, dt, J=10.4 Hz, J=5.2 Hz, H-26'), 3.39 (1H, dt, J=10.5 Hz, J=5.4 Hz, H-26"), 2.76 (1H, sxt, J=6.7 Hz, H-25), 2.67 (1H, t, J=5.0 Hz, OH-26), 2.53-2.64 (1H, m, H-20), 2.20-2.32 (2H, m, H-4, 17), 2.12-2.17 (1H, m, H-15'), 2.08 (3H, s, H-22b), 2.02 (3H, s, H-16b), 1.96-2.04 (2H, m, H-11', 8), 1.59-1.76 (4H, m, H-6', 5, 12', 12"), 1.50-1.59 (1H, m, H-11"), 1.40-1.49 (1H, m, H-7'), 1.35 (1H, dd, J=14.0 Hz, J=4.3 Hz, H-15"), 1.17-1.23 (1H, m, H-7"), 1.16 (3H, s, H-18), 1.08 (3H, d, J=6.7 Hz, H-28), 1.01 (1H, d, J=4.6 Hz, H-19'), 1.03 (3H, d, J=7.0 Hz, H-27), 0.92

(3H, s, H-29), 0.79-0.88 (1H, m, H-6"), 0.83 (3H, d, J=6.7 Hz, H-21), 0.42 (1H, d, J=4.3 Hz, H-19")

$^{13}$C NMR (126 MHz, CD$_3$CN) δ=199.6 (C-23), 171.7 (C-22a), 171.3 (C-16a), 157.9 (C-3), 150.3 (C-24), 144.7 (C-1), 139.7 (C-3b), 129.3 (C-3c, 3g), 129.2 (C-3d, 3H), 128.7 (C-3e), 124.6 (C-24a), 116.9 (C-2), 78.5 (C-22), 76.6 (C-16), 76.3 (C-3a), 66.4 (C-26), 51.2 (C-17), 48.4 (C-14), 46.8 (C-13), 46.6 (C-15), 44.7 (C-8), 43.4 (C-5), 39.8 (C-4), 37.9 (C-25), 33.2 (C-20), 33.0 (C-12), 32.8 (C-10), 28.1 (C-11), 27.5 (C-19), 26.8 (C-9), 24.2 (C-7), 23.7 (C-6), 22.1 (C-16b), 20.9 (C-22b), 19.9 (C-29), 18.1 (C-18), 17.2 (C-27), 13.3 (C-21), 13.1 (C-28)

Example 37

$^{1}$H NMR (500 MHz, CD$_3$CN) δ=7.22-7.42 (10H, m, H-3c, 3d, 3e, 3f, 3g, 24% 24f, 24g, 24h, 24i), 6.67 (1H, d, J=10.4 Hz, H-2), 6.26 (1H, d, J=10.1 Hz, H-1), 5.13 (1H, td, J=7.7 Hz, J=4.4 Hz, H-16), 5.06 (1H, d, J=12.2 Hz, H-3a'), 5.02 (1H, s, H-22), 5.02 (1H, d, J=12.4 Hz, H-3a"), 4.57 (1H, d, J=12.2 Hz, H-24c'), 4.60 (1H, d, J=12.2 Hz, H-24c"), 3.42-3.51 (1H, m, H-26'), 3.34-3.42 (1H, m, H-26"), 3.24 (1H, td, J=7.7 Hz, J=4.4 Hz, H-24), 2.98-3.15 (2H, m, H-24a', 24a"), 2.77-2.83 (1H, m, OH-26), 2.69-2.78 (1H, m, H-20), 2.20-2.31 (1H, m, H-4), 2.12-2.20 (2H, m, H-15', 17), 2.09 (3H, s, H-22b), 2.05 (3H, s, H-16b), 2.00-2.07 (1H, m, H-8), 1.83-1.92 (2H, m, H-25, 11'), 1.52-1.76 (4H, m, H-6', 5, 12', 12"), 1.41-1.50 (1H, m, H-7'), 1.36 (1H, dd, J=13.7 Hz, J=4.3 Hz, H-15"), 1.18 (3H, s, H-18), 1.11-1.23 (1H, m, H-7"), 1.08 (3H, d, J=6.7 Hz, H-28), 1.02 (1H, d, J=4.3 Hz, H-19'), 0.90 (3H, s, H-29), 0.88 (3H, d, J=7.0 Hz, H-27), 0.86 (3H, d, J=6.7 Hz, H-21), 0.78-0.93 (1H, m, H-6"), 0.40 (1H, d, J=4.3 Hz, H-19")

$^{13}$C NMR (126 MHz, CD$_3$CN) δ=210.7 (C-23), 172.3 (C-22a), 171.5 (C-16a), 157.9 (C-3), 144.6 (C-1), 139.7 (C-3b), 139.7 (C-24d), 129.2-129-3 (C-3c, 3d, 3f, 3g, 24e, 24f, 24h, 24i), 128.5-128.7 (C-3e, 24g), 116.9 (C-2), 82.1 (C-22), 76.3 (C-3a), 76.2 (C-16), 76.1 (C-24c), 64.9 (C-26), 52.8 (C-24a), 51.2 (C-17), 48.5 (C-14), 48.4 (C-24), 46.7 (C-13), 46.2 (C-15), 44.2 (C-8), 43.2 (C-5), 39.7 (C-4), 36.4 (C-25), 32.8 (C-10), 32.7 (C-12), 30.8 (C-20), 28.0 (C-11), 27.1 (C-19), 26.9 (C-9), 24.0 (C-7), 23.6 (C-6), 22.0 (C-16b), 21.0 (C-22b), 19.7 (C-29), 17.7 (C-18), 16.2 (C-27), 13.4 (C-21), 13.1 (C-28)

Example 38

24a-O-methyl-neoboutomellerone

Protocol: 36 μl of a sodium hydroxide solution in methanol (c=0.5 N) is added to 10 mg of compound 2 in solution in 200 μl of methanol. The reaction medium is stirred at room temperature for 13 hours. The reaction medium is diluted with water and filtered on Celite®. The filtrate is concentrated in a rotary evaporator and purified by silica gel chromatography (eluent: cyclohexane/AcOEt gradient: 7/3 to 0/10) and then by normal-phase HPLC (eluent: cyclohexane/AcOEt: 65/35+ 5% THF) and by reversed-phase HPLC (eluent: ACN/H$_2$O: 70/30). Compounds 1 (0.75 mg, 8%) and 38 (0.49 mg, 5%) are thus isolated.

$^{1}$H NMR (500 MHz, CD$_3$CN) δ=6.94 (1H, d, J=9.8 Hz, H-1), 5.90 (1H, d, J=10.1 Hz, H-2), 5.21 (1H, td, J=7.9 Hz, J=4.7 Hz, H-16), 4.05 (1H, s, H-22), 3.54 (1H, dd, J=8.9 Hz, J=4.9 Hz, H-24a'), 3.40-3.50 (2H, m, H-26', 26"), 3.40 (1H, t, J=8.9 Hz, H-24a"), 3.22-3.27 (1H, m, H-24), 3.18 (3H, s, H-24b), 2.50-2.61 (1H, m, H-20), 2.34 (1H, dd, J=11.0 Hz, J=7.9 Hz, H-17), 2.14-2.21 (2H, m, H-4,15'), 2.02-2.09 (1H, m, H-8), 2.02 (3H, s, H-16b), 1.93-2.01 (3H, m, H-25, 11', 5), 1.63-1.76 (3H, m, H-6', 12', 12"), 1.54-1.63 (1H, m, H-11"), 1.42-1.51 (1H, m, H-7'), 1.38 (1H, dd, J=13.7 Hz, J=4.6 Hz, H-15"), 1.26 (1H, d, J=4.6 Hz, H-19'), 1.20 (3H, s, H-18), 1.15-1.24 (1H, m, H-7"), 1.02 (3H, d, J=6.7 Hz, H-28), 0.96 (3H, s, H-29), 0.92-0.98 (1H, m, H-6"), 0.89 (3H, d, J=7.0 Hz, H-27), 0.71 (3H, d, J=6.7 Hz, H-21), 0.56 (1H, d, J=4.6 Hz, H-19")

$^{13}$C NMR (126 MHz, CD$_3$CN) δ=216.4 (C-23), 202.4 (C-3), 171.4 (C-16a), 155.6 (C-1), 128.4 (C-2), 80.7 (C-22), 76.1 (C-16), 74.1 (C-24a), 65.1 (C-26), 59.2 (C-24b), 51.6 (C-17), 50.0 (C-24), 48.5 (C-14), 47.6 (C-4), 46.6 (C-13), 46.2 (C-15), 44.8 (C-8), 43.5 (C-5), 35.6 (C-25), 32.8 (C-12), 32.6 (C-20), 28.1 (C-11), 27.3 (C-19), 24.2 (C-7), 24.1 (C-16b), 19.9 (C-29), 18.1 (C-18), 16.2 (C-27), 12.8 (C-21), 11.3 (C-28)

Example 39

26-carboxaldehyde-neoboutomellerone

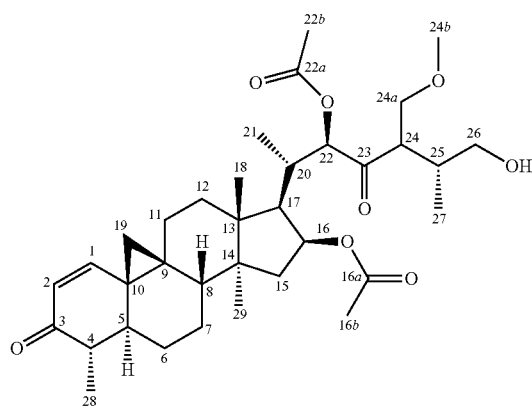

Chemical formula: C$_{35}$H$_{52}$O$_8$
Exact mass: 600.37
Molecular weight: 600.78

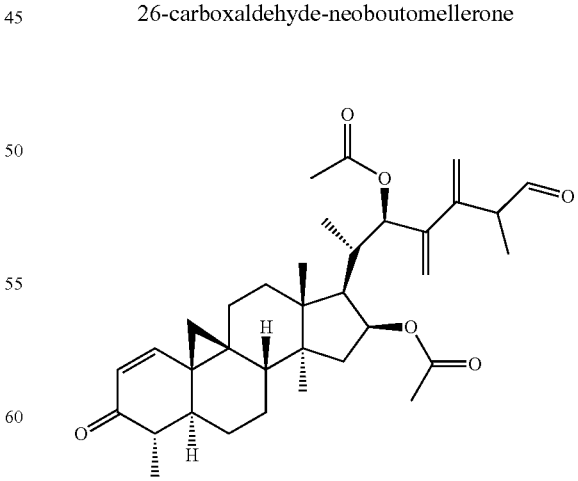

Chemical formula: C$_{35}$H$_{48}$O$_7$
Exact mass: 580.34
Molecular weight: 580.75

Protocol: 100 mg (0.18 mmol) of 2 is solubilized in 3.5 ml of dichloromethane. 350 μl of pyridine (2 ml/mmol) is added and the reaction mixture is cooled to 0° C. Then, 1.76 ml (0.528 mmol, 3 eq, 3 mol/l) of Dess Martin reagent in solution in dichloromethane is added and the temperature of the reaction medium is allowed to rise to room temperature. After 3 h, the reaction medium is diluted with ethyl acetate and saturated sodium thiosulfate solution is added. The aqueous phase is extracted three times in ethyl acetate and the combined organic phases are washed successively with asaturated sodium bicarbonate solution and a saturated sodium chloride solution. The organic phase is dried on $MgSO_4$, filtered and concentrated in a rotary evaporator. The product is purified by silica chromatography (eluent: cyclohexane/AcOEt: 7/3 to 6/4). The aldehyde is obtained with a yield of 66% (66 mg).

$^1$H NMR (500 MHz, $CD_3CN$) δ=9.51 (1H, d, J=0.6 Hz, H-26), 6.94 (1H, d, J=10.1 Hz, H-1), 6.32 (1H, s, H-24a'), 6.06 (1H, s, H-24a"), 5.90 (1H, d, J=10.1 Hz, H-2), 5.58 (1H, d, J=2.1 Hz, H-22), 5.08 (1H, td, J=7.7 Hz, J=4.4 Hz, H-16), 3.45 (1H, q, J=7.2 Hz, H-25), 2.58-2.69 (1H, m, H-20), 2.31 (1H, dd, J=11.0 Hz, J=7.6 Hz, H-17), 2.16-2.23 (2H, m, H-4,15'), 2.09 (3H, s, H-22b), 2.04 (3H, s, H-16b), 1.99-2.07 (2H, m, H-8,11'), 1.92-1.96 (1H, m, H-5), 1.63-1.76 (3H, m, H-6', 12', 12"), 1.52-1.62 (1H, m, H-11"), 1.42-1.49 (1H, m, H-7'), 1.38 (1H, dd, J=13.7 Hz, J=4.0 Hz, H-15"), 1.25 (1H, d, J=4.3 Hz, H-19'), 1.18-1.22 (7H, m, H-7", 27, 18), 1.03 (3H, d, J=6.7 Hz, H-28), 0.96 (3H, s, H-29), 0.94 (1H, qd, J=12.8 Hz, J=3.7 Hz, H-6"), 0.85 (3H, d, J=7.0 Hz, H-21), 0.58 (1H, d, J=4.6 Hz, H-19")

$^{13}$C NMR (126 MHz, $CD_3CN$) δ=202.4 (C-3), 201.7 (C-26), 198.3 (C-23), 171.6 (C-22a), 171.2 (C-16a), 155.5 (C-1), 145.8 (C-24), 128.6 (C-24a), 128.4 (C-2), 78.2 (C-22), 76.8 (C-16), 51.2 (C-17), 48.9 (C-25), 48.3 (C-14), 47.6 (C-4), 46.9 (C-13), 46.7 (C-15), 45.2 (C-8), 43.6 (C-5), 33.8 (C-20), 33.0 (C-12), 28.1 (C-11), 27.6 (C-19), 27.2 (C-9), 24.3 (C-7, 6), 22.1 (C-16b), 20.9 (C-22b), 20.0 (C-29), 18.3 (C-18), 13.8 (C-27), 13.4 (C-21), 11.3 (C-28)

Example 40

1,1-dimethyl-(26-neoboutomelleronylidene)-hydrazone

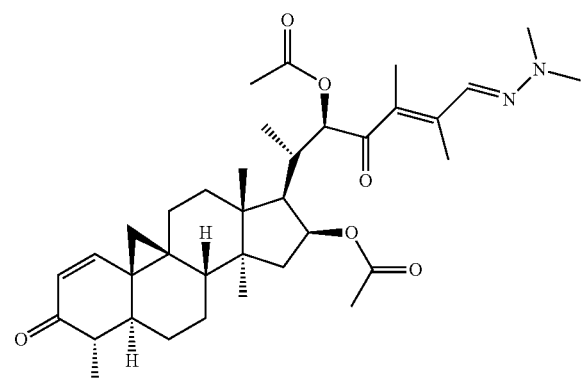

Chemical formula: $C_{37}H_{54}N_2O_6$
Exact mass: 622.40
Molecular weight: 622.83

Protocol: Compound 39 (200 mg, 0.353 mmol) is dissolved in 15 ml of ethanol and 85 mg of hydrazine (0.107 ml, 1.412 mmol, 4 eq) diluted in ethanol is added drop by drop. The reaction is left under stirring for 3 hours at room temperature. The product is then adsorbed on alumina and the solvent is evaporated under reduced pressure. The product is purified on an alumina column with a heptane/ethyl acetate gradient (100/0 to 40/60%) to lead to 40 mg (20%) of compound 40.

$^1$H NMR (500 MHz, ACETONITRILE-$d_3$) δ=7.37 (1H, s, H-26), 6.94 (1H, d, J=10.1 Hz, H-1), 5.83-5.95 (1H, m, H-2), 5.34 (1H, d, J=1.5 Hz, H-22), 5.06 (1H, td, J=7.5 Hz, J=4.3 Hz, H-16), 2.84 (6H, s, H-26a, 26b), 2.51-2.60 (1H, m, H-20), 2.14-2.27 (2H, m, H-15, 4, 17), 2.11 (4H, s, H-22b), 1.96-2.05 (3H, m, H-5a, 8a, 11), 1.93 (8H, br. s., H-27, 24a), 1.88 (3H, s, H-16b), 1.63-1.73 (3H, m, H-12, 6<'>), 1.53-1.62 (1H, m, H-11<">), 1.40-1.48 (1H, m, H-7<'>), 1.32 (1H, dd, J=14.2 Hz, J=3.1 Hz, H-15<">), 1.24 (1H, d, J=4.3 Hz, H-19<'>), 1.20-1.22 (1H, m, H-7<">), 1.19 (3H, s, H-18), 1.03 (3H, d, J=6.7 Hz, H-28), 0.96-0.98 (1H, m, M21), 0.94 (3H, s, H-29), 0.90 (3H, d, J=7.0 Hz, H-21), 0.57 (1H, d, J=4.6 Hz, H-19<">)

$^{13}$C NMR (126 MHz, ACETONITRILE-$d_3$) δ=205.8 (C-23), 202.4 (C-3), 172.0 (C-22a, 16a), 171.4, 155.5 (C-1), 137.5 (C-24), 132.3 (C-26), 132.3 (C-25), 128.5 (C-2), 82.3 (C-22), 75.9 (C-16), 51.2 (C-17), 48.5 (C-14), 47.7 (C-4), 46.9 (C-13), 46.5 (C-15), 45.1 (C-8), 43.6, 43.1 (C-26b, 26a, 5), 33.0 (C-10), 32.9 (C-12), 31.8 (C-20), 28.1 (C-11), 27.6 (C-19), 27.3 (C-9), 24.3 (C-6), 24.3 (C-7), 21.9 (C-16b), 21.0 (C-22b), 20.0 (C-29), 18.2 (C-18), 17.2 (C-24a), 13.8 (C-21, 27), 11.3 (C-28)

Example 41

Neoboutomellerone-26-carboxylic acid

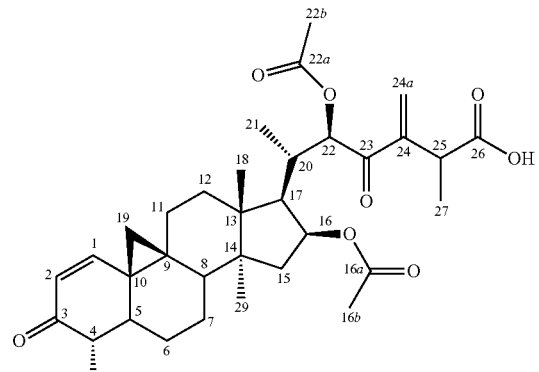

Chemical formula: $C_{34}H_{46}O_8$
Exact mass: 582.32
Molecular weight: 582.72

Protocol: Intermediate aldehyde 39 (45 mg, 0.0795) is solubilized in an acetone/water mixture (1/1, 2 ml) and 84 μl of 2-methyl-2-butylene is added. Then a solution of 55 mg of monosodium phosphate (0.33 mmol, 5 eq) in 100 μl of $H_2O$ and a solution of 22 mg of sodium chlorite (0.24 mmol, 3 eq) in 100 μl of $H_2O$ are added. After 24 h, the reaction medium is diluted with a saturated sodium chloride solution and extracted three times with ethyl acetate. The combined organic phases are dried on $MgSO_4$, filtered and concentrated in a rotary evaporator. The product is purified by silica gel chromatography (eluent: DCM/MeOH: 100/0 to 95/5) in order to obtain a white solid (28 mg, 61%) containing a mixture of C-25 epimers.

$^1$H NMR (500 MHz, CD3CN) δ=6.94 (1H, d, J=10.1 Hz, H-1), 6.20 (1H, br. s., H-24a'), 6.04/6.08 (1H, br. s., H-24a"), 5.89 (1H, d, J=9.8 Hz, H-2), 5.55 (1H, br. s., H-22), 5.02-5.14 (1H, m, H-16), 3.40-3.49/3.51-3.62 (1H, m, H-25), 2.55-2.69 (1H, m, H-20), 2.24-2.33 (1H, m, H-17), 2.12-2.22 (2H, m, H-4,15'), 2.08/2.08 (3H, s, H-22b), 2.03/2.03 (3H, s, H-16b), 1.98-2.05 (3H, m, H-5,8,11'), 1.62-1.75 (3H, m, H-6', 12', 12"), 1.51-1.60 (1H, m, H-11"), 1.40-1.49 (1H, m, H-7'), 1.36 (1H, dd, J=14.0 Hz, J=4.0 Hz, H-15"), 1.22-1.31 (4H, m, H-19', 27), 1.16-1.22 (1H, m, H-7"), 1.18 (3H, s, H-18), 1.02 (3H, d, J=7.0 Hz, H-28), 0.95 (3H, s, H-29), 0.90-0.99 (1H, m, H-6"), 0.84 (3H, d, J=7.0 Hz, H-21), 0.57 (1H, d, J=4.6 Hz, H-19")

$^{13}$C NMR (126 MHz, CD3CN) δ=202.4 (C-3), 197.7 (C-23), 175.5 (C-26), 171.6/171.7 (C-22a), 171.3/171.3 (C-16a), 155.6 (C-1), 147.3 (C-24), 128.4 (C-2), 126.3/127.2 (C-24a), 78.0/78.1 (C-22), 76.7/76.8 (C-16), 51.3/51.3 (C-17), 48.3/48.4 (C-14), 47.6 (C-4), 46.9/46.9 (C-13), 46.7 (C-15), 45.2 (C-8), 43.6 (C-5), 41.5/42.2 (C-25), 33.4/33.7 (C-20), 33.0 (C-12), 32.8 (C-10), 28.1/28.1 (C-11), 27.6 (C-19), 27.2/27.2 (C-9), 24.3 (C-6, 7), 22.1/22.1 (C-16b), 20.9/20.9 (C-22b), 20.0 (C-29), 18.3 (C-18), 15.9/17.2 (C-27), 13.2/13.4 (C-21), 11.3 (C-28)

Example 42

22-deacetyl,23,23a-dihydro-hemiacetal-16,22-neoboutomellerone

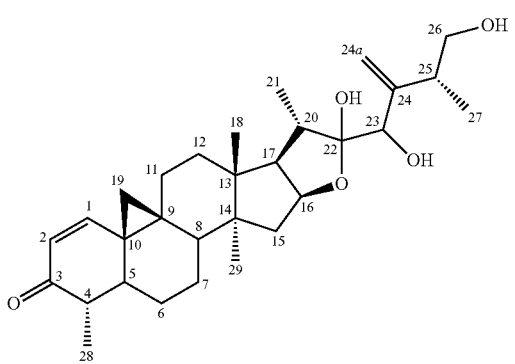

Chemical formula: $C_{30}H_{44}O_5$
Exact mass: 484.32
Molecular weight: 484.67

Protocol: 20 mg of 1 is solubilized in 300 μl of acetonitrile and 570 μl of 1 M NaOH is added. The reaction medium is stirred at room temperature for 22 hours. The reaction medium is diluted with ethyl acetate and filtered on Celite®. After the filtrate is concentrated in a rotary evaporator, the product is purified by silica gel chromatography (eluent: cyclohexane/AcOEt: 5/5) in order to obtain 42 (3 mg, 17%).

$^1$H NMR (500 MHz, CD$_3$CN) δ=6.97 (1H, d, J=10.1 Hz, H-1), 5.91 (1H, d, J=10.1 Hz, H-2), 5.22 (1H, s, H-24a'), 5.12 (1H, s, H-24a"), 4.64 (1H, q, J=6.7 Hz, H-16), 3.98 (1H, d, J=5.5 Hz, H-23), 3.79 (1H, d, J=5.8 Hz, OH-23), 3.49 (1H, s, OH-22), 3.44-3.51 (1H, m, H-26'), 3.40 (1H, ddd, J=9.6 Hz, J=8.7 Hz, J=4.6 Hz, H-26"), 3.24 (1H, t, J=4.7 Hz, OH-26), 2.64 (1H, sxt, J=7.0 Hz, H-25), 2.48 (1H, quin, J=6.8 Hz, H-20), 2.11-2.25 (3H, m, H-4, 8, 17), 1.89-1.99 (2H, m, H5, 11'), 1.60-1.76 (5H, m, H-6', 11", 12', 12", 15alpha), 1.40-1.56 (2H, m, H-7', 15beta), 1.31 (1H, d, J=4.6 Hz, H-19'), 1.22-1.30 (1H, m, H-7"), 1.14 (3H, s, H-18), 1.02 (3H, d, J=6.7 Hz, H-28), 1.01 (3H, d, J=7.0 Hz, H-27), 0.94-0.99 (1H, m, H-6"), 0.96 (3H, d, J=6.7 Hz, H-21), 0.92 (3H, s, H-29), 0.50 (1H, d, J=4.6 Hz, H-19")

$^{13}$C NMR (126 MHz, CD$_3$CN) δ=202.3 (C-3), 155.3 (C-1), 153.3 (C-24), 128.5 (C-2), 114.2 (C-24a), 111.4 (C-22), 82.5 (C-16), 77.8 (C-23), 69.0 (C-26), 60.4 (C-17), 52.4 (C-14), 47.5 (C-4), 44.8 (C-13), 43.6 (C-8), 43.1 (C-5), 41.7 (C-15), 38.3 (C-25), 38.2 (C-20), 33.3 (C-10), 32.8 (C-12), 28.4 (C-11), 27.4 (C-9), 26.5 (C-19), 23.9 (C-6), 23.8 (C-7), 21.3 (C-18), 19.3 (C-29), 17.8 (C-27), 15.8 (C-21), 11.3 (C-28)

Example 43

26-sulfate-neoboutomellerone

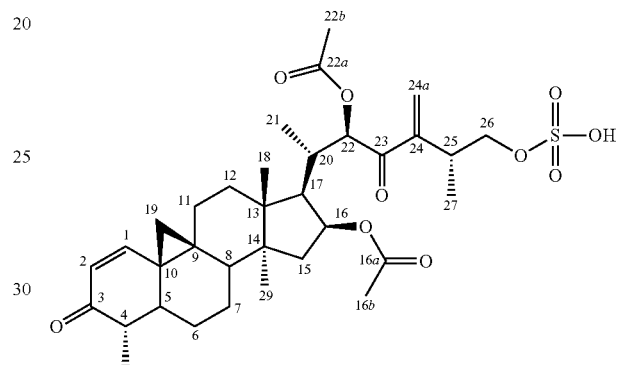

Chemical formula: $C_{34}H_{48}O_{10}S$
Exact mass: 648.30
Molecular weight: 648.80

Protocol: 60 mg (0.088 mmol) of 2 is solubilized in 3 ml of anhydrous tetrahydrofuran under nitrogen and 280 mg (1.76 mmol, 20 eq) of SO$_3$ pyridine complex is added. The reaction medium is stirred at room temperature for 2 hours and then concentrated in a rotary evaporator. The product is purified by silica gel chromatography (eluent: DCM/MeOH: 10/0 to 8/2) in order to obtain a white solid. The white solid is taken up in a saturated sodium bicarbonate solution and the aqueous phase is extracted three times with ethyl acetate. The combined organic phases are dried on MgSO$_4$, filtered and concentrated in a rotary evaporator. A white solid is obtained with a yield of 63% (37 mg).

$^1$H NMR (500 MHz, CD$_3$CN) δ=6.94 (1H, d, J=10.1 Hz, H-1), 6.10 (1H, s, H-24a'), 6.02 (1H, s, H-24a"), 5.89 (1H, d, J=9.8 Hz, H-2), 5.54 (1H, d, J=2.1 Hz, H-22), 5.08 (1H, td, J=7.6 Hz, J=4.6 Hz, H-16), 3.94 (1H, dd, J=9.8 Hz, J=6.4 Hz, H-26'), 3.81 (1H, dd, J=9.8 Hz, J=6.7 Hz, H-26"), 2.99 (1H, sxt, J=6.7 Hz, H-25), 2.60 (1H, dqd, J=11.0 Hz, J=7.0 Hz, J=2.1 Hz, H-20), 2.29 (1H, dd, J=11.0 Hz, J=7.6 Hz, H-17), 2.13-2.22 (2H, m, H-4,15'), 2.10 (3H, s, H-22b), 2.04 (3H, s, H-16b), 1.99-2.07 (2H, m, H-8,11'), 1.96-1.99 (1H, m, H-5), 1.62-1.76 (3H, m, H-6', 12', 12"), 1.51-1.61 (1H, m, H-11"), 1.41-1.49 (1H, m, H-7'), 1.36 (1H, dd, J=14.0 Hz, J=4.0 Hz, H-15"), 1.24 (1H, d, J=4.6 Hz, H-19'), 1.19 (3H, s, H-18), 1.16-1.21 (1H, m, H-7"), 1.06 (3H, d, J=7.0 Hz, H-27), 1.02 (3H, d, J=6.7 Hz, H-28), 0.95 (3H, s, H-29), 0.90-0.98 (1H, m, H-6"), 0.86 (3H, d, J=7.0 Hz, H-21), 0.58 (1H, d, J=4.6 Hz, H-19")

¹³C NMR (126 MHz, CD$_3$CN) δ=202.4 (C-3), 199.1 (C-23), 171.9 (C-22a), 171.4 (C-16a), 155.6 (C-1), 149.5 (C-24), 128.4 (C-2), 125.4 (C-24a), 78.5 (C-22), 76.7 (C-16), 70.6 (C-26), 51.3 (C-17), 48.3 (C-14), 47.6 (C-4), 46.9 (C-13), 46.7 (C-15), 45.2 (C-8), 43.6 (C-5), 35.0 (C-25), 33.3 (C-20), 33.0 (C-12), 32.9 (C-10), 28.1 (C-11), 27.7 (C-19), 27.2 (C-9), 24.3 (C-7, 6), 22.2 (C-16b), 21.0 (C-22b), 20.0 (C-29), 18.3 (C-18), 17.4 (C-27), 13.4 (C-21), 11.3 (C-28)

Example 44

26-sulfate-22-deacetyl-neoboutomellerone

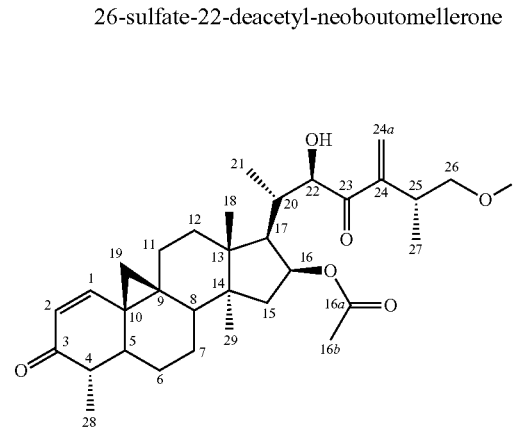

Chemical formula: C$_{32}$H$_{46}$O$_9$S
Exact mass: 606.29
Molecular weight: 606.77

Protocol: 100 mg (0.19 mmol) of compound 1 is dissolved in 0.2 ml of THF and then Burgess reagent solution (54 mg, 1.2 eq, 0.23 mmol) in 0.4 ml of THF is added. The reaction is brought to reflux for 2 h. Once back at room temperature the reaction is hydrolyzed with water and is extracted two times with ethyl ether. The aqueous phase is re-extracted several times with ethyl acetate. These phases are combined, dried on sodium sulfate and then evaporated to isolate compound 44 (50 mg, 43%) which does not require additional purification.

¹H NMR (500 MHz, ACETONITRILE-d$_3$) δ=6.94 (1H, d, J=10.1 Hz, H-1), 6.14 (1H, s, H-24aa), 6.05-6.11 (1H, m, H-24ab), 5.89 (1H, d, J=9.8 Hz, H-2), 5.20 (1H, td, J=7.5 Hz, J=4.6 Hz, H-16), 4.67-4.78 (1H, m, H-22), 3.93 (1H, dd, J=10.0 Hz, J=3.5 Hz, H-26<'>), 3.78 (1H, dd, J=10.0 Hz, J=3.5 Hz, H-26<">), 3.58 (1H, d, J=6.0 Hz, H-30), 3.56 (1H, br. s, H-42), 3.03 (1H, sxt, J=6.5 Hz, H-25), 2.39-2.52 (1H, m, H-17, 20), 2.23 (1H, dd, J=13.5 Hz, J=7.5 Hz, H-15<'>), 2.17 (1H, dq, J=12.5 Hz, J=6.5 Hz, H-4), 2.04-2.06 (1H, m, H-8a), 2.04 (1H, s, H-16b), 1.98-2.02 (1H, m, H-5a, 11<'>), 1.62-1.74 (1H, m, H-12<">, 12<'>, 6<'>), 1.55 (1H, ddd, J=15.0 Hz, J=8.9 Hz, J=6.1 Hz, H-11<">), 1.42-1.50 (1H, m, H-7<'>), 1.38 (1H, dd, J=13.7 Hz, J=4.2 Hz, H-15<">), 1.24 (1H, d, J=4.5 Hz, H-19<'>), 1.18 (1H, s, H-18), 1.13-1.17 (1H, m, H-7<">), 1.07 (1H, d, J=7.0 Hz, H-27), 1.03 (1H, d, J=6.7 Hz, H-28), 0.97 (1H, s, H-29), 0.92-0.94 (1H, m, H-6<">), 0.66 (1H, d, J=6.1 Hz, H-21), 0.57 (1H, d, J=4.5 Hz, H-19<">)

¹³C NMR (126 MHz, ACETONITRILE-d$_3$) δ=205.4 (C-23), 202.4 (C-3), 171.4 (C-16b), 155.6 (C-1), 148.9 (C-24), 128.4 (C-2), 126.7 (C-24a), 77.3 (C-16), 75.8 (C-22), 70.4 (C-26), 51.5 (C-17), 48.4 (C-14), 47.7 (C-4), 47.0 (C-15), 46.7 (C-13), 45.4 (C-8), 43.7 (C-5), 36.3 (C-25), 35.1 (C-20), 33.2 (C-12), 33.0 (C-10), 28.2 (C-11), 27.8 (C-19), 27.3 (C-9), 24.4 (C-7), 24.4 (C-6), 22.2 (C-16b), 20.2 (C-29), 18.5 (C-18), 17.6 (C-27), 12.4 (C-21), 11.3 (C-28)

Example 45

22,26-disulfate-22-deacetyl-neoboutomellerone

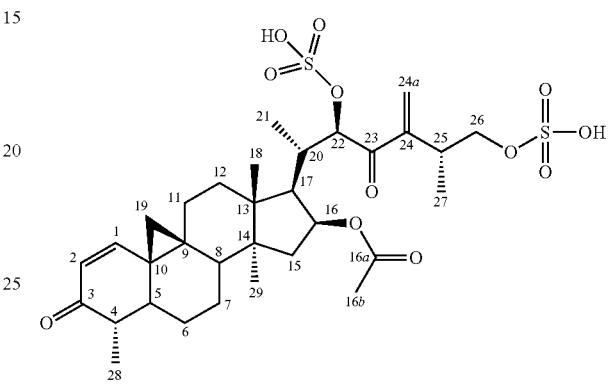

Chemical formula: C$_{32}$H$_{46}$O$_{12}$S$_2$
Exact mass: 686.24
Molecular weight: 686.83

Protocol: The same reaction as carried out before with 2.5 eq of Burgess reagent leads to the formation of compound 45 (21 mg, 16%) in addition to compound 44 (61 mg, 53%).

¹H NMR (500 MHz, ACETONITRILE-d$_3$) δ=6.94 (1H, d, J=10.1 Hz, H-1), 6.22 (1H, s, H-24ab), 6.00 (1H, s, H-24aa), 5.89 (1H, d, J=9.8 Hz, H-2), 5.49 (1H, td, J=7.7 Hz, J=4.3 Hz, H-16), 5.22-5.28 (1H, m, M06), 3.87 (1H, dd, J=10.0 Hz, J=5.5 Hz, H-26<'>), 3.80 (1H, dd, J=10.0 Hz, J=6.7 Hz, H-26<">), 3.12 (1H, sxt, J=7.0 Hz, H-25), 2.44-2.50 (2H, m, H-17, 20), 2.18-2.23 (1H, m, H-15<'>), 2.15-2.18 (1H, m, H-4), 2.04 (3H, s, H-16b), 1.99-2.03 (2H, m, H-8a, 5a), 1.97-1.99 (1H, m, H-11<'>), 1.63-1.75 (3H, m, H-12<">, 12<'>, 6<'>), 1.57 (1H, ddd, J=15.0 Hz, J=9.0 Hz, J=6.0 Hz, H-11<">), 1.42-1.49 (1H, m, H-7<'>), 1.35 (2H, dd, J=7.0 Hz, J=3.5 Hz, H-15<">), 1.24 (1H, d, J=4.0 Hz, H-19<'>), 1.19-1.22 (1H, m, H-7<">), 1.17 (3H, s, H-18), 1.07 (3H, d, J=7.1 Hz, H-27), 1.03 (3H, d, J=7.2 Hz, H-28), 0.96 (3H, s, H-29), 0.91-0.95 (1H, m, H-6<">), 0.82 (3H, d, J=7.0 Hz, H-21), 0.57 (1H, d, J=4.0 Hz, H-19<">)

¹³C NMR (126 MHz, ACETONITRILE-d$_3$) δ=202.4 (C-23), 202.2 (C-3), 171.8 (C-16a), 155.6 (C-1), 150.1 (C-24), 128.4 (C-2), 126.0 (C-24a), 80.8 (C-16), 77.2 (C-22), 71.7 (C-26), 51.1 (C-17), 48.5 (C-14), 47.7 (C-4), 46.7 (C-13), 46.7 (C-15), 45.2 (C-8), 43.6 (C-5), 34.7 (C-25), 34.3

(C-20), 33.1 (C-12), 33.0 (C-10), 28.2 (C-11), 27.7 (C-19), 27.3 (C-9), 24.4 (C-6), 24.3 (C-7),

Example 46

Tosylate-neoboutomellerone

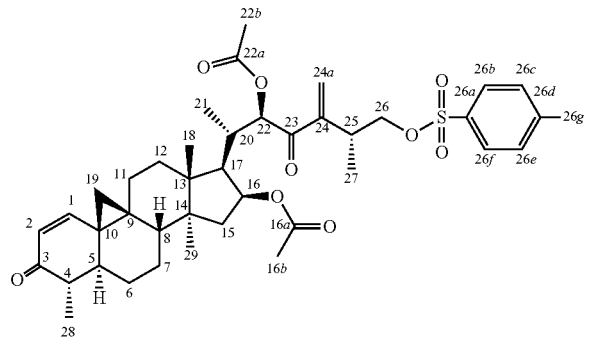

Chemical formula: $C_{41}H_{54}O_9S$
Exact mass: 722.35
Molecular weight: 722.93

Protocol: 100 mg (0.18 mmol) of 2 is solubilized in 1 ml of anhydrous dichloromethane under nitrogen. 49 µl (0.36 mmol, 2 eq) of triethylamine and 46 mg (0.21 mmol, 1.2 eq) of tosyl chloride are added. The reaction medium is stirred for 24 hours and is diluted with ethyl acetate. The organic phase is washed with saturated ammonium chloride solution and dried on $Na_2SO_4$. After concentration in a rotary evaporator, the crude product is purified by silica gel chromatography (eluent: cyclohexane/AcOEt: 7/3 to 6/4). The tosylate is obtained with a yield of 65% (82 mg).

$^1$H NMR (500 MHz, ACETONITRILE-$d_3$) δ=7.75 (2H, d, J=8.2 Hz, H-26f, 26b), 7.43 (2H, d, J=7.9 Hz, H-26e, 26c), 6.94 (1H, d, J=9.8 Hz, H-1), 6.07 (1H, s, H-24a'), 5.89 (1H, d, J=10.1 Hz, H-2), 5.85 (1H, s, H-24a"), 5.48 (1H, d, J=1.8 Hz, H-22), 5.06 (1H, td, J=7.6 Hz, J=4.4 Hz, H-16), 4.05 (1H, dd, J=10.4 Hz, J=6.1 Hz, H-26'), 3.95 (1H, dd, J=9.8 Hz, J=6.1 Hz, H-26"), 2.97 (1H, sxt, J=6.7 Hz, H-25), 2.49-2.55 (1H, m, H-20), 2.44 (3H, s, H-26g), 2.27 (1H, dd, J=11.0 Hz, J=7.6 Hz, H-17), 2.12-2.21 (2H, m, H-4,15'), 2.08 (3H, s, H-22b), 1.99 (3H, s, H-16b), 1.96-2.05 (3H, m, H-5, 8, 11'), 1.61-1.76 (3H, m, H-6', 12', 12"), 1.52-1.60 (1H, m, H-11"), 1.40-1.49 (1H, m, H-7'), 1.36 (1H, dd, J=13.9 Hz, J=3.8 Hz, H-15"), 1.24 (1H, d, J=4.6 Hz, H-19'), 1.16 (3H, s, H-18), 1.13-1.22 (1H, m, H-7"), 1.02 (3H, d, J=6.7 Hz, H-27), 1.01 (3H, d, J=7.0 Hz, H-28), 0.94 (3H, s, H-29), 0.90-0.98 (1H, m, H-6"), 0.80 (3H, d, J=7.0 Hz, H-21), 0.57 (1H, d, J=4.3 Hz, H-19")

$^{13}$C NMR (126 MHz, ACETONITRILE-$d_3$) δ=202.4 (C-3), 198.6 (C-23), 171.6 (C-22a), 171.2 (C-16a), 155.5 (C-1), 147.6 (C-24), 146.5 (C-26d), 133.7 (C-26a), 131.1 (C-26e, 26c), 128.9 (C-26f, 26b), 128.4 (C-2), 126.5 (C-24a), 78.2 (C-22), 76.7 (C-16), 73.9 (C-26), 51.2 (0-17), 48.3 (C-14), 47.6 (C-4), 46.8 (C-13), 46.7 (C-15), 45.2 (C-8), 43.6 (C-5), 35.2 (C-25), 33.3 (C-20), 32.9 (C-12), 28.1 (C-11), 27.7 (C-19), 27.2 (C-9), 24.3 (C-7, 6), 22.1 (C-16b), 21.7 (C-26g), 20.9 (C-22b), 20.0 (C-29), 18.3 (C-18), 16.8 (C-27), 13.3 (C-21), 11.3 (C-28)

Example 47

Azido-methyl-dihydro-furan-neoboutomellerone Derivative

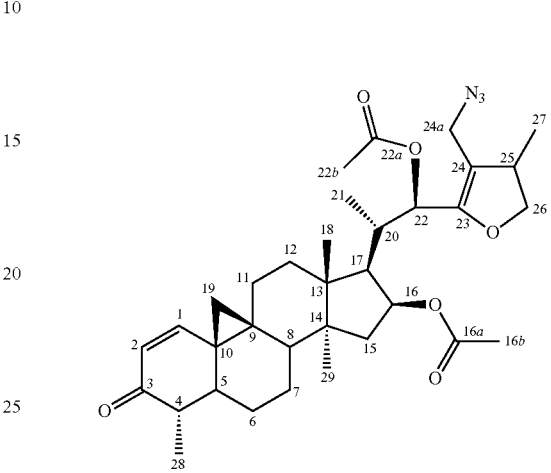

Chemical formula: $C_{34}H_{47}N_3O_6$
Exact mass: 593.35
Molecular weight: 593.75

Protocol: 20 mg (0.027 mmol) of 2 is solubilized in 200 µl of anhydrous DMF under nitrogen. 4 mg (0.054 mmol, 2 eq) of sodium azide is added. The reaction medium is stirred and heated at 50° C. for 24 hours. The reaction medium is diluted with distilled water and is extracted with ethyl acetate (three times). The organic phase is dried on $MgSO_4$, filtered and concentrated in a rotary evaporator. The crude product is purified by silica gel chromatography (eluent: cyclohexane/AcOEt: 8/2 to 4/6). Product 47 is obtained with a yield of 18% (3 mg).

$^1$H NMR (500 MHz, $CD_3CN$) δ=6.94 (1H, d, J=10.1 Hz, H-1), 5.90 (1H, d, J=10.1 Hz, H-2), 5.33 (1H, s, H-22), 5.18 (1H, td, J=7.9 Hz, J=4.6 Hz, H-16), 4.42 (1H, t, J=9.3 Hz, H-26'), 4.21 (1H, d, J=13.7 Hz, H-24a'), 3.82 (1H, dd, J=8.9 Hz, J=7.3 Hz, H-26"), 3.76 (1H, d, J=13.7 Hz, H-24a"), 3.08 (1H, sxt, J=7.1 Hz, H-25), 2.31 (1H, dqd, J=11.0 Hz, J=6.7 Hz, J=1.5 Hz, H-20), 2.14-2.21 (1H, m, H-4), 2.10 (3H, s, H-22b), 1.96-2.00 (3H, m, H-16b), 1.96-2.11 (5H, m, H-5, 8, 11', 15', 17), 1.62-1.73 (3H, m, H-6', 12', H2"), 1.54-1.62 (1H, m, H-11"), 1.40-1.51 (1H, m, H-7'), 1.34 (1H, dd, J=13.9 Hz, J=4.4 Hz, H-15"), 1.25 (1H, d, J=4.3 Hz, H-19'), 1.17-1.23 (1H, m, H-7"), 1.16 (3H, s, H-18), 1.09 (3H, d, J=6.7 Hz, H-27), 1.02 (3H, d, J=7.0 Hz, H-21), 1.01 (3H, d, J=7.0 Hz, H-28), 0.92-1.00 (1H, m, H-6"), 0.90 (3H, s, H-29), 0.56 (1H, d, J=4.3 Hz, H-19")

$^{13}$C NMR (126 MHz, $CD_3CN$) δ=202.3 (C-3), 171.3 (C-16a), 171.0 (C-22a), 155.5 (C-1), 153.7 (C-23), 128.4 (C-2), 110.5 (C-24), 77.1 (C-26), 75.7 (C-16), 72.5 (C-22), 51.0 (C-17), 48.5 (C-14), 47.0 (C-4), 46.7 (C-13), 45.9 (C-24a), 45.8 (C-15), 44.7 (C-8), 43.4 (C-5), 40.0 (C-25), 34.6 (C-20), 32.9 (C-10), 32.7 (C-12), 28.0 (C-11), 27.3

(C-19), 27.0 (C-9), 24.2 (C-6), 24.1 (C-7), 21.5 (C-16b), 21.2 (C-22b), 19.8 (C-29), 18.2 (C-27), 17.9 (C-18), 12.9 (C-21), 11.3 (C-28)

Example 48

Methyl-propanone-dimethyl-dihydro-furan-neoboutomellerone Derivative

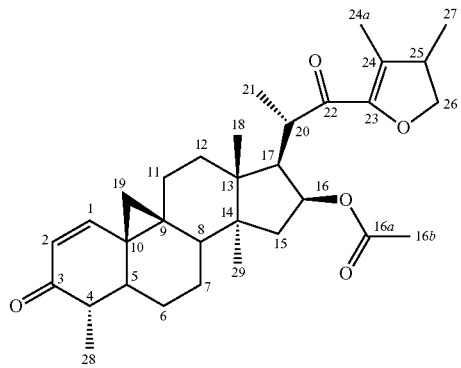

Chemical formula: $C_{32}H_{44}O_5$
Exact mass: 508.32
Molecular weight: 508.69

Protocol: 4.8 mg (0.008 mmol) of 2 is dissolved in 2 ml of deuterated benzene and is mixed with p-toluenesulfonic acid at room temperature. After 5 hours, the product is filtered on silica and the solvent is evaporated to lead to the isolation of 3.8 mg (89%) of compound 48.

The same reaction carried out with 1 leads to the same product 48.

$^1$H NMR (500 MHz, CD$_3$CN) δ=6.95 (1H, d, J=10.1 Hz, H-1), 5.91 (1H, d, J=10.1 Hz, H-2), 5.05 (1H, td, J=8.3 Hz, J=6.0 Hz, H-16), 4.41 (1H, dd, J=9.6 Hz, J=9.0 Hz, H-26'), 3.82 (1H, t, J=8.7 Hz, H-26"), 3.39 (1H, dq, J=11.0 Hz, J=7.1 Hz, H-20), 2.91-3.01 (1H, m, H-25), 2.55 (1H, dd, J=11.0 Hz, J=8.5 Hz, H-17), 2.14-2.21 (1H, m, H-4), 2.04-2.10 (1H, m, H-8), 1.96-2.03 (3H, m, H-5, 11', 15'), 1.91 (3H, d, J=1.5 Hz, H-24a), 1.80 (3H, s, H-16b), 1.71-1.83 (1H, m, H-12'), 1.57-1.70 (3H, m, H-6', 11", 12"), 1.42-1.51 (1H, m, H-7'), 1.27 (1H, d, J=4.3 Hz, H-19'), 1.17-1.30 (2H, m, H-7", 15"), 1.15 (3H, s, H-18), 1.10 (3H, d, J=7.0 Hz, H-27), 1.04 (3H, d, J=7.0 Hz, H-21), 1.02 (3H, d, J=6.7 Hz, H-28), 0.97 (3H, s, H-29), 0.89-1.00 (1H, m, H-6"), 0.55 (1H, d, J=4.6 Hz, H-19")

$^{13}$C NMR (126 MHz, CD$_3$CN) δ=202.3 (C-3), 200.1 (C-22), 170.7 (C-16a), 155.5 (C-1), 147.1 (C-23), 128.5 (C-24), 128.4 (C-2), 75.8 (C-26), 75.3 (C-16), 51.8 (C-17), 48.6 (C-14), 47.6 (C-4), 45.9 (C-13), 44.6 (C-15), 44.3 (C-8), 43.6 (C-25), 43.3 (C-5), 40.7 (C-20), 33.0 (C-10), 32.9 (C-12), 28.0 (C-11), 27.3 (C-9), 27.0 (C-19), 24.1 (C-7), 24.0 (C-6), 21.0 (C-16b), 19.4 (C-29), 18.7 (C-18), 17.5 (C-27), 16.4 (C-21), 11.3 (C-28), 11.1 (C-24a)

Example 49

26-chloro-acetate-neoboutomellerone Derivative

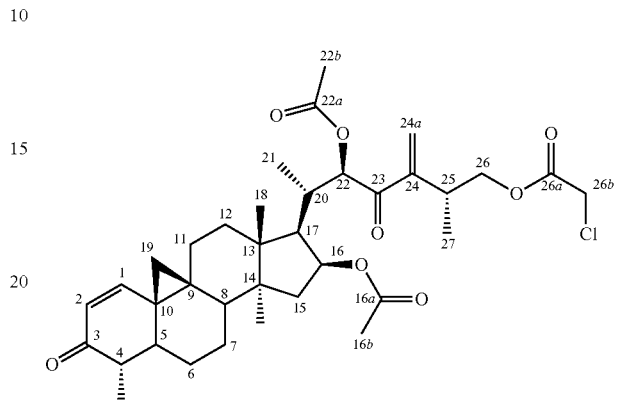

Chemical formula: $C_{36}H_{49}ClO_8$
Exact mass: 644.31
Molecular weight: 645.22

Protocol: 60 mg (0.1 mmol) of 2 is solubilized in 1 ml of anhydrous tetrahydrofuran under nitrogen. 20 μl (0.11, 1.1 eq) of triethylamine is added and the reaction medium is cooled to 0° C. 10 μl (0.11, 1.1 eq) of chloroacetyl chloride is added drop by drop. After 24 hours of stirring at room temperature, the reaction medium is diluted in ethyl acetate and is washed with distilled water and a saturated sodium chloride solution. The organic phase is dried on MgSO$_4$, filtered and concentrated in a rotary evaporator. The crude product is purified by silica gel chromatography (eluent: cyclohexane/ AcOEt: 7/3 to 6/4). The cyclic product 49 and the chloroacetyl product 49 are obtained with yields of 7% (3 mg) and 14% (10 mg), respectively.

$^1$H NMR (500 MHz, CD3CN) δ=6.94 (1H, d, J=10.1 Hz, H-1), 6.15 (1H, s, H-24a'), 6.00 (1H, s, H-24a"), 5.90 (1H, d, J=9.8 Hz, H-2), 5.53 (1H, d, J=2.4 Hz, H-22), 5.09 (1H, td, J=7.6 Hz, J=4.6 Hz, H-16), 4.16 (1H, dd, J=11.0 Hz, J=7.0 Hz, H-26<'>), 4.13 (2H, s, H-26b), 4.12 (1H, dd, J=10.7 Hz, J=6.4 Hz, H-26<">), 3.05 (1H, sxt, J=6.9 Hz, H-25), 2.58 (1H, dqd, J=11.0 Hz, J=7.0 Hz, J=2.4 Hz, H-20), 2.30 (1H, dd, J=11.0 Hz, J=7.6 Hz, H-17), 2.14-2.21 (2H, m, H-4, 15<'>), 2.09 (3H, s, H-22b), 2.03 (3H, s, H-16b), 1.96-2.07 (3H, m, H-5, 8, 11<'>), 1.63-1.77 (3H, m, H-6<'>, 12<'>, 12<">), 1.52-1.61 (1H, m, H-11<">), 1.37 (1H, dd, J=14.3 Hz, J=4.0 Hz, H-15<">), 1.24 (1H, d, J=4.3 Hz, H-19<'>), 1.19 (3H, s, H-18), 1.15-1.23 (1H, m, H-7<">), 1.09 (3H, d, J=7.0 Hz, H-27), 1.03 (3H, d, J=6.7 Hz, H-28), 0.95 (3H, s, M24), 0.88-1.00 (1H, m, H-6<">), 0.85 (3H, d, J=7.0 Hz, H-21), 0.58 (1H, d, J=4.3 Hz, H-19<'>)

$^{13}$C NMR (126 MHz, CD3CN) δ=202.3 (C-3), 198.7 (C-23), 171.6 (C-22a), 171.2 (C-16a), 168.3 (C-26a), 155.5 (C-1), 148.7 (C-24), 128.4 (C-2), 126.1 (C-24a), 78.3 (C-22), 76.7 (C-16), 69.5 (C-26), 51.3 (C-17), 48.4 (C-14), 47.6 (C-4), 46.9 (C-13), 46.7 (C-15), 45.2 (C-8), 43.6 (C-5), 42.1 (C-26b), 34.6 (C-25), 33.4 (C-20), 33.0 (C-12), 32.9 (C-10), 28.1 (C-11), 27.2 (C-9), 24.3 (C-7, 6), 22.1 (C-16b), 20.9 (C-22b), 20.0 (C-29), 18.3 (C-18), 17.0 (C-27), 13.3 (C-21), 11.3 (C-28)

Example 50

16-deacetyl-22-deacetyl-neoboutomellerone-16,26-23-acetal

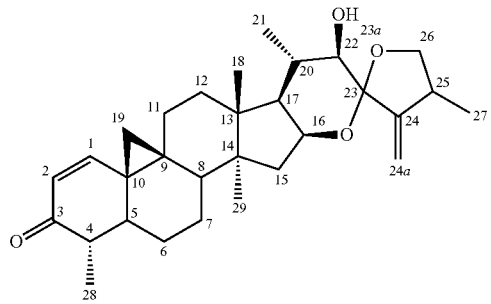

Chemical formula: $C_{30}H_{42}O_4$
Exact mass: 466.31
Molecular weight: 466.65

Protocol: In a sealed test tube, 101 mg (0.178 mmol) of 2' is dissolved in 3.2 ml of tert-butanol. A solution of 122 mg (0.889 mmol) of potassium carbonate in 0.8 ml of water is added and then the test tube is sealed and the reaction is left for 3 days at 70° C. The reaction medium is extracted with ethyl acetate, dried on sodium sulfate and after evaporation of the solvents the various products are purified by preparative TLC and eluted two times with a mixture of 20% ethyl acetate in cyclohexane and then 5 times with a mixture of 5% ethyl acetate in cyclohexane. Among the various products collected is 17 mg (20%) of compound 50 (Rf: 0.81; 50/50 cyclohexane/ethyl acetate).

$^1$H NMR (500 MHz, CD3CN) δ=6.96 (1H, d, J=9.8 Hz, H-1), 5.91 (1H, d, J=9.8 Hz, H-2), 5.26 (1H, d, J=2.7 Hz, H-24aa), 5.00 (1H, d, J=2.7 Hz, H-24ab), 4.15 (1H, t, J=7.9 Hz, H-26<'>), 4.06 (1H, td, J=7.9 Hz, J=6.4 Hz, H-16), 3.56 (1H, t, J=10.8 Hz, H-22), 3.29 (1H, t, J=8.1 Hz, H-26<">), 2.78-2.89 (1H, m, H-25), 2.34 (1H, d, J=10.7 Hz, OH-24b), 2.10-2.20 (2H, m, H-4, 8), 1.89-2.00 (3H, m, H-5, 11<'>, 20), 1.53-1.77 (5H, m, H-15<'>, 6<'>, 12<">, 12<'>, 11<">), 1.45-1.53 (1H, m, H-7<'>), 1.24-1.34 (2H, m, H-15<">, 19<'>), 1.16-1.24 (1H, m, H-7<">), 1.15 (3H, s, H-18), 1.07 (3H, d, J=6.7 Hz, H-27), 1.02 (3H, d, J=7.0 Hz', H-28), 1.00 (3H, d, J=6.4 Hz, H-21), 0.94-1.02 (1H, m, H-6<">), 0.85 (3H, s, H-29), 0.52 (1H, d, J=4.6 Hz, H-19<">)

$^{13}$C NMR (126 MHz, CD3CN) δ=202.3 (C-3), 155.4 (C-1), 154.4 (C-24), 128.4 (C-2), 107.1 (C-23), 105.3 (C-24a), 74.1 (C-26), 73.0 (C-22), 71.8 (C-16), 56.2 (C-17), 48.0 (C-14), 47.5 (C-4), 45.7 (C-13), 44.0 (C-15), 43.6 (C-8), 43.2 (C-5), 36.5 (C-25), 33.4 (C-12), 33.1 (C-10), 32.3 (C-20), 28.1 (C-11), 27.5 (C-9), 26.6 (C-19), 24.0 (C-6), 23.9 (C-7), 20.0 (C-18), 19.1 (C-29), 16.9 (C-21), 15.4 (C-27), 11.3 (C-28)

Example 51

16-deacetyl-26-methoxy-neoboutomellerone-hemiacetal

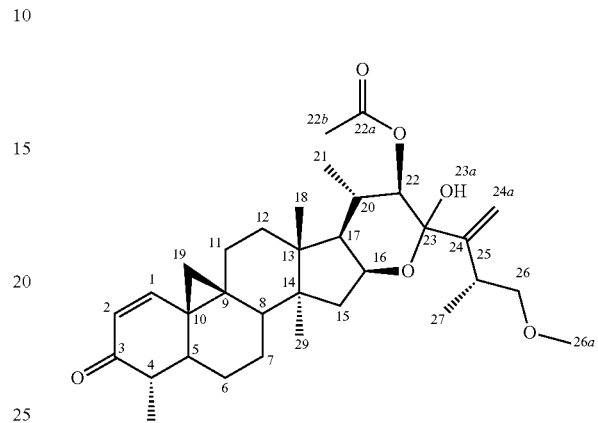

Chemical formula: $C_{33}H_{48}O_6$
Exact mass: 540.35
Molecular weight: 540.73

Protocol: 568 mg (1.0 mmol) of 2 is dissolved in 1 ml of THF which was added at 0° C. to a suspension of 50.4 mg (2.1 eq, 2.1 mmol) of NaH in 1 ml of THF. After 15 minutes of stirring at room temperature, the reaction medium is cooled to 0° C. and then iodomethane (312 μl, 5 eq, 5 mmol) is added and the reaction is left under stirring overnight. After complete disappearance of the starting product, as analyzed by TLC (AcOEt/cyclohexane eluent: 1/1), the reaction is hydrolyzed with 4 ml of 2 N hydrochloric acid and extracted with ethyl acetate. The organic phase is washed successively with water, a thiosulfate solution, water and then brine. 635 mg of crude reaction product is collected which is purified on a silica gel and eluted with a 100/0 to 40/60 cyclohexane/ethyl acetate gradient. Among other products, 80 mg (15%) of compound 51 (Rf: 0.76; 50/50 cyclohexane/ethyl acetate) is collected.

$^1$H NMR (500 MHz, CD3CN) δ=6.96 (1H, d, J=10.1 Hz, H-1), 5.91 (1H, d, J=10.1 Hz, H-2), 5.52 (1H, s, H-24aa), 5.16 (1H, s, H-24ab), 4.99 (1H, s, OH-23a), 4.88 (1H, d, J=11.3 Hz, H-22), 4.49 (1H, td, J=7.9 Hz, J=6.4 Hz, H-16), 3.46 (1H, dd, J=7.9 Hz, J=4.6 Hz, H-26<'>), 3.28 (3H, s, H-26a), 3.03 (1H, dd, J=10.7 Hz, J=7.9 Hz, H-26<">), 2.51-2.63 (1H, m, H-25), 2.09-2.27 (2H, m, H-4, 8), 2.02 (3H, s, H-22b), 1.97 (2H, s, H-5, 11<'>), 1.79-1.88 (3H, m, H-17, 20, 15<'>), 1.55-1.75 (4H, m, H-6<'>, 11<">, 12<">, 12<'>), 1.48-1.55 (1H, m, H-7<'>), 1.41-1.48 (1H, m, H-15<">), 1.29 (1H, d, J=4.6 Hz, H-19<'>), 1.19 (3H, s, H-18), 1.19-1.27 (1H, m, H-7<">), 1.07 (3H, d, J=7.3 Hz, H-27), 1.03 (3H, d, J=7.0 Hz, H-28), 0.94-1.05 (1H, m, H-6<">), 0.91 (3H, s, H-29), 0.78 (3H, d, J=6.1 Hz, H-21), 0.54 (1H, d, J=4.3 Hz, H-19<'>)

$^{13}$C NMR (126 MHz, CD3CN) δ=202.3 (C-3), 171.2 (C-22a), 155.4 (C-1), 154.7 (C-24), 128.5 (C-2), 113.0 (C-24a), 99.9 (C-23), 81.8 (C-26), 81.4 (C-22), 71.3 (C-16), 59.4 (C-26a), 56.8 (C-17), 48.4 (C-14), 47.5 (C-4), 45.8 (C-13), 44.1 (C-8), 43.7 (C-15), 43.3 (C-5), 35.7 (C-25), 33.3 (C-12), 33.1 (C-10), 30.8 (C-20), 28.1 (C-11), 27.4 (C-9), 26.9 (C-19), 24.1 (C-7, 6), 21.1 (C-22b), 19.9 (C-18), 19.1 (C-29), 17.4 (C-27), 15.7 (C-21), 11.3 (C-28)

Example 52

26-TBDMS-neoboutomellerone

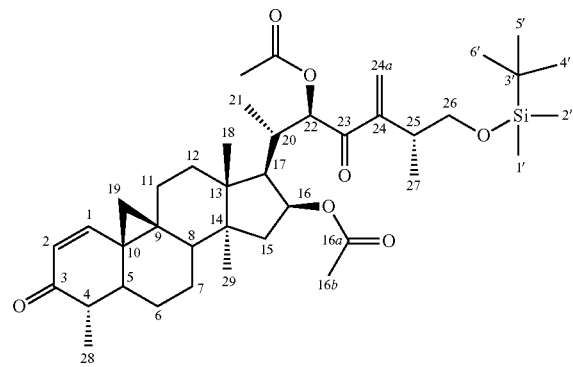

Chemical formula: $C_{40}H_{62}O_7Si$
Exact mass: 682.43
Molecular weight: 683.00

Protocol: 200 mg (0.352 mmol) of compound 2 is dissolved in 3 ml of DCM and then 6.5 eq (2.29 mmol, 157 mg) of imidazol is added. The reaction is cooled to 0° C. at which temperature a solution of TBDMSOTf (3 eq, 1.05 mmol, 0.241 ml) in 6 ml of DCM is added. The reaction is left under stirring at 0° C. for 2 h. The reaction is then hydrolyzed with sodium bicarbonate, extracted three times with 10 ml of DCM and the combined organic phases are washed with brine. After drying on sodium sulfate and evaporation of the solvent, 207 mg of crude reaction product is collected. The product is purified on a silica gel column and is eluted with a 100/0 to 80/20 cyclohexane/ethyl acetate gradient. 141 mg (59%) of product 52 (Rf: 0.32; 80/20 cyclohexane/ethyl acetate) is obtained.

$^1$H NMR (500 MHz, ACETONITRILE-$d_3$) δ=6.94 (1H, d, J=10.1 Hz, H-1), 6.05 (1H, s, H-24a'), 5.90 (1H, d, J=0.9 Hz, H-24a"), 5.90 (1H, d, J=9.8 Hz, H-2), 5.52 (1H, d, J=2.4 Hz, H-22), 5.08 (1H, td, J=7.6 Hz, J=4.3 Hz, H-16), 3.68 (1H, dd, J=9.9 Hz, J=5.6 Hz, H-26<'>), 3.47 (1H, dd, J=9.9 Hz, J=6.6 Hz, H-26<">), 2.77 (1H, sxt, J=6.6 Hz, H-25), 2.58 (1H, dqd, J=10.7 Hz, J=6.7 Hz, J=2.1 Hz, H-20), 2.29 (1H, dd, J=11.0 Hz, J=7.6 Hz, H-17), 2.15-2.20 (2H, m, H-4, 15<'>), 2.08 (3H, s, H-22b), 2.02 (3H, s, H-16b), 1.96-2.06 (3H, m, 5, 8, H-11<'>), 1.62-1.76 (3H, m, H-6<'>, 12<'>, 12<">), 1.51-1.61 (1H, m, H-11<">), 1.41-1.48 (1H, m, H-7<'>), 1.36 (1H, dd, J=14.0 Hz, J=4.3 Hz, H-15<">), 1.24 (1H, d, J=4.3 Hz, H-19<'>), 1.18 (3H, s, H-18), 1.14-1.22 (1H, m, H-7<">), 1.05 (3H, d, J=7.0 Hz, H-27), 1.02 (3H, d, J=6.7 Hz, H-28), 0.95 (3H, s, H-29), 0.91-0.99 (1H, m, H-6<">), 0.88 (9H, s, H-4', 5', 6'), 0.84 (3H, d, J=7.0 Hz, H-21), 0.58 (1H, d, J=4.3 Hz, H-19<">), 0.04 (3H, s, H-1'), 0.03 (3H, s, H-2')

$^{13}$C NMR (126 MHz, ACETONITRILE-$d_3$) δ=202.4 (C-3), 199.3 (C-23), 171.6 (C-22a), 171.2 (C-16a), 155.5 (C-1), 150.0 (C-24), 128.4 (C-2), 125.0 (C-24a), 78.4 (C-22), 76.7 (C-16), 67.4 (C-26), 51.3 (C-17), 48.4 (C-14), 47.6 (C-4), 46.8 (C-13), 46.7 (C-15), 45.2 (C-8), 43.6 (C-5), 38.1 (C-25), 33.3 (C-20), 33.0 (C-12), 32.9 (C-10), 30.7, 28.1 (C-11), 27.7 (C-19), 27.2 (C-9), 26.3 (C-4', 5', 6'), 24.3 (C-6), 24.3 (C-7), 22.1 (C-16b), 20.9 (C-22b), 20.0 (C-29), 18.9 (C-3'), 18.3 (C-18), 17.1 (C-27), 13.4 (C-21), 11.3 (C-28), −5.1 (C-1'), −5.1 (C-2')

Example 53

26-TBDMS-22-deacetyl-neoboutomellerone

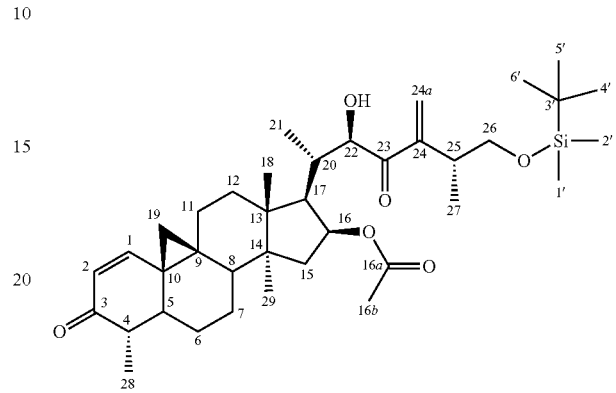

Chemical formula: $C_{38}H_{60}O_6Si$
Exact mass: 640.42
Molecular weight: 640.96

Protocol: 400 mg (0.760 mmol) of 1 is dissolved in 6 ml of DCM and then 6.5 eq (4.94 mmol, 336 mg) of imidazol is added. The reaction is cooled to 0° C. at which temperature a solution of TBDMSOTf (3 eq, 2.27 mmol, 0.520 ml) in 12 ml of DCM is added. The reaction is left under stirring at 0° C. until the starting product disappears (approximately 1 hour). The reaction is then hydrolyzed with sodium bicarbonate, extracted three times with 10 ml of DCM and the combined organic phases are washed with brine. After drying on sodium sulfate and evaporation of the solvent, 750 mg of crude reaction product is collected. The product is purified on a silica gel column and is eluted with a 100/0 to 80/20 cyclohexane/ethyl acetate gradient. 430 mg (88%) of product 53 (Rf: 0.32; 80/20 cyclohexane/ethyl acetate) is obtained.

$^1$H NMR (500 MHz, CD3CN) δ=6.93 (1H, d, J=10.1 Hz, H-1), 6.13 (1H, s, H-24a'), 5.99 (1H, s, H-24a"), 5.89 (1H, d, J=10.1 Hz, H-2), 5.20 (1H, td, J=7.3 Hz, J=4.6 Hz, H-16), 4.70 (1H, dd, J=6.1 Hz, J=1.8 Hz, H-22), 3.70 (1H, dd, J=9.8 Hz, J=5.5 Hz, H-26<'>), 3.53 (1H, d, J=6.1 Hz, OH-22), 3.49 (1H, dd, J=9.8 Hz, J=6.7 Hz, H-26<">), 2.84 (1H, sxt, J=6.5 Hz, H-25), 2.37-2.51 (2H, m, H-17, 20), 2.22 (1H, dd, J=14.0 Hz, J=7.9 Hz, H-15<'>), 2.15-2.21 (1H, m, H-4), 2.02 (3H, s, H-16b), 1.95-2.08 (3H, m, H-5,8,11<'>), 1.59-1.75 (3H, m, H-6<'>, 12<'>, 12<">), 1.50-1.58 (1H, m, H-11<">), 1.41-1.49 (1H, m, H-7<'>), 1.38 (1H, dd, J=14.0 Hz, J=4.0 Hz, H-15<">), 1.23 (1H, d, J=4.3 Hz, H-19<'>), 1.18-1.27 (1H, m, H-7<">), 1.17 (3H, s, H-18), 1.06 (3H, d, J=7.0 Hz, H-27), 1.02 (3H, d, J=6.7 Hz, H-28), 0.96 (3H, s, H-29), 0.91-0.99 (1H, m, H-6<">), 0.88 (9H, s, H-6', 5', 4'), 0.64 (3H, d, J=6.4 Hz, H-21), 0.57 (1H, d, J=4.6 Hz, H-19<">), 0.04 (3H, s, H-1'), 0.03 (3H, s, H-2')

$^{13}$C NMR (126 MHz, CD3CN) δ=205.3 (C-3), 202.4, 171.6 (C-16a), 155.6 (C-1), 148.8 (C-24), 128.4 (C-2), 126.8 (C-24a), 77.2 (C-16), 75.8 (C-22), 67.6 (C-26), 51.4 (C-17), 48.3 (C-14), 47.6 (C-4), 46.9 (C-15), 46.7 (C-13), 45.3 (C-8), 43.6 (C-5), 37.8 (C-25), 36.4 (C-20), 33.1 (C-12), 32.9 (C-10), 28.1 (C-11), 27.7 (C-19), 27.2 (C-9), 26.3 (C-4', 5',

6'), 24.3 (C-6), 24.3 (C-7), 22.1 (C-16b), 20.1 (C-29), 18.9 (C-3'), 18.5 (C-18), 17.1 (C-27), 12.3 (C-21), 11.3 (C-28), −5.1 (C-1'), −5.1 (C-2')

Example 54

22-deacetyl-neoboutomellerone-(26-TBDMS) 22-N-Boc-glycinate

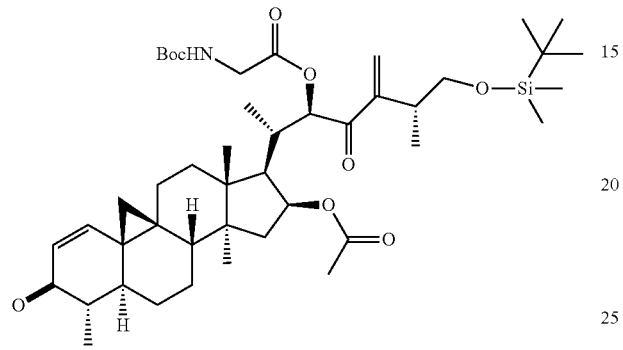

Chemical formula: $C_{32}H_{48}O_6$
Exact mass: 528.35
Molecular weight: 528.72

Protocol: 100 mg of compound 53 is dissolved in 3 ml of DCM and then 2.5 ml (1.6 eq) of a 0.1 M DCC solution is added, followed by a catalytic quantity of DMAP (2 mg, 0.1 eq) and finally 41 mg (1.5 eq) of N-Boc-Gly-OH. The reaction is left under stirring for 4 h at room temperature. The reaction medium is filtered on Celite® and product 54 (Rf: 0.43; 70/30 cyclohexane/ethyl acetate) is purified on a silica gel (eluent: 100/0 to 70/30 cyclohexane/ethyl acetate gradient).

$^1$H NMR (500 MHz, ACETONITRILE-$d_3$) δ=6.94 (1H, d, J=10.1 Hz, H-1), 6.06 (1H, s, H-24aa), 5.92 (1H, s, H-24ab), 5.90 (1H, d, J=10.1 Hz, H-2), 5.58 (1H, d, J=2.1 Hz, H-22), 5.06 (1H, td, J=7.6 Hz, J=4.6 Hz, H-16), 3.93 (1H, dd, J=17.7 Hz, J=6.4 Hz, H-22b<'>), 3.82 (1H, dd, J=17.7 Hz, J=6.1 Hz, H-22b<">), 3.68 (1H, dd, J=10.1 Hz, J=5.5 Hz, H-26<'>), 3.47 (1H, dd, J=9.9 Hz, J=6.6 Hz, H-26<">), 2.78 (1H, sxt, J=6.6 Hz, H-25), 2.54-2.66 (1H, m, H-20), 2.30 (1H, dd, J=10.8 Hz, J=7.5 Hz, H-17), 2.15-2.23 (2H, m, H-4, 15<'>), 2.02 (3H, s, H-16b), 1.96-2.09 (3H, m, H-5,8,11<'>), 1.63-1.74 (3H, m, H-6<'>, 12<">, 12<'>), 1.53-1.63 (1H, m, H-11<">), 1.41 (9H, s, H-22f, 22g, 22h), 1.35-1.45 (1H, m, H-7<'>), 1.24 (1H, d, J=4.3 Hz, H-19<'>), 1.18 (3H, s, H-18), 1.14-1.20 (1H, m, H-6<">), 1.05 (3H, d, J=7.0 Hz, H-27), 1.02 (3H, d, J=6.7 Hz, H-28), 0.97 (3H, s, H-29), 0.91-0.96 (1H, m, H-7<">), 0.88 (9H, s, H-26g, 26f, 26e), 0.84 (3H, d, J=7.0 Hz, H-21), 0.57 (1H, d, J=4.6 Hz, H-19<">), 0.04 (3H, s, H-26c), 0.03 (3H, s, H-26b)

$^{13}$C NMR (126 MHz, ACETONITRILE-$d_3$) δ=202.3 (C-3), 198.7 (C-23), 171.3 (C-22a), 171.2 (C-16a), 156.9 (C-22d), 155.5 (C-1), 149.8 (C-24), 128.4 (C-2), 125.3 (C-24a), 80.0 (C-22e), 78.9 (C-22), 76.7 (C-16), 67.3 (C-26), 51.2 (C-17), 47.6 (C-4), 46.7 (C-15), 45.0 (C-8), 43.5 (C-5), 43.0 (C-22b), 38.1 (C-25), 33.6 (C-20), 33.0 (C-12), 28.6 (C-22h, 22g, 22f), 28.1 (C-11), 27.5 (C-19), 26.3 (C-26g, 26f, 26e), 24.2 (C-6), 24.2 (C-7), 22.1 (C-16b), 20.0 (C-29), 18.9 (C-26d), 18.2 (C-18), 17.1 (C-27), 13.4 (C-21), 11.3 (C-28), −5.1 (C-26c), −5.1 (C-26b)

Example 55

22-deacetyl-neoboutomellerone 22-N-Boc-glycinate

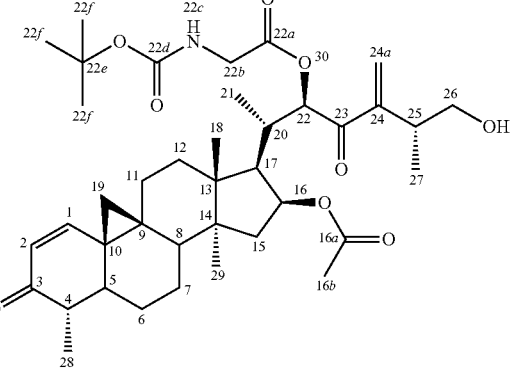

Chemical formula: $C_{39}H_{57}NO_9$
Exact mass: 683.40
Molecular weight: 683.87

Protocol: 118 mg of compound 54 (0.148 mmol) is dissolved in 0.25 ml of THF. 0.32 ml of pyridine is added followed by three times 1.1 ml of a solution of HF in pyridine. The reaction is left under stirring for 21 h at room temperature. The reaction medium is diluted with 2 ml of ethyl acetate and then the medium is neutralized to pH=7 with a sodium bicarbonate solution. The various phases are separated and the organic phase is washed with a copper sulfate solution and rinsed several times with water and then brine. After drying on sodium sulfate and evaporation of the solvent, 84 mg of crude reaction product is collected.

The product is purified on a silica gel column and eluted with a 70/30 to 40/60 cyclohexane/ethyl acetate gradient. 44.5 mg (51%) of product (Rf: 0.24; 60/40 cyclohexane/ethyl acetate) is obtained.

$^1$H NMR (500 MHz, ACETONITRILE-$d_3$) δ=6.93 (1H, d, J=10.0 Hz, H-1), 6.05 (1H, s, H-24ab), 5.91 (2H, s, H-24aa), 5.90 (1H, d, J=10.0 Hz, H-2), 5.59 (1H, d, J=2.0 Hz, H-22), 5.07 (1H, td, J=7.4 Hz, J=4.4 Hz, H-16), 3.94 (1H, dd, J=7.0 Hz, J=2.6 Hz, H-22b<'>), 3.82 (1H, dd, J=7.0 Hz, J=2.5 Hz, H-22b<">), 3.53 (1H, ddd, J=12.0 Hz, J=6.0 Hz, H-26<'>), 3.39 (1H, ddd, J=12.0 Hz, J=6.0 Hz, H-26<">), 2.78 (1H, sxt, J=7.0 Hz, H-25), 2.68-2.73 (1H, m, H-17), 2.59-2.67 (1H, m, H-20), 2.29 (1H, dd, J=11.0 Hz, J=7.0 Hz, H-15<'>), 2.12-2.21 (6H, m, H-11<'>, 22c, 4, 37), 2.03 (3H, s, H-16b), 1.98-2.02 (1H, m, H-5a), 1.62-1.76 (3H, m, H-12<">, 12<'>, 6<'>), 1.52-1.62 (1H, m, H-11<">), 1.42-1.50 (1H, m, $H_{77<}$'>), 1.41 (9H, s, H-22f, 22f, 22f), 1.33-1.36 (1H, m, H-15<">), 1.23-1.26 (1H, m, H-19<'>), 1.18 (3H, s, H-18), 1.03 (4H, d, J=4.0 Hz, H-27), 1.02 (3H, d, J=3.7 Hz, H-28), 0.97 (3H, s, H-29), 0.85 (3H, d, J=7.0 Hz, H-21), 0.57 (1H, d, J=4.5 Hz, H-19<">)

¹³C NMR (126 MHz, ACETONITRILE-d₃) δ=202.4 (C-3), 199.1 (C-23), 171.4 (C-22a), 171.3 (C-16a), 156.8 (C-22d), 155.5 (C-1), 150.2 (C-24), 128.4 (C-2), 124.9 (C-24a), 80.1 (C-22e), 79.0 (C-22), 76.7 (C-16), 66.4 (C-26), 51.2 (C-17), 48.4 (C-14), 47.6 (C-4), 46.8 (C-13), 46.7 (C-15), 45.0 (C-8), 43.5 (C-5), 43.0 (C-22b), 37.9 (C-25), 33.5 (C-20), 33.0 (C-12), 33.0 (C-10), 28.6 (C-40, 46, 22H), 28.1 (C-11), 27.5 (C-19), 27.2 (C-9), 24.2 (C-7), 24.2 (C-6), 22.1 (C-16b), 20.0 (C-29), 18.2 (C-18), 17.2 (C-27), 13.3 (C-21), 11.3 (C-28).

Example 56

Neoboutomellerone 26-N-Boc-glycinate

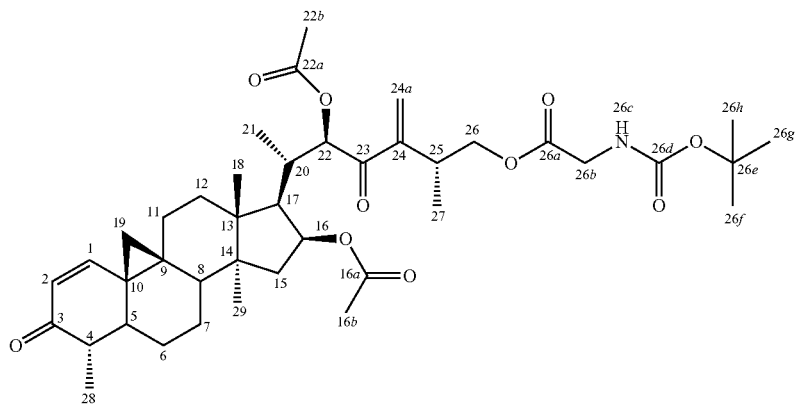

Chemical formula: C₄₁H₅₉NO₁₀
Exact mass: 725.41
Molecular weight: 725.91

Protocol: 100 mg (0.18 mmol) of 2 is solubilized in 1 ml of anhydrous dichloromethane. 40 mg (0.21 mmol, 1.2 eq) of EDC, 37 mg (0.21 mmol, 1.2 eq) of N-Boc-glycine and 2 mg (0.017 mmol, 0.1 eq) of DMAP are added successively. After 18 h of stirring at room temperature, the reaction medium is diluted with ethyl acetate. The organic phase is washed successively with a 4% HCl solution, a saturated sodium bicarbonate solution and a saturated sodium chloride solution. The organic phase is dried on MgSO₉, filtered and concentrated in a rotary evaporator. The product is purified by silica chromatography (eluent: cyclohexane/AcOEt: 6/4). A white solid is obtained with a yield of 85% (80 mg).

¹H NMR (500 MHz, CD₃CN) δ=6.94 (1H, d, J=10.1 Hz, H-1), 6.13 (1H, s, H-24aa), 5.98 (1H, s, H-24ab), 5.90 (1H, d, J=10.1 Hz, H-2), 5.57 (1H, t, J=6.0 Hz, H-26c), 5.53 (1H, d, J=2.1 Hz, H-22), 5.09 (1H, td, J=7.7 Hz, J=4.4 Hz, H-16), 4.11 (1H, dd, J=10.7 Hz, J=6.7 Hz, H-26<'>), 4.01-4.07 (1H, m, H-26<">), 3.72 (2H, d, J=6.4 Hz, H-26b), 3.02 (1H, sxt, J=6.8 Hz, H-25), 2.58 (1H, dqd, J=11.0 Hz, J=6.7 Hz, J=2.1 Hz, H-20), 2.30 (1H, dd, J=10.8 Hz, J=7.5 Hz, H-17), 2.14-2.22 (2H, m, H-4, 15<'>), 2.09 (3H, s, H-22b), 2.04 (3H, s, H-16b), 1.97 (4H, s, H-5,8,11<'>), 1.62-1.76 (3H, m, H-6<'>, 12<">, 12<'>), 1.51-1.60 (1H, m, H-11<">), 1.41-1.48 (1H, m, H-7<'>), 1.41 (9H, s, H-26h, 26g, 26f), 1.37 (1H, dd, J=14.3 Hz, J=4.0 Hz, H-15<">), 1.24 (1H, d, J=4.3 Hz, H-19<'>), 1.19 (3H, s, H-18), 1.16-1.23 (1H, m, H-7<">), 1.08 (3H, d, J=7.0 Hz, H-27), 1.02 (3H, d, J=6.7 Hz, H-28), 0.95 (3H, s, H-29), 0.93 (1H, qd, J=12.8 Hz, J=4.0 Hz, H-6<">), 0.85 (3H, d, J=6.7 Hz, H-21), 0.57 (1H, d, J=4.6 Hz, H-19<">)

¹³C NMR (126 MHz, CD₃CN) δ=202.3 (C-3), 198.8 (C-23), 171.7 (C-22a), 171.4 (C-26a), 171.2 (C-16a), 155.5 (C-1), 148.9 (C-24), 128.4 (C-2), 126.0 (C-24a), 78.3 (C-22), 76.7 (C-16), 68.5 (C-26), 51.3 (C-17), 48.4 (C-14), 47.6 (C-4), 46.9 (C-13), 46.7 (C-15), 45.2 (C-8), 43.6 (C-5), 43.0 (C-26b), 34.7 (C-25), 33.4 (C-20), 32.9 (C-10, 12), 28.6 (C-26h, 26g, 26f), 28.1 (C-11), 27.7 (C-19), 27.2 (C-9), 24.3

(C-7, 6), 22.1 (C-16b), 20.9 (C-22b), 20.0 (C-29), 18.3 (C-18), 17.1 (C-27), 13.3 (C-21), 11.3 (C-28)

Example 57

Neoboutomellerone 26-N-glycinate

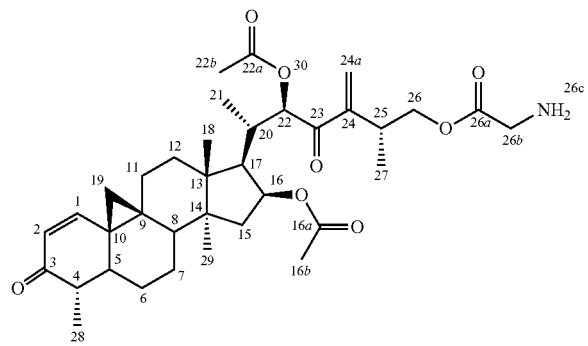

Chemical formula: $C_{34}H_{53}NO_7$
Exact mass: 623.38
Molecular weight: 623.82

Protocol: 29 mg (0.04 mmol, 1 eq) of 56 is solubilized in 600 µl of anhydrous dichloromethane at 0° C. 30 µl (0.4 mmol, 10 eq) of trifluoroacetic acid is added and the reaction medium is stirred at 0° C. After 30 minutes, 30 µl (0.4 mmol, 10 eq) of trifluoroacetic acid is added and the reaction medium is stirred at room temperature for 20 h. The reaction medium is then concentrated in a rotary evaporator. The residue is taken up in water. The aqueous phase is then basified with a saturated sodium carbonate solution. The aqueous phase is then extracted five times with ethyl acetate. The organic phase is washed with a saturated sodium chloride solution, dried on $Na_2SO_4$, filtered and concentrated in a rotary evaporator. The product is purified by silica chromatography (eluent: DCM/MeOH: 95/5). A white solid 57 is obtained with a yield of 24% (6.6 mg).

$^1$H NMR (500 MHz, ACETONITRILE-$d_3$) δ=6.94 (1H, d, J=10.1 Hz, H-1), 6.12 (1H, s, H-24aa), 5.97 (1H, s, H-24ab), 5.90 (1H, d, J=9.8 Hz, H-2), 5.52 (1H, d, J=2.1 Hz, H-22), 5.10 (1H, td, J=7.7 Hz, J=4.4 Hz, H-16), 3.99-4.16 (2H, m, H-26), 3.25-3.31 (2H, m, H-26b), 3.00 (1H, sxt, J=7.0 Hz, H-25), 2.52-2.66 (1H, m, H-20), 2.29 (1H, dd, J=10.9 Hz, J=7.5 Hz, H-17), 2.12-2.22 (2H, m, H-15<'>, 4), 2.09 (3H, s, H-22b), 2.03 (4H, s, H-11<">, 16b), 1.95-1.98 (2H, m, H-8a, 5a), 1.63-1.74 (3H, m, H-12<">, 12<>, 6<'>), 1.52-1.62 (1H, m, H-11<">), 1.40-1.49 (1H, m, H-7<">), 1.37 (1H, dd, J=14.2 Hz, J=4.1 Hz, H-15<">), 1.24 (1H, d, J=4.3 Hz, H-19<>), 1.21-1.23 (1H, m, H-7<'>), 1.18 (3H, s, H-18), 1.08 (3H, d, J=7.0 Hz, H-27), 1.02 (3H, d, J=6.7 Hz, H-28), 0.95 (4H, s, H-29), 0.90-0.93 (1H, m, H-6<">), 0.84 (3H, d, J=7.0 Hz, H-21), 0.58 (1H, d, J=4.6 Hz, H-19<">)

$^{13}$C NMR (126 MHz, ACETONITRILE-$d_3$) δ=202.4 (C-3), 198.9 (C-23), 175.3 (C-26a), 171.7 (C-22a), 171.3 (C-16a), 155.5 (C-1), 149.1 (C-24), 128.4 (C-2), 125.8 (C-24a), 78.3 (C-22), 76.7 (C-16), 68.0 (C-26), 51.3 (C-17), 48.4 (C-14), 47.6 (C-4), 46.8 (C-13), 46.7 (C-15), 45.2 (C-8), 44.7 (C-26b), 43.6 (C-5), 34.9 (C-25), 33.3 (C-20), 32.9 (C-10, 12), 28.1 (C-11), 27.7 (C-19), 27.2 (C-9), 24.3 (C-6, 7), 22.1 (C-16b), 20.9 (C-22b), 20.0 (C-29), 18.3 (C-18), 17.2 (C-27), 13.3 (C-21), 11.3 (C-28)

Example 58

22-deacetyl-neoboutomellerone 26-N-Boc-glycinate

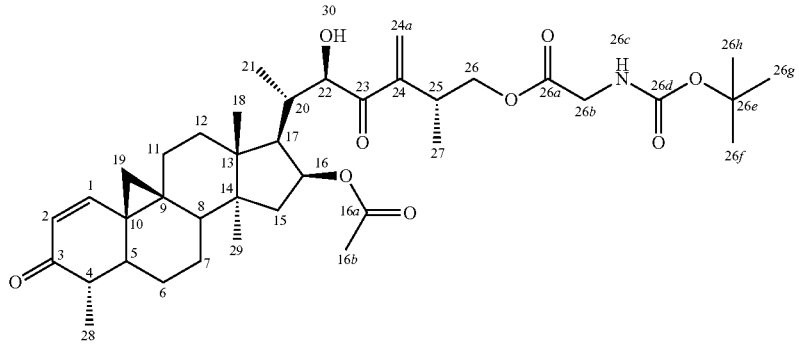

Chemical formula: $C_{39}H_{57}NO_9$
Exact mass: 683.40
Molecular weight: 683.87

Protocol 1: The same reaction as for example 56 was carried out on 100 mg of compound 1 (0.19 mmol) with 36 mg of EDC (0.19 mmol, 1 eq), 33 mg of N-Boc-glycine (0.19 mmol, 1 eq) and 2 mg of DMAP (cat.) in 1 ml of anhydrous dichloromethane. The product is obtained with a yield of 51% after purification on a silica gel (eluent: cyclohexane/AcOEt: 6/4 to 5/5).

Protocol 2: Compound 58 can also be obtained from compound 55. A solution of TBAF in THF is added to a solution of 55 in THF and the reaction medium is left under stirring for 3 hours.

After complete conversion of the substrate (followed by TLC: AcOEt/cyclohexane: 6/4), the reaction medium is diluted with ether and then washed with water and then with brine. After drying on sodium sulfate and evaporation of the solvents, compound 58 is collected and then purified on a silica gel with a 70/30 to 40/60 cyclohexane/ethyl acetate gradient.

$^1$H NMR (500 MHz, $CD_3CN$) δ=6.94 (1H, d, J=9.8 Hz, H-1), 6.19 (1H, s, H-24aa), 6.06 (1H, d, J=0.6 Hz, H-24ab), 5.89 (1H, d, J=10.1 Hz, H-2), 5.56 (1H, t, J=5.2 Hz, NH-26c), 5.20 (1H, td, J=7.4 Hz, J=4.4 Hz, H-16), 4.72 (1H, dd, J=6.1 Hz, J=1.5 Hz, H-22), 4.07-4.19 (2H, m, H-26<">, 26<'>), 3.72 (2H, d, J=6.4 Hz, H-26b), 3.53 (1H, d, J=6.1 Hz, OH-30), 3.06 (1H, sxt, J=6.9 Hz, H-25), 2.38-2.50 (2H, m, H-20, 17), 2.22 (1H, dd, J=14.0 Hz, J=7.9 Hz, H-15<'>), 2.15-2.21 (1H, m, H-4), 2.04 (3H, s, H-16b), 1.95-2.09 (3H, m, H-5,8,11<'>), 1.60-1.75 (3H, m, H-6<'>, 12<">, 12<'>), 1.50-1.59 (1H, m, H-11<">), 1.42-1.49 (1H, m, H-7<'>), 1.40 (9H, s, H-26h, 26g, 26f), 1.34-1.41 (1H, m, H-15<">), 1.24 (1H, d, J=4.3 Hz, H-19<'>), 1.18 (3H, s, H-18), 1.15-1.25 (1H, m, H-7<">), 1.10 (3H, d, J=7.0 Hz, H-27), 1.03 (3H, d, J=7.0 Hz, H-28), 0.96 (3H, s, H-29), 0.89-0.99 (1H, m, H-6<">), 0.64 (3H, d, J=6.4 Hz, H-21), 0.57 (1H, d, J=4.3 Hz, H-19<'>)

$^{13}$C NMR (126 MHz, CD$_3$CN) δ=204.9 (C-23), 202.4 (C-3), 171.4 (C-26a), 171.3 (C-16a), 157.0 (C-26d), 155.6 (C-1), 147.7 (C-24), 128.4 (C-2), 127.7 (C-24a), 80.0 (C-26e), 77.3 (C-16), 75.8 (C-22), 68.5. (C-26), 51.4 (C-17), 48.3 (C-14), 47.6 (C-4), 46.9 (C-15), 46.7 (C-13), 45.3 (C-8), 43.6 (C-5), 43.0 (C-26b), 36.4 (C-20), 34.6 (C-25), 33.1 (C-12), 32.9 (C-10), 28.6 (C-26h, 26g, 26f), 28.1 (C-11), 27.7 (C-19), 27.2 (C-9), 24.3 (C-7), 24.3 (C-6), 22.1 (C-16b), 20.1 (C-29), 18.5 (C-18), 17.1 (C-27), 12.3 (C-21), 11.3 (C-28)

Example 59

22-deacetyl-neoboutomellerone 22,26-bis(N-Boc-glycinate)

acetate. The organic phase is washed successively with a 4% HCl solution, a saturated sodium bicarbonate solution and saturated sodium chloride solution. The organic phase is dried on MgSO$_4$, filtered and concentrated in a rotary evaporator. The mixture is purified by preparative HPLC (SunFire™ column, 250*30; 10 µm; flow rate: 25 ml/min) and eluted with a 6/4 cyclohexane/AcOEt mixture. 153 mg (48%) of compound 59 and 94 mg (36%) of compound 58 are obtained.

$^1$H NMR (500 MHz, ACETONITRILE-d$_3$) δ=6.94 (1H, d, J=9.8 Hz, H-1), 6.15 (1H, s, H-24aa), 6.01 (1H, s, H-24ab), 5.90 (1H, d, J=10.1 Hz, H-2), 5.59 (1H, d, J=2.1 Hz, H-22), 5.07 (1H, td, J=7.7 Hz, J=4.4 Hz, H-16), 4.37 (1H, s, H-26c), 4.32 (1H, d, J=5.8 Hz, H-22c), 4.07-4.12 (2H, m, H-26<">, 26<'>), 3.95 (1H, dd, J=17.7 Hz, J=6.4 Hz, H-22b<'>), 3.82 (1H, dd, J=17.7 Hz, J=6.1 Hz, H-22b<">), 3.70-3.75 (2H, m, H-26b<">, 26b<'>), 3.04 (1H, sxt, J=6.8 Hz, H-25), 2.62 (1H, dtd, J=13.8 Hz, J=6.0 Hz, J=2.1 Hz, H-20), 2.30 (1H, dd, J=10.7 Hz, J=7.6 Hz, H-17), 2.14-2.21 (5H, m, H-15<'>, 4), 2.04 (3H, s, H-16b), 2.01 (1H, dd, J=9.6 Hz, J=3.8 Hz, H-11<'>, 5a, 8a), 1.64-1.81 (3H, m, H-12<">, 12<'>, 6<'>), 1.51-1.62 (1H, m, H-11<">), 1.43-1.48 (1H, m, H-7<'>), 1.41 (18H, s, H-22f, 22f, 22f, 26f, 26f, 26f), 1.34-1.39 (2H, m, H-15">), 1.26-1.29 (1H, m, H-7<">), 1.25 (1H, d, J=4.3 Hz, H-19<'>), 1.19 (3H, d, J=1.2 Hz, H-18), 1.08 (3H, d, J=7.0 Hz, H-27), 1.02 (3H, d, J=6.7 Hz, H-28), 0.97 (3H, s, H-29), 0.92-0.96 (1H, m, H-6<">), 0.84 (3H, d, J=7.0 Hz, H-21), 0.57 (1H, d, J=4.3 Hz, H-19<'>).

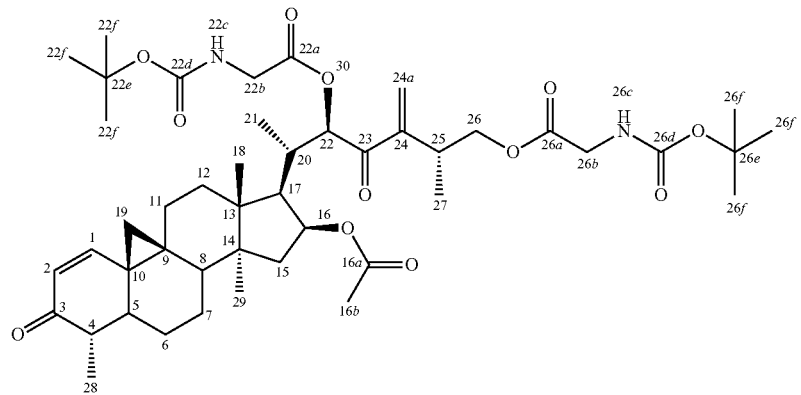

Chemical formula: C$_{46}$H$_{68}$N$_2$O$_{12}$
Exact mass: 840.48
Molecular weight: 841.04

Protocol: 200 mg (0.38 mmol) of 1 is solubilized in 18 ml of anhydrous DCM. 401 mg (2.01 mmol, 5.5 eq) of EDC, 333 mg (1.91 mmol, 5.0 eq) of N-Boc-glycine and 23 mg (0.19 mmol, 0.5 eq) of DMAP are then added. After week at room temperature, the reaction medium is diluted with ethyl $^{13}$C NMR (126 MHz, ACETONITRILE-d$_3$) δ=202.4 (C-3), 198.2 (C-23), 171.5 (C-22a), 171.4 (C-26a), 171.2 (C-16a), 157.0 (C-26d), 156.9 (C-22d), 155.5 (C-1), 148.8 (C-24), 128.4 (C-2), 126.3 (C-24a), 80.0 (C-22e), 80.0 (C-26e), 78.9 (C-22), 76.8 (C-16), 68.6 (C-26), 51.1 (C-17), 48.4 (C-14), 47.6 (C-4), 46.9 (C-13), 46.7 (C-15), 45.0 (C-8), 43.5 (C-5), 43.0 (C-22b), 43.0 (C-26b), 34.5 (C-25), 33.7 (C-20), 33.0 (C-12), 32.9 (C-10), 28.6 (C-26f, 26f, 26f), 28.6 (C-22f, 22f, 22f), 28.1 (C-11), 27.5 (C-19), 27.2 (C-9), 24.2 (C-7), 24.2 (C-6), 22.1 (C-16b), 20.0 (C-29), 18.2 (C-18), 17.0 (C-27), 13.3 (C-21), 11.3 (C-28).

Example 60

22-deacetyl-neoboutomellerone 22-(N-Boc-glycinate)-26-acetyl

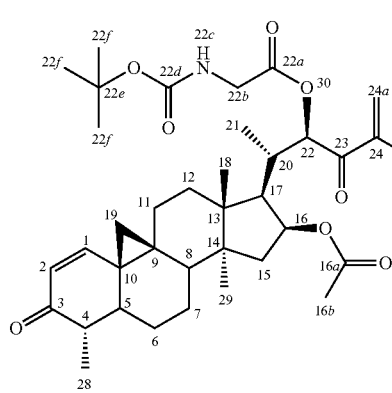

Chemical formula: $C_{46}H_{59}NO_{10}$
Exact mass: 725.41
Molecular weight: 725.91

Protocol: 66 mg (0.118 mmol), of compound 17 is dissolved in 2 ml of DCM. Then, 1.8 ml (1.6 eq) of 0.1 M DCC solution, followed by a catalytic quantity of DMAP (2 mg, 0.1 eq) and finally 31 mg (1.5 eq, 0.176 mmol) of N-Boc-Gly-OH are added. The reaction is left under stirring for 3 h at room temperature. The reaction medium is filtered on Celite® and the product is purified on a silica gel (eluent: cyclohexane/AcOEt gradient: 90/10 to 50/50). 44 mg (52%) of product 60 (Rf: 0.64; 50/50 cyclohexane/ethyl acetate) is obtained.

$^1$H NMR (500 MHz, ACETONITRILE-$d_3$) δ=6.94 (1H, d, J=9.8 Hz, H-1), 6.12 (1H, s, H-24aa), 5.97 (1H, s, H-24ab), 5.90 (1H, d, J=10.1 Hz, H-2), 5.62 (1H, br. s., H-22c), 5.59 (1H, d, J=2.1 Hz, H-22), 5.08 (1H, td, J=7.6 Hz, J=4.6 Hz, H-16), 4.04 (1H, dd, J=10.8 Hz, J=6.4 Hz, H-26<'>), 4.00 (1H, dd, J=10.8 Hz, J=6.4 Hz, H-26<">), 3.94 (1H, dd, J=17.7 Hz, J=6.4 Hz, H-22b<'>), 3.82 (1H, dd, J=17.7 Hz, J=6.2 Hz, H-22b<">), 3.01 (1H, sxt, J=6.9 Hz, H-25), 2.61 (1H, dtd, J=13.9 Hz, J=6.9 Hz, J=2.2 Hz, H-20), 2.30 (1H, dd, J=11.0 Hz, J=7.6 Hz, H-17), 2.19 (1H, d, J=6.7 Hz, H-4, 15<'>), 2.15 (3H, s, H-26b), 2.04-2.06 (1H, m, H-11<'>), 2.03 (3H, s, H-16b), 2.00 (2H, dd, J=6.9 Hz, J=4.1 Hz, H-8a, 5a), 1.64-1.75 (3H, m, H-12<">, 12<'>, 6<'>), 1.52-1.61 (1H, m, H-11<">), 1.43-1.47 (1H, m, H-7<'>), 1.41 (9H, s, H-22f, 22f, 22f), 1.39-1.39 (1H, m, M30), 1.37 (1H, dd, J=13.9 Hz, J=4.1 Hz, H-15<'>), 1.27 (1H, d, J=3.7 Hz, H-7<">), 1.25 (1H, d, J=4.6 Hz, H-19<'>), 1.18 (3H, s, H-18), 1.07 (3H, d, J=7.0 Hz, H-27), 1.02 (3H, d, J=7.0 Hz, H-28), 0.97 (3H, s, H-29), 0.91-0.96 (1H, m, H-6<'>), 0.85 (3H, d, J=6.7 Hz, H-21), 0.57 (1H, d, J=4.3 Hz, H-19<">)

$^{13}$C NMR (126 MHz, ACETONITRILE-$d_3$) δ=202.4 (C-3), 198.4 (C-23), 171.6 (C-26a), 171.4 (C-22a), 171.2 (C-16a), 156.9 (C-22d), 155.5 (C-1), 149.0 (C-24), 128.4 (C-2), 126.0 (C-24a), 80.0 (C-22e), 78.8 (C-22), 76.7 (C-16), 67.8 (C-26), 51.2 (C-17), 48.4 (C-14), 47.6 (C-4), 46.9 (C-13), 46.7 (C-15), 45.0 (C-8), 43.5 (C-5), 43.0 (C-22b), 43.0 (C-26b), 34.5 (C-25), 33.7 (C-20), 33.0 (C-12), 32.9 (C-10), 28.6 (C-26f, 26f, 26f), 28.6 (C-22f, 22f, 22f), 28.1 (C-11), 27.5 (C-19), 27.2 (C-9), 24.2 (C-7), 24.2 (C-6), 22.1 (C-16b), 20.0 (C-29), 18.2 (C-18), 17.0 (C-27), 13.3 (C-21), 11.3 (C-28).

Example 61

22-chloroacetyl-26-acetyl-neoboutomellerone

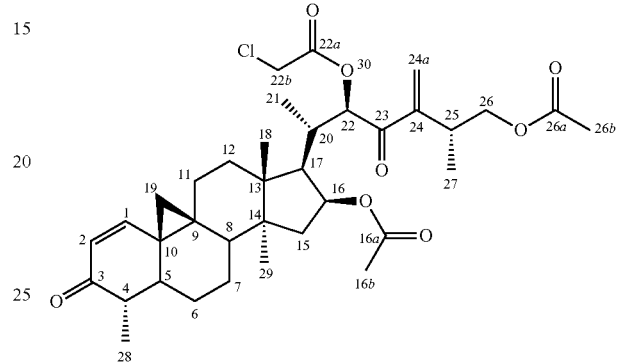

Chemical formula: $C_{36}H_{49}ClO_8$
Exact mass: 644.31
Molecular weight: 645.22

Protocol: 64 mg (0.113 mmol) of compound 17 is dissolved in 2 ml of DCM. Then, 1.8 ml (1.6 eq) of 0.1 M DCC solution, followed by a catalytic quantity of DMAP (2 mg, 0.1 eq) and finally 16 mg (1.5 eq, 0.169 mmol) of chloroacetic acid are added. The reaction is left under stirring for 1 h at room temperature. The reaction medium is filtered on Celite® and the product is purified on a silica gel (eluent: cyclohexane/AcOEt gradient: 90/10 to 50/50). 70 mg (97%) of product 61 (Rf: 0.75; 50/50 cyclohexane/ethyl acetate) is obtained.

$^1$H NMR (500 MHz, ACETONITRILE-$d_3$) δ=6.94 (1H, d, J=10.0 Hz, H-1), 6.14 (1H, s, H-24aa), 6.01 (1H, s, H-24ab), 5.90 (1H, d, J=10.0 Hz, H-2), 5.59 (1H, d, J=2.1 Hz, H-22), 5.10 (1H, td, J=7.7 Hz, J=4.4 Hz, H-16), 4.33 (1H, d, J=15.1 Hz, H-22b<'>), 4.25 (1H, d, J=15.1 Hz, H-22b<">), 3.99-4.08 (3H, m, H-26<">, 26<'>), 3.02 (1H, sxt, J=7.0 Hz, H-25), 2.63 (1H, dtd, J=13.7 Hz, J=7.1 Hz, J=2.3 Hz, H-20), 2.32 (1H, dd, J=11.1 Hz, J=7.6 Hz, H-17), 2.17-2.21 (1H, m, H-4), 2.05-2.10 (1H, m, H-11<'>), 2.04 (3H, s, H-16b), 1.98-2.03 (2H, m, H-5a, 8a), 1.97 (4H, s, H-26b), 1.63-1.75 (4H, m, H-12<">, 12<'>, 6<'>), 1.53-1.61 (1H, m, H-11<">), 1.41-1.49 (1H, m, H-7<'>), 1.38 (1H, dd, J=13.8 Hz, J=4.2 Hz, H-15<">), 1.25 (1H, d, J=4.4 Hz, H-19<'>), 1.19-1.21 (1H, m, H-7<">), 1.19 (3H, s, H-18), 1.12-1.17 (1H, m, M32), 1.08 (4H, d, J=7.0 Hz, H-28), 1.02 (3H, d, J=6.7 Hz, H-27), 0.95 (3H, s, H-29), 0.90-0.94 (1H, m, H-6<'>), 0.86 (3H, d, J=6.9 Hz, H-21), 0.57 (1H, d, J=4.4 Hz, H-19<">).

$^{13}$C NMR (126 MHz, ACETONITRILE-$d_3$) δ=202.4 (C-3), 197.7 (C-23), 171.8 (C-26a), 171.2 (C-16a), 168.2 (C-22a), 155.5 (C-1), 148.9 (C-24), 128.4 (C-2), 126.4 (C-24a), 80.0 (C-22), 76.7 (C-16), 67.8 (C-26), 51.1 (C-17), 48.4 (C-14), 47.6 (C-4), 46.9 (C-13), 46.7 (C-15), 45.1 (C-8), 43.5 (C-5), 42.1 (C-22b), 34.9 (C-25), 34.5 (C-10), 33.6 (C-20), 32.9 (C-12), 28.1 (C-11), 27.6 (C-19), 27.2 (C-9), 24.3 (C-6), 24.2 (C-7), 22.1 (C-16b), 21.1 (C-26b), 19.9 (C-29), 18.2 (C-18), 17.2 (C-27), 13.2 (C-21), 11.3 (C-28).

Examples 62 & 63

Neoboutomellerone 26-N-dimethyl glycinate (62) and neoboutomellerone 26-N-dimethyl glycinate hydrochloride (63)

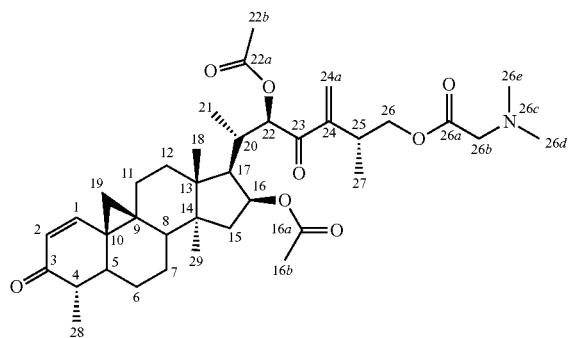

62

Chemical formula: $C_{38}H_{55}NO_8$
Exact mass: 653.39
Molecular weight: 653.85

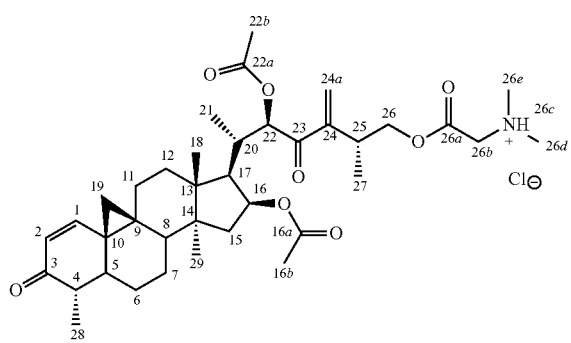

63

Chemical formula: $C_{38}H_{56}NO_8^+$
(counterion: $Cl^-$)
Exact mass: 654.40
Molecular weight: 654.85

Protocol: 3.5 ml (0.1 mol/l, 0.35 mmol, 2 eq) of DCC in dichloromethane solution is placed in a double neck, round bottom flask under nitrogen. 36 mg (0.35 mmol, 2 eq) of dimethylglycine and 2 mg (0.018 mmol, 0.1 eq) of DMAP are added. Finally, 100 mg (0.18 mmol) of 2 is added. The reaction medium is stirred at room temperature for 24 hours. The reaction medium is then filtered and the filtrate is washed with distilled water and dried on $Na_2SO_4$. The product is purified by silica gel chromatography (eluent: cyclohexane/AcOEt: 3/7) in order to obtain amine 62 in the form of a translucent oil with a yield of 23%. 3 ml of 0.1 M HCl is added to 26 mg of dimethylamine 63 and the reaction medium is stirred at room temperature for 1 hour. The reaction medium is then freeze-dried in order to obtain hydrochloride 63 (100%).

Example 62

$^1$H NMR (500 MHz, $CD_3CN$) δ=6.94 (1H, d, J=10.1 Hz, H-1), 6.12 (1H, s, H-24aa), 5.97 (1H, s, H-24ab), 5.90 (1H, d, J=9.8 Hz, H-2), 5.53 (1H, d, J=2.1 Hz, H-22), 5.09 (1H, td, J=7.6 Hz, J=4.6 Hz, H-16), 4.00-4.15 (2H, m, H-26<">, 26<'>), 3.10 (2H, s, H-26b), 3.02 (1H, sxt, J=6.9 Hz, H-25), 2.58 (1H, dqd, J=11.0 Hz, J=7.0 Hz, J=2.1 Hz, H-20), 2.30 (1H, dd, J=11.0 Hz, J=7.3 Hz, H-17), 2.26 (6H, s, H-26e, 26d), 2.13-2.22 (2H, m, H-4, 15<'>), 2.09 (3H, s, H-22b), 2.03 (3H, s, H-16b), 1.95-2.06 (3H, m, H-5,8,11<'>), 1.63-1.77 (3H, m, H-6<'>, 12<">, 12<'>), 1.52-1.60 (1H, m, H-11<'''>), 1.41-1.50 (1H, m, H-7<'>), 1.37 (1H, dd, J=14.2 Hz, J=3.8 Hz, H-15<">), 1.24 (1H, d, J=4.3 Hz, H-19<'>), 1.19 (3H, s, H-18), 1.15-1.22 (1H, m, H-7<">), 1.07 (3H, d, J=7.3 Hz, H-27), 1.02 (3H, d, J=6.7 Hz, H-28), 0.95 (3H, s, H-29), 0.89-0.99 (1H, m, H-6<">), 0.85 (3H, d, J=7.0 Hz, H-21), 0.58 (1H, d, J=4.6 Hz, H-19<">)

$^{13}$C NMR (126 MHz, $CD_3CN$) δ=202.4 (C-3), 198.8 (C-23), 171.6 (C-22a), 171.5 (C-26a), 171.2 (C-16a), 155.5 (C-1), 149.1 (C-24), 128.4 (C-2), 125.8 (C-24a), 78.3 (C-22), 76.7 (C-16), 67.7 (C-26), 60.7 (C-26b), 51.3 (C-17), 48.4 (C-14), 47.6 (C-4), 46.9 (C-13), 46.7 (C-15), 45.3 (C-26d, 26e), 45.2 (C-8), 43.6 (C-5), 34.9 (C-25), 33.3 (C-20), 33.0 (C-12), 32.9 (C-10), 28.1 (C-11), 27.7 (C-19), 27.6, 27.2 (C-9), 24.3 (C-7, 6), 22.1 (C-16b), 20.9 (C-22b), 20.0 (C-29), 18.3 (C-18), 17.3 (C-27), 13.3 (C-21), 11.3 (C-28)

Example 63

$^1$H NMR (500 MHz, $D_2O$) δ=7.19 (1H, d, J=9.8 Hz, H-1), 6.40 (1H, br. s., H-24aa), 6.28 (1H, s, H-24ab), 5.94-6.06 (1H, m, J=5.5 Hz, H-2), 5.67 (1H, br. s., H-22), 5.08 (1H, br. s., H-16), 4.36 (1H, dd, J=10.8 Hz, J=5.6 Hz, H-26<'>), 4.23 (1H, dd, J=11.0 Hz, J=7.9 Hz, H-26<">), 4.11 (1H, d, J=17.1 Hz, H-26b<'>), 4.05 (1H, d, J=17.4 Hz, H-26b<">), 3.09-3.21 (1H, m, H-25), 2.67 (1H, br. s., H-20), 2.29-2.42 (2H, m, H-4, 17), 2.21 (3H, s, H-22b), 2.18-2.28 (1H, m, H-15<'>), 2.15 (3H, s, H-16b), 1.95-2.12 (3H, m, H-5,8,11<'>), 1.71 (3H, br. s., H-6<'>, 12<">, 12<'>), 1.64 (1H, br. s., H-11<'''>), 1.40-1.54 (2H, m, H-7<'>, 15<">), 1.37 (1H, br. s., H-19<'>), 1.19 (3H, br. s., H-18), 1.15-1.27 (1H, m, H-7<">), 1.12 (3H, d, J=7.0 Hz, H-27), 1.04 (3H, d, J=6.7 Hz, H-28), 0.91-1.00 (1H, m, H-6<">), 0.95 (3H, br. s., H-29), 0.88 (3H, d, J=6.4 Hz, H-21), 0.64 (1H, br. s., H-19<">)

$^{13}$C NMR (126 MHz, $D_2O$) δ=174.8 (C-16a, 22a), 167.3 (C-26a), 160.6 (C-1), 147.9 (C-24), 129.2 (C-24a), 127.4 (C-2), 79.4 (C-22), 78.2 (C-16), 70.8 (C-26), 58.0 (C-26b), 51.1 (C-17), 48.2 (C-14), 47.4 (C-4), 46.7 (C-13), 46.1 (C-15), 44.7 (C-26e, 26d), 44.2 (C-8), 42.8 (C-5), 33.7 (C-20), 33.4 (C-10), 33.3 (C-25), 32.6 (C-12), 27.8 (C-11), 27.8 (C-9), 27.2 (C-19), 23.8 (C-6), 23.6 (C-7), 22.3 (C-16b), 21.0 (C-22b), 19.8 (C-29), 17.9 (C-18), 16.7 (C-27), 13.3 (C-21), 11.1 (C-28)

Examples 64 & 65

22-deacetyl-neoboutomellerone 26-N-dimethyl glycinate (64) and 22-deacetyl-neoboutomellerone 26-N dimethyl glycinate hydrochloride (65)

64

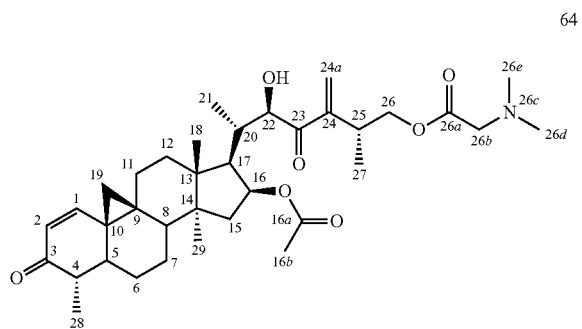

Chemical formula: $C_{36}H_{53}NO_7$
Exact mass: 611.38
Molecular weight: 611.81

65

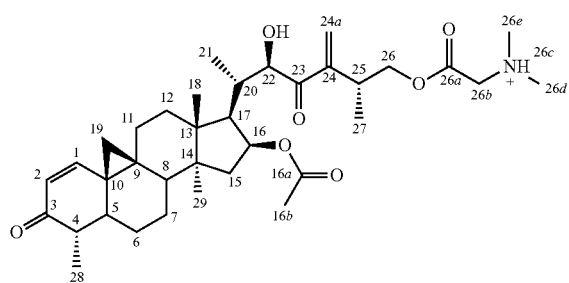

Chemical formula: $C_{36}H_{54}NO_7$
(counterion: $Cl^-$)
Exact mass: 612.38
Molecular weight: 612.82

Protocol: 20 mg (0.19 mmol, 1 eq) of dimethylglycine is solubilized in 1 ml of anhydrous dichloromethane. 80 μl (0.58, 3 eq) of triethylamine and 69 mg (0.21 mmol, 1.1 eq) of TBTU is added and the reaction medium is stirred for 5 minutes. Then, 100 mg (0.19 mmol, 1 eq) of 1 is added. After 16 h of stirring at room temperature, the reaction medium is diluted in ethyl acetate and the organic phase is washed successively with a 4% HCl solution, a saturated sodium bicarbonate solution and a saturated sodium chloride solution. The organic phase is dried on $MgSO_4$, filtered and concentrated in a rotary evaporator. The product is purified by silica gel chromatography (eluent: AcOEt/MeOH: 100/0 to 95/5). A white solid 64 is obtained with a yield of 57% (112 mg). 42 mg (0.068 mmol, 1 eq) of 64 is solubilized in 2 ml of ethanol and 700 μl of 0.1 M HCl (1 eq) is added. The reaction medium is stirred at room temperature for 30 minutes and concentrated in a rotary evaporator. The aqueous solution is then freeze-dried in order to obtain hydrochloride 65 (90%).

Example 64

$^1$H NMR (500 MHz, $CD_3CN$) δ=6.94 (1H, d, J=10.1 Hz, H-1), 6.18 (1H, s, H-24aa), 6.05 (1H, d, J=0.9 Hz, H-24ab), 5.89 (1H, d, J=9.8 Hz, H-2), 5.20 (1H, td, J=7.4 Hz, J=4.4 Hz, H-16), 4.72 (1H, d, J=4.6 Hz, H-22), 4.04-4.15 (2H, m, H-26<'>, 26<''>), 3.54 (1H, d, J=5.8 Hz, OH-30), 3.10 (2H, s, H-26b), 3.07 (1H, sxt, J=7.0 Hz, H-25), 2.37-2.49 (2H, m, H-17, 20), 2.25 (6H, s, H-26d, 26e), 2.16-2.24 (2H, m, H-4, 15<'>), 2.02 (3H, s, H-16b), 2.02 (3H, s, H-5,8,11<'>), 1.60-1.74 (3H, m, H-6<'>, 12<''>, 12<'>), 1.50-1.59 (1H, m, H-11<'''>), 1.41-1.49 (1H, m, H-7<'>), 1.38 (1H, dd, J=14.0 Hz, J=3.7 Hz, H-15<''>), 1.24 (1H, d, J=4.3 Hz, H-19<'>), 1.18 (3H, s, H-18), 1.14-1.26 (1H, m, H-7<''>), 1.10 (3H, d, J=7.0 Hz, H-27), 1.03 (3H, d, J=6.7 Hz, H-28), 0.96 (3H, s, H-29), 0.88-0.99 (1H, m, H-6<''>), 0.64 (3H, d, J=6.1 Hz, H-21), 0.57 (1H, d, J=4.3 Hz, H-19<''>)

$^{13}$C NMR (126 MHz, $CD_3CN$) δ=205.0 (C-23), 202.4 (C-3), 171.5 (C-26a), 171.2 (C-16a), 155.6 (C-1), 148.0 (C-24), 128.4 (C-2), 127.5 (C-24a), 77.3 (C-16), 75.8 (C-22), 67.8 (C-26), 60.7 (C-26b), 51.4 (C-17), 48.3 (C-14), 47.6, 46.9 (C-15), 46.7 (C-13), 45.3 (C-8), 45.3 (C-26d, 26e), 43.6 (C-5), 36.4 (C-20), 34.8 (C-25), 33.1 (C-12), 32.9 (C-10), 28.1 (C-11), 27.7 (C-19), 27.2 (C-9), 24.3 (C-6), 24.3 (C-7), 22.1 (C-16b), 20.1 (C-29), 18.5 (C-18), 17.3 (C-27), 12.3 (C-21), 11.3 (C-28)

Example 65

$^1$H NMR (500 MHz, DMSO-$d_6$) δ=10.15 (1H, br. s, H-26c), 6.96 (1H, d, J=10.0 Hz, H-1), 6.12 (1H, s, H-24ab), 6.07 (1H, s, H-24aa), 5.90 (1H, d, J=10.1 Hz, H-2), 5.12-5.22 (1H, m, H-16), 4.73-4.86 (1H, m, H-30), 4.55-4.66 (1H, m, H-22), 4.19 (2H, m, H-26), 4.07-4.16 (2H, m, H-26b), 3.04 (1H, sxt, J=6.9 Hz, H-25), 2.81 (6H, s, H-26d, 26e), 2.30-2.41 (2H, m, H-20, 17), 2.08-2.18 (2H, m, H-4, 15<'>), 2.02 (3H, s, H-16b), 1.92-2.01 (2H, m, H-11<'>, 8a), 1.86-1.94 (1H, td, J=12.3 Hz, J=4.2 Hz, H-5a), 1.57-1.64 (3H, m, H-6<'>, 12), 1.51-1.56 (1H, m, H-11<''>), 1.38-1.44 (1H, m, H-7<'>), 1.31 (1H, dd, J=14.0 Hz, J=4.0 Hz, H-15<''>), 1.25 (1H, d, J=4.3 Hz, H-19<'>), 1.12 (4H, s, H-7<''>, 18), 1.06 (3H, d, J=7.0 Hz, H-27), 0.98 (4H, d, J=6.7 Hz, H-28), 0.92-0.95 (1H, m, H-6<''>), 0.90 (3H, s, H-29), 0.65 (3H, d, J=6.1 Hz, H-21), 0.57 (1H, d, J=4.3 Hz, H-19<''>)

$^{13}$C NMR (126 MHz, DMSO-$d_6$) δ=203.4 (C-23), 200.6 (C-3), 169.9 (C-16a), 166.0 (C-26a), 154.7 (C-1), 146.9 (C-24), 127.3 (C-2), 125.2 (C-24a), 75.3 (C-16), 74.2 (C-22), 68.5 (C-26), 56.1 (C-26b), 49.5 (C-17), 47.0 (C-14), 46.1 (C-4), 45.3 (C-15), 45.2 (C-13), 43.3 (C-26e, 26d), 43.3 (C-8), 42.0 (C-5), 34.3 (C-20), 32.6 (C-25), 31.8 (C-12), 31.6 (C-10), 26.7 (C-11), 26.2 (C-19), 25.9 (C-9), 22.8 (C-6, 7), 21.4 (C-16b), 19.1 (C-29), 17.6 (C-18), 16.5 (C-27), 11.7 (C-21), 10.8 (C-28)

Examples 66 & 67

26-deacetyl-neoboutomellerone 26-N-diethyl-β-alaninate (66) and 26-deacetyl-neoboutomellerone 26-acrylate (67)

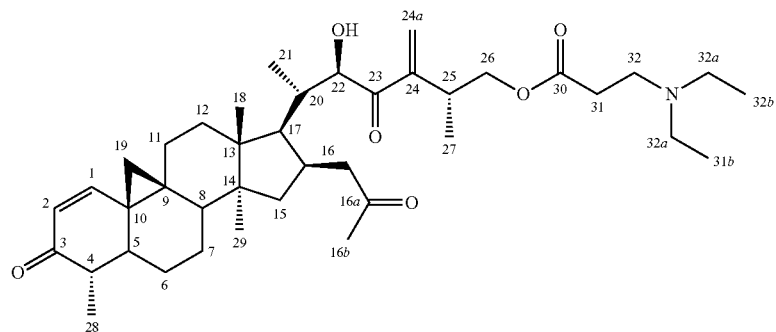

66

Chemical formula: $C_{39}H_{59}NO_7$
Exact mass: 653.43
Molecular weight: 653.89

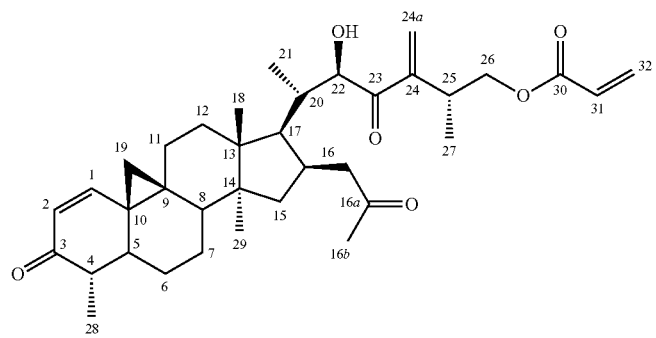

67

Chemical formula: $C_{35}H_{48}O_7$
Exact mass: 580.34
Molecular weight: 580.75

Protocol: Compound 1 (200 mg, 0.38 mmol) is dissolved in 2 ml of DCM and then a solution of diethyl-β-alanine hydrochloride (138 mg, 2 eq, 0.76 mmol), TBTU (254 mg, 2.1 eq, 0.82 mmol) and triethylamine (0.21 ml, 4 eq, 1.52 mmol) in DCM is added. The reaction is left under stirring at room temperature overnight. The reaction is hydrolyzed with water and the organic phase is washed three times with a 3% potassium carbonate solution and then three times with water. This same organic phase is then washed four times with a 5% citric acid solution and the resulting aqueous phases are combined and rebasified with a saturated sodium carbonate solution. The product of this aqueous phase is reextracted with ethyl acetate and the resulting organic phase is washed with water and then with brine. Thus, 215 mg of crude reaction product is collected and then filtered on a silica gel. The residue obtained after evaporation of the solvents is repurified by preparative chromatography (eluent: AcOEt/NEt$_3$: 90/10) to obtain 90 mg of product 66 and 36 mg of compound 67.

Example 66

$^1$H NMR (500 MHz, ACETONITRILE-d$_3$) δ=6.93 (1H, d, J=10.0 Hz, H-1), 6.10 (1H, s, H-24aa), 5.99 (1H, d, J=0.9 Hz, H-24ab), 5.90 (1H, s, H-31, 2), 5.24 (1H, ddd, J=7.3 Hz, J=1.8 Hz, J=1.5 Hz, H-32aa), 5.20 (1H, td, J=7.4 Hz, J=4.3 Hz, H-16), 5.12 (1H, qd, J=15.5 Hz, J=1.5 Hz, H-32ab), 4.71 (1H, dd, J=5.5 Hz, J=1.5 Hz, H-22), 3.93 (1H, dd, J=5.4 Hz, J=1.4 Hz, H-30), 3.51-3.52 (1H, m, H-38), 3.51 (1H, dd, J=9.4 Hz, J=6.4 Hz, H-26<'>), 3.33 (1H, dd, J=9.3 Hz, J=6.6 Hz, H-26<">), 2.97 (1H, sxt, J=6.7 Hz, H-25), 2.38-2.50 (1H, m, H-17, 20), 2.23 (1H, dd, J=13.9 Hz, J=7.8 Hz, H-15<'>), 2.15-2.20 (1H, m, H-4), 2.03-2.09 (1H, m, H-8a, 11<'>), 2.03 (2H, s, H-16b), 1.96-2.02 (2H, m, H-5a), 1.61-1.74 (2H, m, H-12<">, 12<'>, 6<'>), 1.55 (1H, ddd, J=14.9 Hz, J=8.6 Hz, J=6.2 Hz, H-11<'>), 1.42-1.50 (1H, m, H-7<'>), 1.38 (1H, dd, J=14.2 Hz, J=4.2 Hz, H-15<">), 1.24 (1H, d, J=4.5 Hz, H-19<'>), 1.19-1.23 (1H, m, H-7<">), 1.18 (2H, s, H-18), 1.08 (1H, d, J=7.0 Hz, H-27), 1.03 (2H, d, J=6.7 Hz, H-28), 0.97 (2H, s, H-29), 0.91-0.96 (1H, m, H-6<">), 0.65 (1H, d, J=6.1 Hz, H-21), 0.57 (1H, d, J=4.5 Hz, H-19<">).

$^{13}$C NMR (126 MHz, ACETONITRILE-d$_3$) δ=205.4 (C-23), 202.4 (C-3), 171.3 (C-16a), 155.6 (C-1), 149.2 (C-24), 136.4 (C-31), 128.4 (C-2), 126.5 (C-24a), 116.7 (C-32), 77.3 (C-16), 75.9 (C-22), 74.7 (C-26), 72.4 (C-30), 51.5 (C-17), 48.3 (C-14), 47.8 (C-4), 47.0 (C-15), 46.7 (C-13), 45.4 (C-8), 43.7 (C-5), 36.2 (C-25), 35.8 (C-20), 33.2 (C-12), 33.0 (C-10), 28.2 (C-11), 27.8 (C-19), 27.3 (C-9), 24.4 (C-6), 24.4 (C-7), 22.1 (C-16b), 20.1 (C-29), 18.6 (C-18), 17.7 (C-27), 12.3 (C-21), 11.3 (C-28).

Example 67

¹H NMR (500 MHz, ACETONITRILE-d₃) δ=6.93 (1H, d, J=10.0 Hz, H-1), 6.10 (1H, s, H-24aa), 5.99 (1H, d, J=0.9 Hz, H-24ab), 5.90 (1H, s, H-31, 2), 5.24 (1H, ddd, J=7.3 Hz, J=1.8 Hz, J=1.5 Hz, H-32aa), 5.20 (1H, td, J=7.4 Hz, J=4.3 Hz, H-16), 5.12 (1H, qd, J=15.5 Hz, J=1.5 Hz, H-32ab), 4.71 (1H, dd, J=5.5 Hz, J=1.5 Hz, H-22), 3.93 (1H, dd, J=5.4 Hz, J=1.4 Hz, H-30), 3.51-3.52 (1H, m, H-38), 3.51 (1H, dd, J=9.4 Hz, J=6.4 Hz, H-26<'>), 3.33 (1H, dd, J=9.3 Hz, J=6.6 Hz, H-26<">), 2.97 (1H, sxt, J=6.7 Hz, H-25), 2.38-2.50 (1H, m, H-17, 20), 2.23 (1H, dd, J=13.9 Hz, J=7.8 Hz, H-15<'>), 2.15-2.20 (1H, m, H-4), 2.03-2.09 (1H, m, H-8a, 11<'>), 2.03 (2H, s, H-16b), 1.96-2.02 (2H, m, H-5a), 1.61-1.74 (2H, m, H-12<">, 12<'>, 6<'>), 1.55 (1H, ddd, J=14.9 Hz, J=8.6 Hz, J=6.2 Hz, H-11<">), 1.42-1.50 (1H, m, H-7<'>), 1.38 (1H, dd, J=14.2 Hz, J=4.2 Hz, H-15<">), 1.24 (1H, d, J=4.5 Hz, H-19<'>), 1.19-1.23 (1H, m, H-7<">), 1.18 (2H, s, H-18), 1.08 (1H, d, J=7.0 Hz, H-27), 1.03 (2H, d, J=6.7 Hz, H-28), 0.97 (2H, s, H-29), 0.91-0.96 (1H, m, H-6<">), 0.65 (1H, d, J=6.1 Hz, H-21), 0.57 (1H, d, J=4.5 Hz, H-19<">).

¹³C NMR (126 MHz, ACETONITRILE-d₃) δ=205.4 (C-23), 202.4 (C-3), 171.3 (C-16a), 155.6 (C-1), 149.2 (C-24), 136.4 (C-31), 128.4 (C-2), 126.5 (C-24a), 116.7 (C-32), 77.3 (C-16), 75.9 (C-22), 74.7 (C-26), 72.4 (0-30), 51.5 (C-17), 48.3 (C-14), 47.8 (C-4), 47.0 (C-15), 46.7 (C-13), 45.4 (C-8), 43.7 (C-5), 36.2 (C-25), 35.8 (C-20), 33.2 (C-12), 33.0 (C-10), 28.2 (C-11), 27.8 (C-19), 27.3 (C-9), 24.4 (C-6), 24.4 (C-7), 22.1 (C-16b), 20.1 (C-29), 18.6 (C-18), 17.7 (C-27), 12.3 (C-21), 11.3 (C-28).

Examples 68 and 69

26-succinate-neoboutomellerone (68) and 26-succinate-neoboutomellerone N-methyl glutamine salt (69)

68

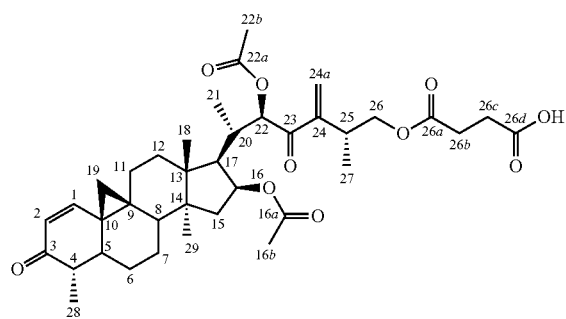

Chemical formula: $C_{38}H_{52}O_{10}$
Exact mass: 668.36
Molecular weight: 668.81

69

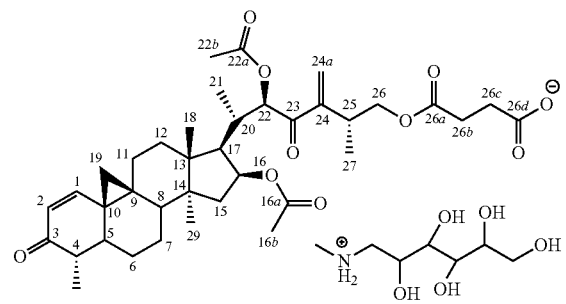

Chemical formula: $C_{38}H_{52}O_{10}$
Exact mass: 667.36
Molecular weight: 667.81

Protocol: 100 mg (0.18 mmol) of 2 is solubilized in 3.5 ml of anhydrous dichloromethane. 75 mg of succinic anhydride (0.70 mmol, 4 eq) and 86 mg of DMAP (0.70 mmol, 4 eq) are added. After 1 h of stirring at room temperature, the reaction is terminated. After dilution in ethyl acetate, the organic phase is washed successively with a 4% HCl solution, a saturated sodium bicarbonate solution and a saturated sodium chloride solution. The organic phase is dried on MgSO₄, filtered and concentrated in a rotary evaporator. The product is purified by silica chromatography (eluent: DCM/MeOH: 100/0 to 95/5) and then by RP-18 HPLC (gradient: H₂O/CH₃CN: 90/10 to 0/100). A white solid 68 is obtained with a yield of 95% (112 mg). 94 mg (0.14 mmol, 1 eq) of 68 is dissolved in 5 ml of ethanol. 27 mg (0.14 mmol, 1 eq) of N-methyl-D-glucamine is dissolved in 2 ml of water and added to the solution prepared previously. The reaction medium is stirred for 10 minutes and concentrated in a rotary evaporator. The residue is taken up in 5 ml of water, filtered on a 45 μm filter and freeze-dried in order to yield 100 mg of 69 (83%).

Example 68

¹H NMR (500 MHz, CD₃CN) δ=6.94 (1H, d, J=10.1 Hz, H-1), 6.13 (1H, s, H-24aa), 5.97 (1H, s, H-24ab), 5.90 (1H, d, J=10.1 Hz, H-2), 5.53 (1H, d, J=2.1 Hz, H-22), 5.09 (1H, td, J=7.6 Hz, J=4.6 Hz, H-16), 3.98-4.12 (2H, m, H-26<">, 26<'>), 3.00 (1H, sxt, J=6.9 Hz, H-25), 2.59 (1H, dqd, J=11.0 Hz, J=6.7 Hz, J=2.1 Hz, H-20), 2.48-2.55 (4H, m, H-26c<">, 26c<'>, 26b<">, 26b<'>), 2.30 (1H, dd, J=11.0 Hz, J=7.6 Hz, H-17), 2.13-2.23 (2H, m, H-4, 15<'>), 2.09 (3H, s, H-22b), 2.04 (3H, s, H-16b), 1.96-2.07 (3H, m, H-5,8,11<'>), 1.62-1.76 (3H, m, H-6<'>, 12<">, 12<'>), 1.52-1.61 (1H, m, H-11<">), 1.41-1.49 (1H, m, H-7<'>), 1.37 (1H, dd, J=14.0 Hz, J=4.0 Hz, H-15<">), 1.24 (1H, d, J=4.3 Hz, H-19<'>), 1.19 (3H, s, H-18), 1.14-1.24 (1H, m, H-7<">), 1.07 (3H, d, J=7.3 Hz, H-27), 1.03 (3H, d, J=7.0 Hz, H-28), 0.95 (3H, s, H-29), 0.94 (1H, qd, J=12.8 Hz, J=4.0 Hz, H-6<">), 0.85 (3H, d, J=7.0 Hz, H-21), 0.58 (1H, d, J=4.6 Hz, H-19<">)

¹³C NMR (126 MHz, CD₃CN) δ=202.4 (C-3), 198.8 (C-23), 174.0 (C-26d), 173.1 (C-26a), 171.7 (C-22a), 171.3 (C-16a), 155.5 (C-1), 148.9 (C-24), 128.4 (C-2), 125.9 (C-24a), 78.4 (C-22), 76.7 (C-16), 67.9 (C-26), 51.3 (C-17), 48.4 (C-14), 47.6 (C-4), 46.8 (C-13), 46.7 (C-15), 45.2 (C-8), 43.6 (C-5), 34.8 (C-25), 33.4 (C-20), 33.0 (C-12), 32.9 (C-10), 29.8 (C-26b), 29.2 (C-26c), 28.1 (C-11), 27.6 (C-19), 27.2 (C-9), 24.3 (C-7, 6), 22.1 (C-16b), 20.9 (C-22b), 20.0 (C-29), 18.3 (C-18), 17.2 (C-27), 13.3 (C-21), 11.3 (C-28)

Example 69

¹H NMR (500 MHz, DEUTERIUM OXIDE) δ=6.99 (1H, d, J=9.5 Hz, H-1), 6.26 (1H, br. s., H-24aa), 6.18 (1H, br. s., H-24ab), 5.94 (1H, d, J=9.5 Hz, H-2), 5.63 (1H, br. s., H-22), 5.08 (1H, d, J=4.0 Hz, H-16), 4.03-4.17 (3H, m, H-26, 5'), 3.79-3.84 (2H, m, H-1'<'>, 4'), 3.73-3.78 (1H, m, H-3'), 3.62-3.67 (2H, m, H-1'<">, 2'), 3.18 (1H, dd, J=12.8 Hz, J=3.4 Hz, H-6'<">), 3.12 (1H, dd, J=12.8 Hz, J=9.5 Hz, H-6'<'>), 3.06 (1H, q, J=6.6 Hz, H-25), 2.72 (3H, s, H-8'), 2.56-2.65 (1H, m, H-20), 2.53 (2H, t, J=6.9 Hz, H-26c), 2.42 (2H, t, J=6.7 Hz, H-26b), 2.25-2.34 (1H, m, H-17), 2.19-2.25 (1H, m, H-15<">, 4), 2.17 (3H, s, H-22b), 2.13 (3H, s, H-16b), 1.89-2.06 (3H, m, H-8a, 5a, 11<'>), 1.61-1.76 (3H, m, H-12, 6<'>), 1.52-1.60 (1H, m, H-11<">), 1.41-1.49 (1H, m, H-7<'>), 1.33-1.41 (1H, m, H-15<'>), 1.23-1.30 (1H, m, H-19<'>), 1.19-1.23 (1H, m, H-7<">), 1.16 (3H, br. s., H-18), 1.10 (3H, d, J=7.0 Hz, H-27), 1.01 (3H, d, J=5.8 Hz, H-28), 0.92 (3H, br. s., H-29), 0.86 (3H, d, J=5.2 Hz, H-21), 0.56 (1H, br. s., H-19<">)

¹³C NMR (126 MHz, DEUTERIUM OXIDE) δ=203.9 (C-3), 199.3 (C-23), 180.5 (C-26d), 175.5 (C-26a), 172.8

(C-22a), 172.6 (C-16a), 156.5 (C-1), 147.5 (C-24), 127.3 (C-2), 126.9 (C-24a), 77.8 (C-22), 76.3 (C-15), 70.8 (C-3'), 70.6 (C-2'), 70.5 (C-4'), 68.3 (C-5'), 67.7 (C-26), 62.6 (C-1'), 51.1 (C-6'), 50.1 (C-17), 47.2 (C-14), 46.6 (C-4), 45.7 (C-15, 13), 43.6 (C-8), 42.1 (C-5), 33.2 (C-25), 33.0 (C-8'), 32.4 (C-20), 32.1 (C-12), 31.9 (C-26b), 30.5 (C-26c), 27.1 (C-11), 26.4 (C-19), 23.0 (C-6, 7), 21.3 (C-16b), 20.1 (C-22b), 19.1 (C-29), 17.3 (C-18), 16.2 (C-27), 12.5 (C-21), 10.5 (C-28)

Examples 70, 71 & 72

22,26-bis-succinate-22-deacetyl-neoboutomellerone (70), 26-succinate-22-deacetyl-neoboutomellerone (71) and 26-succinate-22-deacetyl-neoboutomellerone N-methylglucamine salt (72)

70

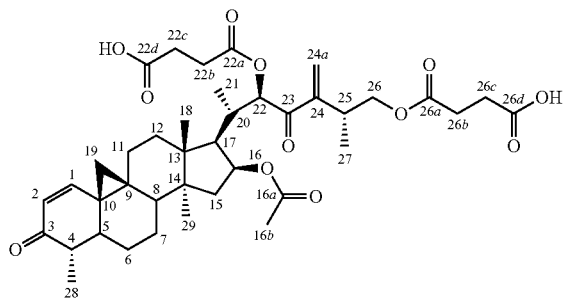

Chemical formula: $C_{40}H_{54}O_{12}$
Exact mass: 726.36
Molecular weight: 726.85

71

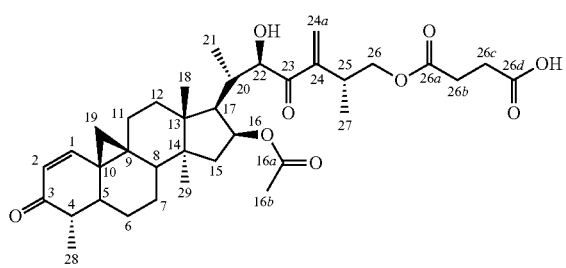

Chemical formula: $C_{36}H_{50}O_9$
Exact mass: 626.35
Molecular weight: 626.78

72

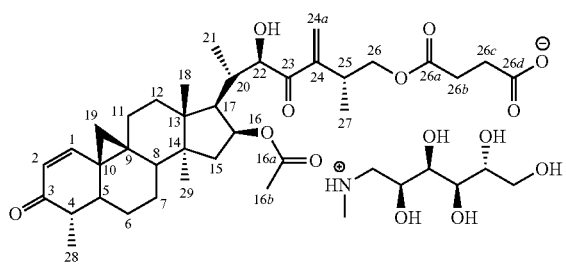

Chemical formula: $C_{43}H_{66}NO_{14}$
Exact mass: 820.45
Molecular weight: 820.98

Protocol: 100 mg (0.19 mmol) of 1 is solubilized in 3.5 ml of anhydrous dichloromethane. 21 mg of succinic anhydride (0.21 mmol, 1.1 eq) and 35 mg of DMAP (0.29 mmol, 1.5 eq) are added. After 20 h of stirring at room temperature, the reaction is terminated. The organic phase is washed with a 4% HCl solution and then extracted three times with ethyl acetate. The combined organic phases are then washed with a saturated sodium bicarbonate solution and a saturated sodium chloride solution. The organic phase is dried on $Na_2SO_4$, filtered and concentrated in a rotary evaporator. The residue is purified by RP-18 HPLC (gradient: $H_2O/CH_3CN$: 90/10 to 30/70). 71 and 70 are obtained with a yield of 66% (78 mg) and 11% (14 mg) in the form of a translucent film and a white solid, respectively. 76 mg (0.12 mmol, 1 eq) of 71 is dissolved in 5 ml of absolute ethanol. 24 mg (0.12 mmol, 1 eq) of N-methyl-D-glucamine is dissolved in 2 ml of water and added to the solution prepared previously. The reaction medium is stirred for 10 minutes and concentrated in a rotary evaporator. The residue is taken up in 5 ml of water, filtered on a 45 m filter and freeze-dried in order to yield 100 mg of 72 (99%).

Example 70

$^1$H NMR (500 MHz, ACETONITRILE-$d_3$) δ=6.95 (1H, d, J=10.1 Hz, H-1), 6.13 (1H, s, H-24aa), 5.97 (1H, s, H-24ab), 5.90 (1H, d, J=10.1 Hz, H-2), 5.57 (1H, d, J=2.1 Hz, H-22), 5.05 (1H, td, J=7.6 Hz, J=4.4 Hz, H-16), 4.07 (1H, dd, J=10.8 Hz, J=6.8 Hz, H-26<'>), 4.03 (1H, dd, J=10.8 Hz, J=6.3 Hz, H-26<''>), 3.00 (1H, sxt, J=6.9 Hz, H-25), 2.66 (1H, s, H-20), 2.55-2.64 (4H, m, H-22c, 22b), 2.48-2.55 (4H, m, H-26b, 26c), 2.29 (1H, dd, J=11.0 Hz, J=7.5 Hz, H-17), 2.12-2.22 (2H, m, H-4, 15<'>), 2.03 (3H, s, H-16b), 1.97-2.03 (2H, m, H-11<'>, 5a, 8a), 1.63-1.76 (3H, m, H-6<'>, 12), 1.56 (1H, qd, J=8.6 Hz, J=6.2 Hz, H-11<''>), 1.41-1.48 (1H, m, H-7<'>), 1.36 (1H, dd, J=13.9 Hz, J=4.1 Hz, H-15<''>), 1.24 (1H, d, J=4.3 Hz, H-19<'>), 1.20-1.22 (1H, m, H-7<''>), 1.18 (3H, s, H-18), 1.06 (3H, d, J=7.0 Hz, H-27), 1.02 (3H, d, J=7.0 Hz, H-28), 0.95 (3H, s, H-29), 0.89-0.93 (1H, m, H-6<''>), 0.85 (3H, d, J=7.0 Hz, H-21), 0.58 (1H, d, J=4.6 Hz, H-19<''>)

$^{13}$C NMR (126 MHz, ACETONITRILE-$d_3$) δ=202.5 (C-3), 198.7 (C-23), 174.2 (C-26d), 174.1 (C-22d), 173.2 (C-26a), 173.0 (C-22a), 171.3 (C-16a), 155.6 (C-1), 148.9 (C-24), 128.4 (C-2), 126.0 (C-24a), 78.5 (C-22), 76.8 (C-16), 68.0 (C-26), 51.2 (C-17), 48.3 (C-14), 47.6 (0-4), 46.8 (C-13), 46.7 (C-15), 45.2 (C-8), 43.6 (C-5), 34.8 (C-25), 33.5 (C-20), 32.9 (C-10, 12), 32.9, 29.9 (C-26b), 29.8 (C-22b), 29.3 (C-22c), 29.3 (C-26c), 28.1 (C-11), 27.6 (C-19), 27.2 (C-9), 24.3 (C-6, 7), 22.1 (C-16b), 20.0 (C-29), 18.3 (C-18), 17.2 (C-27), 13.3 (C-21), 11.3 (C-28)

Example 71

$^1$H NMR (500 MHz, ACETONITRILE-d$_3$) δ=6.94 (1H, d, J=10.1 Hz, H-1), 6.19 (1H, s, H-24aa), 6.05 (1H, s, H-24ab), 5.89 (1H, d, J=10.1 Hz, H-2), 5.20 (1H, td, J=7.6 Hz, J=4.4 Hz, H-16), 4.72 (1H, d, J=1.5 Hz, H-22), 4.10 (1H, dd, J=10.8 Hz, J=6.5 Hz, H-26<'>), 4.07 (1H, dd, J=10.8 Hz, J=6.4 Hz, H-26<''>), 3.06 (1H, sxt, J=6.9 Hz, H-25), 2.48-2.56 (4H, m, H-26c, 26b), 2.39-2.47 (3H, m, H-20, 17), 2.13-2.26 (7H, m, H-15<'>, 4), 2.04 (4H, s, H-16b), 1.96-2.03 (3H, m, H-11<'>, 8a, 5a), 1.63-1.71 (3H, m, H-6<'>, 12), 1.54 (1H, qd, J=8.3 Hz, J=6.6 Hz, H-11<''>), 1.42-1.49 (1H, m, H-7<'>), 1.38 (1H, dd, J=14.0 Hz, J=4.3 Hz, H-15<''>), 1.24 (1H, d, J=4.6 Hz, H-19<'>), 1.19-1.22 (1H, m, H-7<''>), 1.18 (3H, s, H-18), 1.09 (3H, d, J=7.0 Hz, H-27), 1.03 (3H; d, J=7.0 Hz, H-28), 0.96 (3H, s, H-29), 0.89-0.95 (1H, m, H-6<''>), 0.64 (3H, d, J=6.1 Hz, H-21), 0.57 (1H, d, J=4.6 Hz, H-19<''>)

$^{13}$C NMR (126 MHz, ACETONITRILE-d$_3$) δ=204.8 (C-23), 202.3 (C-3), 173.9 (C-26d), 173.1 (C-26a), 171.3 (C-16a), 155.5 (C-1), 147.7 (C-24), 128.3 (C-2), 127.5 (C-24a), 77.2 (C-16), 75.7 (C-22), 68.0 (C-26), 51.3 (C-17), 48.2 (0-14), 47.6 (C-4), 46.8 (C-15), 46.6 (C-13), 45.2 (C-8), 43.5 (C-5), 36.4 (C-20), 34.6 (C-25), 33.0 (C-12), 32.9 (C-10), 29.7 (C-26b), 29.2 (C-26c), 28.0 (C-11), 27.7 (C-19), 27.2 (C-9), 24.2 (C-6, 7), 22.0 (C-16b), 20.0, 18.4 (C-18), 17.1 (C-27), 12.2 (C-21), 11.2 (C-28)

Example 72

$^1$H NMR (500 MHz, DMSO-d$_6$) δ=6.97 (1H, d, J=10.1 Hz, H-1), 6.07 (1H, s, H-24aa), 6.00 (1H, s, H-24ab), 5.89 (1H, d, J=10.1 Hz, H-2), 5.09-5.19 (1H, m, H-16), 4.61 (1H, s, H-22), 4.02 (1H, dd, J=10.7 Hz, J=6.5 Hz, H-26<'>), 3.98 (1H, dd, J=10.7 Hz, J=6.5 Hz, H-26<''>), 3.68-3.73 (1H, m, H-5'), 3.63 (1H, dd, J=5.2 Hz, J=1.5 Hz, H-4'), 3.58 (1H, dd, J=11.0 Hz, J=3.4 Hz, H-1'<'>), 3.45-3.50 (1H, m, H-2'), 3.34-3.41 (1H, m, H-1'<''>), 2.95 (1H, sxt, J=6.8 Hz, H-25), 2.62-2.71 (2H, m, H-6'), 2.41-2.48 (2H, m, H-26c), 2.34-2.40 (3H, m, H-17, 26b), 2.33 (3H, s, H-8'), 2.07-2.16 (2H, m, H-4, 15<'>), 2.02 (3H, s, H-16b), 1.94-2.00 (2H, m, H-8a, 11<'>), 1.89 (2H, s, H-5a), 1.49-1.64 (4H, m, H-12, 6<'>, 11<''>), 1.36-1.45 (1H, m, H-7<'>), 1.29 (1H, dd, J=14.2 Hz, J=4.5 Hz, H-15<''>), 1.24 (1H, d, J=4.3 Hz, H-19<'>), 1.14-1.19 (1H, m, H-7<''>), 1.11 (3H, s, H-18), 1.03 (2H, d, J=7.3 Hz, H-27), 0.98 (3H, d, J=7.0 Hz, H-28), 0.91-0.95 (1H, m, H-6<''>), 0.89 (3H, s, H-29), 0.64 (2H, d, J=6.1 Hz, H-21), 0.57 (1H, d, J=4.3 Hz, H-19<''>)

$^{13}$C NMR (126 MHz, DMSO-d$_6$) δ=203.5 (C-23), 200.7 (C-3), 173.9 (C-26d), 172.3 (C-26a), 170.0 (C-16a), 154.9 (C-1), 147.3 (C-24), 127.3 (C-2), 125.1 (C-24a), 75.3 (C-16), 74.2 (C-22), 71.2 (C-2'), 70.4 (C-3'), 70.3 (C-4'), 70.2 (C-5'), 66.7 (C-26), 63.7 (C-1'), 52.2 (C-6'), 49.6 (C-17), 47.0 (C-14), 46.2 (C-4), 45.5 (C-13), 45.2 (C-15), 43.4 (C-8), 42.1 (C-5), 35.1 (C-8'), 34.3 (C-20), 33.3 (C-25), 31.8 (C-12), 31.6 (C-10), 29.6 (C-26b), 29.3 (C-26c), 26.7 (C-11), 26.3 (C-19), 26.0 (C-9), 22.9 (C-6), 22.8 (C-7), 21.5 (C-16b), 19.2 (C-29), 17.7 (C-18), 16.7 (C-27), 11.8 (C-21), 10.8 (C-28)

Examples 73 & 74

22-deacetyl-22-succinate-26-acetyl-neoboutomellerone (73) and 22-deacetyl-22-succinate-26-acetyl-neoboutomellerone N-methylglucamine salt (74)

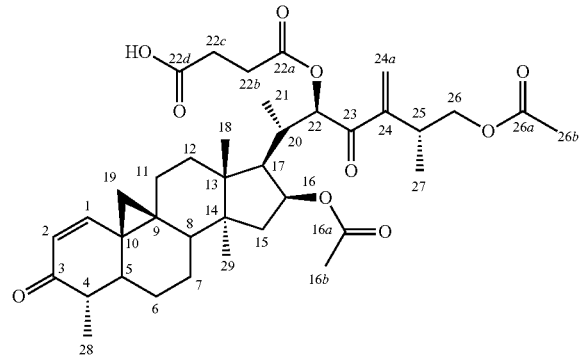

Chemical formula: C$_{38}$H$_{52}$O$_{10}$
Exact mass: 668.36
Molecular weight: 668.81

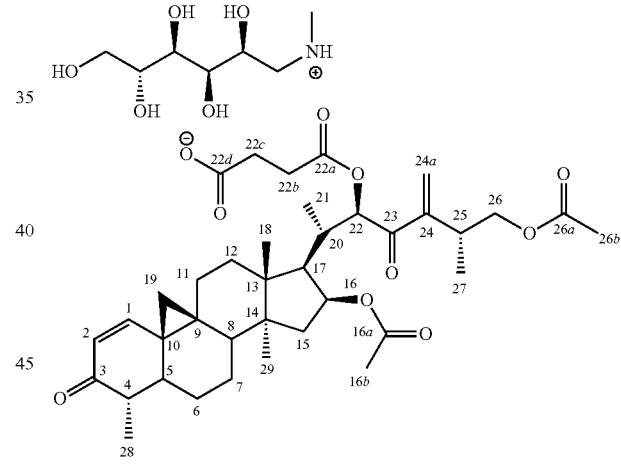

Chemical formula: C$_{45}$H$_{68}$NO$_{15}$
Exact mass: 862.46
Molecular weight: 863.02

Protocol: 59 mg (0.104 mmol) of 17 is solubilized in 2 ml of anhydrous dichloromethane. 42 mg of succinic anhydride (0.418 mmol, 4 eq) and 50 mg of DMAP (0.418 mmol, 4 eq) are added. After 90 h of stirring at room temperature, the reaction is terminated. The organic phase is washed with a 4% HCl solution and then extracted three times with ethyl acetate. The combined organic phases are then washed with a saturated sodium bicarbonate solution and a saturated sodium chloride solution. The organic phase is dried on Na$_2$SO$_4$, filtered and concentrated in a rotary evaporator. The residue is purified by silica gel chromatography (eluent: DCM/MeOH: 95/5) and by RP-18 HPLC (gradient: H$_2$O/CH$_3$CN: 90/10 to 0/100) in order to obtain 54 mg of succinic acid 73 (78%). 35 mg (0.12 mmol, 1 eq) of 73 is dissolved in 5 ml of absolute ethanol. 10 mg (0.05 mmol, 1 eq) of N-methyl-D-glucamine is dissolved in 2 ml of water and added to the solution prepared previously. The reaction medium is stirred for 10 minutes and concentrated in a rotary evaporator. The residue is taken up in 5 ml of water, filtered on a 45 m filter and freeze-dried in order to yield 42 mg of 74 (95%).

Example 73

$^1$H NMR (500 MHz, ACETONITRILE-$d_3$) δ=6.94 (1H, d, J=10.1 Hz, H-1), 6.11 (1H, s, H-24ab), 5.95 (1H, s, 24aa), 5.90 (1H, d, J=10.1 Hz, H-2), 5.56 (1H, d, J=2.1 Hz, H-22), 5.06 (1H, td, J=7.6 Hz, J=4.3 Hz, H-16), 4.03 (1H, dd, J=10.8 Hz, J=7.0 Hz, H-26<'>), 4.01 (1H, dd, J=10.8 Hz, J=6.4 Hz, H-26<">), 3.00 (1H, sxt, J=6.9 Hz, H-25), 2.64-2.71 (1H, m, 20), 2.54-2.64 (4H, m, H-22b, H-22c), 2.28 (1H, dd, J=11.0 Hz, J=7.6 Hz, H-17), 2.14-2.21 (2H, m, H-4, 15<'>), 2.03 (3H, s, H-16b), 1.97-2.02 (3H, m, H-11<'>, 5a, 8a), 1.97 (3H, s, H-26b), 1.63-1.76 (3H, m, H-6<'>, 12), 1.56 (1H, qd, J=8.7 Hz, J=6.2 Hz, H-11<">), 1.44 (1H, s, H-7<'>), 1.36 (1H, dd, J=13.9 Hz, J=4.1 Hz, H-15<">), 1.24 (1H, d, J=4.3 Hz, H-19<'>), 1.19-1.22 (1H, m, H-7<">), 1.18 (3H, s, H-18), 1.07 (3H, d, J=7.0 Hz, H-27), 1.02 (3H, d, J=6.7 Hz, H-28), 0.95 (3H, s, H-29), 0.88-0.94 (1H, m, H-6<">), 0.85 (3H, d, J=7.0 Hz, M25), 0.57 (1H, d, J=4.3 Hz, H-19<">)

$^{13}$C NMR (126 MHz, ACETONITRILE-$d_3$) δ=202.3 (C-3), 198.9 (C-23), 174.2 (C-22d), 173.0 (C-22a), 171.6 (C-26a), 171.3 (C-16a), 155.6 (C-1), 149.0 (C-24), 128.4 (C-2), 125.7 (C-24a), 78.4 (C-22), 76.7 (C-16), 67.8 (C-26), 51.2 (C-17), 48.3 (C-14), 47.6 (C-4), 46.8 (C-13), 46.7 (C-15), 45.2 (C-8), 43.6 (C-5), 34.9 (C-25), 33.4 (C-20), 33.0 (C-10), 32.9 (C-12), 29.9 (C-22b), 29.5 (C-22c), 28.1 (C-11), 27.6 (C-19), 27.2 (C-9), 24.3 (C-6, 7), 22.1 (C-16b), 21.1 (C-26b), 20.0 (C-29), 18.3 (C-18), 17.3 (C-27), 13.3 (C-21), 11.3 (C-28)

Example 74

$^1$H NMR (500 MHz, DMSO-$d_6$) δ=6.97 (1H, d, J=10.1 Hz, H-1), 6.05 (2H, s, H-24ab, 24aa), 5.90 (1H, d, J=10.1 Hz, H-2), 5.48 (1H, d, J=1.5 Hz, H-22), 4.97-5.07 (1H, m, H-16), 3.94-4.04 (2H, m, H-26), 3.66-3.71 (1H, m, H-5'), 3.64 (1H, d, J=4.9 Hz, H-4'), 3.59 (1H, dd, J=10.8 Hz, J=3.5 Hz, H-1'<'>), 3.45-3.50 (1H, m, H-2'), 3.33-3.43 (2H, m, H-3', 1'<">), 2.94 (1H, sxt, J=7.0 Hz, H-25), 2.56-2.68 (3H, m, H-22c, 6'), 2.42-2.48 (3H, m, H-20, 22b), 2.31 (3H, s, H-8'), 2.24 (1H, dd, J=11.0 Hz, J=7.6 Hz, H-17), 2.07-2.18 (2H, m, H-15<'>, 4), 2.04 (3H, s, H-16b), 1.98 (3H, s, H-26b), 1.94-1.97 (2H, m, H-11<'>, 8a), 1.90 (2H, td, J=12.4 Hz, J=4.3 Hz, H-5a), 1.50-1.71 (4H, m, H-12, 6<'>, 11<">), 1.35-1.45 (1H, m, H-7<'>), 1.26-1.33 (1H, dd, J=13.8 Hz, 4.2 Hz, H-15<">), 1.23 (1H, d, J=4.3 Hz, H-19<'>), 1.14-1.17 (1H, m, H-7<">), 1.13 (3H, s, H-18), 1.03 (3H, d, J=7.0 Hz, H-27), 0.98 (3H, d, J=6.7 Hz, H-28), 0.90 (3H, s, H-29), 0.83-0.89 (1H, m, M30), 0.81 (3H, d, J=6.7 Hz, H-21), 0.58 (1H, d, J=4.3 Hz, H-19<">)

$^{13}$C NMR (126 MHz, DMSO-$d_6$) δ=200.6 (C-3), 197.2 (C-23), 173.4 (C-22d), 171.9 (C-22a), 170.1 (C-26a), 169.7 (C-16a), 154.7 (C-1), 147.4 (C-24), 127.3 (C-2), 124.9 (C-24a), 76.5 (C-22), 75.2 (C-16), 71.2 (C-2'), 70.5 (C-4', 3'), 70.4 (C-5'), 66.4 (C-26), 63.7 (C-1'), 52.4 (C-6'), 49.6 (C-17), 46.9 (C-14), 46.1 (C-4), 45.4 (C-13, 15), 43.3 (C-8), 42.0 (C-5), 35.4 (C-8'), 33.5 (C-25), 31.9 (C-20), 31.6 (C-12), 31.6 (C-10), 29.2 (C-22b, 22c), 26.6 (C-9), 26.3 (C-11), 25.9 (C-19), 22.9 (C-6), 22.8 (C-7), 21.4 (C-16b), 20.6 (C-26b), 19.0 (C-29), 17.4 (C-18), 16.6 (C-27), 12.3 (C-21), 10.8 (C-28)

Example 75

22,26-bis(trimethylsilylethoxymethyl)-(26-deacetyl-neoboutomellerone)

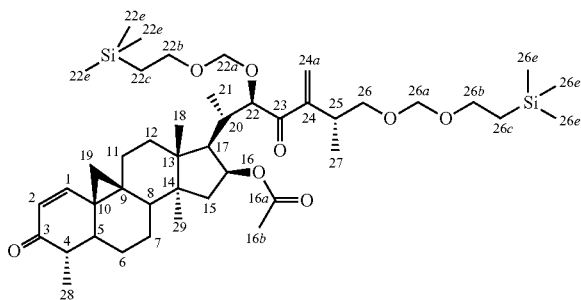

Chemical formula: $C_{44}H_{74}O_8Si_2$
Exact mass: 786.49
Molecular weight: 787.22

Protocol: Compound 1 (50 mg, 0.095 mmol) is dissolved in 0.5 ml of DCM and then 0.37 ml of Hünig's base (270 mg, 22 eq, 2.09 mmol) is added and the reaction medium is cooled in a 0° C. ice bath. 0.25 ml of trimethylsilylethoxymethane chloride (237 mg, 15 eq, 1.42 mmol) is then added and the reaction is allowed to return to room temperature. After 8 h of reaction a mixture of mono-protected compounds (Rf: 0.80; 50/50 cyclohexane/ethyl acetate) and bis-protected 75 (Rf: 0.88; 50/50 cyclohexane/ethyl acetate) are observed; after only one night compound 75 is present in the reaction medium. The reaction is hydrolyzed with an ammonium chloride solution and is extracted with ethyl acetate. The organic phase is washed with water and then with brine, dried on sodium sulfate and the solvents are evaporated. 147 mg of crude reaction product is collected and then purified on a silica gel column (eluent: cyclohexane/AcOEt gradient: 100/0 to 90/10). 71 mg (94%) of product 75 is obtained.

$^1$H NMR (500 MHz, ACETONITRILE-$d_3$) δ=6.93 (1H, d, J=10.0 Hz, H-1), 5.95 (1H, s, H-24ab), 5.89 (1H, d, J=10.0 Hz, H-2), 5.82 (1H, d, J=0.5 Hz, H-24aa), 5.23 (1H, td, J=7.2 Hz, J=4.5 Hz, H-16), 4.67 (1H, d, J=7.2 Hz, H-22a<'>), 4.59 (1H, d, J=6.5 Hz, H-26a<'>), 4.58 (1H, d, J=6.5 Hz, H-26a<">), 4.42 (1H, d, J=7.2 Hz, H-22a<">), 3.64-3.73 (1H, m, H-22b<'>), 3.51-3.61 (4H, m, H-26<'>, 26b<">, 26b<'>, 22b<">), 3.39-3.45 (1H, m, H-26<">), 2.93 (1H, sxt, J=6.6 Hz, H-25), 2.38-2.47 (2H, m, H-20), 2.17-2.22 (2H, m, H-15<'>), 2.13-2.16 (1H, m, H-4), 2.02-2.05 (1H, m, H-8a, 11<'>), 2.01 (4H, s, H-16b), 1.96-1.99 (1H, m, H-5a), 1.62-1.73 (3H, m, H-12<">, 12<'>, 6<'>), 1.50-1.59 (1H, m, H-11<">), 1.44-1.48 (1H, m, H-7<'>), 1.33-1.40 (1H, m, H-15<">), 1.21-1.25 (1H, m, H-19<'>), 1.18-1.21 (1H, m, H-7<">), 1.17 (3H, s, H-18), 1.04 (3H, d, J=7.0 Hz, H-27), 1.02 (3H, d, J=6.7 Hz, M27), 0.96 (3H, s, H-29), 0.87-0.93 (5H, m, H-22c<">, 22c<'>, 26c<">, 26c<'>, 6<'>), 0.77-0.81 (3H, m, H-21), 0.57 (1H, d, J=4.5 Hz, H-19<">), 0.01 (19H, s, H-22e, 22e, 22e, 26e, 26e, 26e).

$^{13}$C NMR (126 MHz, ACETONITRILE-$d_3$) δ=202.9 (C-23), 202.4 (C-3), 171.3 (C-16a), 155.6 (C-1), 151.5 (C-24), 128.4 (C-2), 123.8 (C-24a), 95.6 (C-26a), 95.2

(C-22a), 80.7 (C-22), 76.5 (C-16), 72.0 (C-26), 66.8 (C-26b), 65.7 (C-22b), 51.2 (C-17), 48.4 (C-14), 47.6 (C-4), 46.8 (C-15), 46.8 (C-13), 45.3 (C-8), 43.6 (C-5), 35.8 (C-25), 34.2 (C-20), 33.0 (C-12), 32.9 (C-10), 28.1 (C-11), 27.8 (C-19), 27.2 (C-9), 24.3 (C-6), 24.3 (C-7), 22.2 (C-16b), 20.5 (C-29), 18.8 (C-26c), 18.7 (C-22c), 18.3 (C-18), 17.8 (C-27), 12.9 (C-21), 11.3 (C-28), −1.2 (C-22e, 26e, 22e), −1.3 (C-26e, 26e, 26e).

Example 76

26-trimethylsilylethoxymethyl-neoboutomellerone

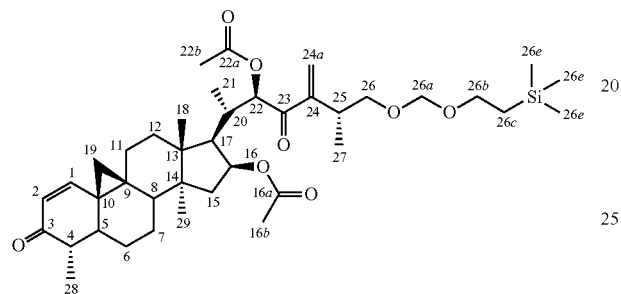

Chemical formula: $C_{38}H_{60}O_7Si$
Exact mass: 656.41
Molecular weight: 656.96

Protocol: Using the same protocol as before but from compound 2 yields compound 76.

$^1$H NMR (500 MHz, ACETONITRILE-$d_3$) δ=6.94 (1H, d, J=10.1 Hz, H-1), 6.04 (1H, s, H-24aa), 5.88-5.92 (2H, m, H-2, 24ab), 5.53 (1H, d, J=2.1 Hz, H-22), 5.09 (1H, td, J=7.7 Hz, J=4.4 Hz, H-16), 4.57-4.61 (2H, m, H-26a<">, 26a<'>), 3.53-3.61 (4H, m, H-26b<">, 26b<'>, 26<'>), 3.42 (1H, dd, J=9.8 Hz, J=6.7 Hz, H-26<">), 2.92 (1H, sxt, J=6.9 Hz, H-25), 2.60 (1H, dtd, J=13.8 Hz, J=6.9 Hz, J=2.2 Hz, H-20), 2.29 (1H, dd, J=11.0 Hz, J=7.3 Hz, H-17), 2.18 (2H, dd, J=13.0 Hz, J=6.6 Hz, H-4, 15<'>), 2.09 (3H, s, H-22b), 2.02-2.03 (3H, m, H-16b), 1.96-2.02 (3H, m, H-11<'>, 8a, 5a), 1.64-1.73 (3H, m, H-6<'>, 12<">, 12<'>), 1.53-1.60 (1H, m, H-11<">), 1.40-1.50 (1H, m, H-7<'>), 1.36 (1H, dd, J=14.3 Hz, J=4.0 Hz, H-15<">), 1.23-1.26 (1H, m, H-19<'>), 1.19 (3H, s, H-18), 1.04-1.07 (3H, m, H-27), 1.03 (3H, d, J=6.7 Hz, H-28), 0.96 (3H, s, H-29), 0.93-0.94 (1H, m, H-6<">), 0.90 (2H, dd, J=8.9 Hz, J=7.6 Hz, H-26c<">, 26c<'>), 0.86 (3H, d, J=7.0 Hz, H-21), 0.58 (1H, d, J$_{19<">,16}$=4.6 Hz, H-19<">), 0.01 (9H, s, H-26e, 26e, 26e).

$^{13}$C NMR (126 MHz, ACETONITRILE-$d_3$) δ=202.4 (C-3), 199.2 (C-23), 171.6 (C-22a), 171.2 (C-16a), 155.5 (C-1), 150.4 (C-24), 128.5 (C-2), 124.6 (C-24a), 95.7 (C-26a), 78.4 (C-22), 76.7 (C-16), 71.9 (C-26), 65.8 (C-26b), 51.4 (C-17), 48.4 (C-14), 47.7 (C-4), 46.9 (C-13), 46.7 (C-15), 45.2 (C-8), 43.6 (C-5), 35.9 (C-25), 33.1 (C-20), 33.0 (C-12), 33.0 (C-10), 28.1 (C-11), 27.7 (C-19), 27.3 (C-9), 24.3 (C-6, 7), 22.1 (C-16b), 21.0 (C-22b), 20.0 (C-29), 18.7 (C-26c), 18.3 (C-18), 17.8 (C-27), 13.3 (C-21), 11.3 (C-28), −1.2 (C-26e, 26e, 26e)

Example 77

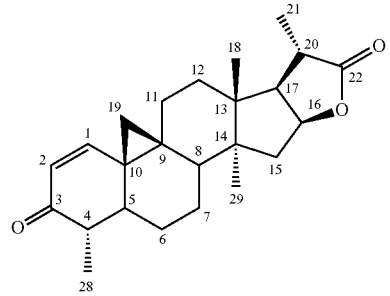

Chemical formula: $C_{24}H_{32}O_3$
Exact mass: 368.24
Molecular weight: 368.51

Protocol: Compound 2 (60 mg, 0.106 mmol) is dissolved in 2 ml of DCM and then 1 ml of a 1 M diisobutylaluminum hydride solution is added. After conversion is complete, the reaction is neutralized with methanol and the solvents are evaporated. The residue is taken up in ethyl acetate, washed with water and then with brine, dried on sodium sulfate and concentrated. After crude purification on silica, 22 mg of a mixture of four diastereoisomers is collected, corresponding to products deacetylated at positions 16 and 22 and reduced at positions 3 and 23 (m/z=488, Rf=0.36, 0.25, 0.19, 0.11; 20/80 cyclohexane/ethyl acetate). This mixture is completely taken up in 6 ml of DCM at room temperature and 65 mg of manganese oxide is added. The reaction is left at room temperature. After disappearance of the initial products the manganese oxide is adsorbed on sodium carbonate and filtered on Celite®. After silica gel chromatography 9 mg of compound 77 (23% in 2 steps) is collected.

$^1$H NMR (500 MHz, ACETONITRILE-$d_3$) δ=6.96 (1H, d, J=10.0 Hz, H-1), 5.92 (1H, d, J=10.0 Hz, H-2), 5.05 (1H, td, J=8.0 Hz, J=5.0 Hz, H-16), 2.63 (1H, qd, J=7.5 Hz, J=1.0 Hz, H-20), 2.45-2.48 (1H, m, H-17), 2.18-2.22 (1H, m, H-4), 2.01-2.06 (1H, m, H-11<'>, 15<'>), 1.96-2.01 (1H, m, H-8a), 1.90-1.92 (1H, m, H-5a), 1.58-1.76 (5H, m, H-11<">, 12<">, 12<'>, 6<'>), 1.45-1.57 (2H, m, H-7<'>, 15<">), 1.30-1.32 (1H, m, H-19<'>), 1.25-1.28 (4H, m, H-21), 1.18-1.24 (1H, m, H-7<">), 1.00-1.04 (6H, m, H-29, 28), 0.88-0.91 (3H, m, H-18), 0.49-0.53 (1H, m, H-19<">).

$^{13}$C NMR (126 MHz, ACETONITRILE-$d_3$) δ=202.2 (C-3), 182.2 (C-22), 155.1 (C-1), 128.6 (C-2), 83.9 (C-16), 66.3, 56.2 (C-17), 50.7 (C-14), 47.4 (C-4), 45.8 (C-13), 43.2 (C-15), 42.9 (C-5, 8), 37.5 (C-20), 33.2 (C-10), 31.0 (C-12), 27.8 (C-11), 27.4 (C-9), 26.0 (C-19), 23.8 (C-6), 23.6 (C-7), 19.0 (C-29), 18.7 (C-18), 18.4 (C-21), 11.3 (C-28).

Example 78

26-allyl-neoboutomellerone ether

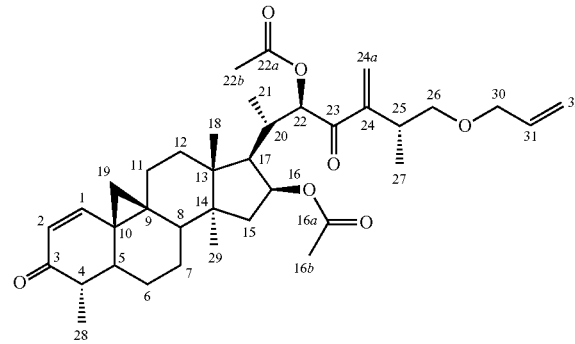

Chemical formula: C$_{37}$H$_{52}$O$_{72}$
Exact mass: 608.37
Molecular weight: 608.80

Protocol: Compound 2 (284 mg, 0.5 mmol) is dissolved at 0° C. in 2 ml of DCM and then 170 µl of 2,6-di-tert-butylpyridine (143 mg, 1.5 eq, 0.75 mmol) is added. The reaction is protected from light with aluminum foil before 141 mg of silver triflate (1.21 eq, 0.55 mmol) and then allyl bromide (52 73 mg, 1.2 eq, 0.6 mmol) are added. The reaction is allowed to return to room temperature and is left under stirring for 4 hours. The reaction is hydrolyzed with a 1 N hydrochloric acid solution and diluted with ethyl acetate. The organic phase is separated, washed with water and then brine and then dried on sodium sulfate and concentrated. The mixture is purified on a silica gel and leads to 107 mg of compound 78 (35%; Rf: 0.87; 50/50 cyclohexane/ethyl acetate) and 116 mg of unreacted compound 2.

$^1$H NMR (500 MHz, ACETONITRILE-d$_3$) δ=6.93 (1H, d, J=9.8 Hz, H-1), 6.02 (1H, s, H-24ab), 5.85-5.93 (3H, m, H-2, 31, 24aa), 5.53 (1H, d, J=2.1 Hz, H-22), 5.24 (1H, ddd, J=17.4 Hz, J=1.8 Hz, J=1.5 Hz, H-32aa), 5.13 (1H, ddd, J=15.0 Hz, J=2.0 Hz, J=1.5 Hz, H-32ab), 5.10 (1H, td, J=7.7 Hz, J=4.3 Hz, H-16), 3.93 (2H, dq, J=5.5 Hz, J=1.3 Hz, H-30<">, 30<'>), 3.45-3.47 (1H, m, M26), 3.48 (1H, dd, J=9.5 Hz, J=6.5 Hz, H-26<'>), 3.32 (1H, dd, J=9.3 Hz, J=6.6 Hz, H-26<">), 2.92 (1H, sxt, J=6.7 Hz, H-25), 2.59 (1H, qdd, J=11.0 Hz, J=6.9 Hz, J=2.3 Hz, H-20), 2.30 (1H, dd, J=11.0 Hz, J=7.6 Hz, H-17), 2.17 (2H, dd, J=13.0 Hz, J=6.9 Hz, H-15<'>), 2.09 (3H, s, H-22b), 2.03-2.06 (2H, m, H-11<'>, 8a), 2.00 (1H, d, J=4.6 Hz, H-5a), 2.02 (5H, s, H-16b), 1.63-1.76 (4H, m, H-12<">, 12<'>, 6<'>), 1.57 (1H, ddd, J=15.0 Hz, J=8.9 Hz, J=6.1 Hz, H-11<">), 1.44-1.50 (1H, m, H-7<'>), 1.36 (1H, dd, J=14.0 Hz, J=3.5 Hz, H-15<">), 1.24 (1H, d, J=4.3 Hz, H-19<'>), 1.20-1.23 (1H, m, H-7<">), 1.18 (3H, s, H-18), 1.06 (3H, d, J=7.0 Hz, H-27), 1.03 (3H, d, J=7.0 Hz, H-28), 0.95 (4H, s, H-29), 0.91-0.93 (1H, m, H-6<'>), 0.85 (4H, d, J=7.0 Hz, H-21), 0.57 (1H, d, J=4.6 Hz, H-19<">).

$^{13}$C NMR (126 MHz, ACETONITRILE-d$_3$) δ=202.3 (C-3), 199.3 (C-23), 171.6 (C-22a), 171.2 (C-16a), 155.4 (C-1), 150.3 (C-24), 136.4 (C-31), 128.5 (C-2), 124.8 (C-24a), 116.8 (C-32), 78.4 (C-22), 76.6 (C-16), 74.3 (C-26), 72.4 (C-30), 51.4 (C-17), 48.4 (C-14), 47.7 (C-4), 46.9 (C-13), 46.7 (C-15), 45.2 (C-8), 43.6 (C-5), 36.3 (C-25), 33.1 (C-20), 33.0 (C-12), 33.0 (C-10), 28.1 (C-11), 27.7 (C-19), 27.2 (C-9), 24.3 (C-7, 6), 22.1 (C-16b), 21.0 (C-22b), 20.1 (C-29), 18.3 (C-18), 17.7 (C-27), 13.3 (C-21), 11.3 (C-28).

Example 79

26-allyl-22-deacetyl-neoboutomellerone

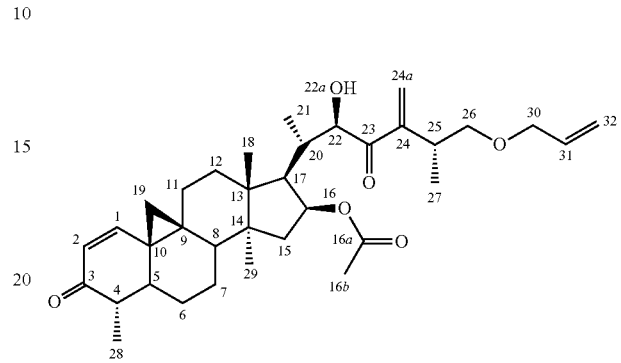

Chemical formula: C$_{35}$H$_{50}$O$_6$
Exact mass: 566.36
Molecular weight: 566.77

Protocol: Compound 1 (263 mg, 0.5 mmol) is dissolved in 2.5 ml of DCM and then 135 mg of magnesium sulfate (1.1 eq, 0.55 mmol) is added. The reaction is protected from light with aluminum foil before 340 mg of silver oxide (3 eq, 1.5 mmol) is added and, after 1 hour of stirring at room temperature, allyl bromide (650 µl, 907 mg, 15 eq, 7.5 mmol) is added. The reaction is left under stirring until conversion is complete. The reaction is hydrolyzed with a 1 N hydrochloric acid solution and diluted with ethyl acetate. The organic phase is separated, washed with water and then brine and then dried on sodium sulfate and concentrated. The mixture is purified on a silica gel and leads to 220 mg of compound 79 (78%; Rf: 0.78; 50/50 cyclohexane/ethyl acetate).

$^1$H NMR (500 MHz, ACETONITRILE-d$_3$) δ=6.93 (1H, d, J=10.0 Hz, H-1), 6.10 (1H, s, H-24aa), 5.99 (1H, d, J=0.9 Hz, H-24ab), 5.90 (1H, s, H-31, 2), 5.24 (1H, ddd, J=7.3 Hz, J=1.8 Hz, J=1.5 Hz, H-32aa), 5.20 (1H, td, J=7.4 Hz, J=4.3 Hz, H-16), 5.12 (1H, qd, J=15.5 Hz, J=1.5 Hz, H-32ab), 4.71 (1H, dd, J=5.5 Hz, J=1.5 Hz, H-22), 3.93 (1H, dd, J=5.4 Hz, J=1.4 Hz, H-30), 3.51-3.52 (1H, m, H-38), 3.51 (1H, dd, J=9.4 Hz, J=6.4 Hz, H-26<'>), 3.33 (1H, dd, J=9.3 Hz, J=6.6 Hz, H-26<">), 2.97 (1H, sxt, J=6.7 Hz, H-25), 2.38-2.50 (1H, m, H-17, 20), 2.23 (1H, dd, J=13.9 Hz, J=7.8 Hz, H-15<'>), 2.15-2.20 (1H, m, H-4), 2.03-2.09 (1H, m, H-8a, 11<'>), 2.03 (2H, s, H-16b), 1.96-2.02 (2H, m, H-5a), 1.61-1.74 (2H, m, H-12<">, 12<'>, 6<'>), 1.55 (1H, ddd, J=14.9 Hz, J=8.6 Hz, J=6.2 Hz, H-11<">), 1.42-1.50 (1H, m, H-7<'>), 1.38 (1H, dd, J=14.2 Hz, J=4.2 Hz, H-15<">), 1.24 (1H, d, J=4.5 Hz, H-19<'>), 1.19-1.23 (1H, m, H-7<">), 1.18 (2H, s, H-18), 1.08 (1H, d, J=7.0 Hz, H-27), 1.03 (2H, d, J=6.7 Hz, H-28), 0.97 (2H, s, H-29), 0.91-0.96 (1H, m, H-6<'>), 0.65 (1H, d, J=6.1 Hz, H-21), 0.57 (1H, d, J=4.5 Hz, H-19<">).

$^{13}$C NMR (126 MHz, ACETONITRILE-d$_3$) δ=205.4 (C-23), 202.4 (0-3), 171.3 (C-16a), 155.6 (C-1), 149.2 (C-24), 136.4 (C-31), 128.4 (C-2), 126.5 (C-24a), 116.7 (C-32), 77.3 (C-16), 75.9 (C-22), 74.7 (C-26), 72.4 (C-30), 51.5 (C-17), 48.3 (C-14), 47.8 (C-4), 47.0 (C-15), 46.7 (C-13), 45.4 (C-8), 43.7 (C-5), 36.2 (C-25), 35.8 (C-20), 33.2 (C-12), 33.0 (C-10), 28.2 (C-11), 27.8 (C-19), 27.3 (C-9), 24.4 (C-6), 24.4 (C-7), 22.1 (C-16b), 20.1 (C-29), 18.6 (C-18), 17.7 (C-27), 12.3 (C-21), 11.3 (C-28).

Example 80

1,2-dihydroxy-26-sn1-glycerylether-neoboutomellerone

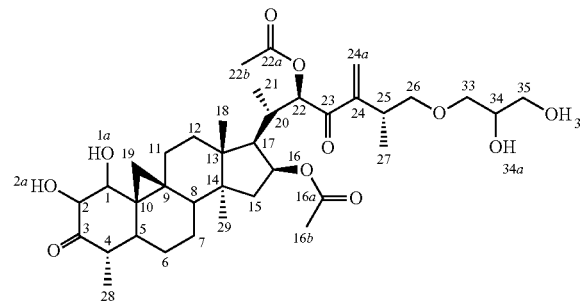

Chemical formula: $C_{37}H_{58}O_{11}$
Exact mass: 676.38
Molecular weight: 676.83

Protocol: Compound 78 (38 mg, 0.063 mmol) is dissolved in 1.5 ml of a tert-butanol/water mixture (9/1) in which 17.5 mg (1.1 eq, 0.069 mmol) of N-methylmorpholine oxide and 1 µl (0.05 eq, 0.003 mmol) of an osmium tetroxide solution in tert-butanol are added. The reaction is quenched with a sodium bisulfite solution and extracted with ethyl acetate. The organic phase is washed with a sodium bicarbonate solution, water and then brine, and then is dried on sodium sulfate and concentrated. The crude reaction product (42 mg) is purified on a silica gel (eluent: AcOEt gradient/cyclohexane: 70/30 to 90/10) to provide compound 80 (38%) and other polyhydroxylated compounds.

$^1$H NMR (500 MHz, ACETONITRILE-d$_3$) δ=6.05 (1H, d, J=1.2 Hz, H-24ab), 5.91 (1H, s, H-24aa), 5.53 (1H, d, J=2.1 Hz, H-22), 5.09 (1H, td, J=7.6 Hz, J=4.3 Hz, H-16), 4.20-4.27 (1H, m, H-1), 3.74-3.79 (1H, m, H-2), 3.70 (1H, d, J=4.9 Hz, H-1a), 3.66 (1H, dt, J=6.0 Hz, J=4.7 Hz, H-34), 3.46-3.52 (1H, m, H-33<'>, 26<'>), 3.39-3.44 (2H, m, H-35<''>, 35<'>, 26<''>), 3.32-3.39 (1H, m, H-33<''>), 3.02 (1H, d, J=2.1 Hz, H-2a), 2.92 (1H, d, J=5.5 Hz, H-34a), 2.69 (1H, t, J=6.0 Hz, H-35a), 2.59 (1H, dtd, J=13.9 Hz, J=6.9 Hz, J=2.2 Hz, H-20), 2.32-2.38 (1H, m, H-25), 2.28-2.34 (1H, m, H-4, 8a), 2.29 (1H, dd, J=10.8 Hz, J=7.5 Hz, H-17), 2.23-2.26 (1H, m, H-11<'>), 2.23-2.28 (1H, m, M30), 2.20 (1H, dd, J=13.9 Hz, J=7.8 Hz, H-15<'>), 2.09 (2H, s, H-22b), 2.03-2.09 (1H, m, H-5a), 2.03 (1H, d, J=0.6 Hz, H-16b), 1.66-1.81 (2H, m, H-6<'>, 12<''>, 12<'>), 1.40-1.46 (2H, m, H-11<''>), 1.36 (2H, dd, J=13.8 Hz, J=4.3 Hz, H-15<''>), 1.30-1.34 (1H, m, H-7<'>), 1.27 (1H, s, M34), 1.22 (2H, s, H-18), 1.08-1.19 (3H, m, H-7<''>), 1.05 (5H, d, J=7.0 Hz, H-27), 0.99-1.02 (1H, m, H-29), 0.98 (5H, d, J=6.4 Hz, H-28), 0.88-0.94 (1H, m, H-6<''>), 0.86 (2H, d, J=6.7 Hz, H-21), 0.81 (2H, d, J=4.6 Hz, H-19<'>), 0.57 (1H, d, J=4.6 Hz, H-19<''>).

$^{13}$C NMR (126 MHz, ACETONITRILE-d$_3$) δ=212.6 (C-3), 199.3 (C-23), 171.7 (C-22a), 171.3 (C-16a), 150.3 (C-24), 124.9 (C-24a), 78.5 (C-22), 78.0 (C-1), 77.9 (C-2), 76.9 (C-16), 75.6 (C-35), 75.5 (C-35), 73.4 (C-33), 73.4 (C-33), 71.7 (C-34), 71.7 (C-34), 64.5 (C-26), 51.5 (C-17), 48.1 (C-14), 48.0 (C-4), 48.0 (C-4), 47.6 (C-15), 46.9 (C-13), 40.3 (C-5), 35.8 (C-25), 35.8 (C-8), 33.2 (C-20), 33.2 (C-12), 32.1 (C-10), 27.4 (C-19), 26.8 (C-11), 26.1 (C-7), 25.7 (C-6), 25.0 (C-9), 22.1 (C-16b), 21.0 (C-22b), 20.6 (C-29), 19.2 (C-18), 17.6 (C-27), 13.3 (C-21), 10.7 (C-28).

Example 81

26-acetoxymethyl-(22-deacetyl-neoboutomellerone) ether

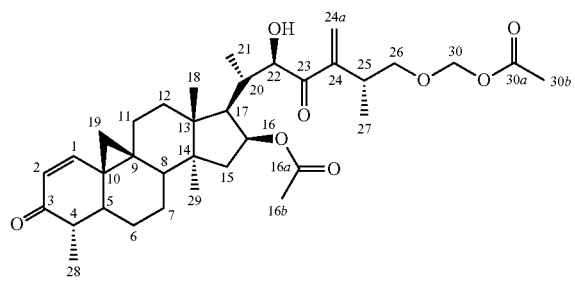

Chemical formula: $C_{38}H_{52}O_8$
Exact mass: 598.35
Molecular weight: 598.77

Protocol: 50 mg (0.095 mmol) of compound 1 is dissolved in 0.5 ml of DCM with 0.33 ml (20 eq, 1.9 mmol) of Hünig's base. The reaction medium is cooled to 0° C. and at this temperature 0.095 ml (10 eq, 0.95 mmol) of bromomethyl acetate is added. After 1 h, the ice bath is removed and stirring is maintained overnight. The reaction medium is hydrolyzed with water and extracted with ethyl acetate. The organic phases are combined, washed with water and then brine and dried on sodium sulfate. The crude reaction product (66 mg) is purified on a silica gel (eluent: cyclohexane/AcOEt gradient: 80/20 to 30/70). 33 mg (59%) of product 81 (Rf: 0.75; 50/50 cyclohexane/ethyl acetate) and 21 mg (42%) of compound 1 are obtained.

¹H NMR (500 MHz, ACETONITRILE-d₃) δ=6.93 (1H, d, J=9.8 Hz, H-1), 6.14 (1H, s, H-24ab), 6.00 (1H, d, J=0.9 Hz, H-24aa), 5.89 (1H, d, J=10.1 Hz, H-2), 5.20-5.23 (1H, m, H-16), 5.19-5.21 (1H, m, H-30<'>), 5.18 (1H, s, H-30<''>), 4.72 (2H, dd, J=5.8 Hz, J=1.5 Hz, H-22), 3.71 (1H, dd, J=9.8 Hz, J=6.4 Hz, H-26<'>), 3.55 (1H, dd, J=9.6 Hz, J=6.6 Hz, H-26<''>), 3.51 (1H, dd, J=6.1 Hz, J=0.6 Hz, H-38), 2.98 (1H, sxt, J=6.6 Hz, H-25), 2.43 (2H, d, J=6.4 Hz, H-17, 20), 2.22 (1H, dd, J=13.7 Hz, J=7.9 Hz, H-15<'>), 2.18 (1H, dd, J=12.8 Hz, J=6.7 Hz, H-4), 2.03 (4H, s, H-30b), 2.02 (2H, s, H-16b), 2.01 (1H, br. s., H-11<'>), 1.96-1.98 (16H, m, H-8a, 5a), 1.63-1.72 (27H, m, H-6<'>, 12<''>, 12<'>), 1.55 (1H, ddd, J=13.9 Hz, J=8.9 Hz, J=6.0 Hz, H-11<''>), 1.46 (1H, dtd, J=10.1 Hz, J=6.7 Hz, J=4.0 Hz, H-7<'>), 1.38 (1H, dd, J=14.0 Hz, J=4.3 Hz, H-15<''>), 1.24 (1H, d, J=4.3 Hz, H-19<'>), 1.19-1.22 (1H, m, H-7<''>), 1.19-1.19 (1H, m, M08), 1.18 (3H, s, H-18), 1.06 (2H, d, J=7.0 Hz, H-27), 1.03 (3H, d, J=7.0 Hz, H-28), 0.97 (3H, s, H-29), 0.91-0.95 (1H, m, H-6<''>), 0.65 (3H, d, J=6.1 Hz, H-21), 0.57 (1H, d, J=4.3 Hz, H-19<''>).

¹³C NMR (126 MHz, ACETONITRILE-d₃) δ=205.2 (C-3), 202.4 (C-23), 171.4 (C-30a), 171.3 (C-16a), 155.6 (C-1), 148.6 (C-24), 128.4 (C-2), 127.0 (C-24a), 89.9 (C-30), 77.3 (C-16), 75.9 (C-22), 74.4 (C-26), 51.5 (C-17), 48.4 (C-14), 47.7 (C-4), 46.9 (C-15), 46.7 (C-13), 45.3 (C-8), 43.7 (C-5), 36.4 (C-25), 35.5 (C-20), 33.2 (C-12), 33.0 (C-10), 28.2 (C-11), 27.8 (C-19), 27.3 (C-9), 24.4 (C-6), 24.4 (C-7), 22.1 (C-16b), 21.3 (C-30b), 20.2 (C-29), 18.5 (C-18), 17.5 (C-27), 12.3 (C-21), 11.3 (C-28).

Example 82

Neoboutomellerone 26-(2,3,4,6-tetraacetyl-glucosylate)

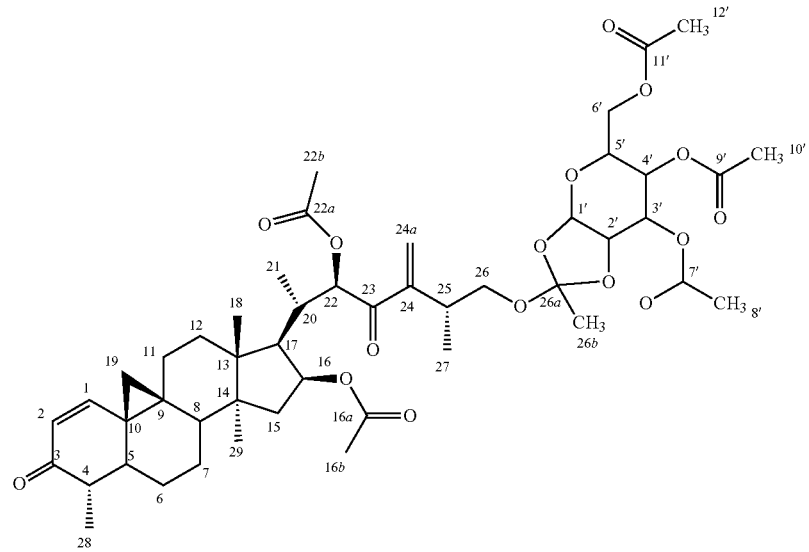

Chemical formula: C₄₈H₆₆O₁₆
Exact mass: 898.44
Molecular weight: 899.03

Step 1: Synthesis of peracetyl-glucose

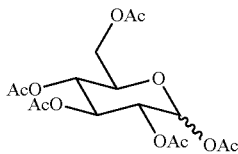

5 g (25.2 mmol) of glucose (α/β mixture: 3/1) is dissolved in acetic anhydride in the presence of sodium acetate. The reaction mixture is left under stirring for 2 h at 100° C. The reaction medium is diluted with ethyl acetate and then filtered. The filtrate is then washed with water, a sodium bicarbonate solution and then brine. After drying on sodium sulfate and evaporation of the solvent, 240 mg of crude reaction product is collected. The product is purified on a silica gel column and eluted with an 80/20 cyclohexane/ethyl acetate mixture. 7.27 g of product is collected with a yield of 74% (Rf: 0.60; 50/50 cyclohexane/ethyl acetate).

Step 2: Synthesis of 2,3,4,6-tetraacetyl-glucose

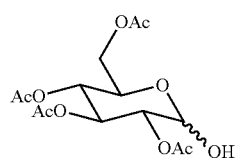 [SMILES: CC(=O)OCC1OC(O)C(OC(C)=O)C(OC(C)=O)C1OC(C)=O]

3.5 g (8.97 mmol) of peracetyl-glucose is dissolved in 10 ml of DMF and then 1.07 g (1.61 mmol, 0.18 eq) of hydrazine acetate is added. The mixture is heated for 20 minutes at 50° C. and then, after it returns to room temperature, diluted with ethyl acetate and filtered. The filtrate is washed successively with water, a sodium bicarbonate solution, water, a 15% aqueous lithium chloride solution, water and finally brine. After drying on sodium sulfate and evaporation of the solvent, 240 mg of crude reaction product is collected. The product is purified on a silica gel column and eluted with a 50/50 cyclohexane/ethyl acetate mixture. 2.57 g of product is collected (82%; Rf: 0.20; 60/40 cyclohexane/ethyl acetate).

Step 3: Synthesis of (1-trichloroacetimidate)-(2,3,4,6-tetraacetyl)-glucose

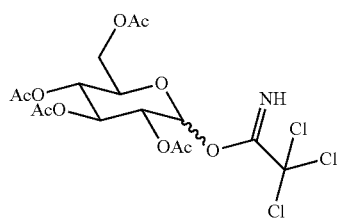 [SMILES: CC(=O)OCC1OC(OC(=N)C(Cl)(Cl)Cl)C(OC(C)=O)C(OC(C)=O)C1OC(C)=O]

2.57 g (7.39 mmol) of 2,3,4,6-tetraacetyl-glucose is dissolved in 10 ml of DCM and then 7.5 ml (75 mmol) of trichloroacetonitrile and 107 μl (10%) of DBU are added successively. The reaction mixture is left under stirring at 0° C. for 2 h. After evaporation of the solvents, the mixture is purified on a silica gel column with a 60/40 to 40/60 cyclohexane/ethyl acetate gradient. 2.36 g (65%) of (1-trichloroacetimidate)-(2,3,4,6-tetraacetyl)-glucose is obtained (Rf: 0.50; 60/40 cyclohexane/ethyl acetate).

Step 4: Synthesis of neoboutomellerone 26-(2,3,4,6-tetraacetyl-glucosylate)

500 mg (0.88 mmol) of 2 and 650 mg of (1-trichloroacetimidate)-(2,3,4,6-tetraacetyl)-glucose (1.5 eq, 1.32 mmol) is dissolved in 10 ml of acetonitrile. A catalytic quantity of trimethylsilyl triflate (20%, 0.088 mmol, 32 μl) is then added and the reaction is left under stirring overnight. The reaction medium is diluted with ethyl acetate and then filtered on sintered glass. The filtrate is washed with water and then brine. After drying on sodium sulfate and evaporation of the solvent, 1.174 g of crude reaction product is collected. The product is purified on a silica gel column and eluted with a 60/40 to 50/50 cyclohexane/ethyl acetate gradient. Among other products, 65.7 mg of neoboutomellerone 26-(2,3,4,6-tetraacetyl-glucosylate) is collected.

$^1$H NMR (500 MHz, ACETONITRILE-d$_3$) δ=6.94 (1H, d, J=10.1 Hz, H-1), 6.14 (1H, s, H-24aa), 5.95 (1H, s, H-24ab), 5.90 (1H, d, J=10.1 Hz, H-2), 5.60 (1H, d, J=5.2 Hz, H-1'), 5.52 (1H, d, J=2.1 Hz, H-22), 5.06 (1H, td, J=7.6 Hz, J=4.4 Hz, H-16), 5.02 (1H, t, J=2.1 Hz, H-3'), 4.83 (1H, ddt, J=9.5 Hz, J=2.1 Hz, J=1.1 Hz, H-4'), 4.29 (1H, ddd, J=5.1 Hz, J=2.8 Hz, J=0.9 Hz, H-2'), 4.13 (1H, dd, J=12.5 Hz, J=3.1 Hz, H-6'<'>), 4.09 (1H, dd, J=12.5 Hz, J=5.5 Hz, H-6'<">), 3.88 (1H, ddd, J=8.9 Hz, J=4.9 Hz, J=2.7 Hz, H-5'), 3.38-3.51 (2H, m, H-26<">, 26<'>), 2.91 (1H, sxt, J=6.4 Hz, H-25), 2.51-2.63 (1H, m, H-20), 2.30 (1H, dd, J=10.8 Hz, J=7.5 Hz, H-17), 2.15-2.23 (2H, m, H-4, 15<'>), 1.95-2.11 (18H, m, H-5,8,8', 10', 12', 16b, 22b, 11<'>), 1.64 (3H, s, H-26b), 1.61-1.75 (3H, m, H-6<'>, 12<">, 12<'>), 1.51-1.60 (1H, m, H-11<">), 1.40-1.49 (1H, m, H-7<'>), 1.37 (1H, dd, J=14.3 Hz, J=4.9 Hz, H-15<">), 1.24 (1H, d, J=4.6 Hz, H-19<'>), 1.18 (3H, s, H-18), 1.16-1.21 (1H, m, H-7<">), 1.03 (3H, d, J=6.7 Hz, H-28), 1.02 (3H, d, J=7.0 Hz, H-27), 0.96 (3H, s, H-29), 0.88-0.97 (1H, m, H-6<">), 0.83 (3H, d, J=7.0 Hz, H-21), 0.58 (1H, d, J=4.6 Hz, H-19<">)

$^{13}$C NMR (126 MHz, ACETONITRILE-d$_3$) δ=202.4 (C-3), 198.6 (C-23), 171.7 (C-22a), 171.5 (C-7'), 171.3 (C-16a), 170.8 (C-9'), 170.4 (C-11'), 155.5 (C-1), 150.0 (C-24), 128.4 (C-2), 125.6 (C-24a), 122.2 (C-26a), 97.7 (C-1'), 78.3 (C-22), 76.7 (C-16), 73.4 (C-2'), 70.7 (C-3'), 69.0 (C-4'), 68.0 (C-26), 67.8 (C-5'), 64.2 (C-6'), 51.2 (C-17), 48.3 (C-14), 47.6 (C-4), 46.9 (C-13), 46.8 (C-15), 45.2 (C-8), 43.6 (C-5), 34.9 (C-25), 33.3 (C-20), 33.0 (C-12), 32.9 (C-10), 28.1 (C-11), 27.7 (C-19), 27.2 (C-9), 24.3 (C-7, 6), 22.2 (C-16b), 21.2 (C-12'), 21.1 (C-10'), 21.1 (C-8'), 21.0, 21.0 (C-26b), 20.9 (C-22b), 20.0 (C-29), 18.3 (C-18), 17.6 (C-27), 13.3 (C-21), 11.3 (C-28)

Example 83

Neoboutomellerone tetraBoc spermine acetate

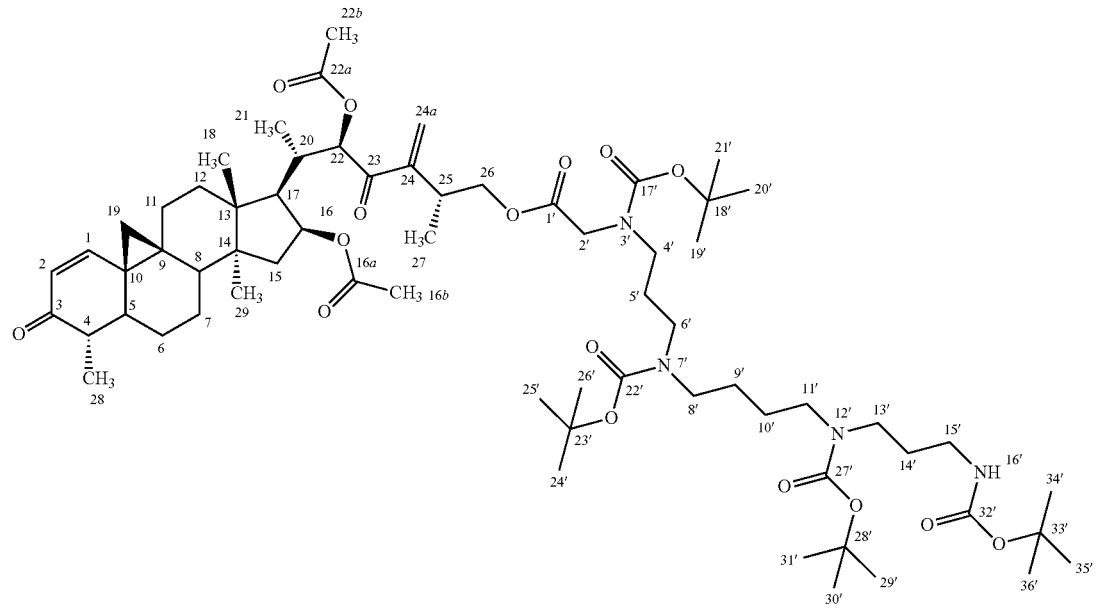 [SMILES: C=C(C(=O)[C@H](OC(C)=O)[C@@H](C)[C@H]1[C@@H](OC(C)=O)C[C@@]2(C)C3CCC4[C@H](C)C(=O)C=C[C@@]45C[C@@]35CC[C@]12C)[C@@H](C)COC(=O)CN(CCCN(CCCCN(CCCNC(=O)OC(C)(C)C)C(=O)OC(C)(C)C)C(=O)OC(C)(C)C)C(=O)OC(C)(C)C]

Chemical formula: $C_{66}H_{106}N_4O_{16}$
Exact mass: 1210.76; Molecular weight: 1211.57

Step 1: Synthesis of triBoc Spermine Ethyl Acetate

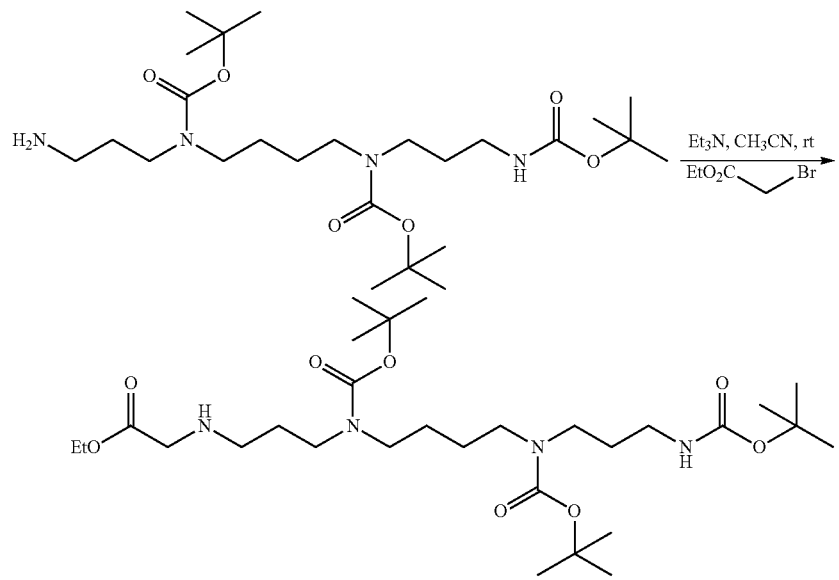

2.6 ml of triethylamine (18.4 mmol, 2.5 eq) is added to a solution of 3.96 g of triBoc spermine (7.3 mmol, 1 eq) in 100 ml of acetonitrile. 0.81 ml of ethyl bromoacetate (7.3 mmol, 1 eq) is then quickly added to this solution under stirring. After 5 h of stirring at room temperature, the reaction medium is dumped into a saturated NaCl solution (100 ml) and extracted with ethyl acetate (2*100 ml). After the organic phases are dried, filtered and evaporated, the residue obtained is purified by flash chromatography on $SiO_2$ (elution with a gradient from pure heptane to pure $CH_2Cl_2$, then with 90/10 $CH_2Cl_2$/MeOH). 2.77 g of a colorless oil is obtained (Yield=64%; TLC Rf=0.57; 90/10 CH$_2$Cl$_2$/MeOH) and 1.05 g of the starting triBoc spermine is recovered (adjusted yield=87%).

Step 2: Synthesis of tetraBoc Spermine Ethyl Acetate

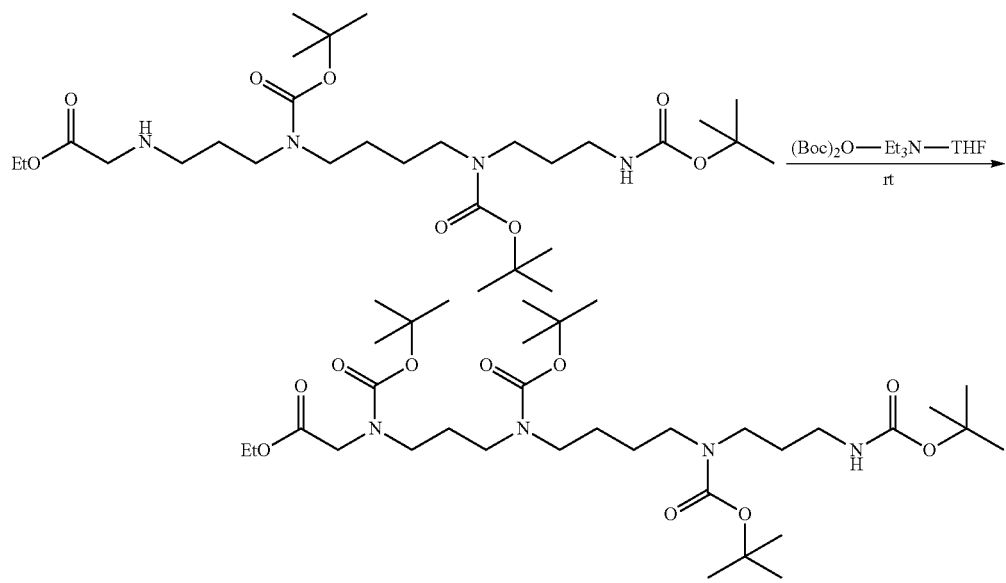

1 ml of triethylamine (6.8 mmol, 1.2 eq) is added at room temperature to a solution of 3.35 g of the intermediate obtained in step 1 (5.7 mmol, 1 eq) in 60 ml of THF. Then, under stirring, a solution of 1.36 g of Boc$_2$O (6.2 mmol, 1.1 eq) is added and the mixture is left under stirring for 2 h. The reaction medium is then dumped into water (300 ml) and extracted with ethyl acetate. (3*200 ml). The organic phases are dried on sodium sulfate, filtered, evaporated and then flash chromatographed on SiO$_2$ (elution by a gradient of pure heptane to pure ethyl acetate) to provide 2.52 g of a colorless oil (Yield=64%; TLC Rf: 0.43; SiO$_2$ 50/50 heptane/AcOEt).

Step 3: Synthesis of tetraBoc Spermine Acetic Acid

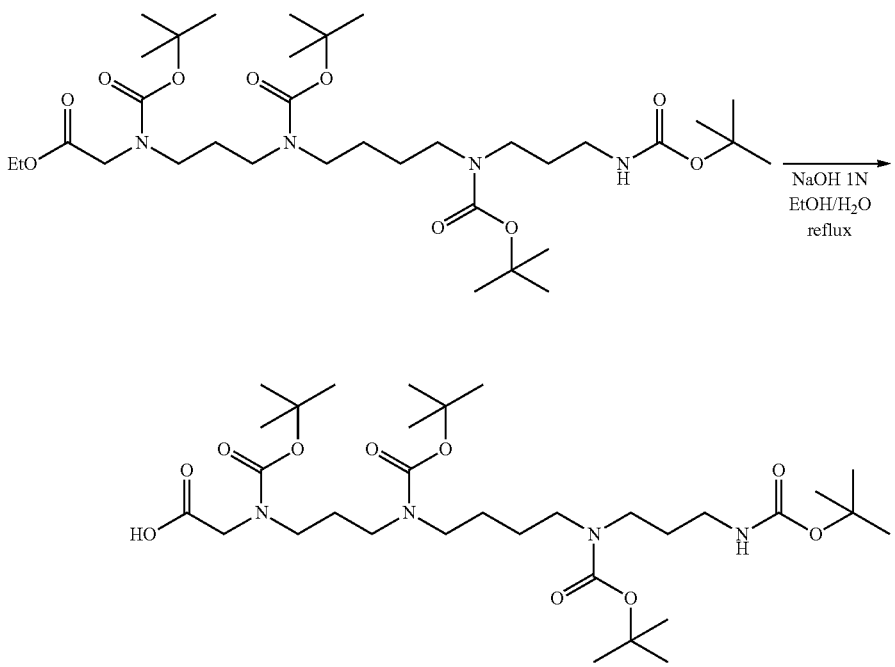

The intermediate ester obtained in step 2 (2.52 g, 3.6 mmol, 1 eq) is heated to reflux under stirring in 50 ml of an EtOH/H₂O mixture and 5.5 ml of a 1 N soda solution for 3 h and then dumped into ice water (300 ml) and acidified with 1 N HCl (5.6 ml). After extraction with CH₂Cl₂, drying on Na₂SO₄, filtration and evaporation, the reaction medium is purified by flash chromatography on SiO₂ (elution gradient of pure heptane to pure CH₂Cl₂ and then 90/10 CH₂Cl₂/MeOH). 2.27 g of tetraBoc spermine acetic acid is obtained in the form of a colorless oil (Yiel=94%; TLC Rf.: 0.4; SiO₂ 90/10 CH₂Cl₂/MeOH).

Step 4: Synthesis of Neoboutomellerone tetraBoc Spermine Acetate

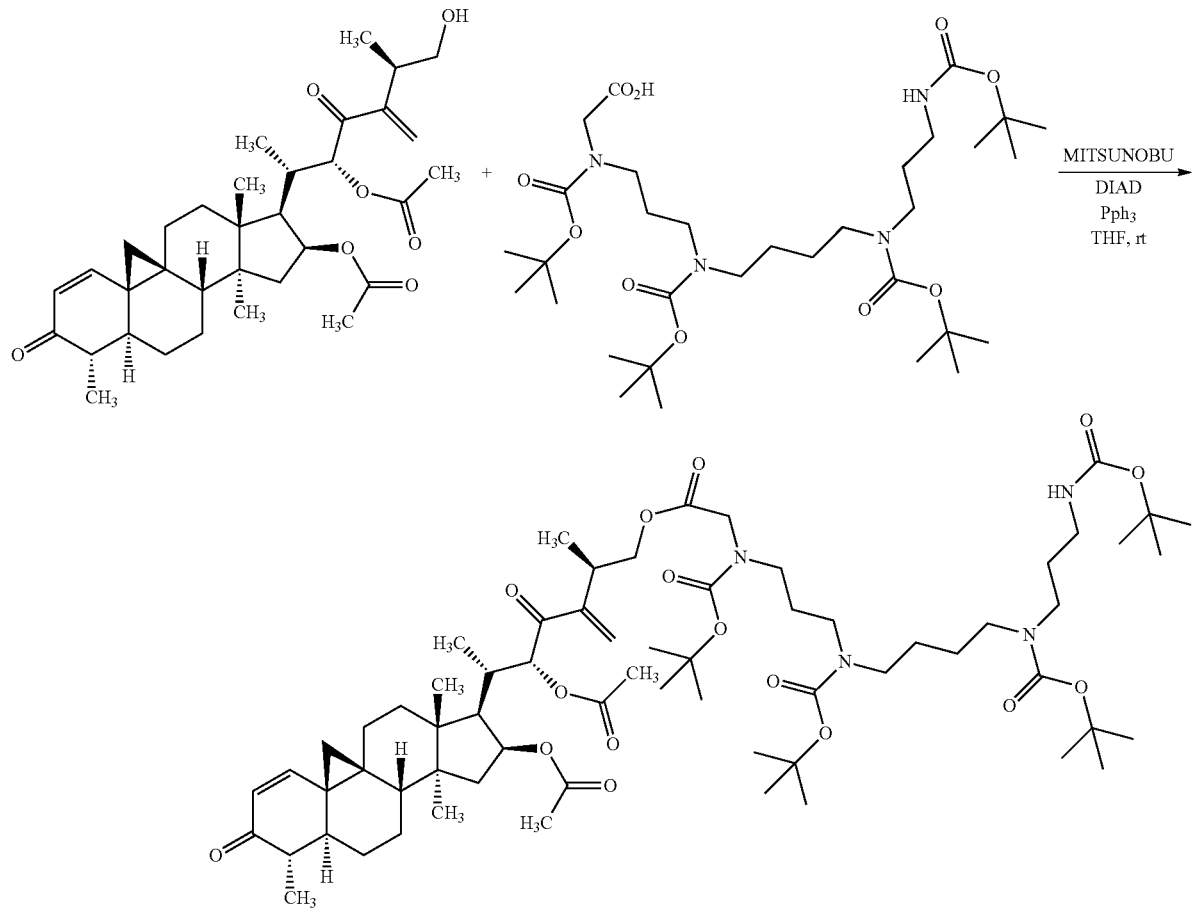

DIAD is added drop by drop at room temperature to a solution comprised of compound 2, the compound obtained in step 3 and triphenylphosphine in THF. After 30 minutes the reaction is complete (as analyzed by SiO₂ TLC: 30/70 heptane/AcOEt). The reaction medium is loaded on silica and then flash chromatographed (elution gradient: 100% heptane to 60/40 heptane/AcOEt) to obtain 520 mg of impure product. Purification is supplemented with reversed-phase preparative HPLC on a Waters 5 μm C8-XBridge™ column (λ: 220 nm; 50/50 CH₂CN/H₂O gradient; product injected in DMSO). The pure fractions concerned are evaporated to eliminate the acetonitrile and then extracted with ethyl acetate. After drying on anhydrous sodium sulfate and filtration, the organic phase is evaporated under reduced pressure to give 250 mg of a clear and colorless oil with a yield of 47%.

$^1$H NMR (500 MHz, DMSO-d₆) δ=6.97 (1H, d, J=10.1 Hz, H-1), 6.74 (1H, br. s., NH-16'), 6.09 (2H, s, H-24a), 5.89 (1H, d, J=9.8 Hz, H-2), 5.45 (1H, s, H-22), 5.02 (1H, td, J=7.5 Hz, J=4.6 Hz, H-16), 4.05-4.17 (1H, m, H-26<'>), 3.97-4.04 (1H, m, H-26<''>), 3.81-3.96 (2H, m, H-2'<''>, 2'<'>), 3.02-3.22 (10H, m, H-4', 6', 8', 11', 13'), 2.95 (1H, dt, J=14.5 Hz, J=7.1 Hz, H-25), 2.87 (2H, q, J=6.5 Hz, H-15'), 2.22 (1H, dd, J=10.8 Hz, J=7.5 Hz, H-17), 2.09 (3H, s, H-22b), 2.07-2.16 (2H, m, H-4, 15<'>), 2.05 (3H, s, H-16b), 1.93-2.01 (2H, m, H-8, 11<'>), 1.89 (1H, td, J=12.4 Hz, J=4.1 Hz, H-5), 1.47-1.71 (8H, m, H-5', 14', 6<'>, 11<''>, 12<''>, 12<'>), 1.26-1.44 (42H, m, H-7<'>, 9', 10', 15<''>, 19', 20', 21', 24', 25', 26', 29', 30', 31', 34', 35', 36'), 1.24 (1H, d, J=4.3 Hz, H-19<'>), 1.13 (4H, s, H-7<''>, 18), 1.03 (3H, d, J=7.0 Hz, H-27), 0.98 (3H, d, J=6.7 Hz, H-28), 0.89 (4H, s, H-6<''>, 29), 0.79 (3H, d, J=6.7 Hz, H-21), 0.57 (1H, br. s., H-19<''>)

$^{13}$C NMR (126 MHz, DMSO-d₆) δ=200.7 (C-3), 197.1, 197.0, 170.2 (C-22a), 170.2 (C-22a), 170.0 (C-1'), 169.9 (C-16a), 169.7 (C-1'), 155.6 (C-32'), 154.8 (C-1), 154.6 (C-17', 22', 27'), 154.5 (C-17', 22', 27'), 147.1 (C-24), 127.3 (C-2), 125.4 (C-24a), 125.3 (C-24a), 79.2 (C-18', 23', 28', 33'), 79.1 (C-18', 23', 28', 33'), 78.3 (C-18', 28', 23', 33'), 77.5 (C-18', 23', 28', 33'), 76.7 (C-22), 75.2 (C-16), 67.2 (C-26), 67.1 (C-26), 49.7 (C-17), 48.9 (C-2'), 48.6 (C-6', 8', 11', 13'), 47.0 (C-14), 46.5 (C-6', 8', 11', 13'), 46.2 (C-4), 46.0 (C-6', 8', 11', 13'), 45.5 (C-15), 45.4 (C-4'), 44.4 (C-6', 8', 11', 13'), 43.5 (C-8), 42.1 (C-5), 37.6 (C-15'), 33.3 (C-25), 33.1 (C-25), 32.0

(C-20), 31.7 (C-12), 31.6, 28.9 (C-5', 9', 10', 14'), 28.3, 28.1, 28.0, 27.8, 26.7 (C-11), 26.5 (C-5', 9', 10', 14'), 26.0 (C-19), 25.7 (C-9', 10', 14'), 25.1 (C-5'), 23.0 (C-6), 22.9 (C-7), 21.5 (C-16b), 20.5 (C-22b), 19.2 (C-29), 17.6 (C-18), 16.6 (C-27), 12.5 (C-21), 10.8 (C-28)
Example 84
Neoboutomellerone Spermine Acetate Tetrahydrochloride Salt
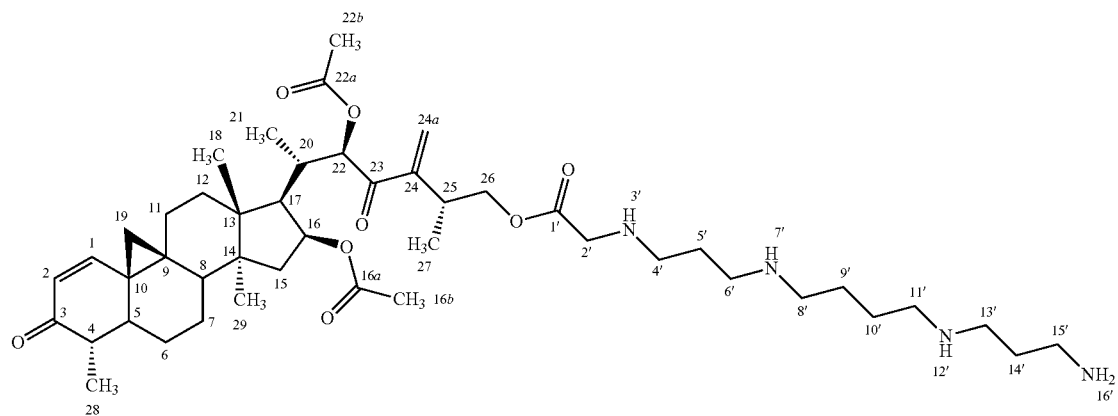
Chemical formula: C$_{46}$H$_{74}$N$_4$O$_8$
Exact mass: 810.55;
Molecular weight: 811.10
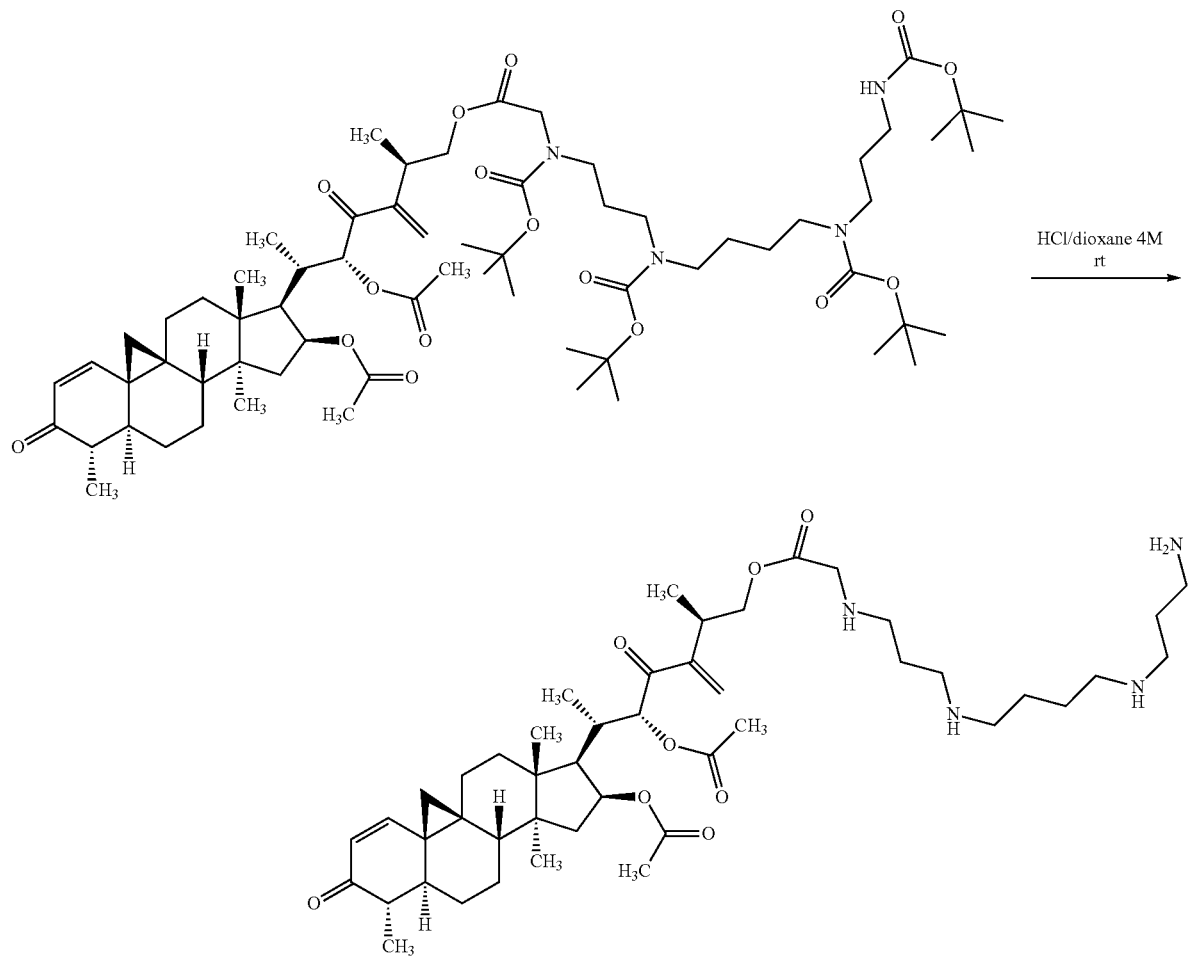

Protocol: Intermediate 83 is left under stirring for 3 hours at room temperature in a 4 M HCl solution in dioxane. The white precipitate obtained (160 mg) is filtered and then rinsed with isopropyl ether.

The product is purified by reversed-phase preparative HPLC on a Waters 5 μm C8-XBridge™ column (λ: 220 nm; 80%/20% 5 mM HCl/CH$_3$CN to 65%/35% 5 mM HCl/CH$_3$CN gradient). After monitoring with analytical HPLC, the fractions concerned are evaporated under reduced pressure to eliminate the acetonitrile and then freeze-dried to give 20 mg of the expected product in its tetrahydrochloride form (white powder).

$^1$H NMR (500 MHz, DMSO-d$_6$) δ=9.53 (1H, br. s., NH-3'), 9.21 (2H, br. s., NH-12', 7'), 8.11 (2H, br. s., H-16'), 6.97 (1H, d, J=10.1 Hz, H-1), 6.18 (1H, s, H-24aa), 6.14 (1H, s, H-24ab), 5.90 (1H, d, J=9.8 Hz, H-2), 5.46 (1H, d, J=1.8 Hz, H-22), 5.03 (1H, td, J=7.4 Hz, J=4.7 Hz, H-16), 4.19 (1H, dd, J=10.7 Hz, J=6.4 Hz, H-26<'>), 4.13 (1H, dd, J=10.7 Hz, J=7.0 Hz, H-26<''>), 3.96 (2H, br. s., H-2'<''>, 2'<'>), 3.00-3.14 (3H, m, H-4', 25), 2.98 (4H, br. s., H-6', 13'), 2.89 (6H, br. s., H-8', 11', 15'), 2.47-2.52 (1H, m, H-20), 2.23 (1H, dd, J=11.0 Hz, J=7.3 Hz, H-17), 2.11 (3H, s, H-22b), 2.04-2.16 (4H, m, H-15<$^{1>, 4, 5'}$>), 2.07 (3H, s, H-16b), 1.98 (4H, m, H-11<'>, 8, 14'), 1.89 (1H, td, J=12.4 Hz, J=4.4 Hz, H-5), 1.67-1.78 (4H, m, H-10', 9'), 1.50-1.67 (4H, m, H-6<'>, 11<''>, 12<''>, 12<'>), 1.34-1.45 (1H, m, H-7<'>), 1.31 (1H, dd, J=13.9 Hz, J=4.1 Hz, H-15<''>), 1.24 (1H, m, J=4.3 Hz, H-19<'>), 1.13 (3H, s, H-18), 1.17 (1H, d, J=3.1 Hz, H-7<''>), 1.06 (3H, d, J=7.0 Hz, H-27), 0.98 (3H, d, J=6.7 Hz, H-28), 0.90 (3H, s, H-29), 0.86-0.95 (1H, m, H-6<''>), 0.80 (3H, d, J=6.7 Hz, H-21), 0.58 (1H, d, J=4.0 Hz, H-19<''>)

$^{13}$C NMR (126 MHz, DMSO-d$_6$) δ=200.7 (C-3), 197.1 (C-23), 170.4 (C-22a), 170.0 (C-16a), 154.9 (C-1), 146.8 (C-24), 127.3 (C-2), 125.6 (C-24a), 76.7 (C-22), 75.2 (C-16), 68.2 (C-26), 49.7 (C-17), 47.0 (C-14), 46.6 (C-2'), 46.2 (C-4), 46.0 (C-11'), 45.9 (C-8'), 45.5 (C-13), 45.4 (C-15), 44.0 (C-4'), 43.8 (C-6', 13'), 43.4 (C-8), 42.1 (C-5), 36.2 (C-15'), 32.6 (C-25), 32.1 (C-20), 31.7 (C-12), 31.6 (C-10), 26.7 (C-11), 26.4 (C-19), 25.9 (C-9), 23.6 (C-14'), 23.0 (C-7), 22.8 (C-6), 22.6 (C-10'), 22.6 (C-9'), 22.1 (C-5'), 21.6 (C-16b), 20.6 (C-22b), 19.2 (C-29), 17.6 (C-18), 16.5 (C-27), 12.5 (C-21), 10.8 (C-28)

Example 85

Trichloroacetamide Dihydro Furan Neoboutomellerone Derivative

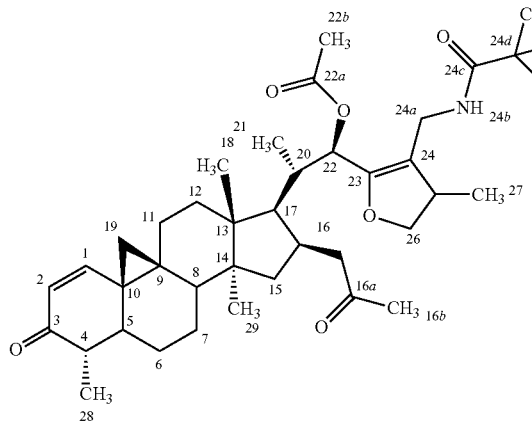

Chemical formula: C$_{36}$H$_{48}$NO$_7$
Exact mass: 711.25
Molecular weight: 713.13

Step 1

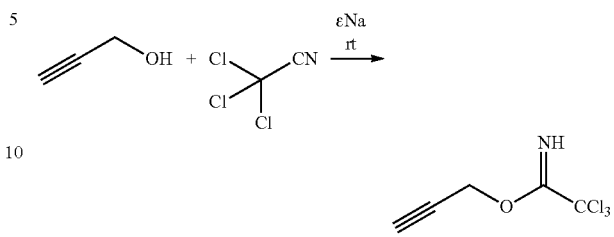

Add sodium to the mixture of reagents and leave in contact at room temperature for 4 hours. Take up the reaction medium in isopropyl ether, wash with saturated NaCl solution, decant, dry on anhydrous sodium sulfate, filter and evaporate the solvent under reduced pressure. Distill in a Kugelrohr apparatus (T$_{Eb}$: 100° C. at 5 mm Hg). A colorless and clear liquid is obtained.

Step 2: Synthesis of Trichloroacetamide Dihydro Furan Neoboutomellerone Derivative

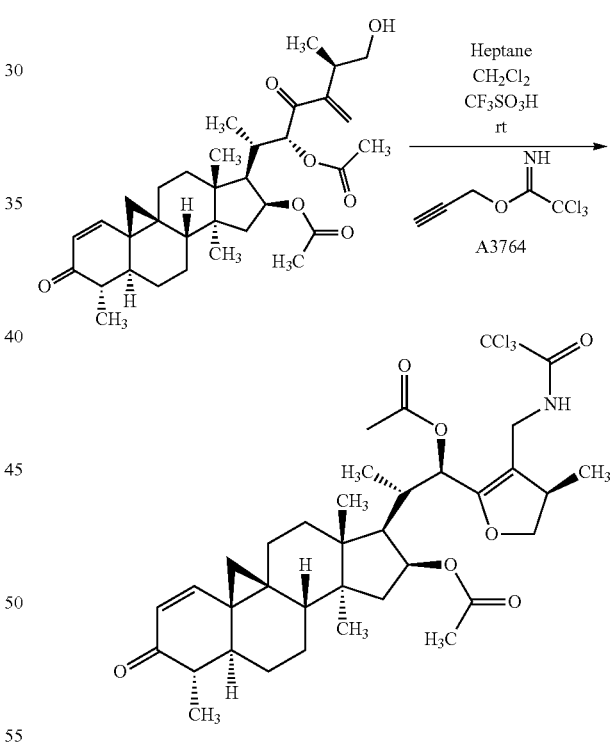

To a solution of 2 and the compound obtained in step 1, in a Heptane/CH$_2$Cl$_2$ mixture, add a drop of triflic acid at room temperature. Leave in contact for 10 minutes under stirring and then dump the reaction medium into a NaHCO$_3$ solution, decant, dry on anhydrous sodium sulfate, filter and evaporate under reduced pressure. Perform flash chromatography on silica with a 100% heptane to 100% isopropyl ether gradient over 15 minutes. Evaporate the fractions concerned to obtain a white foam.

$^1$H NMR (500 MHz, ACETONITRILE-d$_3$) δ=7.37 (1H, br. s., NH-24b), 6.94 (1H, d, J=9.8 Hz, H-1), 5.90 (1H, d, H-2), 5.37 (1H, s, H-22), 5.24 (1H, td, J=7.9 Hz, J=4.6 Hz, H-16), 4.34 (1H, dd, J=9.5 Hz, J=8.9 Hz, H-26<'>), 4.24 (1H, dd, J=14.8 Hz, J=4.7 Hz, H-24a<'>), 3.94 (1H, dd, J=14.6 Hz, J=6.1 Hz, H-24a<">), 3.82 (1H, dd, J=8.9 Hz, J=6.4 Hz, H-26<">), 3.00 (1H, sxt, J=7.2 Hz, H-25), 2.29-2.40 (1H, m, H-20), 2.15-2.21 (2H, m, H-15<'>, 4), 2.08 (3H, s, H-22b), 1.97 (3H, s, H-16b), 1.95-2.12 (4H, m, H-11<'>, 5, 17, 8), 1.62-1.73 (3H, m, H-6<'>, 12<">, 12<'>), 1.54-1.62 (1H, m, H-11<">), 1.41-1.50 (1H, m, H-7<'>), 1.34 (1H, dd, J=13.7 Hz, J=4.0 Hz, H-15<">), 1.25 (1H, d, J=4.6 Hz, H-19<'>), 1.16 (3H, s, H-18), 1.13-1.23 (1H, m, H-7<">), 1.07 (3H, d, J=7.0 Hz, H-27), 1.02 (3H, d, J=6.7 Hz, H-28), 1.02 (3H, d, J=7.0 Hz, H-21), 0.91-0.99 (1H, m, H-6<">), 0.90 (3H, s, H-29), 0.56 (1H, d, J=4.6 Hz, H-19<">)

$^{13}C$ NMR (126 MHz, ACETONITRILE-$d_3$) δ=202.3 (C-3), 171.4 (C-22a), 171.4 (C-16a), 162.6 (C-24c), 155.5 (C-1), 151.7 (C-23), 128.4 (C-2), 111.8 (C-24), 76.9 (C-26), 75.7 (C-16), 72.4 (C-22), 51.1 (C-17), 48.5 (C-14), 47.6 (C-4), 46.7 (C-13), 45.8 (C-15), 44.7 (C-8), 43.4 (C-5), 39.7 (C-25), 36.2 (C-24a), 34.5 (C-20), 32.9 (C-10), 32.7 (C-12), 28.0 (C-11), 27.3 (C-19), 24.2 (C-6), 24.1 (C-7), 21.6 (C-16b), 21.3 (C-22b), 19.8 (C-29), 18.5 (C-27), 17.9 (C-18), 13.1 (C-21), 11.3 (C-28)

Example 86

O-benzoyl N-methyl Hydroxylamine Methyl Dihydro Furan Neoboutomellerone

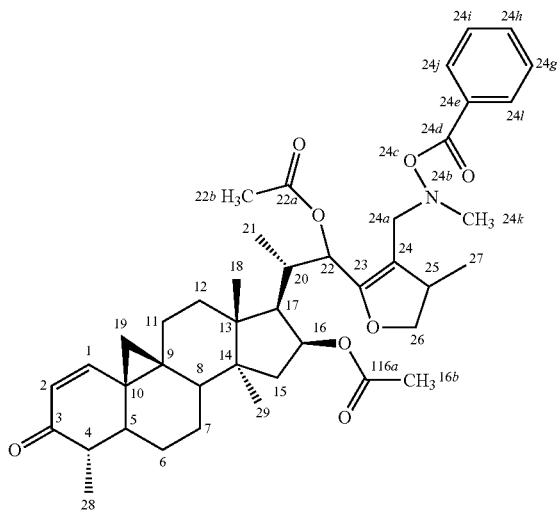

Chemical formula: $C_{42}H_5O_8$
Exact mass: 701.39
Molecular weight: 701.89

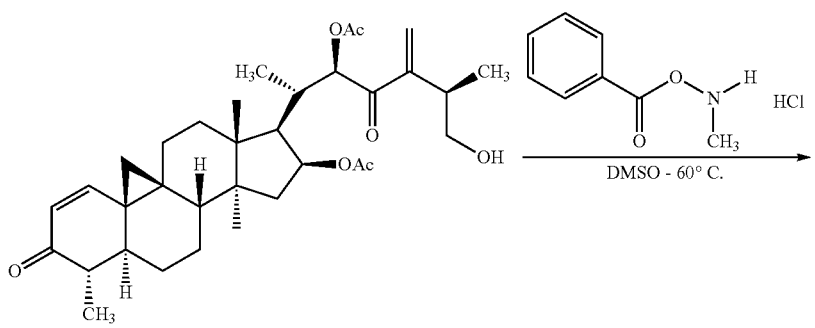

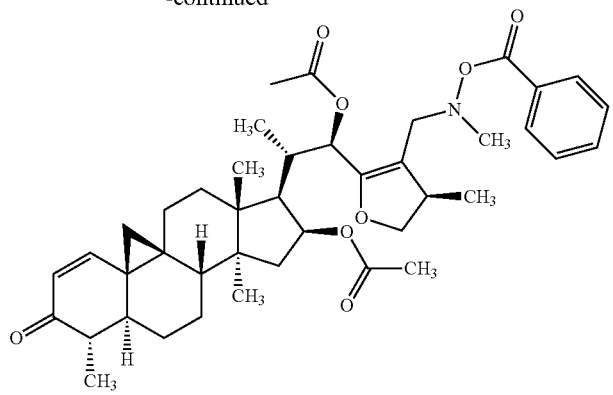

Protocol: The reaction mixture is left under stirring at 60° C. for 1 hour and then hydrolyzed with water and extracted with ethyl acetate. After decantation, drying on anhydrous sodium sulfate and filtration, the organic phase is evaporated under reduced pressure. The product is first purified by flash chromatography on 35-70 µm silica with a 100% heptane to 100% isopropyl ether gradient. The fractions concerned are evaporated to give 45 mg of product in the form of white powder.

The product is then repurified by isocratic flash chromatography on 15-40 µm silica with 80/20 cyclohexane/ethyl acetate. The fractions concerned are evaporated to yield 28 mg.

$^1$H NMR (500 MHz, CD$_3$CN) δ=7.90 (2H, d, J=7.3 Hz, H-24j, 24f), 7.61 (1H, t, J=7.6 Hz, H-24h), 7.48 (2H, dd, J=8.2 Hz, J=7.3 Hz, H-24g, 24i), 6.94 (1H, d, J=9.8 Hz, H-1), 5.90 (1H, d, J=10.1 Hz, H-2), 5.31 (1H, s, H-22), 5.14 (1H, td, J=7.8 Hz, J=4.6 Hz, H-16), 4.23 (1H, t, J=9.2 Hz, H-26<'>), 3.89 (1H, d, J=13.4 Hz, H-24a<'>), 3.75 (1H, dd, J=8.7 Hz, J=6.6 Hz, H-26<">), 3.60 (1H, d, J=13.4 Hz, H-24a<">), 3.15 (1H, sxt, J=7.0 Hz, H-25), 2.81 (3H, s, H-24k), 2.27-2.38 (1H, m, H-20), 2.17 (1H, dq, J=13.0 Hz, J=6.7 Hz, H-4), 2.12 (3H, s, H-22b), 1.99 (3H, s, H-16b), 1.96-2.11 (5H, m, H-5, 8, 11<'>, 15<'>, 17), 1.62-1.70 (3H, m, H-6<'>, 12<">, 12<'>), 1.52-1.61 (1H, m, H-11<">), 1.41-1.49 (1H, m, H-7<'>), 1.29-1.36 (1H, m, H-15<">), 1.25 (1H, d, J=4.3 Hz, H-19<'>), 1.15-1.21 (1H, m, H-7<">), 1.14 (3H, s, H-18), 1.11 (3H, d, J=6.7 Hz, H-27), 1.02 (3H, d, J=6.7 Hz, H-28), 0.96 (3H, d, J=6.7 Hz, H-21), 0.90-0.95 (1H, m, H-6<">), 0.90 (3H, s, H-29), 0.56 (1H, d, J=4.3 Hz, H-19<">)

$^{13}$C NMR (126 MHz, CD$_3$CN) δ=202.3 (C-3), 171.3 (C-16a), 171.1 (C-22a), 165.7 (C-24d), 155.5 (C-1), 134.1 (C-24h), 130.7 (C-24e), 130.1 (C-24f, 24j), 129.6 (C-24g, 24i), 128.4 (C-2), 76.7 (C-26), 75.8 (C-16), 72.5 (C-22), 55.1 (C-24a), 50.8 (C-17), 48.3 (C-14), 47.6 (C-4), 46.7 (C-24k), 46.7 (C-13), 46.0 (C-15), 44.8 (C-8), 43.5 (C-5), 40.2 (C-25), 34.8 (C-20), 32.9 (C-10), 32.7 (C-12), 28.0 (C-11), 27.3 (C-19), 27.3 (C-9), 24.2 (C-6), 24.1 (C-7), 21.8 (C-16b), 21.4 (C-22b), 19.9 (C-29), 18.3 (C-27), 18.0 (C-18), 13.1 (C-21), 11.3 (C-28)

Example 87

Methyl Propanone Methyl Chloromethyl Tetrahydrofuran-Neoboutomellerone Derivative

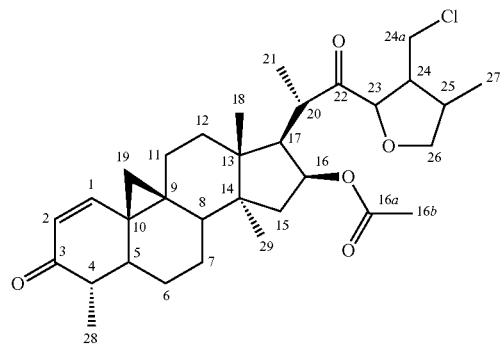

Chemical formula: C$_{32}$H$_{45}$ClO$_5$
Exact mass: 544.30
Molecular weight: 545.15

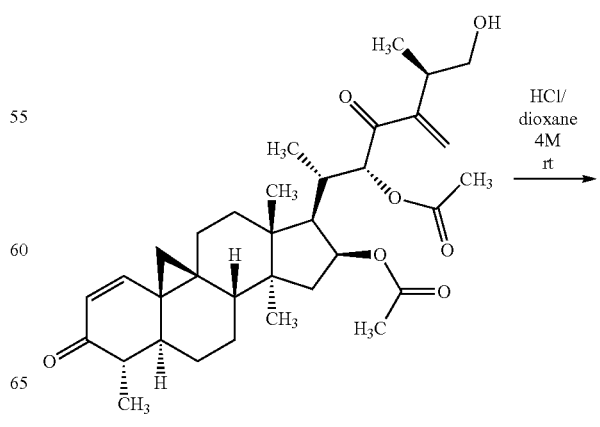

-continued

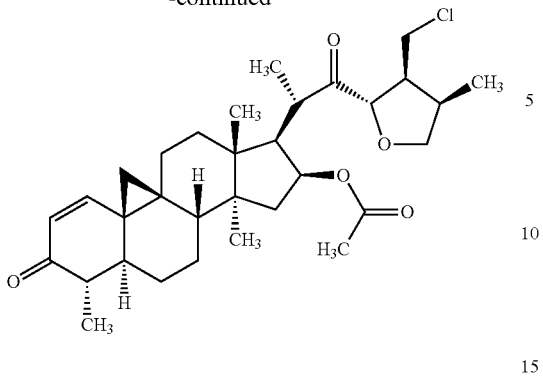

Protocol: Leave the mixture of reagents in contact for 1 hour under stirring at room temperature. Dump the reaction medium into a NaHCO₃ solution, extract with ethyl acetate, decant, dry the organic phase on anhydrous sodium sulfate, filter and evaporate under reduced pressure. Pre-purify by flash chromatography on silica with a 100% heptane to 100% isopropyl ether gradient to obtain 5.5 mg in the form of a foam.

Purify the product by preparative HPLC with a LiChrospher® 100 RP-18 column (5 µm; 10*250 mm; λ: 270 nm; flow rate: 6 ml/min; injection in 100% acetonitrile; mobile phase: 20/80 H₂0/CH₃CN). After monitoring with analytical HPLC, the pure fractions related to the product are evaporated under reduced pressure (1.6 mg).

¹H NMR (500 MHz, CD₃CN) δ=6.95 (1H, d, J=10.1 Hz, H-1), 5.90 (1H, d, J=10.1 Hz, H-2), 5.04 (1H, td, J=8.1 Hz, J=5.5 Hz, H-16), 4.29 (1H, d, J=7.0 Hz, H-23), 3.99 (1H, dd, J=8.4 Hz, J=5.6 Hz, H-26<'>), 3.64-3.74 (2H, m, H-24a<'>, 24a<''>), 3.62 (1H, dd, J=8.2 Hz, J=4.3 Hz, H-26<''>), 3.35 (1H, dq, J=10.9 Hz, J=7.2 Hz, H-20), 2.36-2.64 (3H, m, H-17, 25, 24), 2.14-2.21 (1H, m, H-4), 1.95-2.13 (4H, m, H-5,8, 11<'>, 15<'>), 1.91 (3H, s, H-16b), 1.71-1.82 (1H, m, H-12<'>), 1.56-1.70 (3H, m, H-6<'>, 11<''>, 12<''>), 1.41-1.50 (1H, m, H-7<'>), 1.26 (2H, d, J=4.6 Hz, H-7<''>, 19<'>), 1.18 (3H, s, H-18), 1.15 (3H, d, J=7.0 Hz, H-21), 1.02 (3H, d, J=6.7 Hz, H-27), 1.01 (3H, d, J=6.7 Hz, H-28), 0.98-1.05 (1H, m, H-6<''>), 0.97 (3H, s, H-29), 0.56 (1H, d, J=4.3 Hz, H-19<''>)

¹³C NMR (126 MHz, CD₃CN) δ=215.1 (C-22), 202.3 (C-3), 170.9 (C-16a), 155.5 (C-1), 128.4 (C-2), 84.3 (C-23), 76.1 (C-26), 76.1 (C-16), 51.0 (C-17), 49.2 (C-24), 47.6 (C-4), 45.7 (C-15), 44.5 (C-8), 44.2 (C-24a), 43.4 (C-5), 41.1 (C-20), 36.6 (C-25), 33.0 (C-12), 28.0 (C-11), 27.1 (C-19), 24.2 (C-6), 24.1 (C-7), 21.7 (C-16b), 19.6 (C-29), 18.5 (C-18), 16.6 (C-21), 12.4 (C-27), 11.3 (C-28)

Example 88

Neoboutomellerone Resorcinol Derivative

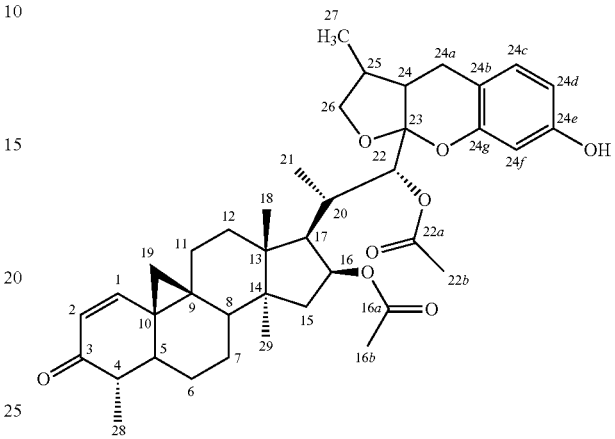

Chemical formula: C₄₀H₅₂O₈
Exact mass: 660.37
Molecular weight: 660.84

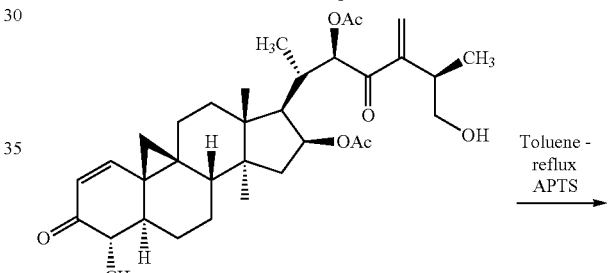

F200158

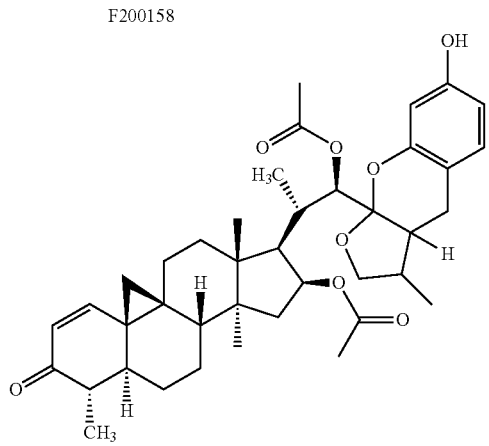

F98690

Protocol: The reaction mixture of the starting materials in toluene is brought to reflux for 15 minutes. After evaporation of the toluene, the residue obtained is pre-purified by flash chromatography on 35-75 µm silica with 100% isopropyl ether elution to give 16 mg of a white solid.

The product is purified by preparative HPLC on a LiChrospher® 100 RP-18 column (5 µm; 25*250 mm; λ: 200 nm;

flow rate: 30 ml/min; injection in 100% acetonitrile; mobile phase: 35/65 to 10/90 H₂O/CH₃CN gradient over 40 min). After monitoring with analytical HPLC, the pure fractions related to the product are evaporated under reduced pressure (4.9 mg).

¹H NMR (500 MHz, CD₃CN) δ=6.94 (1H, d, J=9.8 Hz, H-1), 6.90 (1H, d, J=7.9 Hz, H-24c), 6.84 (1H, br. s., OH-24e), 6.34 (1H, dd, J=7.9 Hz, J=2.4 Hz, H-24d), 6.21 (1H, d, J=2.4 Hz, H-24f), 5.89 (1H, d, J=9.8 Hz, H-2), 5.26 (1H, td, J=7.9 Hz, J=4.7 Hz, H-16), 5.03 (1H, s, H-22), 3.99 (1H, t, J=8.1 Hz, H-26<'>), 3.35 (1H, dd, J=9.2 Hz, J=8.2 Hz, H-26<">), 2.68-2.82 (2H, m, H-20, 24a<'>), 2.59 (1H, dd, J=16.3 Hz, J=1.7 Hz, H-24a<">), 2.11-2.22 (1H, m, H-4), 2.00 (3H, s, H-22b), 1.95-2.07 (4H, m, H-5,8,11<'>, 15<'>), 1.90-1.96 (1H, m, H-24), 1.89 (1H, dd, J=11.4 Hz, J=7.8 Hz, H-17), 1.77-1.85 (1H, m, H-25), 1.68-1.74 (2H, m, H-12<">, 12<'>), 1.61-1.68 (1H, m, H-6<'>), 1.54-1.62 (1H, m, H-11<">), 1.37-1.47 (1H, m, H-7<'>), 1.40 (3H, s, H-16b), 1.24 (1H, d, J=4.6 Hz, H-19<'>), 1.22-1.29 (1H, m, H-15<">), 1.18 (3H, s, H-18), 1.18 (3H, d, J=7.6 Hz, H-21), 1.11-1.21 (1H, m, H-7<">), 1.01 (3H, d, J=6.7 Hz, H-28), 0.96 (3H, d, J=6.4 Hz, H-27), 0.93 (1H, qd, J=13.0 Hz, J=4.1 Hz, H-6<">), 0.86 (3H, s, H-29), 0.56 (1H, d, J=4.6 Hz, H-19<'>)

¹³C NMR (126 MHz, CD₃CN) δ=202.4 (C-3), 172.2 (C-22a), 171.3 (C-16a), 157.7 (C-24e), 155.6 (C-1), 154.8 (C-24g), 130.9 (C-24c), 128.4 (C-2), 113.1 (C-24b), 110.0 (C-23), 109.5 (C-24d), 104.3 (C-24f), 75.7 (C-16), 75.4 (C-26), 74.7 (C-22), 52.3 (C-17), 48.4 (C-14), 47.6 (C-4), 46.9 (C-24), 46.7 (C-13), 45.9 (C-15), 44.7 (C-8), 43.4 (C-5), 34.9 (C-25), 33.0 (C-12), 32.9 (C-10), 31.2 (C-20), 28.1 (C-11), 27.3 (C-9), 27.2 (C-19), 24.2 (C-6), 24.1 (C-7), 21.0 (C-22b), 20.7 (C-16b), 19.9 (C-29), 17.9 (C-18), 15.3 (C-27), 14.1 (C-21), 11.2 (C-28)

Example 89

26-phosphate-neoboutomellerone

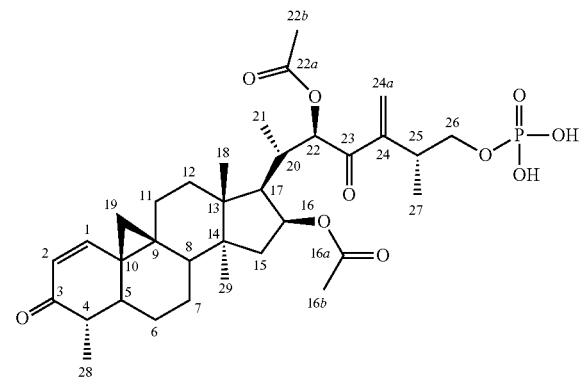

Chemical formula: C₃₄H₄₉O₁₀P
Exact mass: 648.31
Molecular weight: 648.72

Protocol: To a solution of 2, Et₃N and THF at 0° C. add POCl₃ drop by drop at 0° C. and leave in contact at this temperature for 2 hours. Add 1 N HCl and leave under stirring for 1 hour. Extract two times with AcOEt, decant and dry the organic phase on anhydrous sodium sulfate. Filter and evaporate the solvent under reduced pressure to obtain a white foam (150 mg).

Purify the product by preparative HPLC on a Waters 5 μm C8-XBridge™ column (30*250 mm, λ: 220 nm, flow rate: 40 ml/min; injection in 100% DMSO; mobile phase: 80%/20% to 50%/50% 5 mM HCl/CH₃CN gradient). The pure fractions related to the product are evaporated under reduced pressure to eliminate the acetonitrile and then extracted with ethyl acetate, dried on anhydrous sodium sulfate, filtered and evaporated under reduced pressure to lead to 85 mg of white crystallized product with a purity of 98.6%.

¹H NMR (500 MHz, CD₃CN) δ=6.94 (1H, d, J=10.1 Hz, H-1), 6.12 (1H, s, H-24aa), 5.99 (1H, s, H-24ab), 5.89 (1H, d, J=9.8 Hz, H-2), 5.53 (1H, d, J=1.8 Hz, H-22), 5.09 (1H, td, J=7.6 Hz, J=4.4 Hz, H-16), 3.97-4.04 (1H, m, H-26<'>), 3.80-3.94 (1H, m, H-26<">), 3.00 (1H, sxt, J=6.8 Hz, H-25), 2.54-2.65 (1H, m, H-20), 2.29 (1H, dd, J=11.0 Hz, J=7.6 Hz, H-17), 2.12-2.22 (2H, m, H-4, 15<'>), 2.10 (3H, s, H-22b), 2.03 (3H, s, H-16b), 1.98-2.07 (1H, m, H-8, 11<'>), 1.94-1.97 (1H, m, H-5), 1.63-1.76 (3H, m, H-7<'>, 12<">, 12<'>), 1.51-1.61 (1H, m, H-11<">), 1.40-1.49 (1H, m, H-6<'>), 1.36 (1H, dd, J=14.0 Hz, J=4.0 Hz, H-15<">), 1.24 (1H, d, J=4.3 Hz, H-19<'>), 1.19 (3H, s, H-18), 1.15-1.23 (1H, m, H-6<">), 1.08 (3H, d, J=7.0 Hz, H-27), 1.02 (3H, d, J=6.7 Hz, H-28), 0.95 (3H, s, H-29), 0.93 (1H, qd, J=12.5 Hz, J=3.7 Hz, H-7<">), 0.86 (3H, d, J=6.7 Hz, H-21), 0.58 (1H, d, J=4.3 Hz, H-19<">)

¹³C NMR (126 MHz, CD₃CN) δ=202.4 (C-3), 199.0 (C-23), 171.8 (C-22a), 171.3 (C-16a), 155.5 (C-1), 148.6 (C-24), 128.4 (C-2), 125.9 (C-24a), 78.4 (C-22), 76.7 (C-16), 70.1 (C-26), 51.3 (C-17), 48.4 (C-14), 47.6 (C-4), 46.9 (C-13), 46.7 (C-15), 45.2 (C-8), 43.6 (C-5), 36.3 (C-25), 33.3 (C-20), 33.0 (C-12), 32.9 (C-10), 28.1 (C-11), 27.7 (C-19), 27.2 (C-9), 24.3 (C-7, 6), 22.2 (C-16b), 21.0 (C-22b), 20.0 (C-29), 18.3 (C-18), 17.0 (C-27), 13.4 (C-21), 11.3 (C-28)

Example 90

26-phosphate-neoboutomellerone N-methyl Glutamine Salt

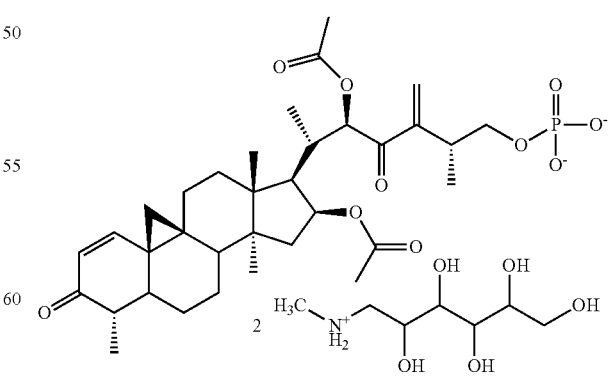

Chemical formula: C₄₁H₆₇NO₁₅P⁺
Exact mass: 844.42
Molecular weight: 844.94

-continued

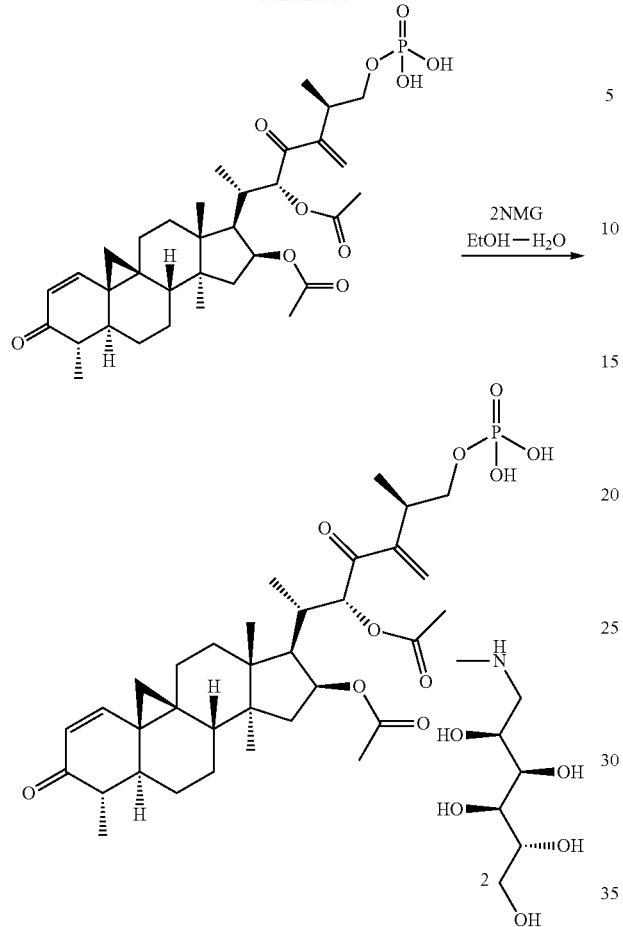

Protocol: Dissolve compound 89 in ethanol and then add 2 eq of NMG in solution in water. The solution obtained is evaporated under reduced pressure, taken up in 5 ml of H$_2$O and filtered on a 0.45 m filter. The solution obtained is frozen and freeze-dried to give 55 mg of a white solid (purity by HPLC: 98.6%). NMR analysis indicates the presence of roughly 2.5 eq of NMG.

$^1$H NMR (500 MHz, D$_2$O) δ=7.22 (1H, d, J=9.8 Hz, H-1), 6.29 (1H, s, H-24aa), 6.22 (1H, s, H-24ab), 6.02 (1H, d, J=9.8 Hz, H-2), 5.74 (1H, d, J=2.1 Hz, H-22), 5.02-5.12 (1H, m, H-16), 4.06 (2H, ddd, J=9.2 Hz, J=5.3 Hz, J=3.5 Hz, H-5'), 3.78-3.88 (5H, m, H-2', 26<'>, 1'<'>), 3.73-3.78 (2H, m, H-3'), 3.67-3.71 (1H, m, H-26<''>), 3.61-3.68 (4H, m, H-4', 1'<''>), 3.12 (2H, dd, J=12.8 Hz, J=3.4 Hz, H-6'<'>), 3.06 (2H, dd, J=12.8 Hz, J=9.5 Hz, H-6'<''>), 2.93 (1H, sxt, J=6.9 Hz, H-25), 2.67-2.74 (1H, m, H-20), 2.68 (6H, s, H-8'), 2.26-2.41 (2H, m, H-4, 17), 2.21 (3H, s, H-22b), 2.19-2.26 (1H, m, H-15<'>), 2.17 (3H, s, H-16b), 1.97-2.13 (3H, m, H-5,8, 11<'>), 1.59-1.78 (4H, m, H-7<'>, 11<''>, 12<''>, 12<'>), 1.41-1.54 (2H, m, H-6<'>, 15<''>), 1.39 (1H, d, J=4.3 Hz, H-19<'>), 1.19 (3H, s, H-18), 1.15-1.27 (1H, m, J=6.4 Hz, H-6<''>), 1.07 (3H, d, J=7.0 Hz, H-27), 1.04 (3H, d, J=6.7 Hz, H-28), 0.95 (3H, s, H-29), 0.92-1.00 (1H, m, H-7<''>), 0.90 (3H, d, J=6.7 Hz, H-21), 0.65 (1H, d, J=4.6 Hz, H-19<''>)

$^{13}$C NMR (126 MHz, D$_2$O) δ=208.1 (C-3), 201.7 (C-23), 174.2 (C-16a), 173.8 (C-22a), 160.0 (C-1), 148.0 (C-24), 127.2 (C-24a), 126.2 (C-2), 78.4 (C-22), 77.2 (C-16), 70.8 (C-3'), 70.6 (C-4'), 70.6 (C-2'), 68.6 (C-5'), 67.0 (C-26), 62.6 (C-1'), 51.3 (C-6'), 50.1 (C-17), 47.2 (C-14), 46.3 (C-4), 45.6 (C-13), 45.1 (C-15), 43.0 (C-8), 41.8 (C-5), 34.4 (C-25), 33.2 (C-8'), 32.5 (C-20), 32.4 (C-10), 31.5 (C-12), 26.8 (C-9), 26.8 (C-11), 26.1 (C-19), 22.7 (C-7), 22.5 (C-6), 21.3 (C-16b), 19.9 (C-22b), 18.7 (C-29), 16.7 (C-18), 16.5 (C-27), 12.2 (C-21), 10.0 (C-28)

Example 91

Neoboutomellerone 26-phosphonoacetate

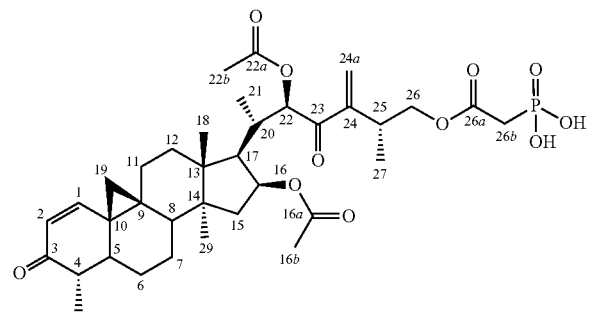

Chemical formula: C$_{37}$H$_{53}$O$_{10}$P
Exact mass: 688.34
Molecular weight: 688.78

Protocol: Compound 2 (250 mg, 0.44 mmol) is solubilized in 40 ml of acetonitrile in the presence of phosphonoacetic acid (185 mg, 1.32 mmol, 3 eq). DCC (272 mg, 1.32 mmol, 3 eq) is added and the reaction medium is left under stirring at room temperature. After conversion of the starting product and filtration of the white precipitate, the acetonitrile is evaporated. The product is purified by preparative HPLC on a Waters 10 µm C8-XBridge™ column (30*250 mm; λ: 220 nm; flow rate: 40 ml/min; mobile phase: 100% 5 mM HCl to 50% 5 mM HCl/50% acetonitrile gradient). The acetonitrile is evaporated under reduced pressure from the fractions concerned and the product is extracted with ethyl acetate to obtain 76 mg (25%) of the expected product in the form of a white foam.

$^1$H NMR (500 MHz, DMSO-d$_6$) δ=6.97 (1H, d, J=10.1 Hz, H-1), 6.12 (1H, s, H-24aa), 6.07 (1H, s, H-24ab), 5.89 (1H, d, J=10.1 Hz, H-2), 5.46 (1H, d, J=1.5 Hz, H-22), 5.02 (1H, td, J=7.6 Hz, J=4.3 Hz, H-16), 4.06 (1H, dd, J=10.4 Hz, J=5.8 Hz, H-26<'>), 3.91 (1H, dd, J=10.7 Hz, J=7.0 Hz, H-26<''>), 2.94 (1H, dq, J=13.2 Hz, J=6.7 Hz, H-25), 2.70 (2H, d, J=21.1 Hz, H-26b), 2.46-2.51 (1H, m, H-20), 2.22 (1H, dd, J=10.8 Hz, J=7.5 Hz, H-17), 2.10 (3H, s, H-22b), 2.07-2.16 (2H, m, H-4, 15<'>), 2.05 (3H, s, H-16b), 1.93-2.01 (2H, m, H-11<'>, 8), 1.89 (1H, td, J=12.5 Hz, J=3.7 Hz, H-5), 1.48-1.69 (4H, m, H-6<'>, 11<''>, 12<''>, 12<'>), 1.34-1.44 (1H, m, H-7<'>), 1.30 (1H, dd, J=14.3 Hz, J=3.7 Hz, H-15<''>), 1.24 (1H, d, J=4.6 Hz, H-19<'>), 1.13 (3H, s, H-18), 1.08-1.19 (1H, m, H-7<''>), 1.04 (3H, d, J=7.0 Hz, H-27), 0.98 (3H, d, J=6.7 Hz, H-28), 0.90 (3H, s, H-29), 0.84-0.94 (1H, m, H-6<''>), 0.79 (3H, d, J=6.7 Hz, H-21), 0.58 (1H, d, J=4.3 Hz, H-19<''>)

$^{13}$C NMR (126 MHz, DMSO-d$_6$) δ=200.7 (C-3), 197.2 (C-23), 170.3 (C-22a), 170.0 (C-16a), 154.9 (C-1), 147.2 (C-24), 127.3 (C-2), 125.4 (C-24a), 76.7 (C-22), 75.1 (C-16), 66.8 (C-26), 49.7 (C-17), 48.6, 47.0 (C-14), 46.2 (C-4), 45.4 (C-15, 13), 43.5 (C-8), 42.1, 36.7 (C-26b), 33.2 (C-25), 31.9 (C-20), 31.7 (C-12), 31.6 (C-10), 26.7 (C-11), 26.5 (C-19), 26.0 (C-9), 23.0 (C-7), 22.9 (C-6), 21.5 (C-16b), 20.5 (C-22b), 19.2 (C-29), 17.6 (C-18), 16.6 (C-27), 12.5 (C-21), 10.8 (C-28)

Example 92

26-(diethylphosphate)-neoboutomellerone

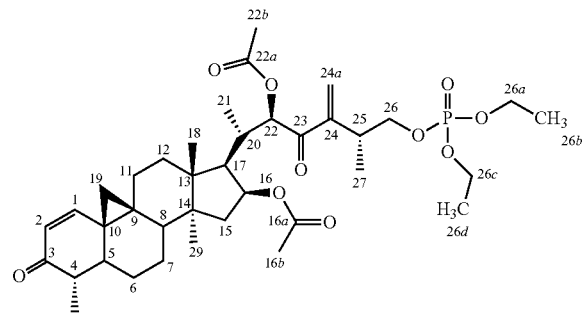

Chemical formula: $C_{38}H_{57}O_{10}P$
Exact mass: 704.37
Molecular weight: 704.83

Protocol: 300 mg (0.528 mmol) of 2 is dissolved in 5 ml of DCM and then 2.3 ml (4 eq, 2.11 mmol) of lutidine is added. The reaction is cooled to 0° C. and then phosphoryl chloride (0.89 ml, 2 eq, 1.06 mmol) is added and the temperature is allowed to rise overnight. The reaction is hydrolyzed with water. The organic phase is washed successively with water, a copper sulfate solution, water and brine. The product is purified by preparative TLC comprising three runs with a 30% ethyl acetate in cyclohexane mixture and then three runs with a 50% ethyl acetate in cyclohexane mixture. 43 mg (11%) of compound 92 is collected (Rf: 0.14; 60/40 cyclohexane/ethyl acetate).

$^1$H NMR (500 MHz, $CD_3CN$) δ=6.94 (1H, d, J=10.1 Hz, H-1), 6.15 (1H, s, H-24a'), 6.00 (1H, s, H-24a"), 5.90 (1H, d, J=10.1 Hz, H-2), 5.53 (1H, d, J=2.1 Hz, H-22), 5.08 (1H, dt, J=7.7 Hz, J=3.9 Hz, H-16), 3.96-4.12 (5H, m, H-26a, 26c, 26<'>), 3.89 (1H, dt, J=10.1 Hz, J=6.3 Hz, H-26<''>), 3.01 (1H, sxt, J=6.7 Hz, H-25), 2.54-2.63 (1H, m, H-20), 2.30 (1H, dd, J=11.1 Hz, J=7.5 Hz, H-17), 2.14-2.22 (2H, m, H-4, 15<'>), 2.09 (3H, s, H-22b), 2.03 (3H, s, H-16b), 1.96-2.09 (3H, m, H-5, 8, 11<'>), 1.63-1.76 (3H, m, H-6<'>, 12<'>, 12<''>), 1.52-1.62 (1H, m, H-11<''>), 1.41-1.50 (1H, m, H-7<'>), 1.37 (1H, dd, J=13.7 Hz, J=4.6 Hz, H-15<''>), 1.27 (6H, td, J=7.0 Hz, J=0.9 Hz, H-26b, 26d), 1.24 (1H, d, J=4.9 Hz, H-19<'>), 1.19 (3H, s, H-18), 1.20 (1H, s, H-7<''>), 1.09 (3H, d, J=7.0 Hz, H-27), 1.03 (3H, d, J=6.7 Hz, H-28), 0.95 (3H, s, H-29), 0.88-0.94 (1H, m, H-6<''>), 0.85 (3H, d, J=7.0 Hz, H-21), 0.58 (1H, d, J=4.6 Hz, H-19<''>)

$^{13}$C NMR (126 MHz, $CD_3CN$) δ=202.4 (C-3), 198.8 (C-23), 171.6 (C-22a), 171.2 (C-16a), 155.5 (C-1), 148.4 (C-24), 128.4 (C-2), 126.1 (C-24a), 78.3 (C-22), 76.7 (C-16), 70.6 (C-26), 64.6 (C-26c, 26a), 51.3 (C-17), 48.4 (C-14), 47.6 (C-4), 46.9 (C-13), 46.7 (C-15), 45.2 (C-8), 43.6 (C-5), 36.2 (C-25), 33.3 (C-20), 33.0 (C-12), 32.7 (C-10), 28.1 (C-11), 27.7 (C-19), 24.3 (C-7, 6), 22.1 (C-16b), 20.9 (C-22b), 20.0 (C-29), 18.3 (C-18), 16.9 (C-27), 16.5 (C-26b, 26d), 13.4 (C-21), 11.3 (C-28)

2. Biological Results

Biological tests were carried out according to protocols described in the following articles: Ausseil F. et al. *J. Biomol Screen.* 2007, 12, 106-116 and Vandenberghe I. et al. *Biochemical Pharmacology* 2008, 76, 453-462.

In order to select novel proteasome inhibitor compounds, it is necessary to indirectly measure the activity of this proteasome within cells. To this end, we constructed a stable cell line, DLD-1 4Ub-Luc, arising from a human colon cancer cell line, which produces a chimeric reporter protein called 4Ub-Luc. This protein is a fusion between a 4-ubiquitin (4Ub) label and luciferase (Luc). This label is capable to direct every proteins that carry it toward the proteasome. The 4Ub-Luc protein is thus efficiently degraded by the proteasome, in contrast to the "wild" non-fused Luc protein. When the DLD-1 4Ub-Luc cell line is treated with a proteasome inhibitor, the fusion protein is much less efficiently degraded and accumulates in the cell. This accumulation is detected by an increase in luciferase activity in the treated extract compared to the extract from untreated cells. The control consists of verifying that the inhibitor has no effect on accumulation of the wild Luc protein produced by the stable DLD-1 RF cell line. For both cell lines and for each product an induction factor is determined for the product tested (or the reference) corresponding to the ratio between the luciferase activities measured in cells treated with this product (or the reference) and cells treated with solvent alone.

The product's activity is then defined by its relative induction factor, i.e., the ratio of its induction factor (IF % luminescence) to that of the reference molecule epoxomicin (IF=100%; see data presented in the table below).

Thus, the test established by Pierre-Fabre is a cellular test that has the advantage, compared to a purely enzymatic test, of detecting only products capable of penetrating the cell.

Procedure:

Two cell lines are used for this test: DLD-1 RF and DLD-1 4Ub-Luc. The culture medium used is as follows:
MEM
5% fetal calf serum
5 ml of penicillin-streptomycin
2.5 ml of FUNGIZONE® (Amphotericin B)
10 ml of α-glutamine Day 1: Inoculate white 96-well culture-treated plates (PerkinElmer White ViewPlate, product no. 6005181) with 100 μl of $1·10^5$ c/ml cell suspension per well. Incubate for 24 hours so that the cells adhere. On each plate five columns will be inoculated with DLD-1 4Ub-Luc and five others with DLD-1 RF according to diagram 1 below.

Day 2: Remove the medium by turning the plates upside down on cotton, and then carry out the treatment with the compounds of the invention, with solvent alone or with a reference compound such as epoxomicin. Each reference compound is used at a concentration of $10^{-7}$ M, whereas the compounds of the invention are tested at concentrations of $10^{-6}$ M, $7.5·10^{-7}$ M, $5·10^{-7}$ M and $2.5·10^{-7}$ M for a period of 8 hours.

| Diagram 1: | | | | | | | | | | | |
|---|---|---|---|---|---|---|---|---|---|---|---|
| DLD-1 4Ub-Luc cell line | | | | | | DLD-1 RF cell line | | | | | |
| 1/A | 2 | 3 | 4 | 5 | 6 | 7 | 8 | 9 | 10 | 11 | 12 |
| B | Test compound | | | | | Control | Control | Test compound | | | |
| C | | | | | | Control | Control | | | | |
| D | | | | | | Control | Control | | | | |
| E | | | | | | Control | Control | | | | |

Diagram 1:

| DLD-1 4Ub-Luc cell line | | | | | | DLD-1 RF cell line | | | | | |
|---|---|---|---|---|---|---|---|---|---|---|---|
| 1/A | 2 | 3 | 4 | 5 | 6 | 7 | 8 | 9 | 10 | 11 | 12 |
| F | | | | | $10^{-7}$ M | $10^{-7}$ M | | | | | |
| G | | | | | epoxo | epoxo | | | | | |
| H | | | | | | | | | | | |

The columns are paired (examples 2 and 8, 3 and 9, 4 and 10 and 5 and 11) and treated with the same compound. Columns 6 and 7 receive the experimental control, namely 0.1% DMSO in culture medium for wells B, C, D, and E of columns 6 and 7, and the positive control ($10^{-7}$ M epoxomicin) in wells F and G.

After incubation, turn the plate upside down on cotton to empty the wells, rinse with 50 µl of PBS to remove any trace of the cytotoxin tested and then add 50 µl of 5× passive lysis buffer (Promega, product no. E1941) diluted to ⅕ in water. Shake energetically using a plate shaker for 5 to 10 minutes at room temperature before freezing at −20° C.

Measurement of Luciferase Activity:

Luciferase activity is measured using a Luciferase Assay System 10-Pack kit (Promega, product no. E1501).

On the day luciferase activity is to be measured, defrost the plates and wait until they have returned to room temperature. The optimal temperature for luciferase activity is 20-25° C.

Reconstitute the firefly luciferase substrate by defrosting the buffer and then adding 10 ml of buffer to the bottle containing the freeze-dried substrate. Wait until the solution is at room temperature before beginning the assay. Light emission is quantified on a luminometer (place white adhesive paper under the plate before reading on the luminometer).

Luminometer (Luminoskan, model RT):
volume injected: 100 µl
integration time (total time): 15 seconds
The results obtained are as follows:

| Compound tested | Concentration tested (M) | | | | Reference: epoxomicin |
|---|---|---|---|---|---|
| | $10^{-5}$ | $5 \cdot 10^{-6}$ | $10^{-6}$ | $5 \cdot 10^{-7}$ | |
| 1 | 3 | 28 | 45 | 1 | 100% |
| 2 | 4 | 37 | 48 | 2 | 100% |
| 4 | 24 | 84 | 2 | — | 100% |
| 6 | — | 31 | 5 | — | 100% |
| 7 | 21 | 65 | 2 | — | 100% |
| 8 | 19 | 74 | 7 | — | 100% |
| 9 | 44 | 34 | 1 | — | 100% |
| 10 | 53 | 5 | 1 | — | 100% |
| 11 | 48 | 45 | 1 | — | 100% |
| 12 | 15 | 72 | 3 | — | 100% |
| 13 | 60 | 71 | 2 | — | 100% |
| 14 | 77 | 10 | 1 | — | 100% |
| 15 | 74 | 11 | 2 | — | 100% |
| 16 | — | 35 | 1 | — | 100% |
| 17 | 6 | 29 | 26 | 2 | 100% |
| 18 | — | 48 | 12 | 1 | 100% |
| 19 | — | 45 | 40 | 1 | 100% |
| 20 | — | 60 | 42 | 6 | 100% |
| 22 | 1 | 4 | 68 | 8 | 100% |
| 23 | 2 | 7 | 69 | 15 | 100% |
| 24 | 1 | 5 | 70 | 12 | 100% |
| 25 | 60 | 51 | 49 | 19 | 100% |
| 26 | 37 | 54 | 53 | 11 | 100% |
| 27 | — | 103 | 1 | 1 | 100% |
| 35 | 30 | 99 | 1 | — | 100% |
| 36 | 6 | 12 | 1 | — | 100% |
| 47 | 36 | 78 | 7 | — | 100% |
| 49 | 15 | 44 | 19 | — | 100% |
| 51 | 60 | 31 | 1 | — | 100% |
| 56 | 7 | 34 | 21 | — | 100% |
| 58 | 10 | 46 | 8 | — | 100% |
| 60 | 2 | 4 | 71 | 76 | 100% |
| 61 | 6 | 21 | 64 | 23 | 100% |
| 62 | 7 | 49 | 11 | — | 100% |
| 63 | 3 | 11 | 50 | 66 | 100% |
| 64 | 7 | 35 | 22 | — | 100% |
| 65 | 4 | 34 | 17 | 1 | 100% |
| 66 | 2 | 9 | 13 | — | 100% |
| 68 | 4 | 18 | 52 | 1 | 100% |
| 71 | 4 | 11 | 62 | 6 | 100% |
| 74 | 2 | 14 | 60 | — | 100% |
| 82 | 48 | 59 | 2 | — | 100% |
| 88 | 78 | 47 | 1 | — | 100% |
| 89 | 40 | 3 | 1 | — | 100% |
| 90 | 51 | 4 | 1 | — | 100% |
| 92 | 2 | 16 | 43 | 3 | 100% |

A dash (—) indicates that the compound was not tested at the given concentration.

The invention claimed is:
1. The compound of following formula (I):

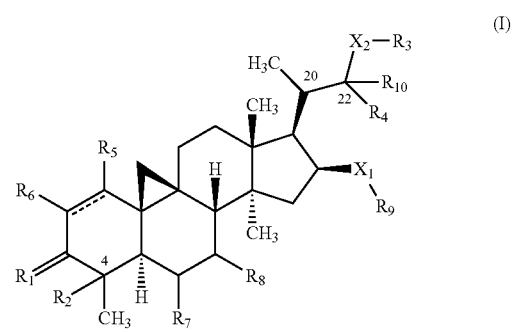

or a pharmaceutically acceptable salt thereof,
wherein:
⸺ indicates a single bond or a double bond,
$X_1$ and $X_2$ represent, independently of each other, an oxygen or sulfur atom,
$R_1$ represents an oxygen atom, a sulfur atom or an N—$OR_{11}$ or N—NHCO—$NH_2$ group,
$R_2$ represents a hydrogen atom or an $OR_{12}$ or $SR_{12}$ group,
$R_3$ represents a hydrogen atom, —$SO_2R_{55}$, —$CH_2OCH_2CH_2SiR_{61}R_{62}R_{63}$, a —CO—($C_1$-$C_6$)alkyl, or —CO—($C_2$-$C_6$)alkenyl group, wherein said group is optionally substituted by a halogen atom or a COOH or $NR_{56}R_{57}$ group,
$R_4$ represents a group selected from:
  a hydrogen atom,
  a saturated or unsaturated linear or branched hydrocarbon chain comprising 1 to 15 carbon atoms, one or more non-consecutive carbon atoms may be replaced by an oxygen atom, wherein said chain is optionally substituted by one or more groups selected from a halogen atom, =O, —OH, —$OSO_2R_{13}$, —$N_3$, ($C_1$-$C_6$)alkoxy, —$Z_1C(X)R_{14}$, —$C(X)Z_2R_{15}$, —$Z_3C(X)Z_4R_{16}$, —NH—$OR_{17}$, =N—$OR_{18}$, =N—$NR_{53}R_{54}$, —$OSiR_{19}R_{20}R_{21}$, —$SiR_{58}R_{59}R_{60}$, —OP(O)($OR_{22}$)($OR_{23}$), —$NR_{24}R_{25}$, a heterocycle with 5 or 6 members, an epoxide, a sugar residue and an inositol residue, one or more hydroxy groups of said sugar and inositol residues are optionally substituted by an acetyl group or —P(O)(OH)$_2$, and a heterocycle with 5 or 6 members or a polycycle with 10 to 15 members, wherein said heterocycle or polycycle comprises at least one oxygen atom and is optionally substituted by one or more groups selected from —OH, =O, —NH$_2$, —N$_3$, =CH$_2$, —COOR$_{26}$, (C$_2$-C$_6$)alkenyl, (C$_1$-C$_6$)alkoxy, and a (C$_1$-C$_6$)alkyl group optionally substituted by a halogen atom or an —N$_3$, —OH, (C$_1$-C$_6$)alkoxy, —NHCOR$_{27}$ or —NR$_{28}$—OC(O)R$_{29}$ group, $R_5$ and $R_6$ each represent a hydrogen atom when ==== represents a double bond, or $R_5$ and $R_6$ each represent, independently of each other, a hydrogen atom or an OR$_{48}$ group, or $R_5$ and $R_6$ together form, with the carbon atoms that carry them, an epoxide ring, when ==== represents a single bond, $R_7$ represents a hydrogen atom or a OR$_{49}$ group, $R_8$ represents a hydrogen atom, or $R_7$ and $R_8$ together form, with the carbon atoms that carry them, an epoxide ring, $R_9$ represents a —CO—(C$_1$-C$_6$)alkyl or —CO—(C$_2$-C$_6$) alkenyl group, or $R_9$ and $R_4$ together form a bond, or $R_9$ forms a bond with the carbon atom of the $R_4$ group located in the a position relative to carbon atom 22, $R_{10}$ represents a hydrogen atom, or $R_{10}$ and $R_3$ together form a bond, or $R_{10}$ and $R_9$ together form a bond, with:

$R_{11}$, $R_{26}$, $R_{28}$, $R_{30}$, $R_{31}$, $R_{36}$, $R_{37}$, $R_{41}$, $R_{42}$, $R_{43}$, $R_{48}$, $R_{49}$ and $R_{50}$ representing, independently of one another, a hydrogen atom or a (C$_1$-C$_6$)alkyl, (C$_2$-C$_6$)alkenyl, aryl or aryl-(C$_1$-C$_6$)alkyl group, $R_{12}$ representing a hydrogen atom or a (C$_1$-C$_6$)alkyl or (C$_2$-C$_6$)alkenyl group, $R_{13}$ and $R_{55}$ represent, independently of each other, an —OH, (C$_1$-C$_6$)alkoxy, aryl, —NR$_{30}$R$_{31}$ or (C$_1$-C$_6$)alkyl-aryl group, or a (C$_1$-C$_6$)alkyl group optionally substituted by an —NR$_{30}$R$_{31}$ group, $R_{14}$ representing a (C$_1$-C$_6$)alkyl, (C$_2$-C$_6$)alkenyl, aryl, (C$_1$-C$_6$)alkyl-aryl or aryl -(C$_1$-C$_6$)alkyl group, wherein said group is optionally substituted by a group selected from a halogen atom, an —NR$_{32}$—[(CH$_2$)$_a$—NR$_{33}$]$_d$—[(CH$_2$)$_b$—NR$_{34}$—(CH$_2$)$_c$—NR$_{35}$]$_e$—R$_{52}$, —P(O)(OH)$_2$ or —COOH group, with a, b and c representing an integer between 1 and 5 and d and e each representing 0 or 1, $R_{15}$ and $R_{16}$ representing, independently of each other, a hydrogen atom or a (C$_1$-C$_6$)alkyl, (C$_2$-C$_6$)alkenyl, aryl, (C$_1$-C$_6$)alkyl-aryl or aryl-(C$_1$-C$_6$)alkyl group, wherein said group is optionally substituted by a group selected from a halogen atom, an —NR$_{32}$—[(CH$_2$)$_a$—NR$_{33}$]$_d$—[(CH$_2$)$_b$—NR$_{34}$—(CH$_2$)$_c$—NR$_{35}$]$_e$—R$_{52}$ or —COOH group, with a, b, c, d and e as defined above, $R_{17}$ and $R_{18}$ representing, independently of each other, a hydrogen atom or a (C$_1$-C$_6$)alkyl, (C$_2$-C$_6$)alkenyl, aryl or aryl-(C$_1$-C$_6$)alkyl group, $R_{19}$, $R_{20}$, $R_{21}$, $R_{58}$, $R_{59}$, $R_{60}$, $R_{61}$, $R_{62}$ and $R_{63}$ representing, independently of one another, a (C$_1$-C$_6$)alkyl, (C$_2$-C$_6$)alkenyl or aryl group, $R_{22}$ and $R_{23}$, identical or different, representing a hydrogen atom or a (C$_1$-C$_6$)alkyl or (C$_2$-C$_6$)alkenyl group, wherein said group is optionally substituted by an —OC(O)—(C$_1$-C$_6$)alkyl, NR$_{36}$R$_{37}$ and —N$^+$R$_{38}$R$_{39}$R$_{40}$ group, or R$_{22}$ and R$_{23}$ together form, with the oxygen atoms that carry them and the phosphorous atom, a ring, $R_{24}$ and $R_{25}$, representing, independently of each other, a hydrogen atom or a —CO—(C$_1$-C$_6$)alkyl, —CO—(C$_2$-C$_6$)alkenyl, (C$_2$-C$_6$)alkenyl, (C$_3$-C$_7$)cycloalkyl or (C$_1$-C$_6$)alkyl group optionally substituted by an NR$_{41}$R$_{42}$ group, or R$_{24}$ and R$_{25}$ together form, with the nitrogen atom that carries them, a heterocycle with 5 or 6 members, wherein said heterocycle may comprise, in addition to the nitrogen atom carrying R$_{24}$ and R$_{25}$, one or more heteroatoms selected from nitrogen, oxygen and sulfur, and is optionally substituted by a (C$_1$-C$_6$)alkyl group, $R_{27}$ representing an aryl, (C$_1$-C$_6$)alkyl or (C$_2$-C$_6$)alkenyl group, wherein said group is optionally substituted by one or more halogen atoms, $R_{29}$ representing a (C$_1$-C$_6$)alkyl, (C$_2$-C$_6$)alkenyl, aryl or aryl-(C$_1$-C$_6$)alkyl group, $R_{32}$, $R_{33}$, $R_{34}$, $R_{35}$, $R_{52}$, $R_{53}$, $R_{54}$, $R_{56}$ and $R_{57}$ representing, independently of one another, a hydrogen atom or a (C$_1$-C$_6$)alkyl, (C$_2$-C$_6$)alkenyl, —CO—(C$_1$-C$_6$)alkyl, —CO—(C$_2$-C$_6$)alkenyl, —CO$_2$—(C$_1$-C$_6$)alkyl or —CO$_2$—(C$_2$-C$_6$)alkenyl group, $R_{38}$, $R_{39}$ and $R_{40}$ representing, independently of one another, a (C$_1$-C$_6$)alkyl or (C$_2$-C$_6$)alkenyl group, X representing O, S or NR$_{50}$, $Z_1$, $Z_2$, $Z_3$ and $Z_4$ representing, independently of one another, O or NR$_{43}$, or $Z_2$R$_{15}$ and/or $Z_4$R$_{16}$ representing, independently of each other, a heterocycle with 5 or 6 members optionally substituted by a (C$_1$-C$_6$)alkyl group, wherein the heterocycle comprises at least one nitrogen atom by which it is linked to the rest of the molecule.

2. The compound according to claim 1, wherein that $R_1$ is selected from an oxygen atom, an N—OH, —N—OMe, —N—OBn and —N—NHCO—NH$_2$ group.

3. The compound according to claim 1, wherein $R_2$ represents a hydrogen atom.

4. The compound according to claim 1, wherein $R_5$ and $R_6$ each represent a hydrogen atom and ==== represents a double bond.

5. The compound according to claim 1, wherein $R_7$ and $R_8$ each represent a hydrogen atom.

6. The compound according to claim 1, wherein $R_9$ represents a —CO—(C$_1$-C$_6$)alkyl group.

7. The compound according to claim 1, wherein $X_2$-$R_3$ represents an OH or OC(O)CH$_3$ group and $R_{10}$ represents a hydrogen atom or $R_3$ and $R_{10}$ together form a bond.

8. The compound according to claim 1 of the following formula (Ia) or (Ib):

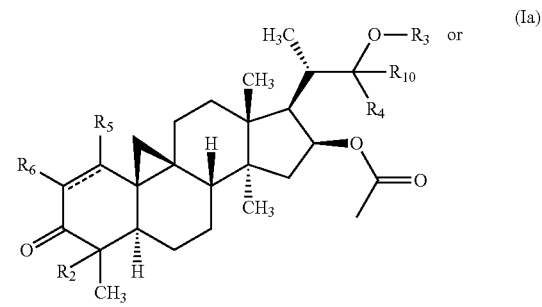

-continued

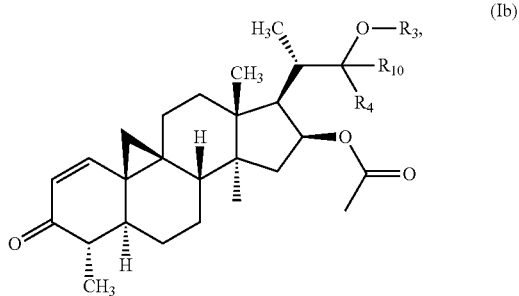

(Ib)

with $R_2$, $R_3$, $R_4$, $R_5$, $R_6$ and $R_{10}$ as defined in claim 1.

9. The compound according to claim 1, wherein $R_4$ represents a chain:

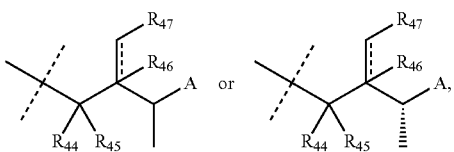

wherein:
- - - - represents a single bond or a double bond, $R_{44}$ represents a hydrogen atom and $R_{45}$ represents an OH group, or $R_{44}$ and $R_{45}$ together form an $=O$ or $=N-OR_{48}$ group, $R_{46}$ represents a hydrogen atom and $R_{47}$ represents a hydrogen atom, a $(C_1-C_6)$alkoxy group, $-NH-OR_{49}$ or a heterocycle with 5 or 6 members linked to the rest of the molecule via a nitrogen atom, when - - - - represents a single bond, or $R_{46}$ is absent and $R_{47}$ represents a hydrogen atom when - - - - represents a double bond, and A represents a $-CHO$, $-COOH$, $-CH_2A_1$ or $-CH_2OCH_2A_1$ group with $A_l$ representing a hydrogen atom, a halogen atom, $-OH$, $-OSO_2R_{13}$, $-N_3$, $(C_1-C_6)$alkoxy optionally substituted by one or more $-OH$ groups; $(C_2-C_6)$alkenoxy, $-OCH_2OR_{66}$, $-Z_1C(X)R_{14}$, $-Z_3C(X)Z_4R_{16}$, $-NH-OR_{17}$, $-OSiR_{19}R_{20}R_{21}$, $-OP(O)(OR_{22})(OR_{23})$, $-NR_{24}R_{25}$, a heterocycle with 5 or 6 members or a sugar residue, wherein one or more hydroxy groups of said sugar residue are optionally substituted by an acetyl or $-P(O)(OH)_2$ group, $R_{48}$ and $R_{49}$ representing, independently of each other, a hydrogen atom, a $(C_1-C_6)$alkyl, aryl or aryl-$(C_1-C_6)$alkyl group, $R_{66}$ representing a $-CO-((C_1-C_6)$alkyl$)$ or $(C_1-C_6)$alkyl group optionally substituted by an $SiR_{67}R_{68}R_{69}$ group, and $R_{67}$, $R_{68}$ and $R_{69}$ representing, independently of one another, a $(C_1-C_6)$alkyl group.

10. The compound according to claim 1, wherein $R_4$ represents the ring:

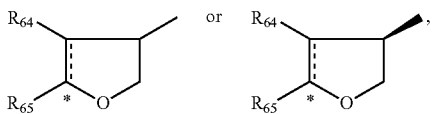

linked to the rest of the molecule via the carbon atom marked with an asterisk (*) and wherein,

- - - - represents a single bond or a double bond, $R_{64}$ represents a $(C_1-C_6)$alkyl group, optionally substituted by a halogen atom or an $-N_3$, $-OH$, $(C_1-C_6)$alkoxy, $-NHCOR_{27}$ or $-NR_{28}-OC(O)R_{29}$ group; or a $=CH_2$ group, wherein this $=CH_2$ group is present only when - - - - represents a single bond, and $R_{65}$ is not present when - - - - represents a double bond, or $R_{65}$ represents a hydrogen atom or a $(C_1-C_6)$alkoxy group when - - - - represents a single bond, or $R_{64}$ and $R_{65}$ together form, with the carbon atoms that carry them, when - - - - represents a single bond, a cyclic system comprising 1 or 2 fused saturated, unsaturated or aromatic rings, each with 5 to 7 members, wherein said cyclic system comprises at least one oxygen atom linked to the carbon atom marked with an asterisk and optionally comprises one or more additional heteroatoms selected from O, S and N, and wherein said cyclic system is optionally substituted by one or more groups selected from $=O$, $-OH$, $-COOR_{26}$, and $(C_1-C_6)$alkyl optionally substituted by an $-OH$ group.

11. The compound according to claim 1, selected from:

Compound 1

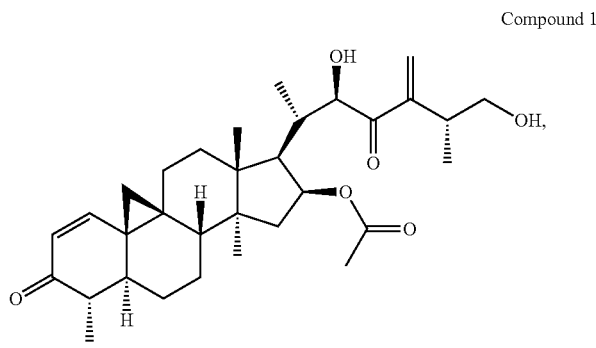

Compound 2

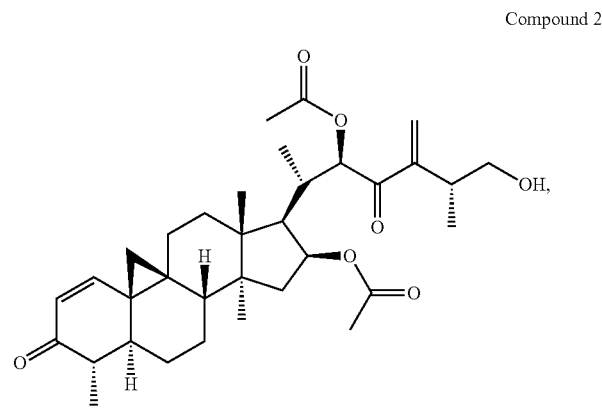

-continued
Compound 3
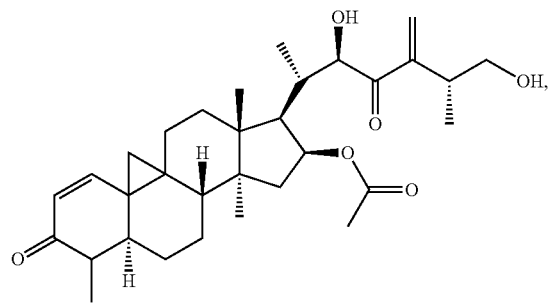
Compound 4
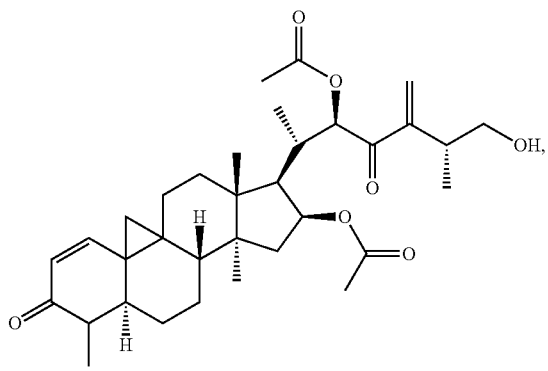
Compound 5
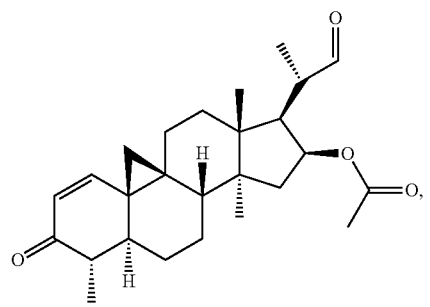
Compound 6
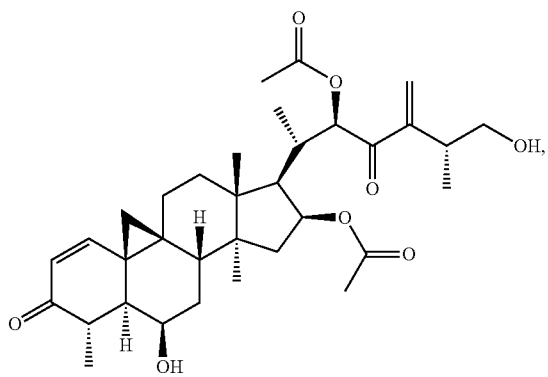
Compound 7
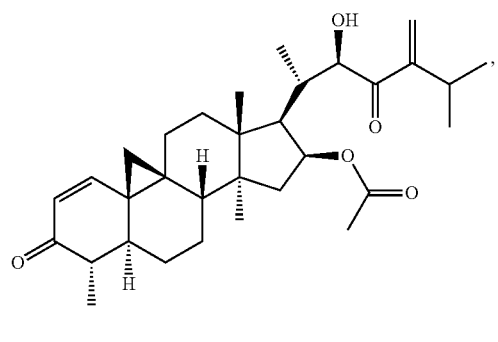
Compound 8
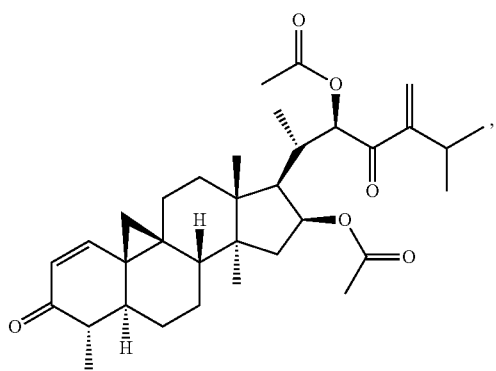
Compound 9
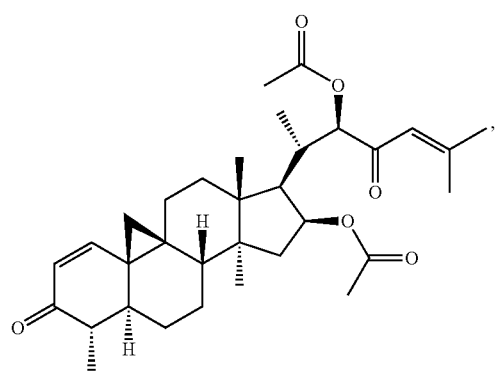
Compound 10
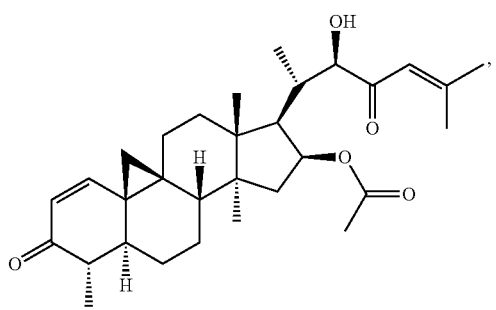

-continued
Compound 11
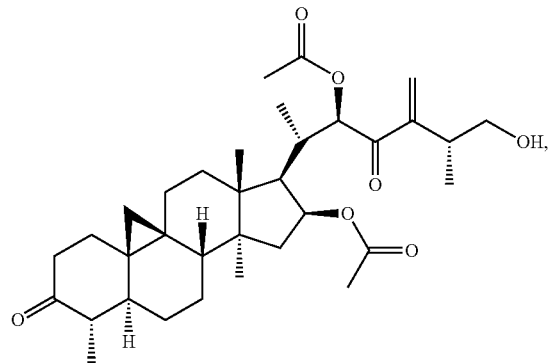
Compound 12
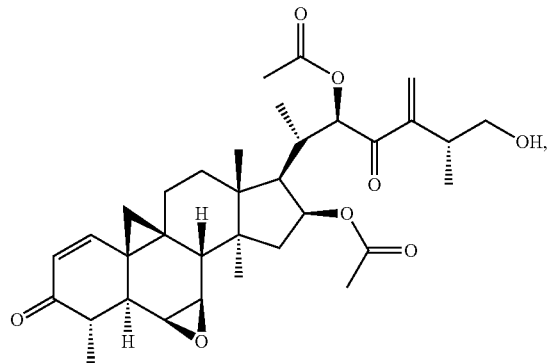
Compound 13
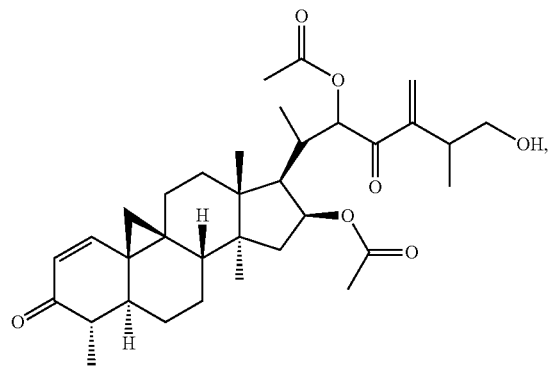
Compound 14
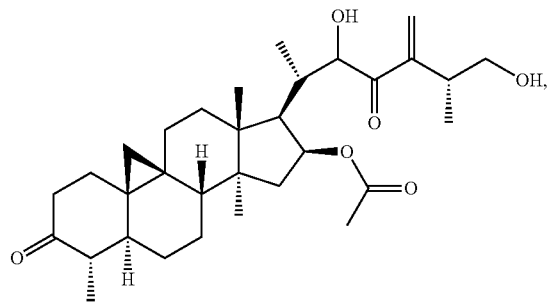
Compound 15
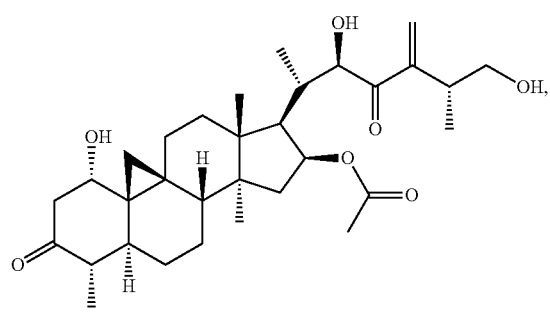
Compound 16
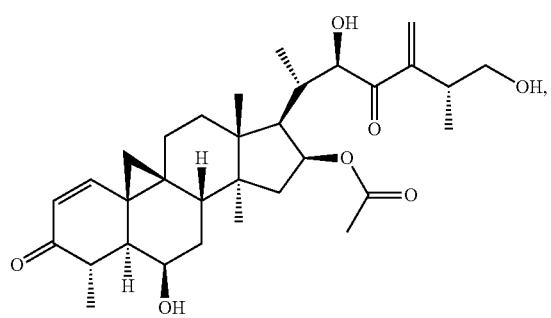
Compound 17
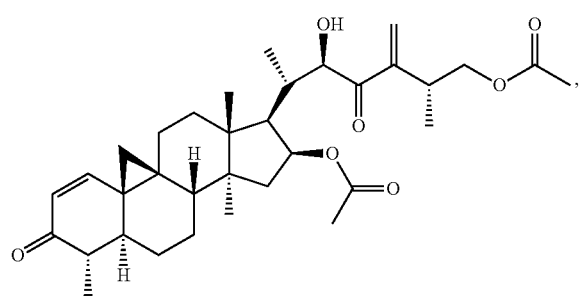
Compound 18
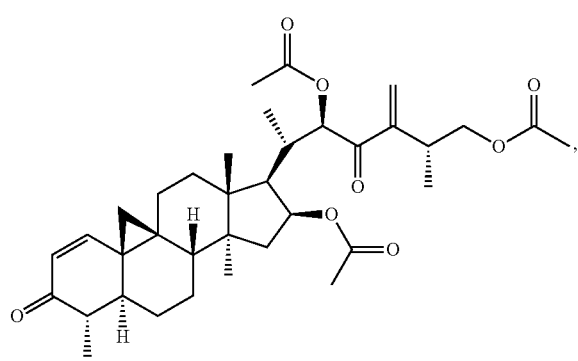

-continued
Compound 19
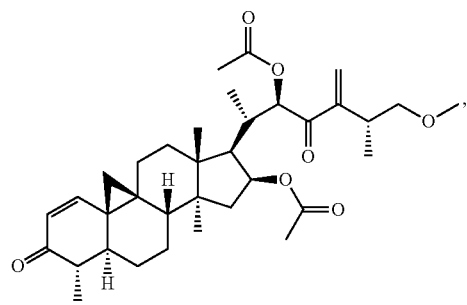
Compound 20
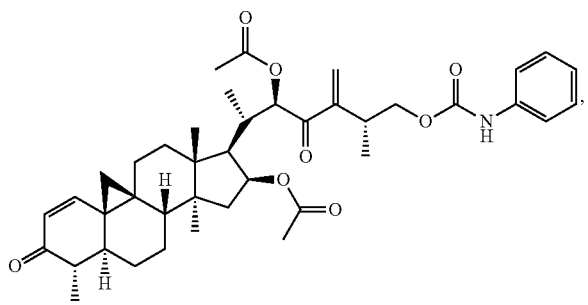
Compound 21
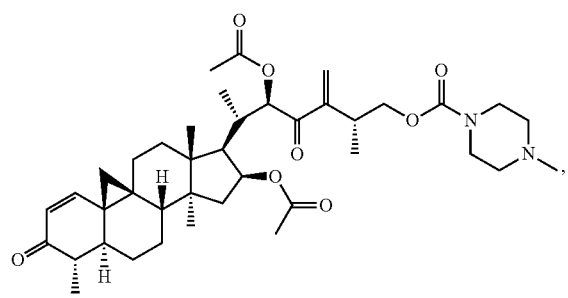
Compound 22
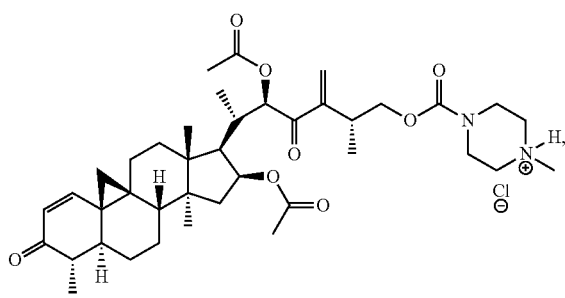
Compound 23
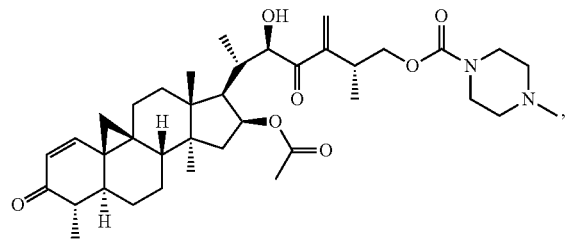
Compound 24
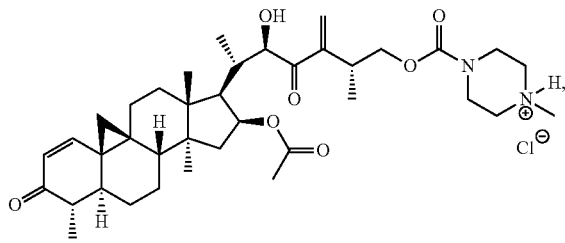
Compound 25
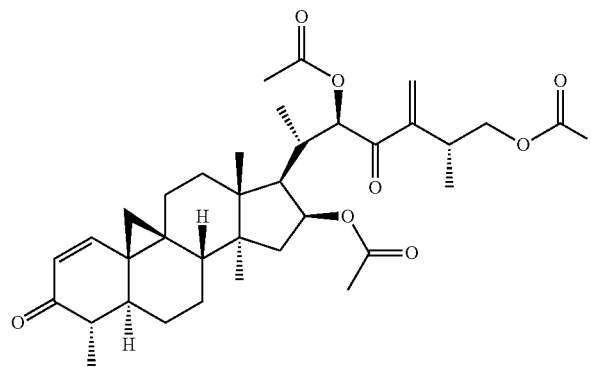
Compound 26
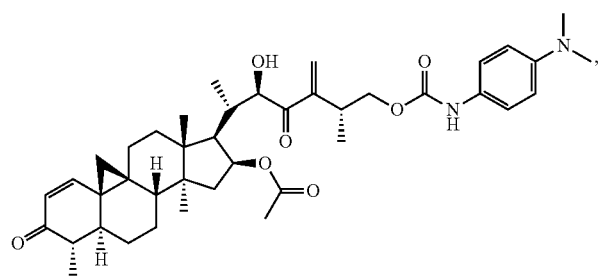
Compound 27
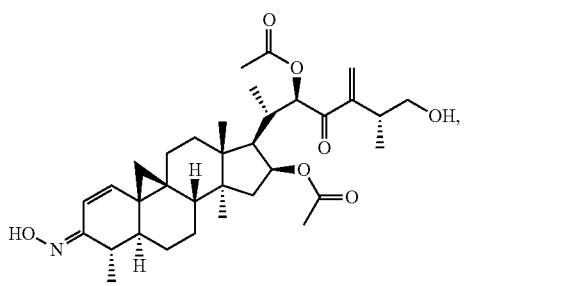

-continued
Compound 28
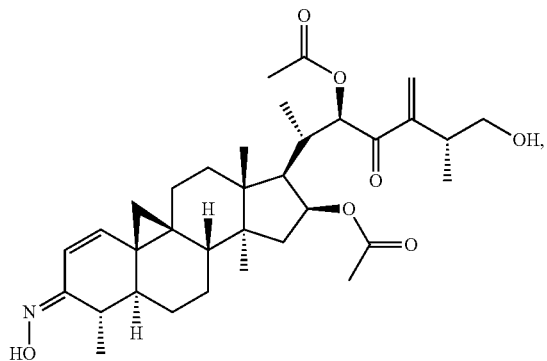
Compound 29
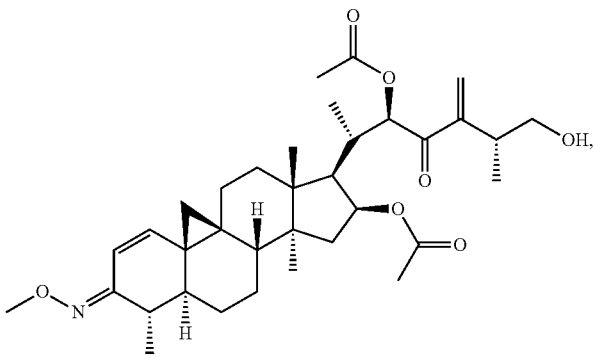
Compound 30
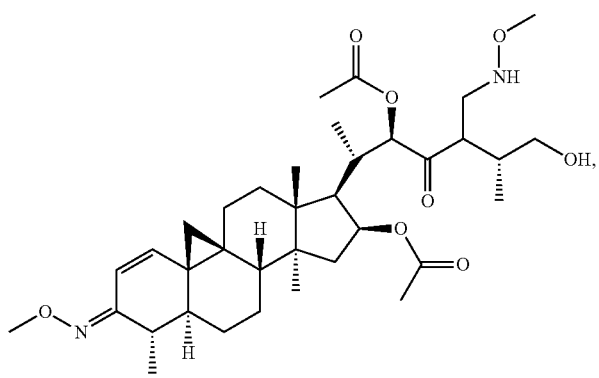
Compound 31
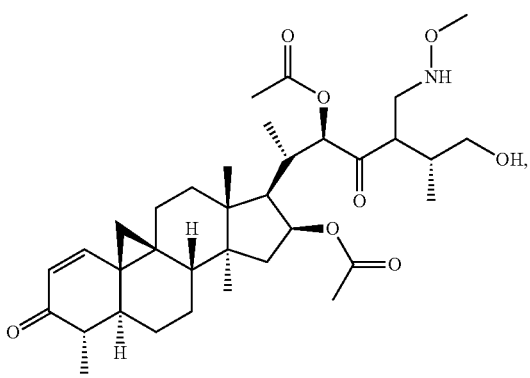
Compound 32
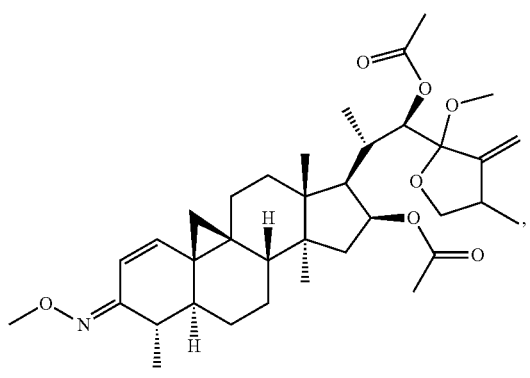
Compound 33
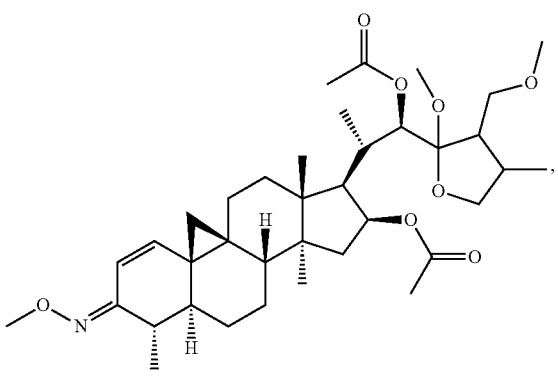
Compound 34
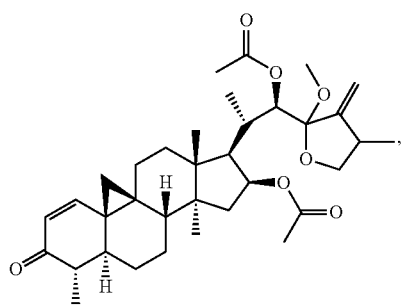
Compound 35
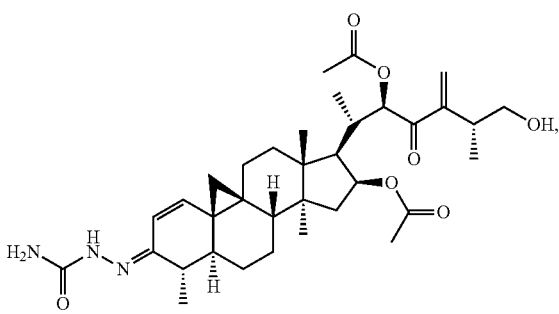

-continued
Compound 36
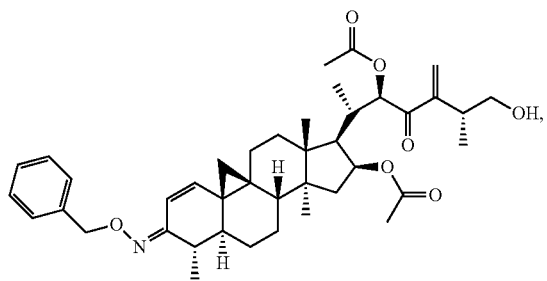
Compound 37
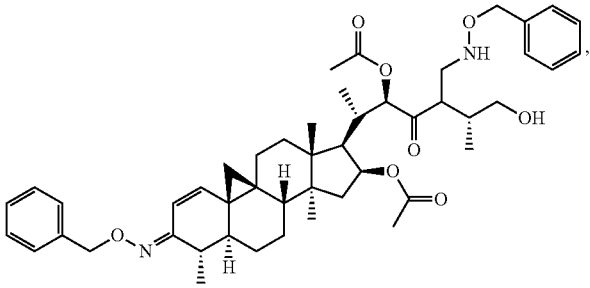
Compound 38
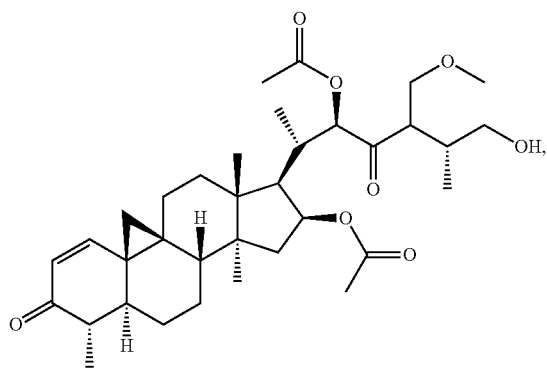
Compound 39
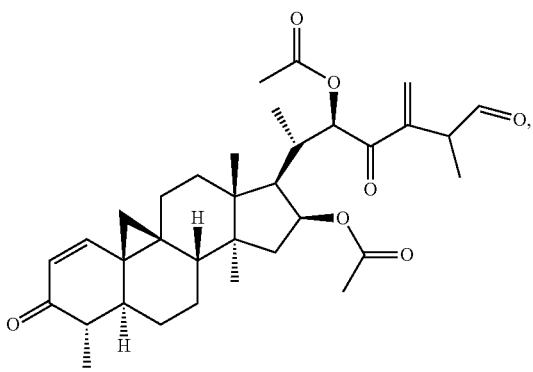
Compound 40
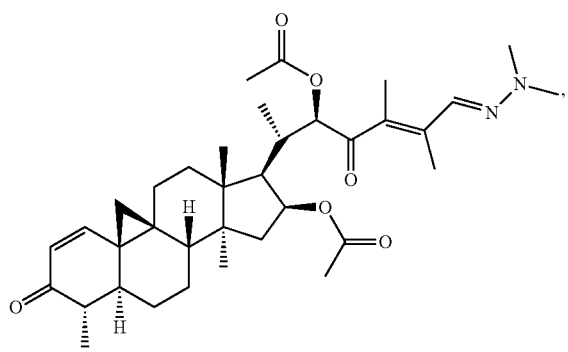
Compound 41
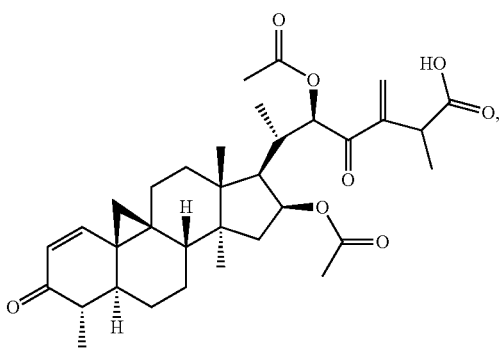
Compound 42
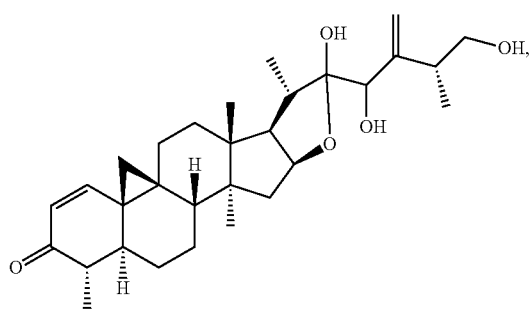
Compound 43
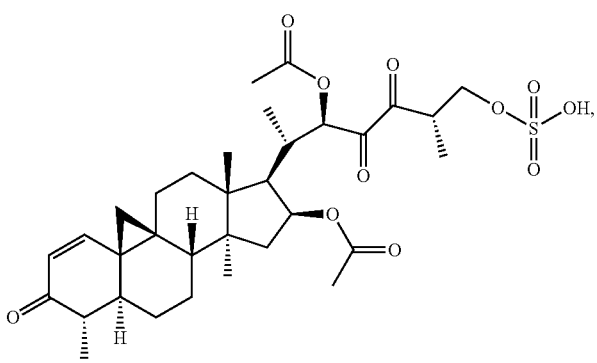

-continued
Compound 44
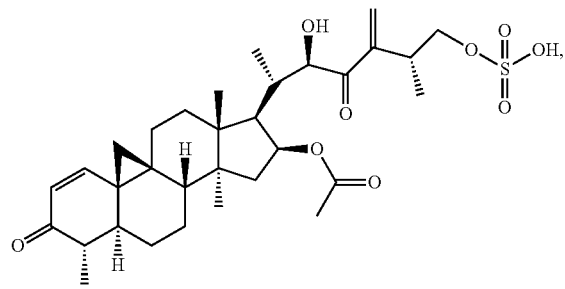
Compound 45
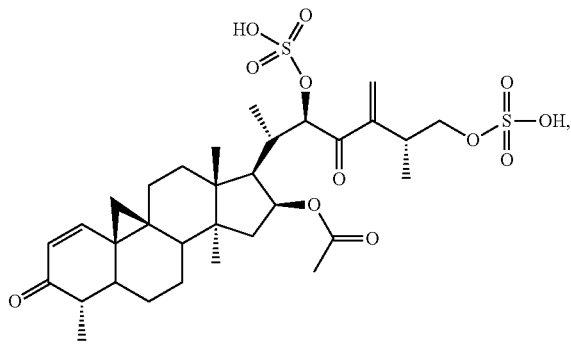
Compound 46
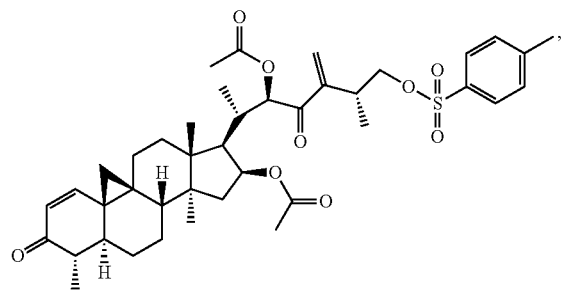
Compound 47
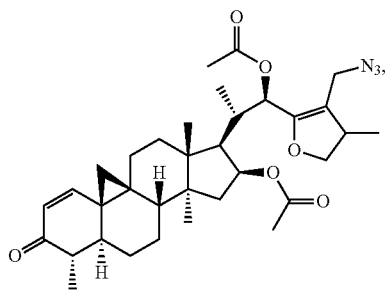
Compound 48
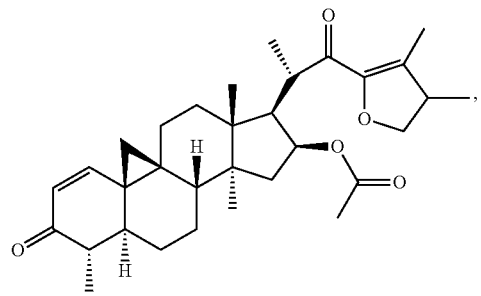
Compound 49
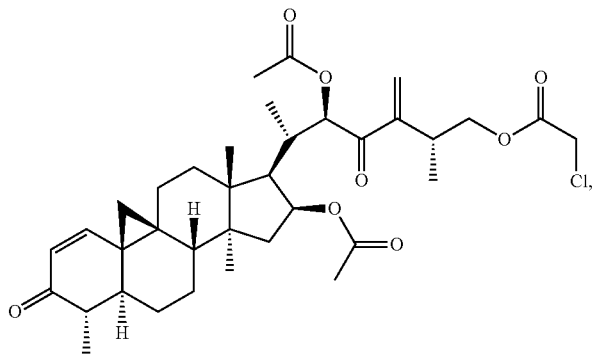
Compound 50
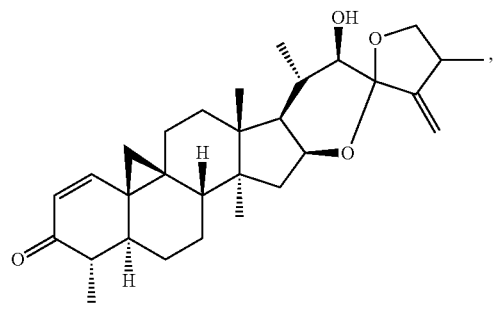
Compound 51
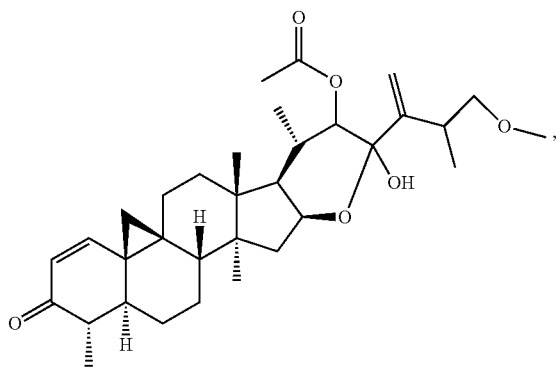

-continued
Compound 52
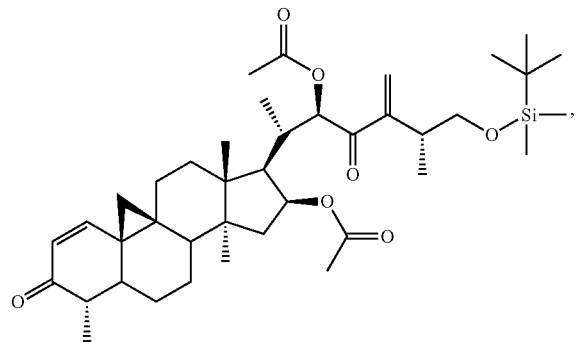
Compound 53
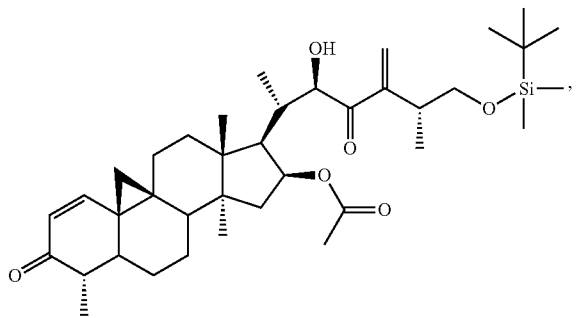
Compound 54
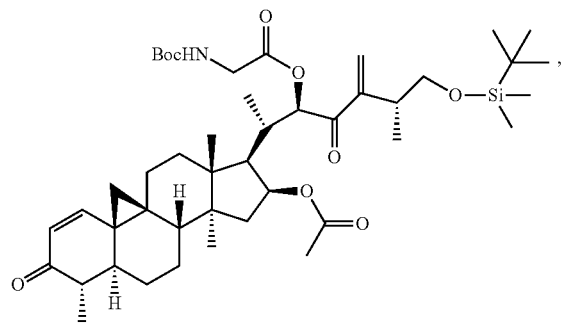
Compound 55
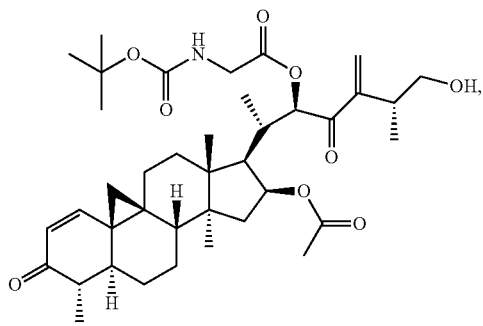
Compound 56
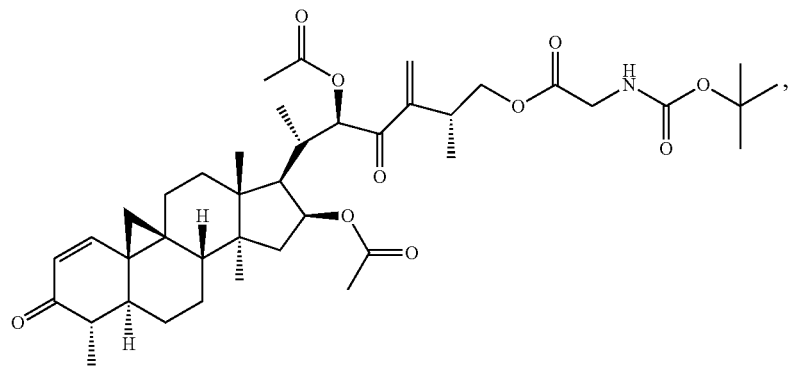
Compound 57
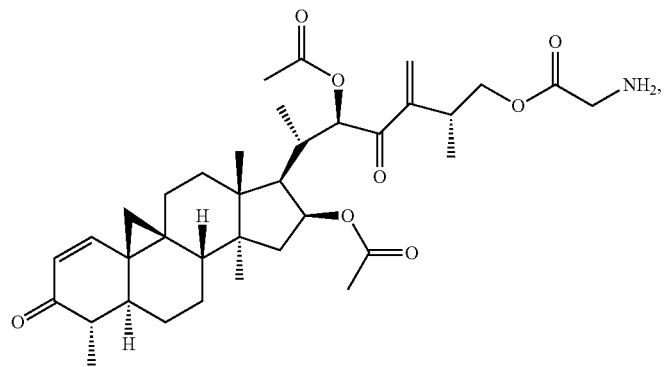

-continued
Compound 58
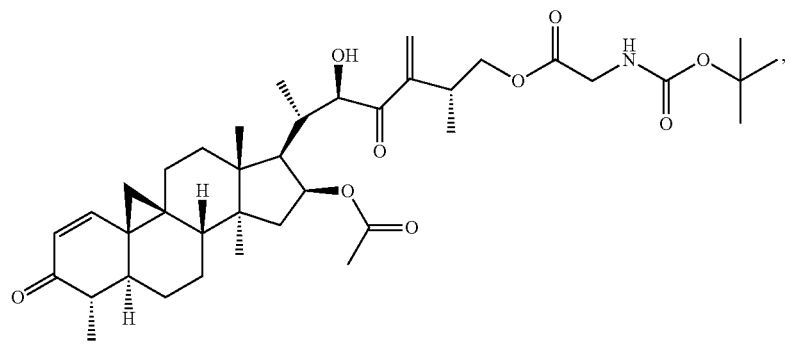
Compound 59
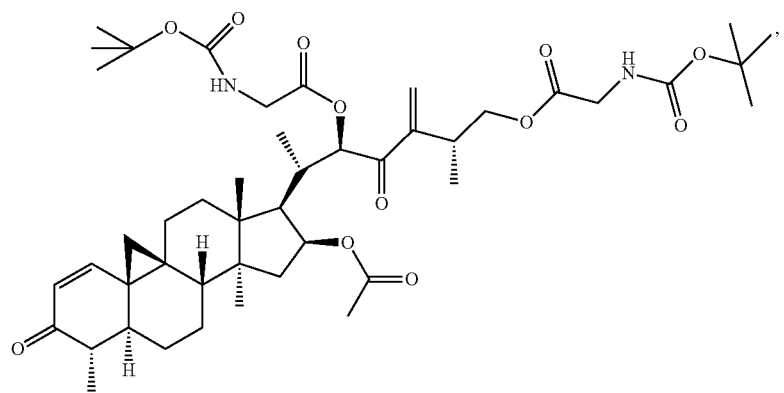
Compound 60
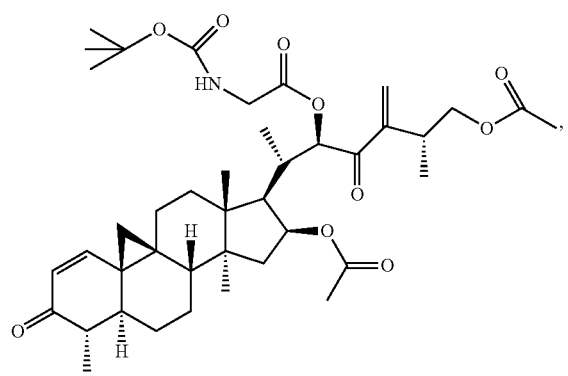
Compound 61
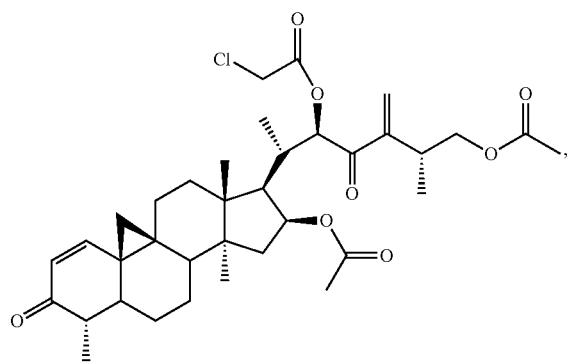
Compound 62
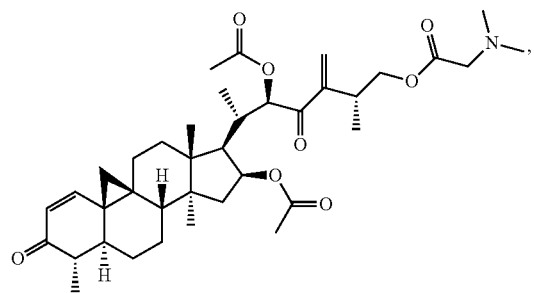
Compound 63
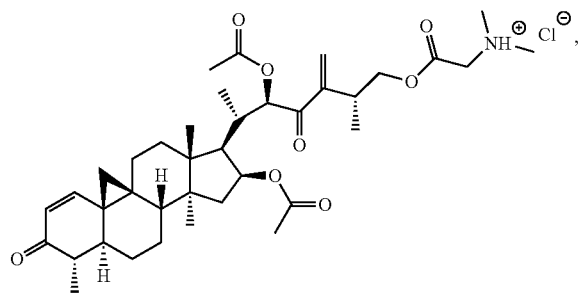

-continued
Compound 64
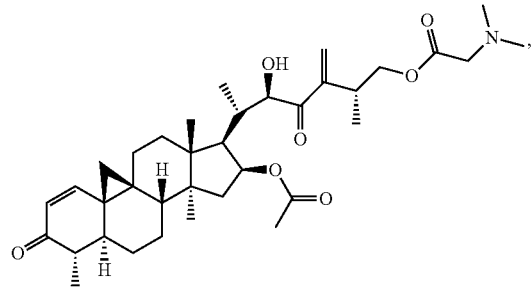
Compound 65
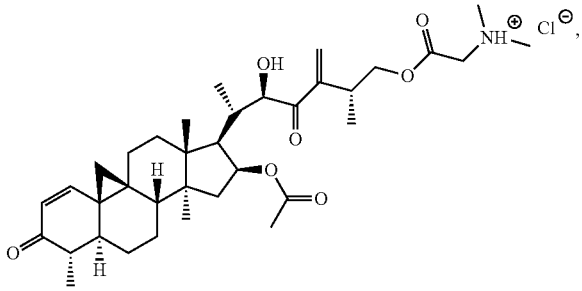
Compound 66
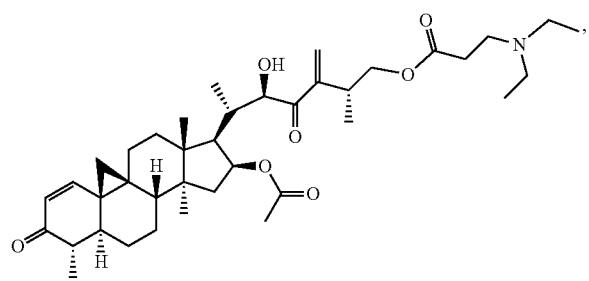
Compound 67
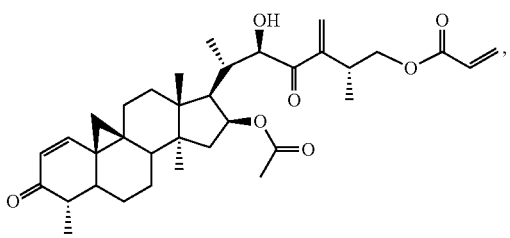
Compound 68
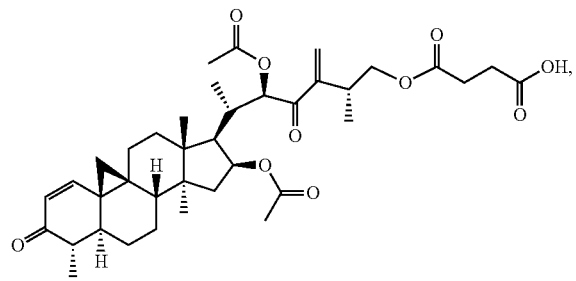
Compound 69
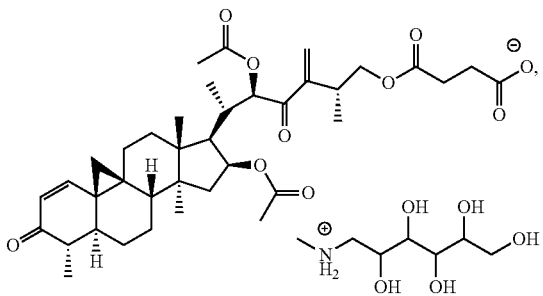
Compound 70
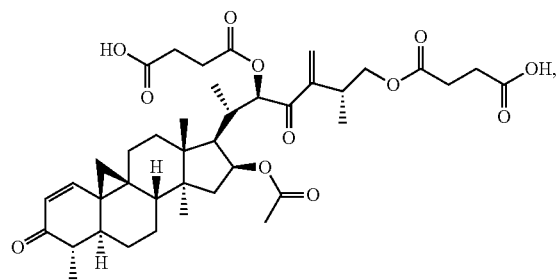
Compound 71
Compound 72
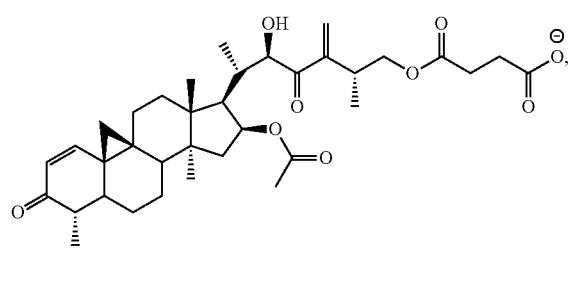
Compound 73
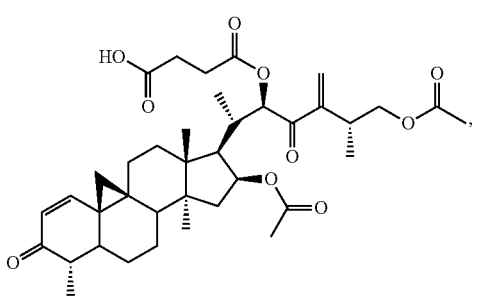

-continued
Compound 75
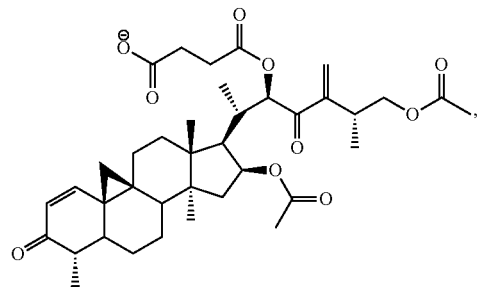
Compound 76
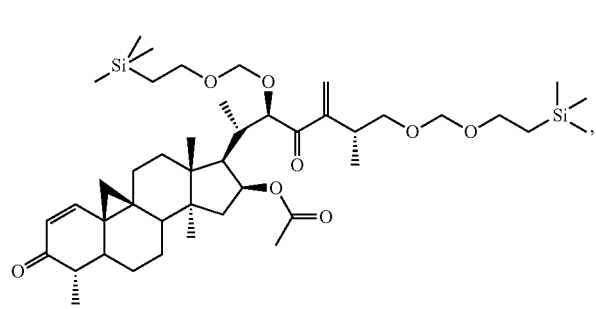
Compound 77
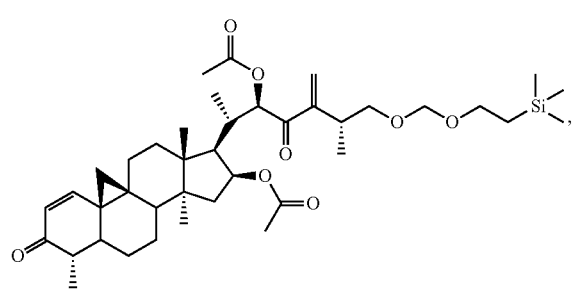
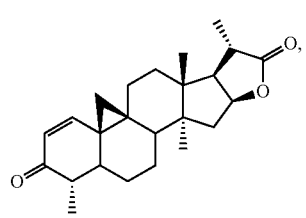
Compound 78
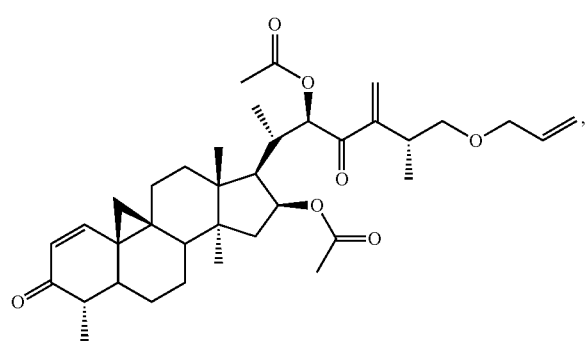
Compound 79
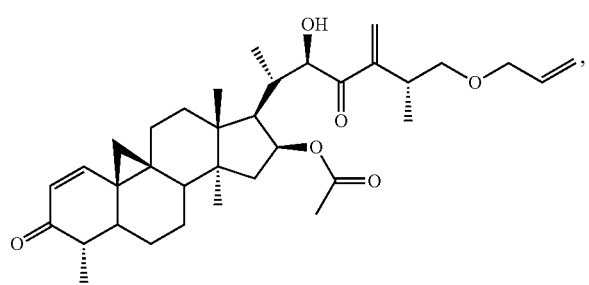
Compound 80
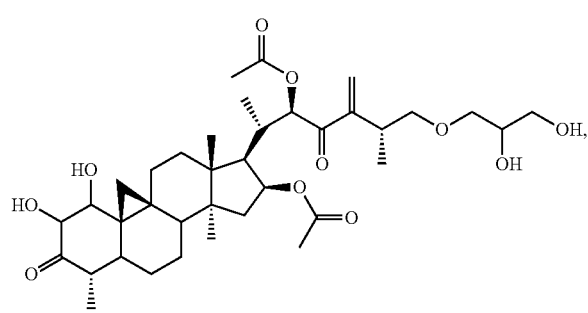
Compound 81
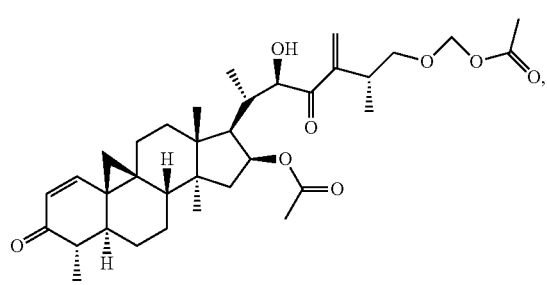

-continued
Compound 82
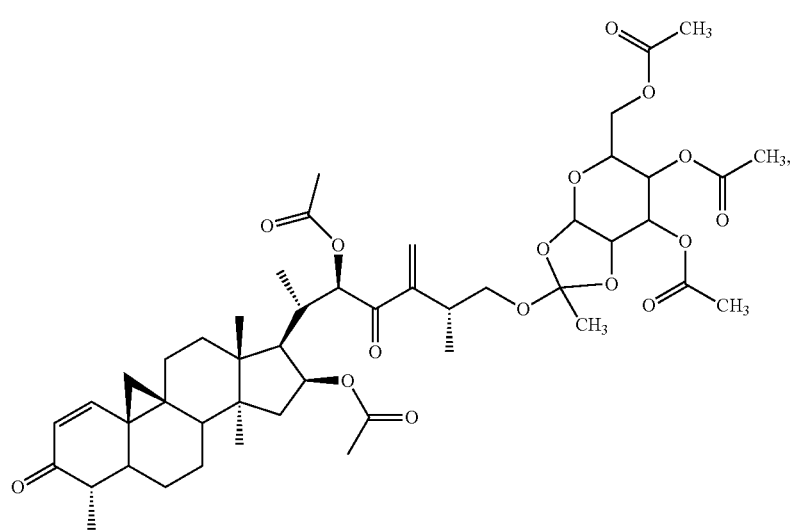
Compound 83
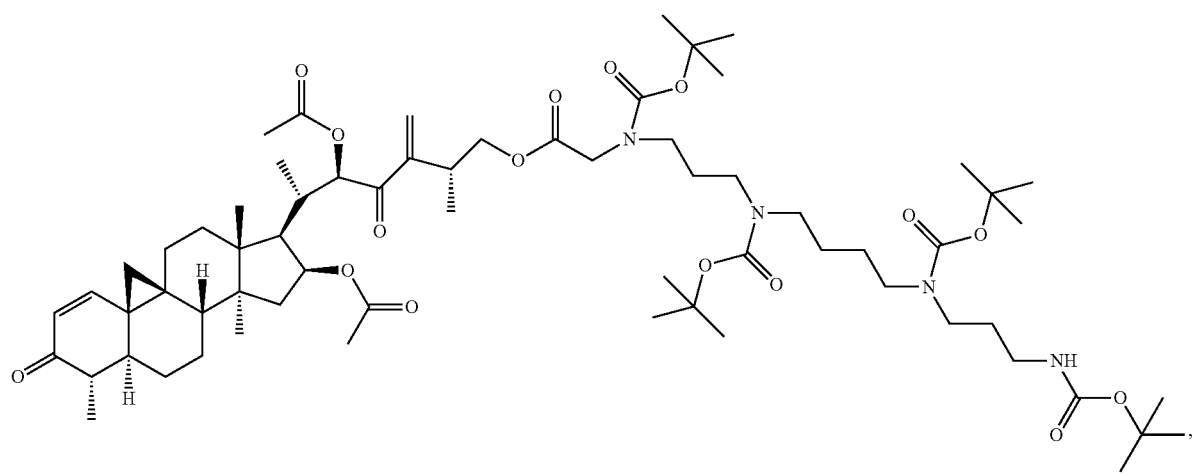
Compound 84
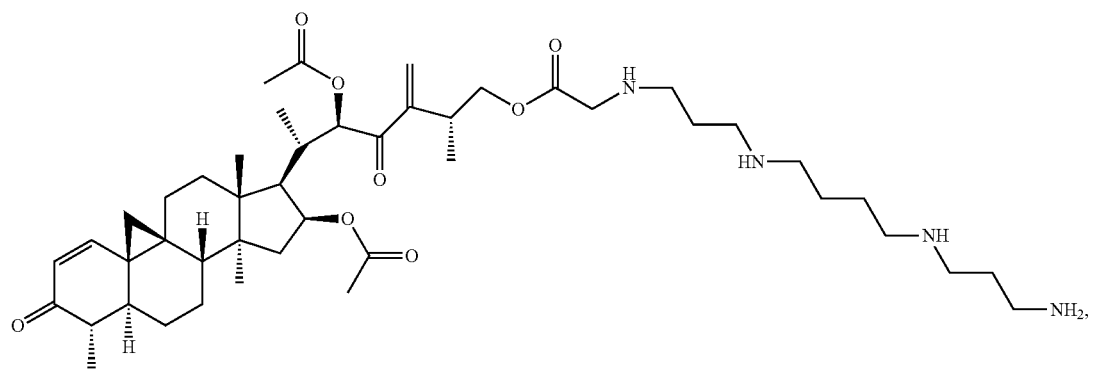

-continued
Compound 85
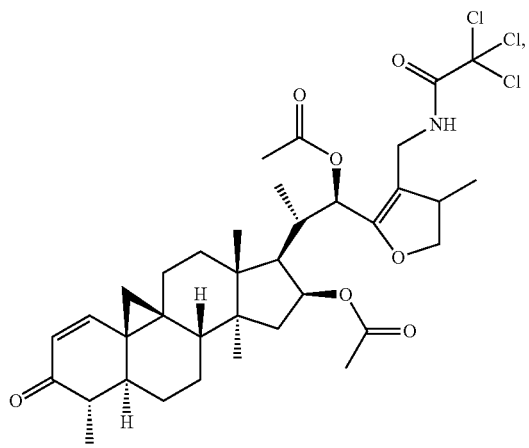
Compound 86
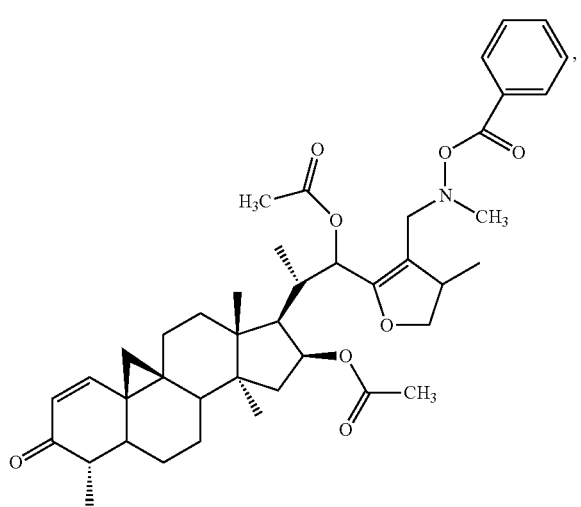
Compound 87
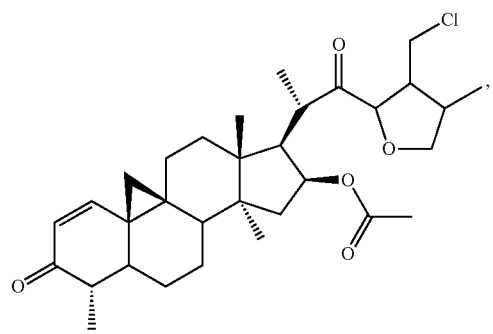
Compound 88
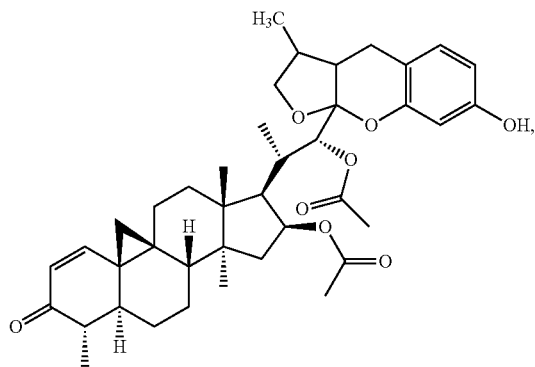
Compound 89
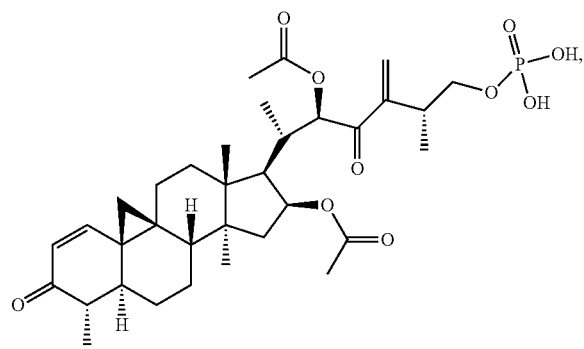

-continued

Compound 90

Compound 91

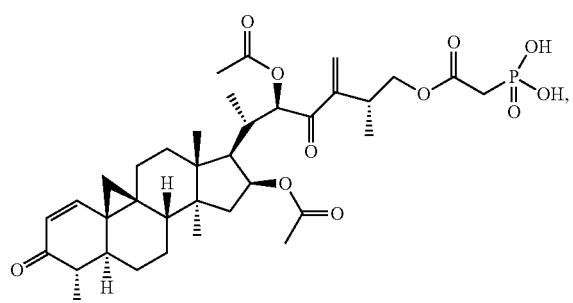

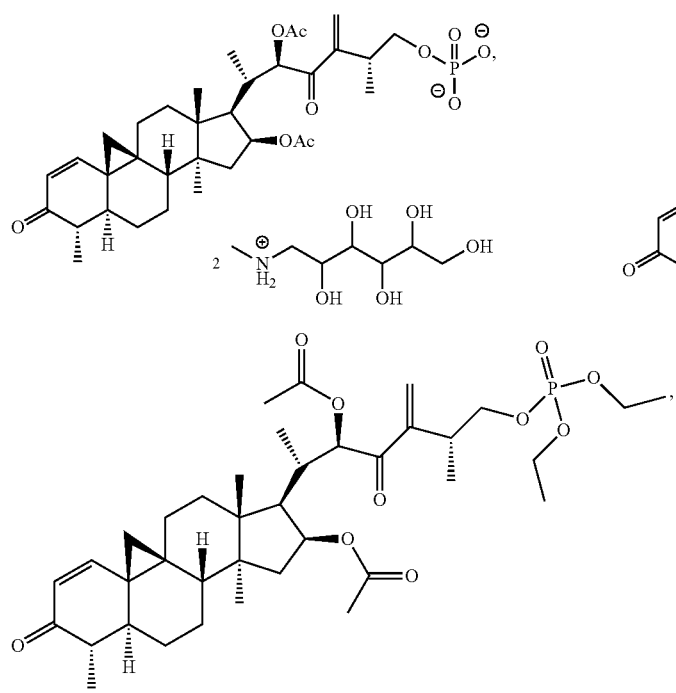

Compound 92.

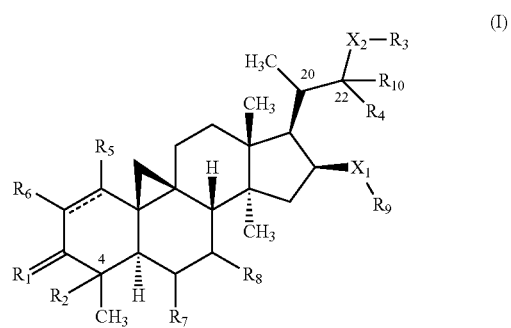

12. A compound according to claim 1, wherein $X_1$ and $X_2$ represent an oxygen atom.

13. A compound according to claim 1, wherein $R_2$ represents a hydrogen atom or an OH or SH group.

14. A compound according to claim 1, wherein $R_7$ represents a hydrogen atom or a OH group.

15. A compound according to claim 1, wherein X represents O.

16. A compound according to claim 1, wherein $R_1$ is an oxygen atom.

17. A compound according to claim 1, wherein $R_9$ represents a —CO—CH$_3$ group.

18. A pharmaceutical composition comprising at least one compound according to claim 1 and at least one pharmaceutically acceptable carrier.

19. The pharmaceutical composition according to claim 18, further comprising at least one other active ingredient.

20. A pharmaceutical composition comprising:
(i) at least one compound according to claim 1, and
(ii) at least one other active ingredient,
as combination products for simultaneous, separate or sequential use.

21. The pharmaceutical composition according to claim 19 or 20, wherein the other active ingredient is an anticancer agent.

22. A method to treat colon cancer, comprising the administration of an effective amount for treatment of a subject in need thereof of a compound according to the following formula (I):

(I)

or a pharmaceutically acceptable salt thereof,
wherein:
≡≡≡ indicates a single bond or a double bond,
$X_1$ and $X_2$ represent, independently of each other, an oxygen or sulfur atom,
$R_1$ represents an oxygen atom, a sulfur atom or an N—OR$_{11}$ or N—NHCO—NH$_2$ group,
$R_2$ represents a hydrogen atom or an OR$_{12}$ or SR$_{12}$ group,
$R_3$ represents a hydrogen atom, —SO$_2$R$_{55}$, —CH$_2$OCH$_2$CH$_2$SiR$_{61}$R$_{62}$R$_{63}$, a —CO—(C$_1$-C$_6$)alkyl, or —CO—(C$_2$-C$_6$)alkenyl group, wherein said group is optionally substituted by a halogen atom or a COOH or NR$_{56}$R$_{57}$ group,
$R_4$ represents a group selected from:
a hydrogen atom,
a saturated or unsaturated linear or branched hydrocarbon chain comprising 1 to 15 carbon atoms, one or more non-consecutive carbon atoms may be replaced by an oxygen atom, wherein said chain is optionally substituted by one or more groups selected from a halogen atom, =O, —OH, —OSO$_2$R$_{13}$, —N$_3$, (C$_1$-C$_6$)alkoxy, —Z$_1$C(X)R$_{14}$, —C(X)Z$_2$R$_{15}$, —Z$_3$C(X)Z$_4$R$_{16}$, —NH—OR$_{17}$, =N—OR$_{18}$, =N—NR$_{53}$R$_{54}$, —OSiR$_{19}$R$_{20}$R$_{21}$, —SiR$_{58}$R$_{59}$R$_{60}$, —OP(O)(OR$_{22}$)(OR$_{23}$), —NR$_{24}$R$_{25}$, a heterocycle with 5 or 6 members, an epoxide, a sugar residue and an inositol residue, one or more hydroxy groups of said sugar and inositol residues are optionally substituted by an acetyl group or —P(O)(OH)$_2$, and a heterocycle with 5 or 6 members or a polycycle with 10 to 15 members, wherein said heterocycle or polycycle comprises at least one oxygen atom and is optionally substituted by one or more groups selected from -OH, =O, —NH$_2$, —N$_3$, =CH$_2$, —COOR$_{26}$, (C$_2$-C$_6$)alkenyl, (C$_1$-C$_6$)alkoxy, and a (C$_1$-C$_6$)alkyl group optionally substituted by a halogen atom or an —N$_3$, —OH, (C$_1$-C$_6$)alkoxy, —NHCOR$_{27}$ or —NR$_{28}$—OC(O)R$_{29}$ group, R$_5$ and R$_6$ each represent a hydrogen atom when ⁻⁻⁻ represents a double bond, or R$_5$ and R$_6$ each represent, independently of each other, a hydrogen atom or an OR$_{48}$ group, or R$_5$ and R$_6$ together form, with the carbon atoms that carry them, an epoxide ring, when ⁻⁻⁻ represents a single bond, R$_7$ represents a hydrogen atom or a OR$_{49}$ group, R$_8$ represents a hydrogen atom, or R$_7$ and R$_8$ together form, with the carbon atoms that carry them, an epoxide ring, R$_9$ represents a —CO—(C$_1$-C$_6$)alkyl or —CO—(C$_2$-C$_6$)alkenyl group, or R$_9$ and R$_4$ together form a bond, or R$_9$ forms a bond with the carbon atom of the R$_4$ group located in the α position relative to carbon atom 22, R$_{10}$ represents a hydrogen atom, or R$_{10}$ and R$_3$ together form a bond, or R$_{10}$ and R$_9$ together form a bond, with:

R$_{11}$, R$_{26}$, R$_{28}$, R$_{30}$, R$_{31}$, R$_{36}$, R$_{37}$, R$_{41}$, R$_{42}$, R$_{43}$, R$_{48}$, R$_{49}$ and R$_{50}$ representing, independently of one another, a hydrogen atom or a (C$_1$-C$_6$)alkyl, (C$_2$-C$_6$)alkenyl, aryl or aryl-(C$_1$-C$_6$)alkyl group, R$_{12}$ representing a hydrogen atom or a (C$_1$-C$_6$)alkyl or (C$_2$-C$_6$)alkenyl group, R$_{13}$ and R$_{55}$ represent, independently of each other, an —OH, (C$_1$-C$_6$)alkoxy, aryl, —NR$_{30}$R$_{31}$ or (C$_1$-C$_6$)alkyl-aryl group, or a (C$_1$-C$_6$)alkyl group optionally substituted by an —NR$_{30}$R$_{31}$ group, R$_{14}$ representing a (C$_1$-C$_6$)alkyl, (C$_2$-C$_6$)alkenyl, aryl, (C$_1$-C$_6$)alkyl-aryl or aryl -(C$_1$-C$_6$)alkyl group, wherein said group is optionally substituted by a group selected from a halogen atom, an —NR$_{32}$—[(CH$_2$)$_a$—NR$_{33}$]$_d$—[(CH$_2$)$_b$—NR$_{34}$—(CH$_2$)$_c$—NR$_{35}$]$_e$—R$_{52}$, —P(O)(OH)$_2$ or —COOH group, with a, b and c representing an integer between 1 and 5 and d and e each representing 0 or 1, R$_{15}$ and R$_{16}$ representing, independently of each other, a hydrogen atom or a (C$_1$-C$_6$)alkyl, (C$_2$-C$_6$)alkenyl, aryl, (C$_1$-C$_6$)alkyl-aryl or aryl-(C$_1$-C$_6$)alkyl group, wherein said group is optionally substituted by a group selected from a halogen atom, an —NR$_{32}$—[(CH$_2$)$_a$—NR$_{33}$]$_d$—[(CH$_2$)$_b$—NR$_{34}$—(CH$_2$)$_c$—N—R$_{35}$]$_e$-R$_{52}$ or —COOH group, with a, b, c, d and e as defined above, R$_{17}$ and R$_{18}$ representing, independently of each other, a hydrogen atom or a (C$_1$-C$_6$)alkyl, (C$_2$-C$_6$)alkenyl, aryl or aryl-(C$_1$-C$_6$)alkyl group, R$_{19}$, R$_{20}$, R$_{21}$, R$_{58}$, R$_{59}$, R$_{60}$, R$_{61}$, R$_{62}$ and R$_{63}$ representing, independently of one another, a (C$_1$-C$_6$)alkyl, (C$_2$-C$_6$)alkenyl or aryl group, R$_{22}$ and R$_{23}$, identical or different, representing a hydrogen atom or a (C$_1$-C$_6$)alkyl or (C$_2$-C$_6$)alkenyl group, wherein said group is optionally substituted by an —OC(O)—(C$_1$-C$_6$)alkyl, NR$_{36}$R$_{37}$ and —N$^+$R$_{38}$R$_{39}$R$_{40}$ group, or R$_{22}$ and R$_{23}$ together form, with the oxygen atoms that carry them and the phosphorous atom, a ring, R$_{24}$ and R$_{25}$, representing, independently of each other, a hydrogen atom or a —CO—(C$_1$-C$_6$)alkyl, —CO—(C$_2$-C$_6$)alkenyl, (C$_2$-C$_6$)alkenyl, (C$_3$-C$_7$)cycloalkyl or (C$_1$-C$_6$)alkyl group optionally substituted by an NR$_{41}$R$_{42}$ group, or R$_{24}$ and R$_{25}$ together form, with the nitrogen atom that carries them, a heterocycle with 5 or 6 members, wherein said heterocycle may comprise, in addition to the nitrogen atom carrying R$_{24}$ and R$_{25}$, one or more heteroatoms selected from nitrogen, oxygen and sulfur, and is optionally substituted by a (C$_1$-C$_6$)alkyl group, R$_{27}$ representing an aryl, (C$_1$-C$_6$)alkyl or (C$_2$-C$_6$)alkenyl group, wherein said group is optionally substituted by one or more halogen atoms, R$_{29}$ representing a (C$_1$-C$_6$)alkyl, (C$_2$-C$_6$)alkenyl, aryl or aryl-(C$_1$-C$_6$)alkyl group, R$_{32}$, R$_{33}$, R$_{34}$, R$_{35}$, R$_{52}$, R$_{53}$, R$_{54}$, R$_{56}$ and R$_{57}$ representing, independently of one another, a hydrogen atom or a (C$_1$-C$_6$)alkyl, (C$_2$-C$_6$)alkenyl, —CO—(C$_1$-C$_6$)alkyl, —CO—(C$_2$-C$_6$)alkenyl, —CO$_2$—(C$_1$-C$_6$)alkyl or —CO$_2$—(C$_2$-C$_6$)alkenyl group, R$_{38}$, R$_{39}$ and R$_{40}$ representing, independently of one another, a (C$_1$-C$_6$)alkyl or (C$_2$-C$_6$)alkenyl group, X representing O, S or NR$_{50}$, Z$_1$, Z$_2$, Z$_3$ and Z$_4$ representing, independently of one another, O or NR$_{43}$, or Z$_2$R$_{15}$ and/or Z$_4$R$_{16}$ representing, independently of each other, a heterocycle with 5 or 6 members optionally substituted by a (C$_1$-C$_6$)alkyl group, wherein the heterocycle comprises at least one nitrogen atom by which it is linked to the rest of the molecule;

or a pharmaceutical composition according to claim 18 or 20 to a person in need thereof.

* * * * *